(12) United States Patent
Shockey et al.

(10) Patent No.: US 7,105,722 B2
(45) Date of Patent: Sep. 12, 2006

(54) PLANT ACYL-COA SYNTHETASES

(75) Inventors: Jay M. Shockey, Pullman, WA (US); Judy Schnurr, Pullman, WA (US); John A. Browse, Pullman, WA (US)

(73) Assignee: Washington State University

( * ) Notice: Subject to any disclaimer, the term of this patent is extended or adjusted under 35 U.S.C. 154(b) by 325 days.

(21) Appl. No.: 10/119,136

(22) Filed: Apr. 9, 2002

(65) Prior Publication Data

US 2003/0097676 A1 May 22, 2003

Related U.S. Application Data

(63) Continuation-in-part of application No. 09/906,419, filed on Jul. 16, 2001, now abandoned.

(60) Provisional application No. 60/220,474, filed on Jul. 21, 2000.

(51) Int. Cl.
*A01H 15/82* (2006.01)
*C12P 21/06* (2006.01)

(52) U.S. Cl. .................... 800/281; 536/23.6; 435/69.1

(58) Field of Classification Search ................ 800/281, 800/298; 435/6, 252.3; 536/23.2
See application file for complete search history.

(56) References Cited

U.S. PATENT DOCUMENTS 5,380,831 A * 1/1995 Adang et al. ............. 536/23.71
5,955,329 A * 9/1999 Yuan et al. .................. 435/468

OTHER PUBLICATIONS

Fulda et al, PMB 33(5) 911-922, 1997.*
Ohlrogge, J (1994) Plant Physiol. 104:821-26.
Ohlrogge, J (1999) Curr. Opin. Plant Biol. 2:121-22.
Fulda et al., Plant Molec. Biol. 33:911-22 (1997).
Steinberg, S.J et al. (2000) Journal of Biological Chemistry 275(45) 35162-35169.
Iijima, H. et al. (1996) Eur J Biochem 242(2): 186-90.
Johnson, DR et al. (1994) J Cell Biol 127(3): 751-62.
Kang, MJ et al. (1997) Proc Natl Acad Sci U S A 94(7): 2880-4.
Uchiyama, A et al. (1996) J Biol Chem 271(48): 30360-5.
Berger, J et al. (1998) FEBS Lett 425(2): 305-9.
Min, KT and Benzer, S (1999) Science 284(5422): 1985-8.
Choi, JY and Martin, CE (1999) J Biol Chem 274(8): 4671-83.
Steinberg, SJ et al. (1999) Biochem and Biophys Res Comm 257(2): 615-621.
Lee, M et al. (1995) Science 280(5365): 915-918.
Ke et al., Plant Physiology (2000) 123:497-508.
Ehlting, J et al. (1999) Plant J 19(1): 9-20.
Shockey et al., Platn Physiology (2002) 129:1710-1277.
Knoll, LJ et al. (1995) J Biol Chem 270(18): 10861-7.
Ohlrogge and Browse (1995) Plant Cell 7(7): 957-70).
Black et al., (1997) J. of Biol. Chem. 272:4896-4903.
Newman et al., Plant Physiol. (1994) 106:1241-1255.

* cited by examiner

*Primary Examiner*—Elizabeth F. McElwain
(74) *Attorney, Agent, or Firm*—Medlen & Carroll, LLP

(57) ABSTRACT

The present invention relates to genes encoding plant acyl-CoA synthetases and methods of their use. In particular, the present invention is related to plant acyl-coenzyme A synthetases. The present invention encompasses both native and recombinant wild-type forms of the enzymes, as well as mutant and variant forms, some of which possess altered characteristics relative to the wild-type enzyme. The present invention also relates to methods of using acyl-CoA synthetases, including altered expression in transgenic plants and expression in prokaryotes and cell culture systems.

6 Claims, 74 Drawing Sheets

| | | | |
|---|---|---|---|
| AtACS1A | PRVLDRVYS₃₃₁GL | N=39 | DKLVFS₃₇₈KVK |
| AtACS1B | PRVLDRVYT₃₃₁GL | N=39 | DKLVFN₃₇₈KVK |
| AtACS1C | PRVLERTYT₃₃₁GL | N=39 | DKTVFK₃₇₈KVK |
| AtACS2  | PRVYDKLYA₃₃₁GI | N=39 | DRLMFD₃₇₈KIK |
| AtACS3A | PRLYNRIYA₃₆₄GI | N=36 | DRLVFN₄₀₈KIK |
| AtACS3B | PRLYNRIYD₃₆₄GI | N=36 | DKLVFN₄₀₈KIK |
| AtACS4A | PLVYETLYS₃₆₂GI | N=70 | KKLIYK₄₄₀KIH |
| AtACS4B | PLVYETLYS₃₆₄GI | N=70 | EKLVHR₄₄₂KIR |
| AtACS5  | PRVFERTHE₃₂₈GI | N=39 | DFIAFR₃₇₅KIR |
| AtACS6A | PAILDRVRE₃₈₇GV | N=41 | DALVFK₄₃₆KIR |
| AtACS6B | PAILDRVRD₃₅₈GV | N=41 | DVLVFR₄₀₇KIR |

FIGURE 3

SEDQ ID NO: 1   AtACS1A Original cDNA Nucleotide Sequence

```
   1 ATGACGCAGC AGAAGAAATA CATCTTCCAA GTTGAAGAAG GCAAAGAAGG
  51 TAGCGATGGA AGACCATCAG TTGGTCCAGT GTACCGGAGT ATCTTTGCCA
 101 AGGACGGRTT TCCCGACCCG ATCGAAGGAA TGGATAGTTG TTGGGATGTT
 151 TTCCGCATGT CTGTTGAGAA GTATCCAAAC AATCCAATGC TGGGACGCCG
 201 CGAGATTGTA GATGGAAAGC CGGGTAAGTA TGTCTGGCAA ACATACCAAG
 251 AAGTCTACGA CATTGTCATG AAACTTGGAA ATTCTCTCAG AAGTGTTGGA
 301 GTTAAGGACG AAGCAAAATG TGGTATCTAT GGTGCAAATT CTCCTGAGTG
 351 GATTATCAGC ATGGAGGCTT GTAATGCACA TGGACTCTAT TGTGTACCGT
 401 TATATGATAC ACTAGGTGCT GATGCTGTGG AATTCATCAT TTCCCATTCA
 451 GAGGTTTCAA TTGTCTTTGT GGAAGAGAAG AAGATCTCTG AGTTGTTCAA
 501 GACATGCCCA AACTCGACAG AGTACATGAA AACTGTTGTG AGCTTCGGGG
 551 GTGTCTCACG TGAACAAAAA GAAGAAGCTG AAACTTTTGG GTTGGTTATA
 601 TATGCTTGGG ATGAATTTTT GAAGCTGGGT GAAGGAAAGC AATATGATCT
 651 CCCAATCAAA AAGAAAGCG ACATTTGCAC GATTATGTAT ACGAGTGGAA
 701 CCACTGGTGA CCCAAAGGGA GTGATGATAT CTAACGAAAG CATTGTGACT
 751 CTAATCGCTG GAGTGATCCG TCTACTGAAA AGTGCTAACG AGGCTCTGAC
 801 TGTGAAAGAT GTGTATCTTT CTTATCTTCC TCTTGCCCAC ATCTTTGACC
 851 GAGTTATCGA GGAGTGTTTC ATTCAACATG GTGCTGCAAT TGGCTTCTGG
 901 CGAGGGGATG TAAAATTGTT GATCGAAGAC CTTGCTGAGC TTAAACCAAC
 951 TATTTTTTGT GCTGTACCTC GTGTCCTGGA TAGAGTATAC CCAGGTCTTC
1001 AGAAGAAGCT TTCTGATGGT GGATTCTTAA AAAGTTCAT ATTTGATTCT
1051 GCATTTTCCT ATAAATTTGG TTATATGAAG AAGGGACAGT CTCATGTGGA
1101 GGCCTCTCCA CTTTTTGACA AACTTGTGTT CAGCAAGGTT AAACAAGGAC
1151 TCGGAGGCAA TGTGAGGATT ATTCTATCTG GAGCTGCTCC TCTTGCTAGT
1201 CACGTAGAGT CATTTCTAAG AGTGGTGGCA TGCTGTCATG TTCTCCAAGG
1251 ATACGGTCTT ACTGAAAGCT GTGCTGGAAC TTTTGTCTCG CTGCCAGATG
1301 AACTAGGTAT GCTCGGCACA GTTGGTCCAC CAGTGCCAAA CGTTGATATA
1351 CGCCTTGAAT CCGTCCCCGA GATGGAATAT GATACTCTTG CGAGTACTGC
1401 ACGTGGTGAA ATCTGCATTC GGGGAAAGAC CCTTTTCTCT GGTTACTACA
1451 AACGTGAAGA TCTCACGAAA GAGGTTCTCA TTGATGGATG GCTGCACACA
1501 GGTGATGTTG GTGAGTGGCA ACCAGATGGA AGCATGAAGA TAATTGACAG
1551 GAAGAAGAAT ATCTTTAAAC TCTCACAAGG AGAGTATGTT GCGGTGGAGA
1601 ACATAGAAAA CATATACGGT GAAGTACAAG CTGTTGATTC CGTGTGGGTG
1651 TACGGTAACA GCTTTGAGTC CTTCCTAATA GCTATCGCCA ACCCAAACCA
1701 GCATATCCTT GAACGCTGGG CTGCAGAAAA CGGTGTGAGT GGTGACTATG
1751 ACGCCCTCTG TCAAAATGAA AAGGCAAAGG AATTCATTCT CGGAGAACTT
1801 GTTAAAATGG CCAAAGAGAA AAAGATGAAA GGGTTCGAGA TCATCAAGGC
1851 GATTCATCTT GACCCAGTGC CATTTGACAT GGAACGAGAT CTTCTTACGC
1901 CGACCTTCAA AAAGAAAAGG CCTCAGTTGC TGAAATACTA CCAGAGTGTG
1951 ATCGACGAAA TGTACAAGAC CATAAATGCA AAATTTGCTT CCAGAGGGTA
2001 G
```

FIGURE 4

SEQ ID NO:2 AtACS1B Original cDNA Nucleotide Sequence

```
   1  ATGACGTCGC AGAAAAGATT CATCTTTGAG GTGGAAGCCG CTAAGGAAGC
  51  CACAGATGGA AATCCCTCGG TTGGTCCTGT CTATCGTAGT ACTTTTGCTC
 101  AGAACGGATT CCCGAACCCG ATCGATGGTA TCCAAAGCTG CTGGGATATT
 151  TTCCGCACGG CTGTTGAGAA GTATCCAAAC AATCGAATGC TTGGTCGCCG
 201  TGAGATTTCG AACGGGAAGG CAGGAAAGTA CGTGTGGAAA ACATACAAAG
 251  AAGTATACGA CATTGTCATA AAACTTGGAA ATTCTCTACG TAGTTGCGGG
 301  ATTAAGGAGG GAGAAAAATG TGGTATATAT GGTATAAATT GTTGTGAGTG
 351  GATCATTAGC ATGGAGGCAT GTAATGCACA TGGCCTTTAT TGTGTCCCTT
 401  TATACGATAC GTTAGGCGCT GGTGCAGTGG AATTCATCAT TTCTCATGCA
 451  GAGGTTTCAA TTGCTTTCGT GGAGGAGAAG AAGATCCCTG AGCTTTTTAA
 501  GACTTGTCCA AACTCAACAA AATATATGAA GACTGTTGTG AGCTTTGGCG
 551  GTGTCAAACC GGAACAAAAA GAAGAAGCTG AAAAATTGGG ATTGGTAATA
 601  CATTCGTGGG ATGAGTTTTT GAAGCTGGGT GAGGGTAAGC AATATGAGCT
 651  TCCCATTAAA AAGCCAAGCG ACATATGCAC GATTATGTAT ACTAGCGGAA
 701  CAACTGGTGA CCCGAAGGGA GTTATGATTT CAAATGAAAG CATTGTTACT
 751  ATAACTACTG GAGTGATGCA TTTCCTAGGG AATGTGAATG CAAGCCTATC
 801  TGAGAAGGAT GTGTATATTT CTTATCTTCC TCTCGCGCAC GTCTTTGATC
 851  GGGCAATCGA GGAATGTATT ATTCAAGTAG GTGGTTCAAT GGTTTCTGG
 901  CGCGGGGATG TCAAATTGTT GATTGAAGAC CTTGGTGAGC TAAAACCAAG
 951  TATCTTTTGC GCCGTTCCTC GTGTCCTAGA TCGAGTATAC ACAGGACTAC
1001  AGCAGAAACT ATCTGGTGGT GGTTTCTTCA AAAAGAAGAA ATTTGGAAAT
1051  ATGAAGAAAG GACAGTCTCA TGTGGCAGCT TCTCCATTTT GTGACAAACT
1101  TGTATTCAAC AAGGTTAAAC AAGGACTTGG AGGCAATGTG AGGATTATTC
1151  TGTCTGGAGC GGCTCCTCTC GCTAGTCACA TAGAATCTTT TCTAAGAGTT
1201  GTTGCATGTT GTAATGTTCT ACAAGGATAT GGTCTAACTG AGAGTTGTGC
1251  TGGAACTTTT GCAACGTTCC CAGACGAACT AGACATGCTT GGGACTGTTG
1301  GTCCACCCGT GCCAAACGTC GATATACGCC TTGAATCTGT CCCGGAAATG
1351  AATTATGATG CTCTTGGAAG TACTCCGCGA GGCGAAATAT GCATACGAGG
1401  AAAAACTTTA TTTTCAGGGT ACTACAAACG TGAAGACCTC ACAAAAGAGG
1451  TTTTTATCGA CGGATGGTTG CACACAGGTG ATGTTGGTGA GTGGCAACCA
1501  AATGGAAGCA TGAAGATAAT TGACCGGAAA AAGAACATCT TCAAACTCGC
1551  GCAAGGAGAG TATGTCGCTG TTGAGAATTT AGAAAATGTC TACAGTCAAG
1601  TAGAAGTTAT TGAATCGATA TGGGTATATG GAAACAGCTT TGAGTCCTTC
1651  CTTGTCGCAA TCGCTAACCC GGCCCAACAA ACTCTTGAAC GATGGGCTGT
1701  GGAGAATGGA GTGAATGGAG ACTTCAACTC CATCTGCCAA AACGCAAAGG
1751  CAAAAGCATT CATACTTGGA GAACTCGTTA AACAGCCAA AGAGAACAAG
1801  TTGAAGGGTT TTGAGATCAT AAAAGATGTT CATCTGGAAC CAGTGGCGTT
1851  CGACATGGAA CGAGACCTTC TTACTCCAAC CTACAAAAAG AAGAGGCCTC
1901  AATTGCTCAA ATACTATCAG AATGTGATCC ATGAAATGTA CAAGACAACA
1951  AAGGAAAGTC TAGCTTCCGG ACAGTAA
```

FIGURE 5

SEQ ID NO:3 AtACS1C Original cDNA Nucleotide Sequence

```
   1  ATGGCGACTG GTCGATACAT CGTTGAGGTT GAGAAGGGAA AGCAAGGCGT
  51  TGATGGAGGA AGTCCATCGG TCGGTCCAGT TTACCGGAGT ATCTATGCTA
 101  AAGACGGTTT TCCTGAACCG CCTGATGATC TCGTCAGTGC ATGGGATATT
 151  TTCCGTTTAT CTGTGGAGAA ATCTCCAAAT AATCCTATGC TTGGTCGTAG
 201  AGAAATAGTT GATGGAAAAG CTGGGAAATA TGTATGGCAA ACTTACAAAG
 251  AAGTACATAA TGTAGTGATT AAGCTTGGAA ACTCTATCAG AACTATTGGA
 301  GTTGGAAAAG GAGATAAATG CGGTATTTAT GGCGCCAATA GTCCTGAATG
 351  GATTATAAGC ATGGAGGCTT GCAATGCTCA TGGACTCTAC TGTGTACCTT
 401  TATATGACAC TCTAGGTGCT GGAGCAATAG AATTCATCAT TGTCATGCT
 451  GAGGTCTCAC TTGCTTTTGC TGAGGAGAAC AAAATCTCTG AGTTATTGAA
 501  GACAGCTCCT AAATCAACTA AATATTTGAA GTATATTGTG AGCTTTGGTG
 551  AGGTTACAAA TAATCAGAGA GTAGAAGCTG AGAGGCACAG ATTAACAATA
 601  TATTCATGGG ACCAATTCTT GAAGCTAGGC GAGGGTAAAC ATTATGAATT
 651  ACCAGAGAAG AGAAGAAGCG ATGTTTGCAC CATAATGTAT ACAAGTGGCA
 701  CAACTGGTGA TCCTAAAGGA GTATTGCTTA CAAATGAGAG CATTATTCAT
 751  CTCCTTGAAG GTGTTAAAAA ATTGCTTAAA ACTATTGACG AAGAGTTAAC
 801  CAGTAAAGAT GTATATCTCT CATATCTACC TCTGGCTCAT ATCTTCGATC
 851  GTGTGATTGA GGAGCTGTGT ATTTATGAAG CAGCCTCTAT CGGATTCTGG
 901  CGAGGGGATG TTAAGATATT GATAGAAGAC ATTGCTGCAT GAAACCTAC
 951  TGTTTTCTGC GCTGTTCCTC GCGTGCTAGA GAGAATATAC ACCGGTCTTC
1001  AGCAGAAACT TTCTGATGGT GGTTTTGTAA AGAAGAAATT ATTCAACTTT
1051  GCATTCAAAT ACAAACATAA AAACATGGAG AAAGGGCAGC TCATGAACA
1101  AGCATCTCCA ATAGCTGACA AAATTGTATT TAAAAAGGTA AAAGAAGGGT
1151  TGGGAGGAAA CGTGCGTCTT ATCCTCTCAG GAGCAGCTCC TCTTGCAGCT
1201  CACATCGAAT CTTTCCTTCG AGTTGTCGCG TGTGCTCATG TTTTGCAAGG
1251  ATACGGTCTA ACAGAGAGTT GTGGTGGGAC TTTTGTGTCC ATTCCAAACG
1301  AGCTTTCAAT GCTTGGAACG GTTGGTCCAC CGGTTCCAAA CGTTGACATA
1351  AGGCTAGAGT CAGTTCCAGA GATGGGTTAT GACGCTCTTG CAAGCAATCC
1401  ACGTGGAGAG ATTTGCATCA GGGGAAAGAC TTTGTTCTCT GGATACTACA
1451  AACGTGAAGA TCTCACTCAA GAAGTCTTCA TTGATGGATG GCTTCACACT
1501  GGTGATGTCG GTGAGTGGCA CCAGATGGA GCCATGAAGA TCATCGACCG
1551  TAAGAAGAAC ATCTTTAAAC TGTCTCAAGG AGAATACGTT GCCGTTGAGA
1601  ACTTGGAGAA CATATACAGT CATGTCGCCG CCATTGAATC GATATGGGTA
1651  TATGGAAACA GCTATGAGTC TTACTTAGTG GCTGTGGTAT GTCCAAGCAA
1701  GATCCAGATC GAGCATTGGG CCAAAGAACA CAAAGTTTCA GGAGACTTTG
1751  AGTCTATCTG CCGAAACCAA AAGACTAAAG AGTTTGTCCT GGAGAGTTC
1801  AACAGAGTAG CCAAAGACAA AAAGCTGAAG GATTTGAGC TGATCAAAGG
1851  TGTTCATTTG GACACAGTCC CGTTCGACAT GGAAAGAGAT CTCATCACTC
1901  CTTCTTACAA GATGAAAAGA CCTCAGCTTC TCAAGTACTA TCAGAAAGAG
1951  ATTGATGAAA TGTATAAGAA AAACAGAGAA GTGCAGCTAC GAGTGTAA
```

FIGURE 6

SEQ ID NO:4   AtACS2 Original cDNA Nucleotide Sequence

```
   1  ATGTCTTTAG CCGCGGATAA TGTGTTGTTG GTGGAAGAAG GAAGGCCAGC
  51  CACAGCGGAA CATCCATCGG CCGGACCGGT TTATCGATGT AAATACGCTA
 101  AAGATGGCCT CCTCGATCTC CCTACCGATA TTGATTCTCC TTGGCAGTTC
 151  TTTAGTGAGG CTGTGAAGAA ATATCCGAAT GAGCAAATGT TGGGCCAACG
 201  CGTAACGACT GATTCTAAGG TCGGTCCATA CACGTGGATC ACATATAAGG
 251  AAGCGCACGA CGCTGCAATT CGGATTGGAT CAGCAATCAG AAGCCGAGGC
 301  GTTGATCCGG ACACTGTTG TGGTATTTAC GGAGCTAATT GTCCAGAATG
 351  GATTATTGCA ATGGAGGCCT GCATGAGCCA AGGGATCACC TACGTGCCTC
 401  TATACGATTC TTTAGGCGTA AACGCAGTTG AATTCATCAT CAACCACGCC
 451  GAGGTTTCGC TAGTATTTGT TCAAGAGAAG ACAGTTTCAT CGATCTTATC
 501  GTGCCAAAAG GGATGTTCTT CGAATTTGAA GACTATTGTG AGCTTCGGGG
 551  AAGTCTCGAG TACACAAAAG GAAGAAGCTA AGAACCAATG TGTTTCTTTA
 601  TTTTCATGGA ATGAGTTCTC ACTAATGGGA AACTTAGATG AGGCAAATCT
 651  ACCTCGTAAG CGAAAGACAG ACATCTGCAC AATAATGTAC ACAAGCGGGA
 701  CGACTGGAGA ACCCAAAGGT GTAATCTTAA CAACGCAGC AATTTCGGTC
 751  CAGGTTTTAT CCATAGACAA AATGCTTGAA GTCACTGATC GATCGTGTGA
 801  CACGAGCGAT GTGTTCTTCT CGTACTTGCC ATTAGCACAT GCTATGATC
 851  AAGTCATGGA GATTTACTTT TTATCTAGAG GCTCCTCTGT TGGATACTGG
 901  CGTGGCGACA TTCGGTACCT GATGGATGAT GTTCAAGCTC TTAAACCTAC
 951  TGTGTTTTGC GGTGTTCCAC GAGTTTACGA CAAACTATAT GCCGGTATAA
1001  TGCAAAAAAT ATCAGCTAGT GGCTTGATAC GCAAGAAACT GTTTGATTTT
1051  GCTTATAACT ACAAATTGGG AAATATGAGA AAAGGATTCT CTCAAGAAGA
1101  AGCTTCTCCT CGTCTAGACA GACTTATGTT CGATAAGATA AAGAAGCAT
1151  TAGGAGGAAG AGCTCATATG TTGTTATCAG GAGCAGCGCC TCTACCTCGT
1201  CATGTAGAGG AGTTCTTGAG AATCATTCCT GCCTCTAATC TCTCTCAAGG
1251  TTATGGATTG ACTGAGAGTT GTGGGGGAAG CTTCACGACC TTAGCCGGAG
1301  TATTTCTAT GGTGGGGACA GTGGGTGTGC AATGCCCAC GGTGGAGGCA
1351  AGGCTAGTGT CCGTACCAGA GATGGGTTAC GACGCCTTTT CCGCTGACGT
1401  GCCGAGAGGA GAGATTTGTC TTAGAGGAAA TTCAATGTTT TCTGGTTACC
1451  ATAAAAGACA AGATCTAACT GATCAAGTCC TAATCGATGG ATGGTTCCAC
1501  ACAGGAGATA TTGGAGAATG GCAAGAAGAT GGATCAATGA AGATCATCGA
1551  TAGGAAGAAG AACATCTTCA AGTTGTCTCA AGGTGAATAT GTTGCTGTTG
1601  AAAACCTCGA AAACACTTAC TCAAGATGTC CCTCATTGC TCAGGTATGG
1651  GTCTATGGCA ACAGCTTCGA GTCATTTTTG GTAGGTGTGG TTGTACCTGA
1701  TAGAAAAGCT ATTGAAGATT GGGCTAAACT CAATTACCAA TCTCCCAATG
1751  ATTTCGAATC TCTATGTCAA AATCTCAAAG CTCAAAAATA CTTCTTGGAT
1801  GAGCTTAACT CTACCGCAAA GCAATATCAA CTTAAGGAT TTGAAATGTT
1851  AAAAGCTATT CATTTAGAAC CAAACCCTTT TGATATTGAA AGAGATCTTA
1901  TTACTCCAAC TTTCAAGCTG AAAAGGCCAC AGCTCCTCCA ACATTACAAG
1951  GGCATAGTTG ATCAACTTTA TTCAGAAGCA AAGAGGTCCA TGGCATAG
```

FIGURE 7

SEQ ID NO:5   AtACS3A Original cDNA Nucleotide Sequence

```
   1  ATGGATTCTT CTTCTTCGTC TTCCTCCGCC GCCGCACGCC GCCGTATCAA
  51  CGCTATCCAC TCTCACCTCG TCACCTCTTC TCGCTCTTCC CCTCTCCTCC
 101  GCTCCAATCC CACCGCCGGC GAGTTCTGTC TTGATAATGG CTATAGTGTT
 151  GTTCTTCCCG AGAAACTGAA TACTGGCAGT TGGAACGTCT ACAGATCTGC
 201  AAAATCCCCG TTCAAGCTCG TTAGCAGATT CCCAGATCAT CCTGACATCG
 251  CTACTCTCCA TGACAATTTT GAGCATGCTG TTCATGATTT TCGAGATTAC
 301  AAGTATTTAG GAACTCGTGT TCGTGTCGAC GGAACTGTTG AGACTACAA
 351  ATGGATGACA TATGGAGAAG CTGGTACAGC AAGAACTGCT TTAGGTTCTG
 401  GTTTGGTTCA TCACGtAATC CCCATGGGAT CTTCTGTTGG AATTTACTTC
 451  ATCAATCGCC CAGAGTGGCT CATTGTTGAT CATGCTTGTT CTTCTTATTC
 501  TTATGTGTCT GTTCCTTTGT ATGATACTCT TGGTCCTGAT GCTGTGAAAT
 551  TTATTGTCAA TCATGCAACT GTGCAAGCCA TATTTGTGT GGCAGAGACT
 601  TTAAACTCTT TACTTAGCTG TTTGTCTGAG ATGCCAAGTG TACGCCTGGT
 651  GGTGGTTGTT GGAGGGTTAA TTGAATCTTT ACCCTCGCTT CCCTCATCAT
 701  CAGGAGTGAA AGTTGTATCC TATTCGGTGT TACTGAATCA GGGTCGTAGT
 751  AACCCTCAGC GATTTTTTCC ACCAAAACCC GATGATGTTG CAACCATATG
 801  CTATACAAGC GGAACAACTG GGACACCCAA GGGAGTCGTA TTAACTCATG
 851  CAAACTTGAT TGCCAATGTT GCTGGCTCCA GCTTAGTGT GAAGTTTTC
 901  TCTTCAGATG TTTACATTTC GTATCTTCCA CTTGCTCACA TTTACGAACG
 951  AGCTAATCAG ATCCTAACAG TGTACTTTGG AGTTGCTGTT GGATTCTACC
1001  AAGGGGACAA TATGAAACTA CTGGATGATT TGGCTGCTCT GAGACCTACT
1051  GTATTTAGCA GTGTCCCTCG ATTATACAAT AGAATATATG CTGGTATCAT
1101  TAATGCAGTA AAAACCTCTG GTGGTCTGAA AGAGAGACTC TTCAATGCTG
1151  CCTATAATGC AAAGAAGCAG GCTCTCTTGA ATGGAAAGAG TGCTTCTCCC
1201  ATATGGGACA GGTTGGTATT TAATAAAATA AAGGACAGAC TTGGAGGGCG
1251  GGTTCGTTTT ATGACGTCTG GTGCTTCACC TCTCTCTCCT gAAGTGATGG
1301  AATTTTTGAA AGTATGCTTT GGAGGAAGGG TAACAGAGGG ATATGGAATG
1351  ACTGAAACAT CTTGTGTTAT AAGTGGAATG GACGAGGGTG ATAACCTCAC
1401  TGGACATGTT GGCTCTCCTA ATCCAGCTTG TGAAATAAAG CTTGTGGATG
1451  TCCCAGAAAT GAACTATACA TCAGCGGATC AGCCCCATCC CCGTGGCGAA
1501  ATATGTGTTA GGGGTCCTAT CATTTTTACA GGCTATTACA AAGATGAAAT
1551  TCAAACGAAA GAGGTGATTG ATGAAGATGG ATGGCTTCAC ACTGGAGATA
1601  TAGGTCTGTG GCTGCCGGGA GGACGTCTAA AAATTATTGA CAGAAAGAAG
1651  AACATCTTCA AATTGGCGCA GGGGGAGTAT ATAGCTCCAG AGAAAATTGA
1701  AAACGTCTAT GCCAAATGCA AATTTGTGGG CCAGTGCTTC ATATATGGTG
1751  ATAGCTTTAA TTCATCATTG GTAGCTGTTG TATCGGTTGA TCCAGATGTG
1801  CTGAAAAGCT GGGCAGCTTC AGAAGGCATT AAGGGAGGAG ATCTGAGAGA
1851  ATTGTGTAAT AATCCGAGAG TGAAAGCAGC AGTACTATCT GACATGGACA
1901  CTGTTGGAAG AGAAGCTCAG TTGAGAGGCT TCGAGTTTGC AAAGGCTGTG
1951  ACATTGGTGC TGGAACCATT TACTCTGGAA AATGGCTTGT TGACTCCGAC
2001  GTTCAAGATT AAGAGACCAC AAGCAAAGGA ATATTTCGCA GAAGCAATAA
2051  CAAACATGTA CAAGGAGCTT GGTGCTTCTG ATCCCTCTGC TAATAGAGGT
2101  TTGTGAGCGG CCGCACTCGA GCACCACCAC CACCACCACT GAGATCCGGC
2151  TGCTAACAAA GCCCGAAAGG AAGCTGAGTT GGCTGCTGCC ACCGCTGAGC
2201  AATAACTAGC ATAACCCCTT GGGGCCTCTA AACGGGTCTT GAGGGGTTTT
2251  TTGCTGA
```

FIGURE 8

SEQ ID NO:6   AtACS3B Original cDNA Nucleotide Sequence

```
   1  ATGGAATTTG CTTCGCCGGA ACAACGTCGT CTCGAAACCA TTCGATCTCA
  51  CATCGATACT TCTCCGACCA ACGATCAATC ATCATCTaTA TTCCTCAACG
 101  CCACCGCTTC TTCTGCTTCA CCTTTCTTTA AGAGGATAG CTACAGTGTT
 151  GTGCTTCCAG AAAAGCTTGA TACTGGAAAA TGGAATGTCT ACAGATCTAA
 201  AAGATCGCCT ACGAAACTCG TTAGTAGGTT CCCGGATCAT CCTGAAATCG
 251  GGACTTTACA TGACAATTTT GTACATGCTG TTGAAACATA TGCTGAAAAC
 301  AAGTATCTTG GTACACGAGT TCGGTCCGAT GGAACCATTG AGAGTATTC
 351  ATGGATGACA TATGGAGAAG CAGCGTCTGA GCGACAAGCC ATTGGTTCAG
 401  GACTCTTGTT TCATGGAGTT AACCAAGGAG cTTGCGTTGG ACTCTATTTT
 451  ATTAACAGAC CAGAGTGGTT GGTTGTGGAT CATGCTTGTG CAGCATATTC
 501  ATTTGTCTCT GTTCCTTTAT ATGATACACT TGGTCCAGAC GCTGTTAAGT
 551  TTGTGGTGAA TCATGCTAAT CTGCAAGCTA TATTTGTGT ACCACAAACC
 601  TTGAATATTT TGCTAAGCTT CCTAGCGGAA ATCCCATCCA TTCGTCTCAT
 651  TGTGGTGGTG GGAGGGGCTG ATGAGCATTT GCCATCACTT CCTCGAGGAA
 701  CTGGAGTCAC AATTGTATCA TACCAAAAGC TATTGAGTCA GGGTCGAAGT
 751  AGCTTACATC CATTTTCGCC TCCAAAGCCA GAAGACATTG CAACCATATG
 801  CTACACAAGT GGAACCACAG GAACACCAAA GGGTGTTGTG TTGACTCATG
 851  GAAACTTGAT CGCGAATGTC GCTGGTTCCA GTGTGGAAGC AGAATTCTTT
 901  CCTTCAGATG TTTACATATC ATATCTTCCT TTGGCGCACA TATATGAACG
 951  TGCAAATCAG ATTATGGGGG TGTATGGTGG TGtTGCTGTC GGTTTCTATC
1001  AGGGGGATGT CTTgAAGCTG ATGGATGATT TTGCTGTGTT AAGACCAACA
1051  ATATTCTGTA GTGTCCCTCG CTTrTATAAT CGAATATATG ATGGCATTAC
1101  AAGTGCCGTA AAATCATCTG GGGTTGTGAA AAAAAGGCTT TTCGAAATTG
1151  CCTATAACTC AAAGAAGCAA GCGATCATTA ATGGgCGGAC TCCTTCTGCA
1201  TTTTGGGACA AGCTGGTGTT CAACAAAATA AAAGAAAAGC TTGGTGGACG
1251  GGTTCGGTTT ATGGGGTCTG GTGCTTCTCC TTTGTCACCT GATGTCATGG
1301  ATTTCTTGAG AATATGCTTT GGATGTTCGG TGCGTGAAGG GTATGGTATG
1351  ACCGAGACTT CTTGTGTCAT AAGcGCTATG GATGATGGTG ACAATTTATC
1401  TGGCCAcGTC GGaTCCCCTA ATCCAGCTTG CGAGGTAAAg CTTGTGGATG
1451  TTCCCGAAAT GAATTACACA TCgGAaGATC AACCATACCC ACGTGGTGAA
1501  ATCTGTGTAA GAGGACCAAT CATCTTCAAA GGCTAyTACA AAGATGAAGA
1551  ACAAACGAGA GAAATTCTTG ATGGAGATGG CTGGCTACAC ACAGGAGATA
1601  TCGGGTTGTG GTTACCTGGT GGTCGGCTCA AGATCATAGA CAGGAAGAAG
1651  AACATATTTA AGTTGGCGCA AGGAGAATAT ATAGCACCAG AGAAGATCGA
1701  AAATGTTTAT ACCAAATGTA GATTCGTTTC GCAGTGTTTC ATTCACGGTG
1751  ATAGCTTCAA TTCCTCTCTA GTAGCTATAG TTTCAGTCGA CCCCGAAGTT
1801  ATGAAAGATT GGCTGCATC AGAAGGCATC AAGTATGAGC ATCTAGGACA
1851  GCTCTGTAAC GATCCAAGAG TGCGAAAGAC TGTTCTTGCT GAGATGGATG
1901  ACCTTGGAAG AGAAGCTCAG TTGAGAGGGT TGAGTTTGC AAAGGCTGTG
1951  ACTTTGGTGC CAGAACCATT CACCTTGGAG AATGGACTTC TCACACCAAC
2001  ATTCAAGATA AAGAGACCTC AAGCAAAAGC CTACTTTGCA GAAGCAATTA
2051  GCAAAATGTA TGCGGAAATC GCAGCCTCGA ACCCCATTCC TTCTAAACTG
2101  TGA
```

FIGURE 9

SEQ ID NO:7  AtACS4A Original cDNA Nucleotide Sequence

```
   1  ATGGCTTCGA CTTCTTCTTT GGGACCTTCT ACACTACTCT CTTACGGTTC
  51  TCCTTCTCGT CAGTTTCCTG ATTTTGGGTT CAGATTGATT TCGGGTCACG
 101  AAAGTGTTCG AATTCCATCA TTCCGGCGAT TCGGGTTCA  CTGCGAGTCA
 151  AAGGAAAAAG AAGTGAAGCC GTCTTCTCCA TTTCTTGAAA GCTCCTCGTT
 201  TTCGGGAGAT GCCGCTTTGC GCTCTAGTGA ATGGAAGGCT GTTCCTGATA
 251  TTTGGAGATC ATCTGCAGAA AAGTATGGTG ATAGAGTTGC ATTGGTGGAT
 301  CCTTATCATG ATCCTCCTTT GAAACTGACG TACAAGCAGT TGAACAAGA
 351  AATTTTGGAC TTTGCTGAGG GCTTACGAGT TCTTGGAGTG AAAGCAGATG
 401  AGAAGATTGC ACTTTTTGCT GATAACTCCT GCCGATGGCT TGTTTCAGAT
 451  CAAGGTATAA TGGCCACAGG GGCAGTCAAT GTTGTCAGAG GATCTAGGTC
 501  CTCTGTTGAA GAGTTACTGC AGATATACCG TCATTCTGAA AGCGTAGCCA
 551  TTGTTGTGGA TAATCCTGAG TTTTTCAACC GCATTGCTGA GTCATTTACG
 601  TCAAAGGCAT CTCTGAGATT TTTGATACTT CTCTGGGGTG AGAAATCATC
 651  ACTGGTCACA CAGGGGATGC AGATTCCAGT TTACAGTTAT GCAGAAATTA
 701  TAAACCAAGG ACAGGAGAGT CGTGCAAAAT TATCAGCATC TAATGATACC
 751  AGGAGCTATA GAAATCAATT CATCGATTCA GATGATACAG CTGCAATTAT
 801  GTATACCAGT GGTACCACGG GAAATCCAAA AGGCGTTATG CTTACACATC
 851  GGAATCTCTT ACACCAGATA AACATTTAT  CCAAATATGT ACCTGCTCAA
 901  GCTGGGGATA AATTTCTAAG CATGCTACCA TCATGGCATG CCTATGAACG
 951  TGCTAGTGAA TACTTCATAT TCACTTGTGG AGTTGAGCAA ATGTATACAT
1001  CTATAAGATA CTTAAAGGAT GATCTAAAGC GGTACCAACC GAACTATATT
1051  GTGTCCGTTC CTCTAGTATA TGAGACACTT TACAGTGGGA TTCAAAAGCA
1101  AATTTCTGCA AGTTCTGCTG GCCGTAAATT CTAGCACTT  ACATTGATCA
1151  AAGTCAGTAT GGCATATATG GAGATGAAAA GGATATATGA GGGTATGTGT
1201  CTGACAAAAG AGCAAAAGCC TCCAATGTAT ATTGTTGCTT TTGTGGATTG
1251  GTTGTGGGCG AGAGTAATTG CTGCCTTGTT GTGGCCATTA CATATGTTGG
1301  CCAAAAAGCT TATCTACAAG AAAATTCATT CGTCTATTGG GATATCGAAG
1351  GCTGGTATTA GCGGAGGTGG TAGTTTACCC ATTCATGTTG ACAAGTTTTT
1401  TGAGGCCATC GGTGTGATTC TACAAAATGG TTATGGTTTG ACAGAGACCT
1451  CACCTGTTGT CTGTGCACGG ACACTTAGCT GCAATGTTCT TGGCTCAGCT
1501  GGGCATCCAA TGCATGGTAC AGAATTCAAA ATTGTAGATC CTGAGACTAA
1551  TAATGTACTC CCTCCTGGTT CAAAGGGCAT TATCAAAGTC AGAGGTCCAC
1601  AGGTTATGAA GGGTTATTAT AAGAATCCAT CGACTACAAA GCAAGTTCTA
1651  AATGAGAGTG GATGGTTCAA TACAGGAGAC ACCGGTTGGA TTGCTCCTCA
1701  TCACTCAAAA GGGCGGAGTC GCCACTGTGG AGGTGTCATT GTTCTTGAAG
1751  GCCGTGCAAA AGACACAATT GTACTTTCCA CAGGTGAAAA TGTGGAACCG
1801  TTGGAGATTG AAGAAGCCGC CATGAGAAGC AGGGTGATTG AACAAATTGT
1851  TGTTATTGGA CAGGACCGAC GTCGCCTTGG AGCTATCATT ATCCCAAACA
1901  AAGAGGAAGC ACAAAGAGTA GATCCTGAAA CATCCAAAGA AACACTAAAG
1951  AGCTTGGTCT ACCAAGAACT GAGAAAATGG ACATCAGAAT GTTCGTTTCA
2001  AGTCGGACCA GTCTTGATCG TCGACGACCC TTTCACGATA GACAACGGGT
2051  TAATGACACC AACTATGAAG ATTAGACGGG ACATGGTCGT GGCTAAATAC
2101  AAAGAGGAGA TTGATCAACT CTACAGTTAA
```

FIGURE 10

SEQ ID NO:8  AtACS4B Original cDNA Nucleotide Sequence

```
   1 ATGGCTTCAA CGTCTCTCGG AGCTTCGATT CTCGTTTCTC ACTGCTGCTC
  51 AGCTCCTGAA TTTCAAGTTT CTGGGATGAG ATTGGTGTTT GGTTACAAGG
 101 CTTTTGGCTG CAGAACTTCA CGCAGGGGAT TTCGAGTTCG CTGCGAATCC
 151 AAGATTCAGG AGAAGGAGTT AAGGCGGTGT TCGCCATTCT TAGAACGCTT
 201 ATCATTGCCA AGGGAGGCTG CTTTGAGCTC TAATGAATGG AAGTCTGTTC
 251 CTGATATTTG AGATCATCT GTGGAGAAGT ACGGTGACAG AGTTGCGGTG
 301 GTAGATCCGT ATCATGACCC GCCTTCTACA TTCACGTACA GACAGTTGGA
 351 ACAAGAAATC TTGGACTTTG TTGAGGGTTT ACGAGTCGTT GGAGTGAAAg
 401 CAGACGAGAA GATTGCACTT TTTGCTGATa ACTCCTGTCG ATGGCTTGTT
 451 GCGGATCAAG GTATAATGGC CACAGGAGCA GTCAATGTTG TTAGAGGATC
 501 CAGATCGTCT GTTGAAGAGT TATTGCAGAT ATACTGTCAT TCGGAAAGTG
 551 TAGCCCTTGT TGTGGATAAC CCTGAGTTTT TCAATCGCAT TGCGGAGTCA
 601 TTTTCTTACA AGGCAGCTCC AAAATTTGTG ATTCTTCTCT GGGGGGAAAA
 651 ATCGTCGTTG GTTACAGCGG GTAGGCACAC ACCAGTCTAT AGTTACAACG
 701 AAATTAAAAA GTTTGGACAA GAGAGACGTG CAAAATTTGC AAGATCTAAT
 751 GATTCTGGGA AGTATGAATA TGAATACATC GATCCAGATG ATATAGCCAC
 801 AATTATGTAT ACCAGTGGAA CCACAGGAAA TCCAAAAGGT GTTATGCTCA
 851 CACATCAGAA TTTGTtACAC CAGATAAGAA ACTTGTCCGA TTTTGTGCCT
 901 GCGGAAGCTG GGgAAAGATT TCTGAGTATG TTGCCATCAT GGCATGCTTA
 951 TGAACGGGCT TGTGAATACT TCATATTTAC ATGTGGAGTT GAGCAAAAGT
1001 ATACGTCTAT AAGATTCTTA AAGGATGATC TCAAGCGTTA TCAACCACAC
1051 TATCTTATTT CAGTTCCTTT AGTATATGAG ACACTCTACA GCGGGATTCA
1101 AAAGCAAATT TCTGCAAGCT CCCCTGCTCG TAAATTTTTG GCACTTACAT
1151 TGATCAAAGT CAGCCTGGCA TATACGGAAA TGAAAAGAGT TTATGAGGGT
1201 CTTTGTTTGA CAAAAAATCA AAAGCCTCCA ATGTATATTG TTTCGTTGGT
1251 GGATTGGTTG TGGGCGAGAG TAGTTGCATT TTTCCTATGG CCATTGCATA
1301 TGTTGGCTGA AAAGCTTGTA CACAGAAAAA TTCGTTCGTC TATTGGGATA
1351 ACAAAGGCTG GTGTTAGTGG AGGTGGTAGT TTACCTATGC ATGTTGACAA
1401 GTTTTTTGAG GCCATCGGTG TGAATGTACA AATGGGTAT GGTTTGACAG
1451 AAACCTCACC GGTTGTCTCT GCGCGAAGGC TTAGGTGTAA CGTTCTTGGC
1501 TCAGTTGGGC ATCCTATTAA AGATACAGAG TTCAAAATTG TAGATCATGA
1551 GACTGGTACT GTTCTTCCAC CTGGTTCAAA GGGCATTGTC AAAGTCAGAG
1601 GCCCACCGGT GATGAAAGGT ACTACAAGA ATCCACTGGC CACCAAGCAG
1651 GTTATAGATG ACGATGGATG GTTCAATACT GGAGATATGG GTTGGATTAC
1701 TCCTCAGCAC TCAACAGGAC GGAGTCGTAG CTGTGGAGGT GTCATCGTTC
1751 TTGAAGGGCG TGCCAAGGAC ACTATCGTGC TTTCCACAGG TGAAAATGTG
1801 GAACCATTGG AGATTGAAGA AGCGGCCATG AGAAGCAATT TGATTCAACA
1851 AATAGTGGTT ATTGGACAGG ATCAACGCCG CCTTGGAGCT ATTGTTATCC
1901 CAAACAAAGA AGCAGCAGAA GGAGCAGCAA AGCAGAAAAT TCACCTGTA
1951 GATTCTGAAG TCAATGAACT TAGCAAGGAG ACGATAACAA GCATGGTCTA
2001 TGAAGAACTA AGGAAATGGA CGTCACAATG CTCGTTCCAA GTGGGACCAG
2051 TTCTGATCGT GGATGAACCA TTCACGATAG ACAACGGTTT AATGACACCG
2101 ACAATGAAAA TAAGACGGGA CAAGGTGGTT GATCAATACA GAATGAAAT
2151 AGAAAGACTC TACAAGTAG
```

FIGURE 11

SEQ ID NO:9 AtACS5 Original cDNA Nucleotide Sequence

```
   1 ATGAAGTCTT TTGCGGCTAA GGTAGAAGAG GGAGTTAAAG GAATAGACGG
  51 AAAGCCGTCG GTAGGTCCGG tGTACCGGAA TCTTCTGTCG GAAAAAGGTT
 101 TTCCTCCGAT TGATTCyGAG ATCACCACTG CTTGGGACAT TTTCAGTAAA
 151 TCAGTGGAGA AATTCCCTGA CAATAATATG CTTGGATGGC GTCGAATTGT
 201 TGATGAGAAG GTTGGACCAT ATATGTGGAA AACGTACAAG GAAGTATACG
 251 AAGAAGTTTT GCAGATTGGC TCTGCACTAC GAGCCGCCGG AGCTGAACCT
 301 GGGAGTCGAG TGGGGATCTA CGGTGTTAAT TGTCCTCAGT GGATCATAGC
 351 AATGGAGGCT TGTGCAGCTC ACACTCTAAT CTGTGTACCT CTATATGATA
 401 CATTGGGTTC AGGAGCAGTC GATTACATTG TAGAGCATGC GGAAATCGAC
 451 TTTGTGTTTG TCCAAGACAC CAAAATTAAA GGACTTCTTG AGCCAGATTG
 501 CAAATGTGCT AAACGGCTAA AGCTATAGT TTCCTTCACT AACGTGAGCG
 551 ACGAGCTTAG CCACAAGGCT TCAGAAATTG GAGTCAAAAC ATACTCCTGG
 601 ATCGATTTTC TCCATATGGG ACGTGAGAAA CCGGAAGACA CGAACCCGCC
 651 TAAGGCGTTT AACATATGCA CCATAATGTA CACCAGCGGC ACAAGCGGTG
 701 ATCCTAAAGG TGTGGTTTTG ACTCACCAAG CGGTCGCGAC TTTTGTTGTT
 751 GGGATGGATC TCTATATGGA CCAGTTTGAA GATAAGATGA CACATGATGA
 801 TGTGTATCTC TCCTTCTTGC CCTTGGCTCA TATTCTTGAC CGTATGAACG
 851 AGGAATACTT CTTTCGCAAA GGCGCTTCCG TCGGCTATTA CCATGGAAAT
 901 TTGAACGTGT ACGTGACGA TATTCAAGA CTGAAACCGA CTTATCTAGC
 951 TGGAGTACCA AGAGTGTTTG AGAGAATCCA TGAGGGGATT CAAAAGGCTC
1001 TTCAAGAACT TAACCCAAGA AGGAGATTCA TCTTCAATGC TCTCTACAAA
1051 CACAAGCTTG CGTGGTTGAA TCGTGGGTAC TCTCATAGTA AAGCTTCACC
1101 CATGGCTGAT TCATTGCTT TCAGAAAGAT TAGAgACAAA TTGGGAGGTC
1151 GCATCCGGTT GCTAGTATCT GGAGGAGCAC CTTTGAGCCC cGAGATTGAA
1201 GAGTTTTTGA gAGTTACTTG TTGTTGCTTT GTCGtTCAAG GCTACGGTCT
1251 AACGGAGACA CTTGGAGGAA CGGCTTTGGG TTTCCCGGAC GAgATGTGTA
1301 TGCTAGGGAC AGTCGGTATT CCAgCGGTTT ACAACgAGAT ACGGcTTGAA
1351 GAGGTGTCTG AAATGGGCTA TGACCCGCTC GGAgAAAATC CGGCAGGAgA
1401 GATCTGTATA AGAGGACAAT GTATGTTTTC AGGGTATTAC AAGAACCCTG
1451 AACTCACTGA AGAAGTCATG AAAGATGGAT GGTTCCACAC AGGAGATATA
1501 GGTGAGATTC TTCCAAACGG AGTACTCAAG ATCATCGATC GTAAAAAGAA
1551 TCTGATCAAA CTTTCTCAAG GAGAATATGT TGCTCTCGAG CATTTGGAAA
1601 ACATCTTCGG GCAAAACTCT GTTGTCCAAG ATATATGGGT TTATGGAGAC
1651 AGCTTCAAAT CTATGCTTGT CGCGGTGGTT GTTCCAACC CAGAAACCGT
1701 CAACAGGTGG GCTAAAGATC TCGGTTTTAC TAAACCATTC GAAGAACTCT
1751 GTTCTTTCCC GGAACTAAAA GAACACATCA TTTCAGAACT GAAGTCCACG
1801 GCAGAAAAGA ACAAGCTAAG AAAGTTTGAG TACATCAAAG CGGTGACAGT
1851 GGAGACAAAA CCTTTCGACG TAGAGAGAGA CTTAGTGACT GCGACGCTCA
1901 AGAATCGGAG GAACAATCTT CTCAAATATT ATCAGGTGCA AATCGACGAA
1951 ATGTACCgCA AATTGGCCTC AAAGAAAATC TGA
```

FIGURE 12

SEQ ID NO:10  AtACS6A Original cDNA Nucleotide Sequence

```
   1 ATGGAAGATT CTGGAGTGAA TCCAATGGAT TCACCATCTA AAGGCAGTGA
  51 CTTTGGAGTC TATGGAATCA TAGGAGGTGG AATCGTGGCT TTACTTGTGC
 101 CTGTGTTACT CTCTGTGGTG TTGAATGGAA CCAAAAAGGG GAAAAAGAGA
 151 GGTGTTCCCA TCAAAGTAGG TGGCGAGGAA GGTTACACAA TGCGTCATGC
 201 TCGAGCTCCT GAATTGGTTG ATGTACCTTG GAAGGAGCT GCTACTATGC
 251 CTGCTTTGTT TGAGCAGTCT TGTAAGAAGT ATTCGAAAGA TCGGTTACTA
 301 GGAACTAGAG AGTTTATAGA TAAGGAATTT ATTACTGCTA GTGATGGGAG
 351 GAAGTTTGAG AAGCTTCATT TAGGAGAGTA TAAATGGCAA AGTTATGGAG
 401 AGGTTTTTGA ACGTGTTTGT AACTTTGCGT CGGGGTTAGT TAATGTAGGA
 451 CATAATGTTG ATGATCGTGT TGCTATCTTT TCGGATACTC GTGCTGAGTG
 501 GTTTATCGCG TTTCAGGGAT GTTTCAGGCA GAGCATAACC GTTGTTACTA
 551 TTTATGCTTC TTTAGGAGAA GAGGCTTTGA TTTACTCACT CAATGAGACT
 601 CGAGTGTCAA CCTTAATATG TGACTCAAAA CAACTTAAGA AGTTGTCTGC
 651 GATACAATCA AGCTTGAAAA CTGTGAAGAA CATTATTTAC ATTGAAGAAG
 701 ATGGAGTAGA TGTTGCTTCT AGTGATGTCA ATAGTATGGG TGATATAACT
 751 GTTTCGTCGA CTCTGAAGT TGAGAAACTT GGGCAGAAGA ACGCTGTTCA
 801 ACCGATCTTA CCTTCGAAGA ATGGAGTTGC TGTTATAATG TTTACCAGTG
 851 GTAGTACTGG TCTACCAAAG GGAGTTATGA TTACCCACGG AAATCTTGTC
 901 GCAACTGCTG CAGGAGTTAT GAAGGTGGTT CCAAAGTTGG ATAAAAATGA
 951 TACATATATT GCGTACTTAC CTTTGGCTCA TGTGTTTGAG CTGGAAGCTG
1001 AGATTGTGGT CTTTACCTCA GGTAGTGCCA TCGGTTACGG CTCAGCAATG
1051 ACTTTAACTG ACACTTCAAA TAAAGTTAAG AAAGGAACCA AGGAGATGT
1101 TTCAGCTCTG AAGCCAACTA TAATGACTGC AGTTCCAGCT ATTCTGGATC
1151 GTGTCCGAGA AGGAGTTCTT AAAAAGGTTG AGGAAAAGGG AGGGATGGCG
1201 AAgACCCtTT TTGACTTTGC ATACAAGCGC CGGTTAGCAG CTGTGGATGG
1251 AAGTTGGTTT GGTGCCTGGG GTTTGgAGAA AATGTTATGG GATGCTCTTG
1301 TCTTCAAGAA AATACGCGCT GTGCTTGGAG GACACATCCG TTTTATGCTC
1351 GTTGGAGGAG CTCCTCTGTC TCCTGATTCG CAACGCTTCA TCAATATCTG
1401 CATGGGGTCT CCCATCGGCC AAGGATATGG ATTGACTGAA ACGTGTGCTG
1451 GAGCTACGTT TTCTGAGTGG GACGATCCTG CTGTTGGTCG TGTTGGACCT
1501 CCACTTCCAT GCGGCTACGT TAAGCTCGTT TCTTGGGAAG AAGGTGGCTA
1551 CAGAATTTCA GATAAACCAA TGCCTAGAGG GGAGATTGTG GTAGGTGGTA
1601 ACAGTGTAAC AGCAGGTTAC TTCAACAATC AAGAAAAAAC CGATGAGGTT
1651 TACAAGGTCG ATGAGAAGGG CACAAGGTGG TTTTACACCG GAGATATTGG
1701 GAGATTCCAC CCTGATGGAT GTCTCGAAGT CATCGATAGA AAGAAAGATA
1751 TTGTTAAACT TCAACATGGG GAATACGTAT CCCTTGGAAA GGTGGAGGCA
1801 GCTTTGGGTT CGAGCAATTA CGTTGATAAC ATCATGGTCC ACGCAGACCC
1851 AATTAACAGC TACTGTGTAG CTCTTGTTGT TCCATCACGA GGAGCATTAG
1901 AGAAATGGGC AGAGGAAGCT GGAGTTAAAC ACAGCGAATT CGCTGAGCTA
1951 TGCGAGAAAG GTGAAGCAGT CAAGGAGGTT CAACAATCTC TTACCAAGGC
2001 CGGGAAGGCG GCAAAGCTCG AAAAGTTTGA GCTTCCAGCA AGATCAAGT
2051 TGCTGTCAGA GCCGTGGACA CCGGAGTCGG GATTGGTCAC TGCTGCTCTT
2101 AAGATAAAGA GAGAACAAAT AAAGTCCAAG TTCAAAGATG AACTCAGCAA
2151 GTTATATGCC TAA
```

FIGURE 13

SEQ ID NO:11   AtACS6B Original cDNA Nucleotide Sequence

```
   1 ATGATTCCTT ATGCTGCTGG TGTTATTGTG CCATTGGCTT TGACGTTTCT
  51 GGTTCAGAAA TCTAAGAAAG AAAAGAAAAG AGGTGTTGTT GTTGATGTTG
 101 GTGGTGAACC AGGTTATGCT ATTAGGAATC ACAGGTTTAC TGAGCCTGTT
 151 AGTTCCCATT GGGAACATAT CTCAACGCTT CCAGAGCTCT TTGAGATATC
 201 GTGTAATGCT CACAGTGATA GGGTTTTCCT TGGCACCCGA AAGCTGATCT
 251 CTAGAGAGAT TGAGACTAGT GAGGATGGAA AAACGTTCGA GAAACTGCAT
 301 TTAGGTGACT ACGAGTGGCT CACTTTTGGG AAGACTCTCG AAGCAGTGTG
 351 TGATTTTGCC TCTGGGTTAG TTCAGATTGG GCACAAGACG GAAGAGCGTG
 401 TCGCCATTTT TGCAGATACT AGAGAAGAAT GGTTCATCTC CCTACAGGGT
 451 TGCTTCAGGC GCAACGTCAC TGTGGTAACT ATCTATTCAT CTTTGGGAGA
 501 GGAAGCTCTT TGTCACTCGC TGAATGAGAC AGAGGTCACA ACCGTAATAT
 551 GTGGTAGCAA AGAACTCAAA AAGCTCATGG ACATAAGCCA ACAGCTTGAA
 601 ACTGTGAAAC GTGTGATATG CATGGATGAT GAATTCCCAT CTGATGTGAA
 651 CAGTAATTGG ATGGCGACTT CATTTACTGA TGTTCAGAAA CTTGGCCGCG
 701 AAAATCCTGT GGATCCTAAT TTCCCTCTCT CAGCAGATGT TGCTGTTATA
 751 ATGTACACCA GTGGAAGCAC TGGACTTCCC AAGGGTGTTA TGATGACGCA
 801 TGGTAATGTC CTAGCTACAG TTTCGGCAGT GATGACAATT GTTCCTGACC
 851 TTGGAAAGAG GGATATATAC ATGGCATATT TACCTTTGGC TCACATCCTT
 901 GAGTTAGCAG CTGAGAGCGT AATGGCTACT ATTGGGAGTG CTATTGGATA
 951 TGGGTCTCCC TTGACGCTAA CGGATACTTC AAACAAGATA AAAAAGGGTA
1001 CAAAAGGAGA TGTCACAGCA CTAAAGCCCA CTATAATGAC AGCTGTTCCA
1051 GCCATTCTTG ATCGTGTCAG GGATGGTGTC CGCAAAAAGG TTGATGCAAA
1101 GGGCGGATTG TCAAAGAAAT TGTTTGACTT TGCATATGCT CGGCGATTAT
1151 CTGCAATCAA TGGAAGTTGG TTTGGAGCCT GGGGATTAGA AAAGCTTTTG
1201 TGGGATGTGC TTGTGTTCAG GAAAATCCGT GCAGTTTTGG GAGGTCAAAT
1251 CCGCTATTTG CTCTCTGGTG GTGCCCCTCT TTCTGGTGAC ACTCAGAGAT
1301 TCATTAACAT CTGCGTTGGG GCTCCAATCG GTCAGGGATA TGGGCTCACA
1351 GAGACTTGTG CTGGTGGAAC CTTCTCGGAG TTTGAGGACA CATCCGTTGG
1401 CCGTGTTGGT GCTCCACTTC CTTGCTCCTT TGTAAAGCTA GTAGACTGGG
1451 CGGAAGGTGG GTATCTAACT AGTGATAAGC CGATGCCCCG TGGTGAAATT
1501 GTAATTGGTG GCTCAAATAT CACGCTTGGG TATTTCAAAA ATGAGGAGAA
1551 AACTAAAGAA GTGTACAAGG TTGATGAAAA GGGAATGAGG TGGTTCTACA
1601 CAGGAGACAT AGGACGATTT CACCCTGATG GCTGCCTCGA GATAATAGAC
1651 CGAAAAAGG ATATCGTTAA ACTTCAGCAT GGAGAATATG TCTCCTTGGG
1701 CAAAGTTGAA GCTGCTCTAA GTATAAGTCC CTATGTTGAA AACATAATGG
1751 TTCATGCTGA TTCGTTCTAC AGTTACTGTG TGGCTCTTGT GGTCGCGTCC
1801 CAACATACAG TTGAAGGTTG GCTTCAAAG CAAGGAATAG ACTTTGCCAA
1851 CTTCGAAGAA CTGTGCACGA AAGAGCAAGC CGTGAAAGAA GTGTATGCGT
1901 CCCTTGTGAA GGCGGCTAAA CAATCACGAT GGAGAAGTT TGAGATACCA
1951 GCAAAGATCA AATTATTGGC ATCTCCATGG ACGCCAGAGT CAGGATTAGT
2001 CACAGCAGCT CTAAAGCTGA GAAGAGATGT AATTAGGAGG GAATTCTCTG
2051 AAGATCTCAC CAAGTTATAT GCCTAA
```

FIGURE 14

SEQ ID NO:12 AtACS1A Original Amino Acid Sequence

```
  1  MSQQKKYIFQ  VEEGKEGSDG  RPSVGPVYRS  IFAKDGFPDP  IEGMDSCWDV
 51  FRMSVEKYPN  NPMLGRREIV  DGKPGKYVWQ  TYQEVYDIVM  KLGNSLRSVG
101  VKDEAKCGIY  GANSPEWIIS  MEACNAHGLY  CVPLYDTLGA  DAVEFIISHS
151  EVSIVFVEEK  KISELFKTCP  NSTEYMKTVV  SFGGVSREQK  EEAETFGLVI
201  YAWDEFLKLG  EGKQYDLPIK  KKSDICTIMY  TSGTTGDPKG  VMISNESIVT
251  LIAGVIRLLK  SANEALTVKD  VYLSYLPLAH  IFDRVIEECF  IQHGAAIGFW
301  RGDVKLLIED  LAELKPTIFC  AVPRVLDRVY  PGLQKKLSDG  GFLKKFIFDS
351  AFSYKFGYMK  KGQSHVEASP  LFDKLVFSKV  KQGLGGNVRI  ILSGAAPLAS
401  HVESFLRVVA  CCHVLQGYGL  TESCAGTFVS  LPDELGMLGT  VGPPVPNVDI
451  RLESVPEMEY  DTLASTARGE  ICIRGKTLFS  GYYKREDLTK  EVLIDGWLHT
501  GDVGEWQPDG  SMKIIDRKKN  IFKLSQGEYV  AVENIENIYG  EVQAVDSVWV
551  YGNSFESFLI  AIANPNQHIL  ERWAAENGVS  GDYDALCQNE  KAKEFILGEL
601  VKMAKEKKMK  GFEIIKAIHL  DPVPFDMERD  LLTPTFKKKR  PQLLKYYQSV
651  IDEMYKTINA  KFASRG*
```

FIGURE 15

SEQ ID NO:13  AtACS1B Original Amino Acid Sequence

```
  1  MTSQKRFIFE VEAAKEATDG NPSVGPVYRS TFAQNGFPNP IDGIQSCWDI
 51  FRTAVEKYPN NRMLGRREIS NGKAGKYVWK TYKEVYDIVI KLGNSLRSCG
101  IKEGEKCGIY GINCCEWIIS MEACNAHGLY CVPLYDTLGA GAVEFIISHA
151  EVSIAFVEEK KIPELFKTCP NSTKYMKTVV SFGGVKPEQK EEAEKLGLVI
201  HSWDEFLKLG EGKQYELPIK KPSDICTIMY TSGTTGDPKG VMISNESIVT
251  ITTGVMHFLG NVNASLSEKD VYISYLPLAH VFDRAIEECI IQVGGSIGFW
301  RGDVKLLIED LGELKPSIFC AVPRVLDRVY TGLQQKLSGG GFFKKKKFGN
351  MKKGQSHVAA SPFCDKLVFN KVKQGLGGNV RIILSGAAPL ASHIESFLRV
401  VACCNVLQGY GLTESCAGTF ATFPDELDML GTVGPPVPNV DIRLESVPEM
451  NYDALGSTPR GEICIRGKTL FSGYYKREDL TKEVFIDGWL HTGDVGEWQP
501  NGSMKIIDRK KNIFKLAQGE YVAVENLENV YSQVEVIESI WVYGNSFESF
551  LVAIANPAQQ TLERWAVENG VNGDFNSICQ NAKAKAFILG ELVKTAKENK
601  LKGFEIIKDV HLEPVAFDME RDLLTPTYKK KRPQLLKYYQ NVIHEMYKTT
651  KESLASGQ
```

FIGURE 16

SEQ ID NO:14  AtACS1C Original Amino Acid Sequence

```
  1  MATGRYIVEV EKGKQGVDGG SPSVGPVYRS IYAKDGFPEP PDDLVSAWDI
 51  FRLSVEKSPN NPMLGRREIV DGKAGKYVWQ TYKEVHNVVI KLGNSIRTIG
101  VGKGDKCGIY GANSPEWIIS MEACNAHGLY CVPLYDTLGA GAIEFIICHA
151  EVSLAFAEEN KISELLKTAP KSTKYLKYIV SFGEVTNNQR VEAERHRLTI
201  YSWDQFLKLG EGKHYELPEK RRSDVCTIMY TSGTTGDPKG VLLTNESIIH
251  LLEGVKKLLK TIDEELTSKD VYLSYLPLAH IFDRVIEELC IYEAASIGFW
301  RGDVKILIED IAALKPTVFC AVPRVLERIY TGLQQKLSDG GFVKKKLFNF
351  AFKYKHKNME KGQPHEQASP IADKIVFKKV KEGLGGNVRL ILSGAAPLAA
401  HIESFLRVVA CAHVLQGYGL TESCGGTFVS IPNELSMLGT VGPPVPNVDI
451  RLESVPEMGY DALASNPRGE ICIRGKTLFS GYYKREDLTQ EVFIDGWLHT
501  GDVGEWQPDG AMKIIDRKKN IFKLSQGEYV AVENLENIYS HVAAIESIWV
551  YGNSYESYLV AVVCPSKIQI EHWAKEHKVS GDFESICRNQ KTKEFVLGEF
601  NRVAKDKKLK GFELIKGVHL DTVPFDMERD LITPSYKMKR PQLLKYYQKE
651  IDEMYKKNRE VQLRV
```

FIGURE 17

SEQ ID NO:15    AtACS2 Original Amino Acid Sequence

```
  1  MSLAADNVLL  VEEGRPATAE  HPSAGPVYRC  KYAKDGLLDL  PTDIDSPWQF
 51  FSEAVKKYPN  EQMLGQRVTT  DSKVGPYTWI  TYKEAHDAAI  RIGSAIRSRG
101  VDPGHCCGIY  GANCPEWIIA  MEACMSQGIT  YVPLYDSLGV  NAVEFIINHA
151  EVSLVFVQEK  TVSSILSCQK  GCSSNLKTIV  SFGEVSSTQK  EEAKNQCVSL
201  FSWNEFSLMG  NLDEANLPRK  RKTDICTIMY  TSGTTGEPKG  VILNNAAISV
251  QVLSIDKMLE  VTDRSCDTSD  VFFSYLPLAH  CYDQVMEIYF  LSRGSSVGYW
301  RGDIRYLMDD  VQALKPTVFC  GVPRVYDKLY  AGIMQKISAS  GLIRKKLFDF
351  AYNYKLGNMR  KGFSQEEASP  RLDRLMFDKI  KEALGGRAHM  LLSGAAPLPR
401  HVEEFLRIIP  ASNLSQGYGL  TESCGGSFTT  LAGVFSMVGT  VGVPMPTVEA
451  RLVSVPEMGY  DAFSADVPRG  EICLRGNSMF  SGYHKRQDLT  DQVLIDGWFH
501  TGDIGEWQED  GSMKIIDRKK  NIFKLSQGEY  VAVENLENTY  SRCPLIAQVW
551  VYGNSFESFL  VGVVVPDRKA  IEDWAKLNYQ  SPNDFESLCQ  NLKAQKYFLD
601  ELNSTAKQYQ  LKGFEMLKAI  HLEPNPFDIE  RDLITPTFKL  KRPQLLQHYK
651  GIVDQLYSEA  KRSMA
```

FIGURE 18

SEQ ID NO:16  AtACS3A Original Amino Acid Sequence

```
  1  MDSSSSSSSA AARRRINAIH SHLVTSSRSS PLLRSNPTAG EFCLDNGYSV
 51  VLPEKLNTGS WNVYRSAKSP FKLVSRFPDH PDIATLHDNF EHAVHDFRDY
101  KYLGTRVRVD GTVGDYKWMT YGEAGTARTA LGSGLVHHGI PMGSSVGIYF
151  INRPEWLIVD HACSSYSYVS VPLYDTLGPD AVKFIVNHAT VQAIFCVAET
201  LNSLLSCLSE MPSVRLVVVV GGLIESLPSL PSSSGVKVVS YSVLLNQGRS
251  NPQRFFPPKP DDVATICYTS GTTGTPKGVV LTHANLIANV AGSSFSVKFF
301  SSDVYISYLP LAHIYERANQ ILTVYFGVAV GFYQGDNMKL LDDLAALRPT
351  VFSSVPRLYN RIYAGIINAV KTSGGLKERL FNAAYNAKKQ ALLNGKSASP
401  IWDRLVFNKI KDRLGGRVRF MTSGASPLSP EVMEFLKVCF GGRVTEGYGM
451  TETSCVISGM DEGDNLTGHV GSPNPACEIK LVDVPEMNYT SADQPHPRGE
501  ICVRGPIIFT GYYKDEIQTK EVIDEDGWLH TGDIGLWLPG GRLKIIDRKK
551  NIFKLAQGEY IAPEKIENVY AKCKFVGQCF IYGDSFNSSL VAVVSVDPDV
601  LKSWAASEGI KGGDLRELCN NPRVKAAVLS DMDTVGREAQ LRGFEFAKAV
651  TLVLEPFTLE NGLLTPTFKI KRPQAKEYFA EAITNMYKEL GASDPSANRG
701  L
```

FIGURE 19

SEQ ID NO:17  AtACS3B Original Amino Acid Sequence

```
  1  MEFASPEQRR  LETIRSHIDT  SPTNDQSSSI  FLNATASSAS  PFFKEDSYSV
 51  VLPEKLDTGK  WNVYRSKRSP  TKLVSRFPDH  PEIGTLHDNF  VHAVETYAEN
101  KYLGTRVRSD  GTIGEYSWMT  YGEAASERQA  IGSGLLFHGV  NQGACVGLYF
151  INRPEWLVVD  HACAAYSFVS  VPLYDTLGPD  AVKFVVNHAN  LQAIFCVPQT
201  LNILLSFLAE  IPSIRLIVVV  GGADEHLPSL  PRGTGVTIVS  YQKLLSQGRS
251  SLHPFSPPKP  EDIATICYTS  GTTGTPKGVV  LTHGNLIANV  AGSSVEAEFF
301  PSDVYISYLP  LAHIYERANQ  IMGVYGGVAV  GFYQGDVLKL  MDDFAVLRPT
351  IFCSVPRLYN  RIYDGITSAV  KSSGVVKKRL  FEIAYNSKKQ  AIINGRTPSA
401  FWDKLVFNKI  KEKLGGRVRF  MGSGASPLSP  DVMDFLRICF  GCSVREGYGM
451  TETSCVISAM  DDGDNLSGHV  GSPNPACEVK  LVDVPEMNYT  SEDQPYPRGE
501  ICVRGPIIFK  GYYKDEEQTR  EILDGDGWLH  TGDIGLWLPG  GRLKIIDRKK
551  NIFKLAQGEY  IAPEKIENVY  TKCRFVSQCF  IHGDSFNSSL  VAIVSVDPEV
601  MKDWAASEGI  KYEHLGQLCN  DPRVRKTVLA  EMDDLGREAQ  LRGFEFAKAV
651  TLVPEPFTLE  NGLLTPTFKI  KRPQAKAYFA  EAISKMYAEI  AASNPIPSKL
```

FIGURE 20

SEQ ID NO:18   AtACS4A Original Amino Acid Sequence

```
  1  MASTSSLGPS TLLSYGSPSR QFPDFGFRLI SGHESVRIPS FRRFRVHCES
 51  KEKEVKPSSP FLESSSFSGD AALRSSEWKA VPDIWRSSAE KYGDRVALVD
101  PYHDPPLKLT YKQLEQEILD FAEGLRVLGV KADEKIALFA DNSCRWLVSD
151  QGIMATGAVN VVRGSRSSVE ELLQIYRHSE SVAIVVDNPE FFNRIAESFT
201  SKASLRFLIL LWGEKSSLVT QGMQIPVYSY AEIINQGQES RAKLSASNDT
251  RSYRNQFIDS DDTAAIMYTS GTTGNPKGVM LTHRNLLHQI KHLSKYVPAQ
301  AGDKFLSMLP SWHAYERASE YFIFTCGVEQ MYTSIRYLKD DLKRYQPNYI
351  VSVPLVYETL YSGIQKQISA SSAGRKFLAL TLIKVSMAYM EMKRIYEGMC
401  LTKEQKPPMY IVAFVDWLWA RVIAALLWPL HMLAKKLIYK KIHSSIGISK
451  AGISGGGSLP IHVDKFFEAI GVILQNGYGL TETSPVVCAR TLSCNVLGSA
501  GHPMHGTEFK IVDPETNNVL PPGSKGIIKV RGPQVMKGYY KNPSTTKQVL
551  NESGWFNTGD TGWIAPHHSK GRSRHCGGVI VLEGRAKDTI VLSTGENVEP
601  LEIEEAAMRS RVIEQIVVIG QDRRRLGAII IPNKEEAQRV DPETSKETLK
651  SLVYQELRKW TSECSFQVGP VLIVDDPFTI DNGLMTPTMK IRRDMVVAKY
701  KEEIDQLYS
```

FIGURE 21

SEQ ID NO:19 AtACS4B Original Amino Acid Sequence

```
  1  MASTSLGASI  LVSHCSSAPE  FQVSGMRLVF  GYKAFGCRTS  RRGFRVRCES
 51  KIQEKELRRC  SPFLERLSLP  REAALSSNEW  KSVPDIWRSS  VEKYGDRVAV
101  VDPYHDPPST  FTYRQLEQEI  LDFVEGLRVV  GVKADEKIAL  FADNSCRWLV
151  ADQGIMATGA  VNVVRGSRSS  VEELLQIYCH  SESVALVVDN  PEFFNRIAES
201  FSYKAAPKFV  ILLWGEKSSL  VTAGRHTPVY  SYNEIKKFGQ  ERRAKFARSN
251  DSGKYEYEYI  DPDDIATIMY  TSGTTGNPKG  VMLTHQNLLH  QIRNLSDFVP
301  AEAGERFLSM  LPSWHAYERA  CEYFIFTCGV  EQKYTSIRFL  KDDLKRYQPH
351  YLISVPLVYE  TLYSGIQKQI  SASSPARKFL  ALTLIKVSLA  YTEMKRVYEG
401  LCLTKNQKPP  MYIVSLVDWL  WARVVAFFLW  PLHMLAEKLV  HRKIRSSIGI
451  TKAGVSGGGS  LPMHVDKFFE  AIGVNVQNGY  GLTETSPVVS  ARRLRCNVLG
501  SVGHPIKDTE  FKIVDHETGT  VLPPGSKGIV  KVRGPPVMKG  YYKNPLATKQ
551  VIDDDGWFNT  GDMGWITPQH  STGRSRSCGG  VIVLEGRAKD  TIVLSTGENV
601  EPLEIEEAAM  RSNLIQQIVV  IGQDQRRLGA  IVIPNKEAAE  GAAKQKISPV
651  DSEVNELSKE  TITSMVYEEL  RKWTSQCSFQ  VGPVLIVDEP  FTIDNGLMTP
701  TMKIRRDKVV  DQYKNEIERL  YK
```

FIGURE 22

SEQ ID NO:20  AtACS5 Original Amino Acid Sequence

```
  1  MKSFAAKVEE  GVKGIDGKPS  VGPVYRNLLS  EKGFPPIDSE  ITTAWDIFSK
 51  SVEKFPDNNM  LGWRRIVDEK  VGPYMWKTYK  EVYEEVLQIG  SALRAAGAEP
101  GSRVGIYGVN  CPQWIIAMEA  CAAHTLICVP  LYDTLGSGAV  DYIVEHAEID
151  FVFVQDTKIK  GLLEPDCKCA  KRLKAIVSFT  NVSDELSHKA  SEIGVKTYSW
201  IDFLHMGREK  PEDTNPPKAF  NICTIMYTSG  TSGDPKGVVL  THQAVATFVV
251  GMDLYMDQFE  DKMTHDDVYL  SFLPLAHILD  RMNEEYFFRK  GASVGYYHGN
301  LNVLRDDIQE  LKPTYLAGVP  RVFERIHEGI  QKALQELNPR  RRFIFNALYK
351  HKLAWLNRGY  SHSKASPMAD  FIAFRKIRDK  LGGRIRLLVS  GGAPLSPEIE
401  EFLRVTCCCF  VVQGYGLTET  LGGTALGFPD  EMCMLGTVGI  PAVYNEIRLE
451  EVSEMGYDPL  GENPAGEICI  RGQCMFSGYY  KNPELTEEVM  KDGWFHTGDI
501  GEILPNGVLK  IIDRKKNLIK  LSQGEYVALE  HLENIFGQNS  VVQDIWVYGD
551  SFKSMLVAVV  VPNPETVNRW  AKDLGFTKPF  EELCSFPELK  EHIISELKST
601  AEKNKLRKFE  YIKAVTVETK  PFDVERDLVT  ATLKNRRNNL  LKYYQVQIDE
651  MYRKLASKKI
```

FIGURE 23

SEQ ID NO:21   AtACS6A Original Amino Acid Sequence

```
  1  MEDSGVNPMD SPSKGSDFGV YGIIGGGIVA LLVPVLLSVV LNGTKKGKKR
 51  GVPIKVGGEE GYTMRHARAP ELVDVPWEGA ATMPALFEQS CKKYSKDRLL
101  GTREFIDKEF ITASDGRKFE KLHLGEYKWQ SYGEVFERVC NFASGLVNVG
151  HNVDDRVAIF SDTRAEWFIA FQGCFRQSIT VVTIYASLGE EALIYSLNET
201  RVSTLICDSK QLKKLSAIQS SLKTVKNIIY IEEDGVDVAS SDVNSMGDIT
251  VSSISEVEKL GQKNAVQPIL PSKNGVAVIM FTSGSTGLPK GVMITHGNLV
301  ATAAGVMKVV PKLDKNDTYI AYLPLAHVFE LEAEIVVFTS GSAIGYGSAM
351  TLTDTSNKVK KGTKGDVSAL KPTIMTAVPA ILDRVREGVL KKVEEKGGMA
401  KTLFDFAYKR RLAAVDGSWF GAWGLKKMLW DALVFKKIRA VLGGHIRFML
451  VGGAPLSPDS QRFINICMGS PIGQGYGLTE TCAGATFSEW DDPAVGRVGP
501  PLPCGYVKLV SWEEGGYRIS DKPMPRGEIV VGGNSVTAGY FNNQEKTDEV
551  YKVDEKGTRW FYTGDIGRFH PDGCLEVIDR KKDIVKLQHG EYVSLGKVEA
601  ALGSSNYVDN IMVHADPINS YCVALVVPSR GALEKWAEEA GVKHSEFAEL
651  CEKGEAVKEV QQSLTKAGKA AKLEKFELPA KIKLLSEPWT PESGLVTAAL
701  KIKREQIKSK FKDELSKLYA
```

FIGURE 24

SEQ ID NO:22  AtACS6B Original Amino Acid Sequence

```
  1  MIPYAAGVIV PLALTFLVQK SKKEKKRGVV VDVGGEPGYA IRNHRFTEPV
 51  SSHWEHISTL PELFEISCNA HSDRVFLGTR KLISREIETS EDGKTFEKLH
101  LGDYEWLTFG KTLEAVCDFA SGLVQIGHKT EERVAIFADT REEWFISLQG
151  CFRRNVTVVT IYSSLGEEAL CHSLNETEVT TVICGSKELK KLMDISQQLE
201  TVKRVICMDD EFPSDVNSNW MATSFTDVQK LGRENPVDPN FPLSADVAVI
251  MYTSGSTGLP KGVMMTHGNV LATVSAVMTI VPDLGKRDIY MAYLPLAHIL
301  ELAAESVMAT IGSAIGYGSP LTLTDTSNKI KKGTKGDVTA LKPTIMTAVP
351  AILDRVRDGV RKKVDAKGGL SKKLFDFAYA RRLSAINGSW FGAWGLEKLL
401  WDVLVFRKIR AVLGGQIRYL LSGGAPLSGD TQRFINICVG APIGQGYGLT
451  ETCAGGTFSE FEDTSVGRVG APLPCSFVKL VDWAEGGYLT SDKPMPRGEI
501  VIGGSNITLG YFKNEEKTKE VYKVDEKGMR WFYTGDIGRF HPDGCLEIID
551  RKKDIVKLQH GEYVSLGKVE AALSISPYVE NIMVHADSFY SYCVALVVAS
601  QHTVEGWASK QGIDFANFEE LCTKEQAVKE VYASLVKAAK QSRLEKFEIP
651  AKIKLLASPW TPESGLVTAA LKLRRDVIRR EFSEDLTKLY A
```

FIGURE 25
SEQ ID NO:23  AtAMPBP1 cDNA Nucleotide Sequence

```
   1  ATGGAGGGAA CTATCAAATC TCCGGCCAAC TACGTTCCTC TCACTCCGAT
  51  CAGCTTCCTC GATAGATCTG CTGTCGTCTA CGCTGACAGA GTCTCCATCG
 101  TTTATGGCTC CGTCAAGTAC ACGTGGCGCC AGACTCGTGA CCGCTGCGTC
 151  AGAATCGCCT CCGCTCTCTC CCAGCTCGGA ATCTCTACCG GAGATGTGGT
 201  TTCAGTGTTG GCTCCAAACG TTCCAGCTAT GGTTGAATTG CATTTTGGTG
 251  TTCCTATGGC TGGAGCTTTG CTCTGTACAC TCAACATTCG TCATGATTCA
 301  TCACTTGTTG CTGTCTTGCT TAGACATTCA GGGACAAAAG TGATTTTTGC
 351  AGATCATCAG TTTCTCCAAA TAGCTGAAGG AGCTTGTGAA ATCCTCTCAA
 401  ATAAAGGTGA CAAGGTCCCG ATTTTGGTCT TGATCCCAGA GCCTCTTACT
 451  CAATCTGTTT CAAGGAAGAA GAGATCTGAG GAAATGATGG AATACGAAGA
 501  TGTTGTAGCG ATGGGGAAAT CGGACTTCGA GGTTATACGA CCAACAGATG
 551  AGTGTGATGC TATATCTGTT AATTACACAa gcGGTACCAC TTCAAGCCCC
 601  AAAGGTGTTG TTTATAGTCA CAGAGGTGCT TATTTGAATT CTCTGGCTGC
 651  GGTTTTACTC AACGAAATGC ACTCCTCGCC TACTTATCTA TGGACTAATC
 701  CCATGTTTCA CTGCAATGGC TGGTGCTTAT TGTGGGGTGT TACTGCTATT
 751  GGTGGGACTA ATATATGTTT GAGGAATGTT ACGGCCAAGG CTATATTTGA
 801  TAATATTTCC CAGCATAAGG TGACTCATAT GGGAGGTGCG CCGACGATAT
 851  TGAATATGAT CATCAATGCG CCTGAATCTG AGCAGAAACC GCTTCCCGGG
 901  AAGGTGTCTT TTATAACCGG TGCTGCACCG CCACCAGCTC ATGTGATTTT
 951  CAAGATGGAA GAGTTGGGGT TTTCTATGTT TCATTCCTAT GGGTTAACTG
1001  AAACTTATGG ACCAGGCACA ATCTGTACAT GGAAGCCTGA GTGGGACTCT
1051  TTGCCTAGAG AAGAACAGGC GAAAATGAAA GCTCGACAAG GCGTGAATCA
1101  TTTAGGGCTC GAGGAAATAC AAGTTAAAGA CCCTGTAACC ATGAGAACTT
1151  TGCCAGCTGA TGGTGTGACT ATGGGTGAAG TTGTCTTCAG AGGAAACACG
1201  GTGATGAATG GTTACTTAAA GAACCCTGAA GCAACCAAGG AAGCTTTTAA
1251  AGGAGGTTGG TTTTGGAGTG GCGACTTAGG TGTTAAACAC CCTGACGGAT
1301  ACATAGAGCT GAAAGACAGA TCGAAAGACA TTATAATCTC TGGAGGAGAA
1351  AACATTAGCT CGATTGAAGT CGAGTCTACT CTGTTCACTC ACCCTTGTGT
1401  TCTTGAAGCA GCTGTAGTTG CGAGGCCTGA TGAGTATTGG GGTGAGACTG
1451  CTTGTGCATT TGTGAAACTT AAAGACGGGT CTAAGGCCAG TGCGGAGGAG
1501  CTTATTAGCT ATTGCAGGGA CCGGCTTCCA CATTATATGG CTCCGAGGAG
1551  TATTGTGTTT GAGGATCTTC CTAAAACATC GACTGGAAAA GTCCAGAAGT
1601  TGTTCTGAG GACCAAGGCT AAGGCTTTGG TAAGCTTATC AAAGAAAGGC
1651  AGAAGCAAGT TATGA
```

FIGURE 26
SEQ ID NO:24  AtAMPBP2 cDNA Nucleotide Sequence

```
   1  ATGAGATTCT TGTTAACCAA AAGAGCATTC AGAATCTTCA ACCCACGTTT
  51  CCAGAGACTG TGGTTAACTT CTTCTCCCTT CTCCTCAACC TCAAATTCCG
 101  GCGGATTTCC CGACGATTCC GAGCCGGAAT CATGGAGAAC TATAGAGGGT
 151  CTTCTCCGTT CCCCTGCAAA TTTCTCTCCT TTATCTCCAA TCACGTTCTT
 201  GGAGCGATCC GCTAAGGTTT ACAGAGACAG AACCTCTCTT GTGTTTGGTT
 251  CCGTTAAACA CACTTGGTTC CAAACTTATC AACGTTGTCT CCGTCTTGCC
 301  TCTGCTCTTA CCAATCTCGG AATCTCTCGT GGCGATGTGG TTGCAGCTTT
 351  AGCTCCGAAT GTTCCAGCTA TGCATGAGCT TCATTTCGCT GTTCCTATGG
 401  CTGGTTTGAT TCTTTGTCCG CTTAATACTC GACTTGATCC TTCCACATTG
 451  TCGGTTTTGT TAGCACACTC CGAGGCCAAA ATCCTCTTTG TTGATCATCA
 501  GTTACTTGAG ATTGCTCATG GAGCTCTTGA TCTTCTTGCT AAATCAGATA
 551  AAACTAGAAA AAGTCTGAAG CTTGTGTTGA TCTCTCAGTC TAATGATGAT
 601  GATGATAGTG ATGAAGATAG CTCATCTACC TTTGCCTCAA AGTACTCTTT
 651  TGATTACGAA TATGAAACTC TGCTTAAATC CGGAGATAGC GAGTTTGAGA
 701  TAATCAAACC GAGATGCGAA TGGGATCCTA TTAGTATAAA CTACACTTCA
 751  GGGACGACTT CGAGACCTAA GGGTGTAGTG TATAGCCATA GAGGAGCTTA
 801  TCTCAATTCT CTTGCTACAG TCTTTCTTCA CCAGATGTCT GTTTATCCGG
 851  TGTATTTATG GACAGTGCCG ATGTTTCACT GTAACGGATG GTGTCTTGTT
 901  TGGGGAGTAG CAGCTCAAGG TGGTACTAAT ATCTGTCTCA GGAAAGTCTC
 951  TCCTAAGATG ATCTTTAAGA ACATTGCTAT GCATAAAGTG ACTCACATGG
1001  GAGGAGCCCC AACTGTGTTG AATATGATTG TGAACTATAC TGTGACTGAA
1051  CATAAACCGC TTCCTCACAG GGTTGAGATC ATGACAGGTG GGTCACCGCC
1101  TCTACCGCAG ATCCTGGCTA AGATGGAAGA ATTAGGTTTC AATGTGTCTC
1151  ATCTTTATGG TTTGACAGAG ACATACGGTC CAGGGACACA TTGCGTGTGG
1201  AAACCTGAAT GGGATTCACT TTCGTTGGAG GAGAGAACTA AGTTGAAGGC
1251  TAGACAAGGA GTGCAGCATT TGGGTCTAGA AGGGCTCGAT GTGAAAGATC
1301  CGCTGACAAT GGAGACTGTC CCTGATGATG GTTTAACCAT GGGTGAGGTT
1351  ATGTTCAGAG GAAACACTGT GATGAGTGGA TATTTCAAGG ACATAGAGGC
1401  AACACGAAAA GCTTTCGAGG GAGATTGGTT CCACAGTGGT GATCTCGCTG
1451  TTAAGTATCC AGACGGGTAC ATAGAGATAA AGACCGGTT AAAAGATGTG
1501  ATCATCTCAG GAGGAGAAAA CATAAGCTCA GTGGAGGTTG AGAGAGTTTT
1551  GTGCAGCCAT CAAGCGGTTC TTGAAGCTGC TGTTGTAGCA CGTCCAGATC
1601  ATCACTGGGG ACAGACTCCT TGCGGTTTTG TAAAGCTGAA AGAAGGATTT
1651  GATACCATCA AACCCGAGGA GATTATCGGG TTCTGTCGAG ATCATTTGCC
1701  GCATTACATG GCTCCAAAGA CTATAGTTTT CGGGGACATA CCTAAAACCT
1751  CGACGGGGAA AGTACAAAAG TATCTTCTGA GGAAGAAAGC TGATGAAATG
1801  GGTAGCTTGT AA
```

FIGURE 27
SEQ ID NO:25 AtAMPBP3 cDNA Nucleotide Sequence

```
   1  ATGGATAGCG ATACTCTCTC AGGATTATTG GAAAACGTCG CCAAAAAATT
  51  CCCCGATCGC CGAGCTCTCT CCGTTTCTGG AAAATTCAAT CTCACTCACG
 101  CGCGTCTTCA CGATCTAATC GAACGCGCCG CTTCACGCCT TGTCTCCGAC
 151  GCTGGAATCA AACCCGGCGA TGTCGTTGCT CTCACCTTCC CTAACACCGT
 201  CGAGTTTGTT ATAATGTTTT TAGCGGTGAT AAGAGCTAGA GCCACGGCGG
 251  CGCCGTTGAA CGCAGCGTAC ACGGCGGAGG AATTTGAGTT TTACCTCTCC
 301  GATTCAGATT CAAAGCTATT GTTAACCTCT AAAGAAGGAA ACGCACCGGC
 351  TCAAGAAGCA GCTTCAAAGC TGAAAATCTC TCACGTCACC GCTACGCTGC
 401  TTGACGCTGG CTCGGACCTT GTACTATCCG TTGCGGATTC AGATTCCGTC
 451  GTTGACTCAG CGACGGAACT CGTTAATCAC CCGGACGACG TGCTCTCTT
 501  CCTCCACACT TCTGGCACTA CGAGCCGTCC AAAGGGTGTA CCGCTTACGC
 551  AGCTCAATCT AGCTTCATCC GTCAAGAACA TTAAAGCTGT GTACAAGCTT
 601  ACTGAGTCTG ATTCTACGGT GATTGTTCTC CCTCTGTTCC ATGTTCATGG
 651  ATTGTTAGCT GGGTTGCTTA GCTCGCTTGG AGCTGGTGCT GCTGTAACTC
 701  TTCCAGCTGC TGGTAGATTC TCAGCAACAA CATTTTGGCC AGATATGAAG
 751  AAGTATAACG CTACATGGTA TACTGCTGTG CCGACCATTC ATCAGATCAT
 801  ATTGGACCGC CACGCGAGCC ACCCTGAGAC GGAATATCCT AAACTCCGGT
 851  TCATCAGGAG TTGCAGTGCT TCTTTGGCTC CGGTGATATT GTCCAGGCTT
 901  GAGGAAGCGT TTGGAGCACC GGTGCTCGAG GCCTATGCAA TGACAGAGGC
 951  AACACATTTG ATGAGCTCAA ACCCCTTACC AGAGGAAGGT CCACACAAGC
1001  CTGGGTCTGT TGGGAAACCG GTAGGTCAAG AAATGGCGAT CCTTAATGAG
1051  AAAGGCGAGA TCCAAGAGCC AAATAACAAA GGAGAGGTTT GTATAAGAGG
1101  TCCAAATGTG ACCAAGGGTT ACAAGAATAA CCCAGAAGCC AACAAGGCAG
1151  GTTTCGAGTT TGGGTGGTTC CACACTGGTG ATATCGGTTA CTTTGATACC
1201  GATGGGTATT TGCATCTGGT GGGTCGGATC AAAGAGCTTA TTAACCGTGG
1251  AGGTGAGAAG ATATCTCCAA TTGAAGTGGA TGCAGTACTC TTAACGCATC
1301  CTGACGTTTC TCAGGGTGTT GCATTCGGTG TTCCTGATGA GAAATATGGG
1351  GAAGAGATTA ACTGTGCGGT GATTCCAAGA GAAGGAACTA CTGTAACCGA
1401  AGAGGACATT AAAGCGTTTT GTAAGAAGAA TTTGGCAGCT TTCAAGGTGC
1451  CAAAGAGAGT GTTCATCACT GATAACCTCC CCAAAACTGC CTCTGGTAAG
1501  ATTCAGCGCC GTATCGTCGC ACAACATTTC CTTGAGAAGC CCTGA
```

FIGURE 28
SEQ ID NO:26 AtAMPBP4 cDNA Nucleotide Sequence

```
   1  ATGGAACTTT TACTCCCACA CGCTTCAAAC TCATGTCCTC TCACTGTTCT
  51  TGGCTTCTTA GAACGAGCCG CCTCTGTCTT CGGCGACTCT CCTTCACTCC
 101  TCCACACAAC CACTGTTCAT ACTTGGTCTG AAACTCATTC TCGATGTCTC
 151  CGTATAGCTT CAACTCTCTC TTCCGCTTCC CTCGGAATCA ACCGCGGCCA
 201  AGTTGTCTCT GTTATTGGTC CAAACGTCCC ATCTGTCTAC GAGCTTCAGT
 251  TCGCAGTTCC GATGTCAGGC GCAGTCCTCA CAACATCAA CCCACGTTTA
 301  GACGCTCATG CACTCTCCGT CCTTCTACGT CACAGCGAAT CCAAGCTCGT
 351  GTTTGTTGAC CATCACTTAA GCTCTTTAGT CCTCGAAGCT GTCTCGTTTT
 401  TGCCCAAGGA TGAGAGACCT CGTCTCGTCA TACTCAACGA CGGAAACGAC
 451  ATGCCATCAT CTTCATCAGC TGATATGGAT TTTCTTGACA CGTACGAAGG
 501  GTTTATGGAG AGAGGAGACC TGAGGTTCAA GTGGGTACGT CCTAAAAGCG
 551  AGTGGACTCC AATGGTGCTT AACTACACCT CAGGAACTAC GTCGTCCCCA
 601  AAGGGAGTGG TGCATAGCCA CAGATCGGTT TTCATGAGCA CTATTAACTC
 651  TTTGCTAGAC TGGTCTTTGC CTAACCGTCC GGTATACCTG TGGACACTGC
 701  CGATGTTCCA TGCCAATGGT GGAGCTACA CATGGGCCAC AGCAGCTGTG
 751  GGAGCCAGAA ACATCTGTGT CACAAGAGTT GATGTGCCGA CTATTTTCAA
 801  CTTGATCGAC AAGTATCAAG TGACCCACAT GTGCGCTGCG CCAATGGTTC
 851  TCAACATGTT GACTAATCAC CCAGCCCAGA AACCGCTTCA GAGCCCAGTT
 901  AAGGTTATGA CTGCTGGAGC TCCACCACCA GCTACAGTCA TCTCCAAGGC
 951  TGAGGCGCTT GGTTTCGACG TGAGTCACGG TTACGGGATG ACAGAAACAG
1001  GCGGTCTGGT TGTCTCGTGC GCATTGAAGC TGAGTGGGA TCGTCTAGAA
1051  CCAGACGAGA GAGCAAAACA GAAATCAAGG CAAGGAATTA GAACTGCAGT
1101  ATTCGCGGAA GTCGATGTTA GAGACCCAAT ATCCGGGAAG AGCGTGAAGC
1151  ATGATGGAGC AACTGTGGGA GAGATCGTCT TCAGAGGCGG TTCGGTCATG
1201  CTAGGTTATT ACAAAGACCC AGAAGGCACC GCAGCAAGTA TGAGAGAAGA
1251  CGGATGGTTC TACACCGGAG ACATTGGAGT AATGCACCCA GACGGTTACT
1301  TGGAAGTCAA AGACAGATCA AAGGATGTGG TCATTTGCGG AGGAGAGAAC
1351  ATCAGCAGCA CGGAACTCGA GGCAGTTCTG TACACAAACC CCGCAATTAA
1401  GGAAGCAGCT GTGGTAGCTA AGCCAGACAA GATGTGGGGA GAAACTCCAT
1451  GTGCATTTGT CAGCCTGAAG TATCATGACG GGTCTGTGAC TGAGAGAGAG
1501  ATACGGGAGT TTTGTAAAAC CAAGCTGCCA AGTATATGG TTCCAAGGAA
1551  TGTGGTTTTC CTGGAAGAGC TTCCAAAGAC TTCTACTGGA AAGATTCAAA
1601  AGTTTCTTCT CAGACAAATG GCTAAGTCCT TGCCTTGA
```

FIGURE 29
SEQ ID NO:27 AtAMPBP5 cDNA Nucleotide Sequence

```
   1 ATGGAGCAAA TGAAGCCATG CGCCGCAAAC TCGCCGCCGT TGACGCCGAT
  51 AGGTTTCTTA GAGAGAGCCG CCACCGTTTA CGGTGACTGT ACCTCCATCG
 101 TTTATGGCAG CAACACCGTT TACACGTGGC GTGAAACAAA CCTCCGTTGT
 151 CTCCGCGTGG CGTCTTCTCT GTCTTCAATC GGAATCGGCA GGTCTGACGT
 201 AGTCTCTGTT CTCTCTCCCA ATACTCCGGC TATGTACGAG CTCCAGTTTG
 251 CTGTTCCCAT GTCCGGCGCA ATCCTCAACA ACATCAACAC TCGCCTCGAC
 301 GCACGCACCG TCTCTGTTCT CTCCGTCAC TGTGGATCTA AGCTTCTCTT
 351 CGTCGACGTC TTCTCCGTTG ATCTTGCCGT TGAAGCGATC TCGATGATGA
 401 CGACTGATCC GCCGATTCTT GTCTTCATCG CCGATAAAGA AGAAGAAGGA
 451 GGAGATGCTG ACGTGGCGGA TCGTACCAAA TTCAGTTACA CTTACGATGA
 501 TCTGATCCAT AGAGGTGATC TGGATTTTAA ATGGATCCGA CCCGAAAGCG
 551 AATGGGATCC GGTTGTGCTT AATTACACTT CCGGTACGAC TTCGGCTCCT
 601 AAAGGAGTCG TACACTGCCA CAGAGGAATT TTCGTAATGT CAATTGATTC
 651 TTTAATCGAT TGGACCGTAC CGAAAAATCC GGTTTACTTA TGGACTCTAC
 701 CGATATTTCA CGCTAACGGC TGGAGCTATC CATGGGGAAT CGCCGCCGTC
 751 GGAGGAACTA ACGTCTGTTT GCGTAAATTC GACGCGCCGT TAATCTACCG
 801 TTTGATCCGT GATCACGGCG TCACACACAT GTGTGGAGCT CCGGTAGTGC
 851 TCAACATGTT GTCGGCGACT AACGAATTTC AGCCGTTAAA TCGTCCTGTC
 901 AACATCTTAA CCGCCGGTGC TCCGCCTCCA GCAGCCGTAC TCCTCCGAGC
 951 AGAATCAATT GGATTCGTGA TAAGTCACGG ATACGGGTTA ACGGAAACCG
1001 CCGGATTAAA CGTGTCATGC GCGTGGAAGC CACAGTGGAA TCGTTTACCG
1051 GCGAGCGATC GAGCGAGGTT GAAAGCACGG CAAGGAGTGA GAACCGTCGG
1101 ATTTACTGAA ATCGACGTGG TGGATCCTGA ATCAGGTAGG AGCGTTGAGA
1151 GAAACGGAGA AACCGTCGGA GAAATAGTGA TGAGAGGAAG CTCGATCATG
1201 CTCGGTTACT TAAAAGATCC GGTCGGAACA GAGAAAGCTT TAAAGAACGG
1251 GTGGTTTTAC ACCGGAGATG TTGGTGTGAT TCATTCCGAT GGTTATCTAG
1301 AGATTAAAGA TAGATCGAAA GATATAATTA TAACGGGAGG TGAAAATGTG
1351 AGTAGTGTTG AGGTTGAAAC GGTTTTGTAT ACGAATCCGG CGGTGAATGA
1401 AGTGGCGGTG GTGGCGAGAC CTGATGTGTT TTGGGGAGAG ACGCCGTGTG
1451 CGTTTGTTAG TTTGAAAAGT GGGTTGACTC AAAGACCGAC GGAGGTGGAA
1501 ATGATAGAGT ATTGTAGGAA GAAGATGCCG AAATATATGG TTCCTAAAAC
1551 GGTGTCCTTT GTGGATGAGC TGCCTAAAAC TTCGACGGGG AAGGTTATGA
1601 AGTTTGTACT TAGAGAGATT GCGAAGAAGA TGGGTACGAC GAGGTTGAGT
1651 CGGATGTAA
```

FIGURE 30
SEQ ID NO:28  AtAMPBP6 cDNA Nucleotide Sequence

```
   1 ATGGAGGAAA TGAAGCCATG CGCCGCAAAC TCGCCGCCGT TGACGCCGAT
  51 AGGTTTTTTA GAGAGAGCCG CCACCGTTTA CGGTGACTGT ACCTCCATCG
 101 TTTATGGCAG CAACACCGTT TACACGTGGC GTGAAACAAA CCTCCGTTGT
 151 CTCCGCGTGG CGTCTTCTCT GTCTTCAATC GGAATCGGCA GGTCTGACGT
 201 AGTCTCTGTT CTCTCTCCCA ATACTCCGGC TATGTACGAG CTCCAGTTTG
 251 CTGTTCCCAT GTCCGGCGCA ATCCTCAACA ACATCAACAC ACGCCTCGAC
 301 GCACGCACCG TCTCTGTTCT CTCCGTCAC TGTGAATCTA AGCTTCTTTT
 351 CGTCGACGTC TTCTCCGTTG ATCTCGCCGT TGAAGCGGTC TCGATGATGA
 401 CGACTGATCC GCCGATTCTC GTCGTCATCG CCGATAAAGA AGAGGAAGGA
 451 GGAGTTGCTG ACGTGGCTGA TCTTTCAAAA TTCAGTTACA CTTACGATGA
 501 TCTTATCGAA AGAGGTGATC CGGGTTTTAA ATGGATCCGA CCCGAAAGCG
 551 AATGGGATCC GGTTGTGCTT AATTACACTT CCGGTACGAC TTCAGCTCCT
 601 AAAGGAGTGG TACACTGCCA CAGAGGAATT TTCGTAATGT CAGTTGATTC
 651 ACTAATTGAT TGGGCCGTAC CGAAAAATCC GGTTTACTTA TGGACTCTAC
 701 CGATATTTCA CTCTAACGGT TGGACCAATC CATGGGGAAT CGCCGCCGTC
 751 GGAGGAACTA ACGTCTGTTT GCGTAAATTT GACGCGCCGT TAATCTACCG
 801 TCTGATCCGT GATCACGGCG TCACACACAT GTGTGGAGCT CCGGTGGTGC
 851 TCAACATGTT ATCCGCGACT CAGGAATCTC AGCCTCTTAA CCATCCCGTC
 901 AACATCTTAA CCGCCGGTTC TCCGCCTCCA GCTACCGTCC TCCTCCGAGC
 951 CGAATCAATT GGTTTCGTTA TCAGTCACGG TTACGGATTA ACGGAAACCG
1001 CCGGTGTAAT CGTCTCGTGC GCGTGGAAGC CAAAATGGAA TCATTTACCG
1051 GCAAGCGATC GAGCGAGATT GAAGGCACGG CAAGGAGTGA GAACCGTCGG
1101 GTTTACTGAA ATTGACGTGG TGGATCCTGA ATCGGGTTTG AGCGTTGAGA
1151 GAAATGGAGA AACTGTCGGA GAAATTGTGA TGAGAGGAAG CTCGGTCATG
1201 CTCGGTTACT TAAAAGATCC GGTCGGAACA GAGAAAGCTT TAAAGAACGG
1251 GTGGTTTTAC ACCGGAGATG TTGGTGTGAT TCATTCCGAT GGTTATCTAG
1301 AGATTAAAGA TAGATCGAAA GATATAATTA AACGGGAGG TGAGAATGTG
1351 AGTAGTGTTG AGGTTGAAAC GGTGTTGTAC ACGATTCCGG CGGTGAATGA
1401 AGTGGCGGTG GTGGCTAGAC CTGATGAGTT TTGGGGAGAG ACACCGTGTG
1451 CGTTTGTGAG TTTGAAAAAT GGGTTAGTG GGAAACCTAC GGAGGAGGAA
1501 TTGATGGAGT ATTGTAGAAA GAAGATGCCC AAGTATATGG TTCCTAAAAC
1551 GGTGTCGTTT ATGATGAGT TGCCTAAGAG TTCGACGGGA AAGGTTACGA
1601 AGTTTGTGCT TAGGGACATT GCAAGAAGA TGGGTGATAA GACAATTTCT
1651 TAA
```

FIGURE 31

SEQ ID NO:29  AtAMPBP7 cDNA Nucleotide Sequence

```
   1  ATGGCGGCAA CGAAGTGGCG TGACATCGAT GATCTTCCCA AGATTCCGGC
  51  CAACTACACG GCGTTGACTC CGCTTTGGTT CCTTGATAGG GCTGCCGTGG
 101  TTCATCCGAC CAGAAAATCT GTGATTCACG GATCGCGAGA GTACACGTGG
 151  CGCCAGACTT ATGACCGGTG TCGCCGACTC GCCTCCGCTC TCGCCGATCG
 201  ATCAATCGGT CCCGGTTCAA CGGTGGCTAT TATTGCACCT AACATCCCAG
 251  CAATGTACGA AGCTCATTTC GGAGTACCAA TGTGTGGAGC TGTTCTGAAT
 301  TGTGTCAACA TCCGTCTCAA TGCCCCAACA GTCGCTTTTC TTCTTAGTCA
 351  CTCGCAGAGC TCTGTTATAA TGGTGGATCA GGAGTTCTTT ACTCTGGCTG
 401  AGGATTCTTT GAGACTTATG GAGGAGAAAG CTGGAAGTAG CTTCAAACGC
 451  CCGCTTTTAA TCGTCATTGG TGATCACACC TGTGCTCCTG AGTCACTTAA
 501  CCGGGCTTTG TCGAAGGGAG CTATAGAATA TGAGGATTTT CTTGCAACCG
 551  GAGATCCAAA TTATCCGTGG CAGCCACCAG CTGATGAGTG GCAGAGCATC
 601  GCTCTTGGTT ATACCTCGGG AACAACTGCT AGTCCGAAAG GAGTGGTGCT
 651  TCATCATCGA GGTGCGTATA TAATGGCTTT GAGCAATCCT CTCATTTGGG
 701  GGATGCAAGA TGGTGCTGTT TACTTGTGGA CTCTCCCTAT GTTTCATTGC
 751  AACGGTTGGT GTTTCCCTTG GTCCCTTGCT GTGCTCTCTG GTACAAGCAT
 801  CTGTCTCCGT CAGGTTACGG CGAAGGAAGT GTATTCAATG ATAGCCAAAT
 851  ACAAGGTAAC TCATTTCTGT GCAGCTCCTG TGGTCCTCAA CGCTATTGTC
 901  AATGCTCCTA AGAAGACAC TATCCTTCCT CTTCCCCATA CAGTCCATGT
 951  CATGACAGCA GGAGCTGCTC CTCCACCTTC TGTTCTCTTC TCCATGAACC
1001  AGAAGGGCTT CCGAGTCGCT CACACCTATG GCTTTCCGA GACTTATGGT
1051  CCTTCCACCG TATGCGCTTG GAAACCCGAG TGGGATTCCC TCCCTCCTGA
1101  GACGCAGGCC AAGCTCAATG CTCGCCAAGG TGTCCGCTAT ACTGGCATGG
1151  AGCAGCTTGA TGTCATTGAC ACTCAGACCG GAAAACCTGT TCCTGCAGAT
1201  GGAAAAACCG CAGGAGAAAT TGTTTTCCGA GGGAATATGG TGATGAAAGG
1251  CTATCTAAAG AATCCGGAAG CGAACAAAGA GACATTTGCT GGTGGGTGGT
1301  TCCACTCGGG GGATATTGCA GTGAAACACC CAGACAACTA TATCGAGATC
1351  AAGGACAGGT CAAAGGACGT TATAATCTCT GGGGGCGAGA ATATCAGCAG
1401  TGTCGAAGTC GAAAACGTAG TGTACCATCA CCCCGCGGTT CTTGAAGCCT
1451  CTGTTGTGGC CAGGCCAGAC GAGCGGTGGC AAGAATCTCC GTGTGCGTTT
1501  GTGACACTTA AGAGCGATTA CGAGAAGCAT GACCAGAATA AGTTGGCTCA
1551  GGATATAATG AAATTCTGCC GGGAGAAGCT TCCGGCATAT TGGGTCCCAA
1601  AGTCAGTGGT GTTTGGGCCG TTACCAAAGA CAGCAACTGG AAAAATTCAG
1651  AAGCATATTC TGAGGACCAA GGCCAAAGAG ATGGGACCAG TACCAAGAAG
1701  CAGGTTATAG
```

FIGURE 32
SEQ ID NO:30  AtAMPBP8 cDNA Nucleotide Sequence

```
   1  ATGGAAGAGC CAAGTGCCGC TAACTCGTTA CCATTGACAC TGTTAGGCTT
  51  TCTTGAGAGA GCAGCCACCG TGTATGGAGA CTGTACCTCC ATCGTTTACG
 101  GCAATTCCAC CGTGTACACA TGGCGAGAAA CGAATCACCG TTGCCTCTGC
 151  GTCGCGTCTG CTCTGTCTTC CATTGGAATA GGAAGATCCG ACGTTGTCTC
 201  TGTCCTATCT GCTAATACTC CGGAAATGTA CGAGCTCCAG TTTTCCGTTC
 251  CGATGTCTGG CGCGATCCTT AACAACATCA ATACCCGCCT CGACGCGCGA
 301  ACCGTCTCTG TTCTTCTCCG CCATTGCGAG TCTAAGCTGC TCTTCGTCGA
 351  CTTCTTTTAC TCCGATCTCG CTGTCGAAGC GATCACGATG TTGCTCAATC
 401  CGCCGATTCT CGTCCTAATC GCCAATGAGG AGGAGGAAGA AGGAGGAGCT
 451  GAAGTAACGG AGCGTTCAAA ATTCTGTTAC TTGTACAGTG ATCTAATCAC
 501  TAGAGGGAAT CCGGATTTTA AATGGATCCG ACCCGGAAGT GAATGGGACC
 551  CGATTGTGGT CAATTACACA TCAGGTACGA CGTCGTCTCC TAAAGGAGTG
 601  GTTCATTGCC ACAGGGGTAT ATTCGTCATG ACGCTTGATT CCCTAACCGA
 651  TTGGGCCGTA CCGAAAACCC CGGTTTACTT ATGGACCTTA CCGATATTTC
 701  ACGCCAACGG TTGGACCTAT CCATGGGGAA TCGCCGCCGT CGGAGGAACT
 751  AACGTCTGTG TGCGTAAACT CCACGCGCCG TCAATATACC ATCTAATCCG
 801  TGATCACGGC GTGACTCACA TGTACGGCGC ACCAATAGTG CTTCAGATTC
 851  TATCGGCGAG TCAAGAATCT GATCAGCCTC TTAAGAGTCC GGTCAATTTC
 901  TTAACCGCCG GTTCTTCTCC GCCAGCTACG GTGCTTCTCC GCGCCGAGTC
 951  TCTAGGTTTC ATCGTCAGTC ACGGTTACGG ATTAACGGAG ACAGCCGGTG
1001  TGATCGTCTC CTGCGCGTGG AAGCCAAACT GGAATCGGTT ACCGGCGAGT
1051  GATCAAGCGC AATTGAAATC ACGGCAAGGA GTGAGAACCG TCGGATTTAG
1101  CGAAATCGAT GTAGTGGATC CAGAATCAGG TCGGAGCGTG GAGAGAGACG
1151  GAGAAACAGT CGGAGAAATA GTGTTGAGAG GGAGTTCAAT CATGCTCGGA
1201  TACTTAAAAA ATCCGATCGG AACTCAAAAT TCGTTTAAAA ACGGGTGGTT
1251  CTTCACCGGA GACCTCGGTG TGATTCACGG GGATGGTTAC TTAGAGATTA
1301  AAGATAGATC GAAAGATGTG ATTATTTCAG GAGGAGAGAA TGTGAGTAGT
1351  GTGGAAGTGG AGGCGGTGTT GTACACGAAT CCGGCGGTGA ATGAAGCGGC
1401  GGTGGTGGCT AGACCTGACG AGTTTTGGGG AGAGACGCCG TGTGCTTTTG
1451  TTAGTTTAAA ACCCGGGTTG ACCCGGAAAC CAACGGATAA GGAGATTATA
1501  GAGTATTGCA AATATAAAT GCCACGTTAC ATGGCTCCTA AAACGGTCTC
1551  GTTTCTTGAA GAGTTACCAA AGACTTCCAC TGGGAAGATT ATAAAGTCAT
1601  TGCTTAAAGA GATTGCCAAA AACATGTAA
```

FIGURE 33
SEQ ID NO:31  AtAMPBP9 cDNA Nucleotide Sequence

```
   1  ATGGAACTCT TACTTCCACA CCCTTCGAAC TCAACACCTC TCACCGTCCT
  51  CGGCTTCTTA GACCGAGCCG CCTCTGTCTA CGGCGACTGT CCGTCCATCC
 101  TCCACACCAC TAACACCGTC CACACTTGGT CCGAAACCCA CAACCGCTGT
 151  CTTCGAATCG CCTCGGCTCT CACTTCTTCC TCTCTCGGCA TAAACCGAGG
 201  CCAAGTTGTC TCCGTCGTAG GTCCCAACGT CCCGTCCGTC TACGAGCTTC
 251  AGTTTGCTGT CCCAATGTCC GGAGCCATCT TAAACAACAT CAACCCTCGT
 301  TTGGACGCAC ATGCACTCTC TGTCCTCCTG CGTCACAGTG AATCTAAGCT
 351  CGTTTTCGTC GATCCCAATT CAATCTCCGT AGTCCTCGAA GCAGTCTCGT
 401  TCATGAGGCA AAACGAGAAA CCTCACCTTG TCCTCCTAGA CGACGACCAA
 451  GAGGACGGTT CTTTGTCTCC TTCGGCCGCA TCAGATTTTC TTGACACATA
 501  CCAAGGAGTT ATGGAGAGAG GAGATTCAAG ATTCAAGTGG ATCCGTCCTC
 551  AAACCGAGTG GCAGCCTATG ATTCTCAACT ATACTTCTGG AACAACGTCA
 601  TCTCCCAAAG GAGTAGTGTT GAGCCACAGA GCAATTTTCA TGCTAACCGT
 651  AAGCTCATTG CTTGACTGGC ATTTTCCGAA CAGGCCGGTT TACTTGTGGA
 701  CTCTACCAAT GTTCCACGCC AATGGTTGGG GGTATACATG GGGCACTGCG
 751  GCGGTTGGAG CCACCAACGT CTGCACCCGT AGAGTCGACG CGCCGACTAT
 801  CTATGACTTG ATCGATAAGC ATCACGTAAC TCACATGTGT GCCGCACCAA
 851  TGGTTCTCAA CATGCTAACC AACTACCCGT CTCGTAAACC GCTAAAGAAC
 901  CCGGTTcagg ttATGACCGC CGGAGCTCCA CCTCCAGCAG CCATCATCTC
 951  AAGAGCAGAA ACCCTAGGTT TCAACGTCGG TCATGGGTAC GGTTTAACGG
1001  AAACCGGAGG CCCGGTTGTG TCATGTGCTT GgAAGGCTGA GTGGGATCAT
1051  CTTGATCCAT TGGAAAGAGC AAGACTGAAA TCAAGACAAG GAGTAAGAAC
1101  CATCGGATTC GCGGAAGTTG ATGTTAGGGA CCCGAGAACC GGGAAGAGTG
1151  TGGAACACGA CGGTGTTTCC GTTGGAGAGA TCGTTTTAAA AGGCGGTTCG
1201  GTTATGCTTG GTTACTACAA AGACCCTGAA GGAACCGCAG CGTGTATGAG
1251  AGAGGACGGA TGGTTCTACA GCGGAGACGT AGGAGTTATA CATGAAGACG
1301  GTTACTTGGA AGTTAAAGAC CGGTCAAAGG ATGTGATCAT ATGCGGAGGA
1351  GAGAACATAA GTAGTGCCGA GGTTGAGACG GTTCTGTATA CAAATCCAGT
1401  AGTTAAAGAA GCCGCGGTGG TGGCTAAACC GGATAAGATG TGGGGAGAGA
1451  CACCGTGTGC TTTTGTGAGC TTGAAGTATG ATtcgAATGG TAATGGGTTG
1501  GTGACTGAGA GGGAAATAAG GGAGTTTTGT AAGACGAGGT TACCTAAGTA
1551  TATGGTTCCA AGGAAAGTAA TTTTTCAGGA GGAGCTTCCA AAGACTTCTA
1601  CTGGAAAGAT ACAGAAGTTT CTTCTAAGAC AAATGGCTAA GTCTCTGCCT
1651  TAA
```

FIGURE 34

SEQ ID NO:32 AtAMPBP10 cDNA Nucleotide Sequence

```
   1  ATGGAACTCT TACTTCCACA CCCATCAAAC TCAACTCCAC TCACCGTCCT
  51  CGGCTTCTTA GACCGAGCCG CTTCCGTCTA TGGTGACTGT CCGTCCATCC
 101  TCCACACTGC AAACACCGTT CATACTTGGT CCGAAACACA TAACCGCTGT
 151  CTCCGTATCG CATCGGCTCT AACTTCCTCC TCTATCGGAA TTAAACAAGG
 201  CCAAGTCGTC TCTGTCGTGG GTCCCAACGT CCCGTCCGTC TATGAGCTTC
 251  AGTTTGCTGT CCCAATGTCC GGAGCCATCT TAAACAACAT CAACCCTCGC
 301  TTAGACGCAC ACGCACTCTC TGTCCTCCTG CGTCACAGCG AATCCAGACT
 351  CGTTTTCGTC GACCACCGTT CTATATCCTT AGTCCTTGAA GCAGTTTCAT
 401  TATTCACACA ACACGAGAAA CCTCACCTCG TCCTCCTGGA CGATGACCAA
 451  GAGAACGATT CTTCATCCGC ATCAGATTTT CTTGACACGT ACGAAGAAAT
 501  TATGGAGAGA GGAAATTCAA GATTCAAGTG GATCCGTCCT CAAACCGAAT
 551  GGCAACCAAT GGTTCTTAAC TATACTTCCG GAACGACGTC GTCTCCCAAG
 601  GGAGTGGTAC TTAGCCACAG AGCGATTTTC ATGCTCACTG TTAGCTCCTT
 651  GCTTGATTGG TCAGTACCAA ACCGGCCAGT TTACTTGTGG ACTCTACCGA
 701  TGTTTCACGC CAATGGTTGG GGTTACACTT GGGGCACCGC AGCGGTTGGA
 751  GCCACCAACA TCTGCACGCG TAGAGTCGAC GCACCGACTA TTTACAACTT
 801  GATCGATAAG CACAATGTGA CCCACATGTG TGCTGCACCT ATGGTTCTCA
 851  ACATGCTAAT TAACTATCCA TTAAGTACGC CGCTCAAGAA CCCGGTTATG
 901  ACCTCTGGAG CTCCCCCACC AGCAACCATT ATCTCCCGAG CGGAGTCACT
 951  TGGTTTCAAC GTCAGCCACT CATACGGTTT AACAGAGACT AGCGGTCCGG
1001  TTGTGTCATG TGCTTGGAAG CCTAAGTGGG ACCATCTTGA TCCATTGGAG
1051  AGAGCTAGGC TGAAGTCAAG GCAAGGAGTA AGAACACTCG GATTCACGGA
1101  AGTCGATGTA AGGGATCGAA AAACAGGAAA GAGTGTGAAA CACGACGGAG
1151  TTTCGGTTGG AGAGATTGTT TTCAGAGGCA GCTCAGTCAT GTTGGGATAC
1201  TACAAAGACC CTCAAGGAAC TGCGGCTTGT ATGAGAGAGG ACGGGTGGTT
1251  CTACTCTGGA GACATCGGGG TTATACACAA AGATGGTTAC TTGGAGATCA
1301  AAGATCGGTC AAAAGATGTG ATCATATGCG GAGGAGAAAA TATAAGCAGC
1351  GCAGAGATTG AGACGGTTCT GTATACAAAT CCGGTGGTGA AGGAAGCTGC
1401  GGTGGTGGCT AAACCGGATA AGATGTGGGG AGAGACACCA TGTGCTTTTG
1451  TGAGCTTGAA GTGTGATAAC AATGGTGATG GTTCGGTTCC CGTGACCGAG
1501  AGAGAGATAA GGGAGTTTTG TAAGACGAAG TTACCTAAGT ACATGGTTCC
1551  GAGGAAAGTG ATCTTTCAGG AGGAACTTCC CAAGACTTCC ACAGGAAAAA
1601  TTCAGAAGTT TTTGCTAAGA CAAATGGCTA AGACCCTGTC TTGA
```

FIGURE 35

SEQ ID NO:33  AtAMPBP1 Amino Acid Sequence

```
  1  MEGTIKSPAN YVPLTPISFL DRSAVVYADR VSIVYGSVKY TWRQTRDRCV
 51  RIASALSQLG ISTGDVVSVL APNVPAMVEL HFGVPMAGAL LCTLNIRHDS
101  SLVAVLLRHS GTKVIFADHQ FLQIAEGACE ILSNKGDKVP ILVLIPEPLT
151  QSVSRKKRSE EMMEYEDVVA MGKSDFEVIR PTDECDAISV NYTSGTTSSP
201  KGVVYSHRGA YLNSLAAVLL NEMHSSPTYL WTNPMFHCNG WCLLWGVTAI
251  GGTNICLRNV TAKAIFDNIS QHKVTHMGGA PTILNMIINA PESEQKPLPG
301  KVSFITGAAP PPAHVIFKME ELGFSMFHSY GLTETYGPGT ICTWKPEWDS
351  LPREEQAKMK ARQGVNHLGL EEIQVKDPVT MRTLPADGVT MGEVVFRGNT
401  VMNGYLKNPE ATKEAFKGGW FWSGDLGVKH PDGYIELKDR SKDIIISGGE
451  NISSIEVEST LFTHPCVLEA AVVARPDEYW GETACAFVKL KDGSKASAEE
501  LISYCRDRLP HYMAPRSIVF EDLPKTSTGK VQKFVLRTKA KALVSLSKKG
551  RSKL*
```

FIGURE 36

SEQ ID NO:34  AtAMPBP2 Amino Acid Sequence

```
  1  MRFLLTKRAF  RIFNPRFQRL  WLTSSPFSST  SNSGGFPDDS  EPESWRTIEG
 51  LLRSPANFSP  LSPITFLERS  AKVYRDRTSL  VFGSVKHTWF  QTYQRCLRLA
101  SALTNLGISR  GDVVAALAPN  VPAMHELHFA  VPMAGLILCP  LNTRLDPSTL
151  SVLLAHSEAK  ILFVDHQLLE  IAHGALDLLA  KSDKTRKSLK  LVLISQSNDD
201  DDSDEDSSST  FASKYSFDYE  YETLLKSGDS  EFEIIKPRCE  WDPISINYTS
251  GTTSRPKGVV  YSHRGAYLNS  LATVFLHQMS  VYPVYLWTVP  MFHCNGWCLV
301  WGVAAQGGTN  ICLRKVSPKM  IFKNIAMHKV  THMGGAPTVL  NMIVNYTVTE
351  HKPLPHRVEI  MTGGSPPLPQ  ILAKMEELGF  NVSHLYGLTE  TYGPGTHCVW
401  KPEWDSLSLE  ERTKLKARQG  VQHLGLEGLD  VKDPLTMETV  PDDGLTMGEV
451  MFRGNTVMSG  YFKDIEATRK  AFEGDWFHSG  DLAVKYPDGY  IEIKDRLKDV
501  IISGGENISS  VEVERVLCSH  QAVLEAAVVA  RPDHHWGQTP  CGFVKLKEGF
551  DTIKPEEIIG  FCRDHLPHYM  APKTIVFGDI  PKTSTGKVQK  YLLRKKADEM
601  GSL*
```

FIGURE 37

SEQ ID NO:35   AtAMPBP3 Amino Acid Sequence

```
  1  MDSDTLSGLL  ENVAKKFPDR  RALSVSGKFN  LTHARLHDLI  ERAASRLVSD
 51  AGIKPGDVVA  LTFPNTVEFV  IMFLAVIRAR  ATAAPLNAAY  TAEEFEFYLS
101  DSDSKLLLTS  KEGNAPAQEA  ASKLKISHVT  ATLLDAGSDL  VLSVADSDSV
151  VDSATELVNH  PDDGALFLHT  SGTTSRPKGV  PLTQLNLASS  VKNIKAVYKL
201  TESDSTVIVL  PLFHVHGLLA  GLLSSLGAGA  AVTLPAAGRF  SATTFWPDMK
251  KYNATWYTAV  PTIHQIILDR  HASHPETEYP  KLRFIRSCSA  SLAPVILSRL
301  EEAFGAPVLE  AYAMTEATHL  MSSNPLPEEG  PHKPGSVGKP  VGQEMAILNE
351  KGEIQEPNNK  GEVCIRGPNV  TKGYKNNPEA  NKAGFEFGWF  HTGDIGYFDT
401  DGYLHLVGRI  KELINRGGEK  ISPIEVDAVL  LTHPDVSQGV  AFGVPDEKYG
451  EEINCAVIPR  EGTTVTEEDI  KAFCKKNLAA  FKVPKRVFIT  DNLPKTASGK
501  IQRRIVAQHF  LEKP*
```

FIGURE 38

SEQ ID NO:36  AtAMPBP4 Amino Acid Sequence

```
  1  MELLLPHASN SCPLTVLGFL ERAASVFGDS PSLLHTTTVH TWSETHSRCL
 51  RIASTLSSAS LGINRGQVVS VIGPNVPSVY ELQFAVPMSG AVLNNINPRL
101  DAHALSVLLR HSESKLVFVD HHLSSLVLEA VSFLPKDERP RLVILNDGND
151  MPSSSSADMD FLDTYEGFME RGDLRFKWVR PKSEWTPMVL NYTSGTTSSP
201  KGVVHSHRSV FMSTINSLLD WSLPNRPVYL WTLPMFHANG WSYTWATAAV
251  GARNICVTRV DVPTIFNLID KYQVTHMCAA PMVLNMLTNH PAQKPLQSPV
301  KVMTAGAPPP ATVISKAEAL GFDVSHGYGM TETGGLVVSC ALKPEWDRLE
351  PDERAKQKSR QGIRTAVFAE VDVRDPISGK SVKHDGATVG EIVFRGGSVM
401  LGYYKDPEGT AASMREDGWF YTGDIGVMHP DGYLEVKDRS KDVVICGGEN
451  ISSTELEAVL YTNPAIKEAA VVAKPDKMWG ETPCAFVSLK YHDGSVTERE
501  IREFCKTKLP KYMVPRNVVF LEELPKTSTG KIQKFLLRQM AKSLP*
```

FIGURE 39

SEQ ID NO:37  AtAMPBP5 Amino Acid Sequence

```
  1 MEQMKPCAAN SPPLTPIGFL ERAATVYGDC TSIVYGSNTV YTWRETNLRC
 51 LRVASSLSSI GIGRSDVVSV LSPNTPAMYE LQFAVPMSGA ILNNINTRLD
101 ARTVSVLLRH CGSKLLFVDV FSVDLAVEAI SMMTTDPPIL VFIADKEEEG
151 GDADVADRTK FSYTYDDLIH RGDLDFKWIR PESEWDPVVL NYTSGTTSAP
201 KGVVHCHRGI FVMSIDSLID WTVPKNPVYL WTLPIFHANG WSYPWGIAAV
251 GGTNVCLRKF DAPLIYRLIR DHGVTHMCGA PVVLNMLSAT NEFQPLNRPV
301 NILTAGAPPP AAVLLRAESI GFVISHGYGL TETAGLNVSC AWKPQWNRLP
351 ASDRARLKAR QGVRTVGFTE IDVVDPESGR SVERNGETVG EIVMRGSSIM
401 LGYLKDPVGT EKALKNGWFY TGDVGVIHSD GYLEIKDRSK DIIITGGENV
451 SSVEVETVLY TNPAVNEVAV VARPDVFWGE TPCAFVSLKS GLTQRPTEVE
501 MIEYCRKKMP KYMVPKTVSF VDELPKTSTG KVMKFVLREI AKKMGTTRLS
551 RM*
```

FIGURE 40

SEQ ID NO:38 AtAMPBP6 Amino Acid Sequence

```
  1  MEEMKPCAAN SPPLTPIGFL ERAATVYGDC TSIVYGSNTV YTWRETNLRC
 51  LRVASSLSSI GIGRSDVVSV LSPNTPAMYE LQFAVPMSGA ILNNINTRLD
101  ARTVSVLLRH CESKLLFVDV FSVDLAVEAV SMMTTDPPIL VVIADKEEEG
151  GVADVADLSK FSYTYDDLIE RGDPGFKWIR PESEWDPVVL NYTSGTTSAP
201  KGVVHCHRGI FVMSVDSLID WAVPKNPVYL WTLPIFHSNG WTNPWGIAAV
251  GGTNVCLRKF DAPLIYRLIR DHGVTHMCGA PVVLNMLSAT QESQPLNHPV
301  NILTAGSPPP ATVLLRAESI GFVISHGYGL TETAGVIVSC AWKPKWNHLP
351  ASDRARLKAR QGVRTVGFTE IDVVDPESGL SVERNGETVG EIVMRGSSVM
401  LGYLKDPVGT EKALKNGWFY TGDVGVIHSD GYLEIKDRSK DIIITGGENV
451  SSVEVETVLY TIPAVNEVAV VARPDEFWGE TPCAFVSLKN GFSGKPTEEE
501  LMEYCRKKMP KYMVPKTVSF MDELPKSSTG KVTKFVLRDI AKKMGDKTIS
551  *
```

FIGURE 41

SEQ ID NO:39  AtAMPBP7 Amino Acid Sequence

```
  1  MAATKWRDID  DLPKIPANYT  ALTPLWFLDR  AAVVHPTRKS  VIHGSREYTW
 51  RQTYDRCRRL  ASALADRSIG  PGSTVAIIAP  NIPAMYEAHF  GVPMCGAVLN
101  CVNIRLNAPT  VAFLLSHSQS  SVIMVDQEFF  TLAEDSLRLM  EEKAGSSFKR
151  PLLIVIGDHT  CAPESLNRAL  SKGAIEYEDF  LATGDPNYPW  QPPADEWQSI
201  ALGYTSGTTA  SPKGVVLHHR  GAYIMALSNP  LIWGMQDGAV  YLWTLPMFHC
251  NGWCFPWSLA  VLSGTSICLR  QVTAKEVYSM  IAKYKVTHFC  AAPVVLNAIV
301  NAPKEDTILP  LPHTVHVMTA  GAAPPPSVLF  SMNQKGFRVA  HTYGLSETYG
351  PSTVCAWKPE  WDSLPPETQA  KLNARQGVRY  TGMEQLDVID  TQTGKPVPAD
401  GKTAGEIVFR  GNMVMKGYLK  NPEANKETFA  GGWFHSGDIA  VKHPDNYIEI
451  KDRSKDVIIS  GGENISSVEV  ENVVYHHPAV  LEASVVARPD  ERWQESPCAF
501  VTLKSDYEKH  DQNKLAQDIM  KFCREKLPAY  WVPKSVVFGP  LPKTATGKIQ
551  KHILRTKAKE  MGPVPRSRL*
```

FIGURE 42

SEQ ID NO:40  AtAMPBP8 Amino Acid Sequence

```
  1  MEEPSAANSL PLTLLGFLER AATVYGDCTS IVYGNSTVYT WRETNHRCLC
 51  VASALSSIGI GRSDVVSVLS ANTPEMYELQ FSVPMSGAIL NNINTRLDAR
101  TVSVLLRHCE SKLLFVDFFY SDLAVEAITM LLNPPILVLI ANEEEEEGGA
151  EVTERSKFCY LYSDLITRGN PDFKWIRPGS EWDPIVVNYT SGTTSSPKGV
201  VHCRGIFVM  TLDSLTDWAV PKTPVYLWTL PIFHANGWTY PWGIAAVGGT
251  NVCVRKLHAP SIYHLIRDHG VTHMYGAPIV LQILSASQES DQPLKSPVNF
301  LTAGSSPPAT VLLRAESLGF IVSHGYGLTE TAGVIVSCAW KPNWNRLPAS
351  DQAQLKSRQG VRTVGFSEID VVDPESGRSV ERDGETVGEI VLRGSSIMLG
401  YLKNPIGTQN SFKNGWFFTG DLGVIHGDGY LEIKDRSKDV IISGGENVSS
451  VEVEAVLYTN PAVNEAAVVA RPDEFWGETP CAFVSLKPGL TRKPTDKEII
501  EYCKYKMPRY MAPKTVSFLE ELPKTSTGKI IKSLLKEIAK NM*
```

FIGURE 43

SEQ ID NO:41  AtAMPBP9 Amino Acid Sequence

```
  1  MELLLPHPSN STPLTVLGFL DRAASVYGDC PSILHTTNTV HTWSETHNRC
 51  LRIASALTSS SLGINRGQVV SVVGPNVPSV YELQFAVPMS GAILNNINPR
101  LDAHALSVLL RHSESKLVFV DPNSISVVLE AVSFMRQNEK PHLVLLDDDQ
151  EDGSLSPSAA SDFLDTYQGV MERGDSRFKW IRPQTEWQPM ILNYTSGTTS
201  SPKGVVLSHR AIFMLTVSSL LDWHFPNRPV YLWTLPMFHA NGWGYTWGTA
251  AVGATNVCTR RVDAPTIYDL IDKHHVTHMC AAPMVLNMLT NYPSRKPLKN
301  PVQVMTAGAP PPAAIISRAE TLGFNVGHGY GLTETGGPVV SCAWKAEWDH
351  LDPLERARLK SRQGVRTIGF AEVDVRDPRT GKSVEHDGVS VGEIVLKGGS
401  VMLGYYKDPE GTAACMREDG WFYSGDVGVI HEDGYLEVKD RSKDVIICGG
451  ENISSAEVET VLYTNPVVKE AAVVAKPDKM WGETPCAFVS LKYDSNGNGL
501  VTEREIREFC KTRLPKYMVP RKVIFQEELP KTSTGKIQKF LLRQMAKSLP
551  *
```

FIGURE 44

SEQ ID NO:42  AtAMPBP10 Amino Acid Sequence

```
  1  MELLLPHPSN STPLTVLGFL DRAASVYGDC PSILHTANTV HTWSETHNRC
 51  LRIASALTSS SIGIKQGQVV SVVGPNVPSV YELQFAVPMS GAILNNINPR
101  LDAHALSVLL RHSESRLVFV DHRSISLVLE AVSLFTQHEK PHLVLLDDDQ
151  ENDSSSASDF LDTYEEIMER GNSRFKWIRP QTEWQPMVLN YTSGTTSSPK
201  GVVLSHRAIF MLTVSSLLDW SVPNRPVYLW TLPMFHANGW GYTWGTAAVG
251  ATNICTRRVD APTIYNLIDK HNVTHMCAAP MVLNMLINYP LSTPLKNPVM
301  TSGAPPPATI ISRAESLGFN VSHSYGLTET SGPVVSCAWK PKWDHLDPLE
351  RARLKSRQGV RTLGFTEVDV RDRKTGKSVK HDGVSVGEIV FRGSSVMLGY
401  YKDPQGTAAC MREDGWFYSG DIGVIHKDGY LEIKDRSKDV IICGGENISS
451  AEIETVLYTN PVVKEAAVVA KPDKMWGETP CAFVSLKCDN NGDGSVPVTE
501  REIREFCKTK LPKYMVPRKV IFQEELPKTS TGKIQKFLLR QMAKTLS*
```

FIGURE 45

```
AtACS1A : VPLYDTLG : 8
AtACS1B : VPLYDTLG : 8
AtACS1C : VPLYDTLG : 8
AtACS2  : VPLYDSLG : 8
AtACS3A : VPLYDTLG : 8
AtACS3B : VPLYDTLG : 8
AtACS5  : VPLYDTLG : 8
AtACS6A : VTIYASLG : 8
AtACS6B : VTIYSSLG : 8
```

Motif 1:

V-P/T-L/I-Y-D/A/S-T/S-L-G (SEQ ID NO:43)

FIGURE 46

```
                        *
AtACS1A   : IMYTSGTTGDPKGV : 14
AtACS1B   : IMYTSGTTGDPKGV : 14
AtACS1C   : IMYTSGTTGDPKGV : 14
AtACS2    : IMKTSGTTGEPKGV : 14
AtACS3A   : ICYTSGTTGTPKGV : 14
AtACS3B   : ICYTSGTTGTPKGV : 14
AtACS4A   : IMYTSGTTGNPKGV : 14
AtACS4B   : IMYTSGTTGNPKGV : 14
AtACS5    : IMYTSGTSGDPKGV : 14
AtACS6A   : IMFTSGSTGLPKGV : 14
AtACS6B   : IMYTSGSTGLPKGV : 14
AtAMPBP1  : VNYTSGTTSSPKGV : 14
AtAMPBP2  : INYTSGTTSRPKGV : 14
AtAMPBP3  : FLHTSGTTSRPKGV : 14
AtAMPBP4  : LNYTSGTTSSPKGV : 14
AtAMPBP5  : LNYTSGTTSAPKGV : 14
AtAMPBP6  : LNYTSGTTSAPKGV : 14
AtAMPBP7  : LGYTSGTTASPKGV : 14
AtAMPBP8  : VNYTSGTTSSPKGV : 14
AtAMPBP9  : LNYTSGTTSSPKGV : 14
AtAMPBP10 : LNYTSGTTSSPKGV : 14
```

Motif 2:

I-M/C-Y/F/K-T-S-G-T/S-T/S-G-$X_1$-P-K-G-V $X_1$ = D, L, T, N, or E (SEQ ID NO:44)

FIGURE 47

```
AtACS1A   : SYLPLAH : 7
AtACS1B   : SYLPLAH : 7
AtACS1C   : SYLPLAH : 7
AtACS2    : SYLPLAH : 7
AtACS3A   : SYLPLAH : 7
AtACS3B   : SYLPLAH : 7
AtACS4A   : SMLPSWH : 7
AtACS4B   : SMLPSWH : 7
AtACS5    : SFLPLAH : 7
AtACS6A   : AYLPLAH : 7
AtACS6B   : AYLPLAH : 7

AtAMPBP1  : WTNPMFH : 7
AtAMPBP2  : WTVPMFH : 7
AtAMPBP3  : IVLPLFH : 7
AtAMPBP4  : WTLPMFH : 7
AtAMPBP5  : WTLPIFH : 7
AtAMPBP6  : WTLPIFH : 7
AtAMPBP7  : WTLPMFH : 7
AtAMPBP8  : WTLPIFH : 7
AtAMPBP9  : WTLPMFH : 7
AtAMPBP10 : WTLPMFH : 7
```

Motif 3:

S/A-Y/M/F-L-P-L/S-A/W-H (SEQ ID NO:45)

FIGURE 48

| | | | |
|---|---|---|---|
| AtACS1A | : | LKPT | : 4 |
| AtACS1B | : | LKPS | : 4 |
| AtACS1C | : | LKPT | : 4 |
| AtACS2  | : | LKPT | : 4 |
| AtACS3A | : | LRPT | : 4 |
| AtACS3B | : | LRPT | : 4 |
| AtACS4A | : | QKPP | : 4 |
| AtACS4B | : | QKPP | : 4 |
| AtACS5  | : | LKPT | : 4 |
| AtACS6A | : | LKPT | : 4 |
| AtACS6B | : | LKPT | : 4 |

Motif 4:

L/Q-K/R-P-T/P/S (SEQ ID NO:46)

FIGURE 49

```
AtACS1A   : SGAAPL : 6
AtACS1B   : SGAAPL : 6
AtACS1C   : SGAAPL : 6
AtACS2    : SGAAPL : 6
AtACS3A   : SGASPL : 6
AtACS3B   : SGASPL : 6
AtACS4A   : GGSLPI : 6
AtACS4B   : GGSLPM : 6
AtACS5    : SGGAPL : 6
AtACS6A   : VGGAPL : 6
AtACS6B   : SGGAPL : 6

AtAMPBP1  : TGAAPP : 6
AtAMPBP2  : TGGSPP : 6
AtAMPBP3  : ASLAPV : 6
AtAMPBP4  : AGAPPP : 6
AtAMPBP5  : AGAPPP : 6
AtAMPBP6  : AGSPPP : 6
AtAMPBP7  : AGAAPP : 6
AtAMPBP8  : AGSSPP : 6
AtAMPBP9  : AGAPPP : 6
AtAMPBP10 : SGAPPP : 6
```

Motif 5:

S/G/V-G-A/G/S-A/L/S-P-L/I/M (SEQ ID NO:47)

FIGURE 50

| | | | | |
|---|---|---|---|---|
| AtACS1A | : | GYGLTES | : | 7 |
| AtACS1B | : | GYGLTES | : | 7 |
| AtACS1C | : | GYGLTES | : | 7 |
| AtACS2 | : | GYGLTES | : | 7 |
| AtACS3A | : | GYGMTET | : | 7 |
| AtACS3B | : | GYGMTET | : | 7 |
| AtACS4A | : | GYGLTET | : | 7 |
| AtACS4B | : | GYGLTET | : | 7 |
| AtACS5 | : | GYGLTET | : | 7 |
| AtACS6A | : | GYGLTET | : | 7 |
| AtACS6B | : | GYGLTET | : | 7 |
| | | | | |
| AtAMPBP1 | : | SYGLTET | : | 7 |
| AtAMPBP2 | : | LYGLTET | : | 7 |
| AtAMPBP3 | : | AYAMTEA | : | 7 |
| AtAMPBP4 | : | GYGMTET | : | 7 |
| AtAMPBP5 | : | GYGLTET | : | 7 |
| AtAMPBP6 | : | GYGLTET | : | 7 |
| AtAMPBP7 | : | TYGLSET | : | 7 |
| AtAMPBP8 | : | GYGLTET | : | 7 |
| AtAMPBP9 | : | GYGLTET | : | 7 |
| AtAMPBP10 | : | SYGLTET | : | 7 |

Motif 6:

G-Y-G-L/M-T-E-T/S (SEQ ID NO:48)

FIGURE 51

```
AtACS1A   : ARGEICIRG : 9
AtACS1B   : PRGEICIRG : 9
AtACS1C   : PRGEICIRG : 9
AtACS2    : PRGEICLRG : 9
AtACS3A   : PRGEICVRG : 9
AtACS3B   : PRGEICVRG : 9
AtACS4B   : SKGIVKVRG : 9
AtACS5    : PRAEICIRG : 9
AtACS6A   : PRGEIVVGG : 9
AtACS6B   : PRGEIVIGG : 9

AtAMPBP1  : TMGEVVFRG : 9
AtAMPBP2  : TMGEVMFRG : 9
AtAMPBP3  : NKGEVCIRG : 9
AtAMPBP4  : TVGEIVFRG : 9
AtAMPBP5  : TMGEIVMRG : 9
AtAMPBP6  : TMGEIVMRG : 9
AtAMPBP7  : TAGEIVFRG : 9
AtAMPBP8  : TVGEIVLRG : 9
AtAMPBP9  : SVGEIVLKG : 9
AtAMPBP10 : SVGEIVFRG : 9
```

Motif 7:

P/S/A-R/K-G/A-E/I-I/V-C/K/V-I/V/L-R/G-G (SEQ ID NO:49)

FIGURE 52

```
                      *         20
consensus    : DGWLHTGDIGXWXPXGXLKIIDRKK : 25

AtACS1A      : DGWLHTGDVGEWQPDGSMKIIDRKK : 25
AtACS1B      : DGWLHTGDVGEWQPNGSMKIIDRKK : 25
AtACS1C      : DGWLHTGDVGEWQPDGAMKIIDRKK : 25
AtACS2       : DGWFHTGDIGEWQEDGSMKIIDRKK : 25
AtACS3A      : DGWLHTGDIGLWLPGGRLKIIDRKK : 25
AtACS3B      : DGWLHTGDIGLWLPGGRLKIIDRKK : 25
AtACS4A      : SGWFNTGDTGWIAPH---HSKGRSR : 22
AtACS4B      : DGWFNTGDMGWITPQ---HSKGRSR : 22
AtACS5       : DGWFHTGDIGEILPNGVLKIIDRKK : 25
AtACS6A      : TRWFYTGDIGRFHPDGCLEVIDRKK : 25
AtACS6B      : MRWFYTGDIGRFHPDGCLEIIDRKK : 25

AtAMPBP1     : GGWFWSGDLGVKHPDGYIELKDRSK : 25
AtAMPBP2     : GDWFHSGDLAVKYPDGYIEIKDRLK : 25
AtAMPBP3     : FGWFHTGDIGNFDTGGYLHLVGRIK : 25
AtAMPBP4     : DGWFYTGDIGVMHPDGYLEVKDRSK : 25
AtAMPBP5     : NGWFYTGDVGVIHSDGYLEIKDRSK : 25
AtAMPBP6     : NGWFYTGDVGVIHSDGYLEIKDRSK : 25
AtAMPBP7     : GGWFHSGDIAVKHPDNYIEIKDRSK : 25
AtAMPBP8     : NGWFFTGDLGVIHGDYLEIKDRSK  : 25
AtAMPBP9     : DGWFYSGDVGVIHEDGYLEVKDRSK : 25
AtAMPBP10    : DGWFYSGDIGVIHKDGYLEIKDRSK : 25
```

Motif 8:

I-I-D-R-K-K (SEQ ID NO:50)

FIGURE 53

```
AtACS1A    : LLTPTFKKKRPQ : 12
AtACS1B    : LLTPTYKKKRPQ : 12
AtACS1C    : LITPSYKMKRPQ : 12
AtACS2     : LITPTFKIKRPQ : 12
AtACS3A    : LLTPTFKIKRPQ : 12
AtACS3B    : LLTPTFKIKRPQ : 12
AtACS4A    : LMTPTMKIRRDM : 12
AtACS4B    : LMTPTMKIRRDK : 12
AtACS5     : LVTATLKNRRNN : 12
AtACS6A    : LVTAALKIKREQ : 12
AtACS6B    : LVTAALKLRRDV : 12

AtAMPBP1   : PKTSTGKVQKFV : 12
AtAMPBP2   : PKTSTGKVQKYL : 12
AtAMPBP3   : PKTASGKIQRRI : 12
AtAMPBP4   : PKTSTGKIQKFL : 12
AtAMPBP5   : PKTSTGKVMKFV : 12
AtAMPBP6   : PKSSTGKVTKFV : 12
AtAMPBP7   : PKTATGKIQKHI : 12
AtAMPBP8   : PKTSTGKIIKSL : 12
AtAMPBP9   : PKTSTGKIQKFL : 12
AtAMPBP10  : PKTSTGKIQKFL : 12
```

Motif 9:

L-L/V/M/I-T-P/A-T/A/S-F/L/M/Y-K-$X_1$-K/R-R $X_1$ = I, K, M, N, or L (SEQ ID NO:51)

FIGURE 56A
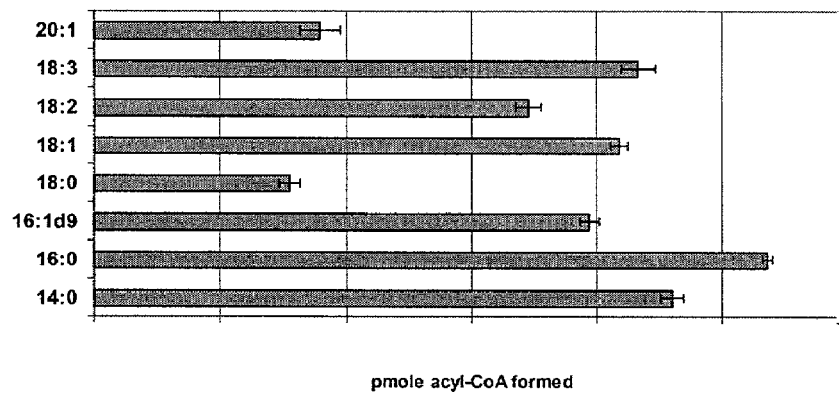
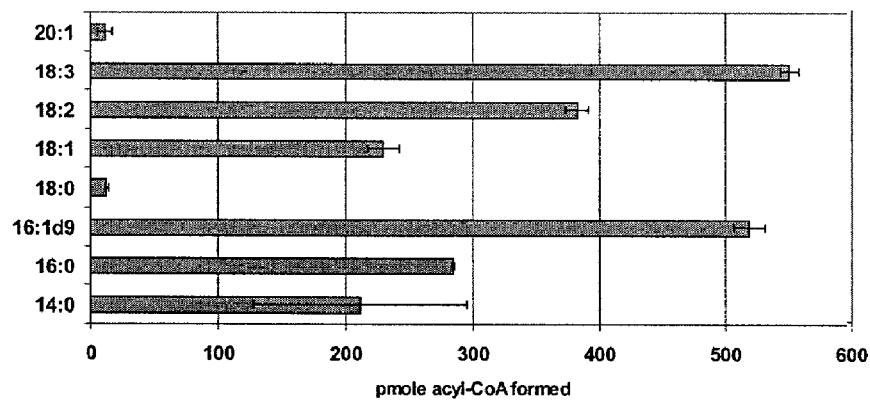
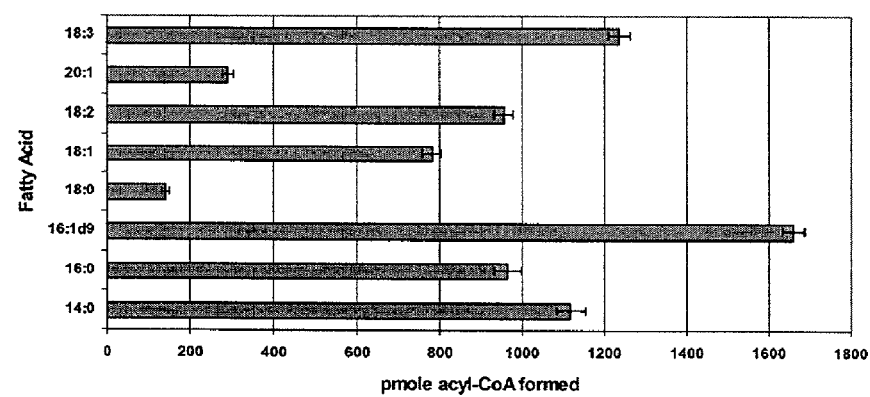

FIGURE 56B
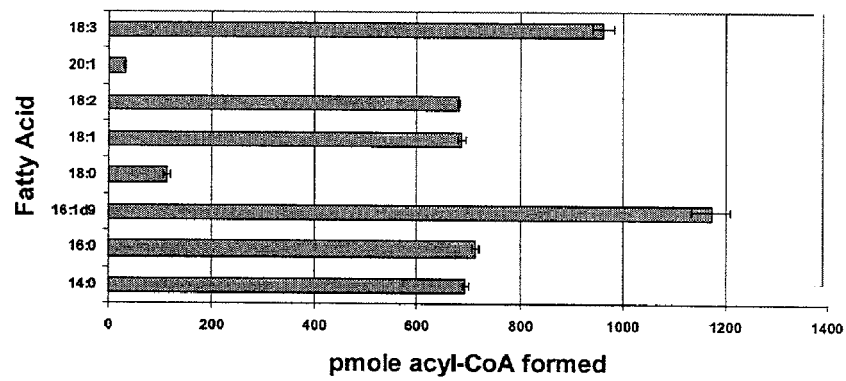
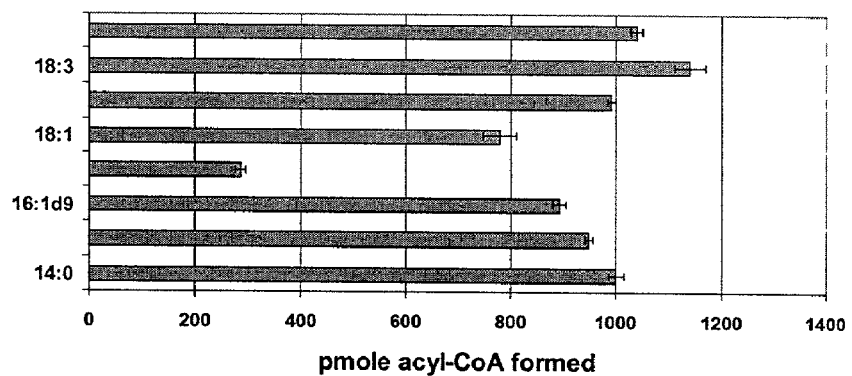
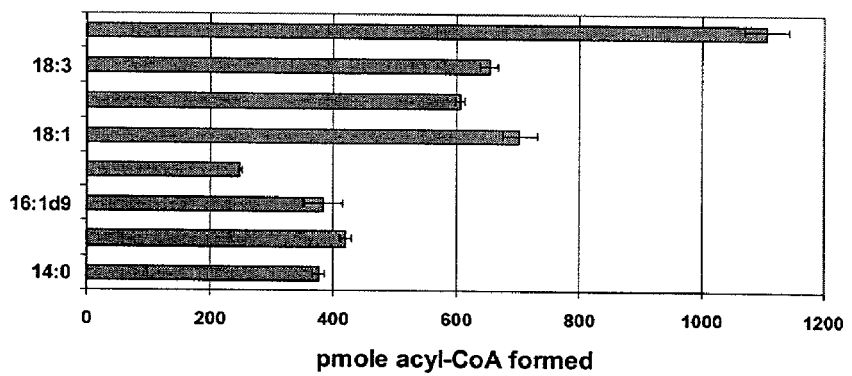

FIGURE 56C
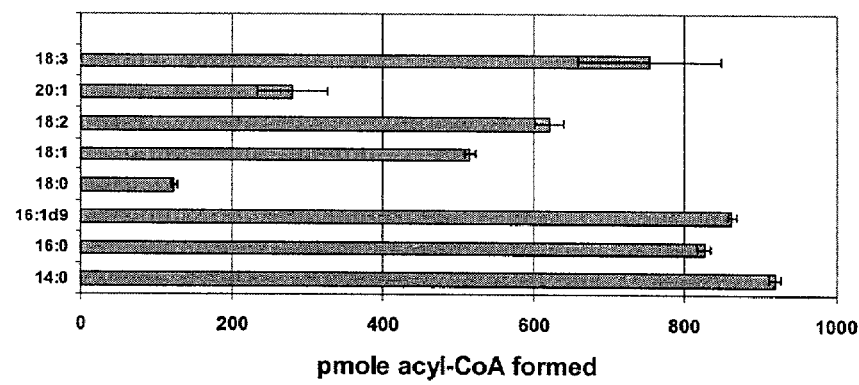
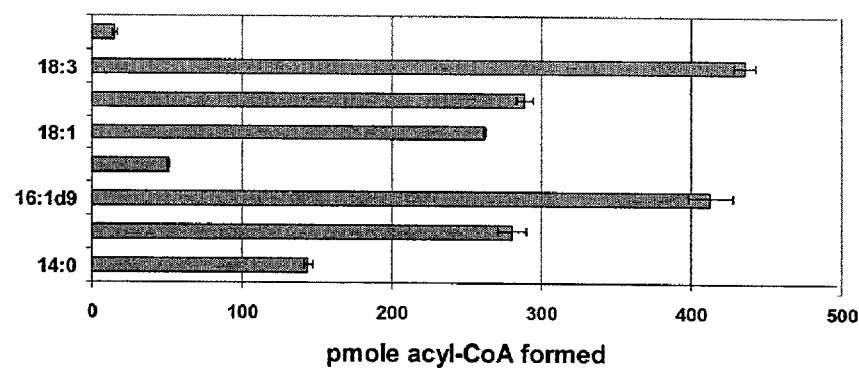
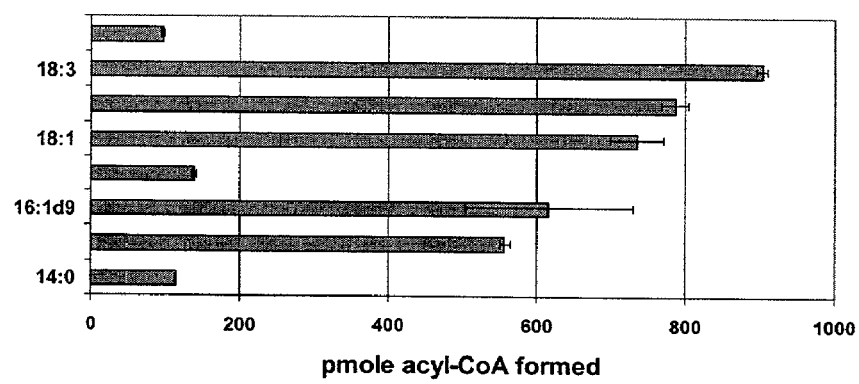

FIGURE 58

SEQ ID NO:121  AtACS1A Modified cDNA Nucleotide Sequence

```
   1  ATGTCGCAGC AGAAGAAATA CATCTTCCAA GTTGAAGAAG GCAAAGAAGG
  51  TAGCGATGGA AGACCATCAG TTGGTCCAGT GTACCGGAGT ATCTTTGCCA
 101  AGGACGGATT TCCCGACCCG ATCGAAGGAA TGGATAGTTG TTGGGATGTT
 151  TTCCGCATGT CTGTTGAGAA GTATCCAAAC AATCCAATGC TGGGACGCCG
 201  CGAGATTGTA GATGGAAAGC CGGGTAAGTA TGTCTGGCAA ACATACCAAG
 251  AAGTCTACGA CATTGTCATG AAACTTGGAA ATTCTCTCAG AAGTGTTGGA
 301  GTTAAGGACG AAGCAAAATG TGGTATCTAT GGTGCAAATT CTCCTGAGTG
 351  GATTATCAGC ATGGAGGCTT GTAATGCACA TGGACTCTAT TGTGTACCGT
 401  TATATGATAC ACTAGGTGCT GATGCTGTGG AATTCATCAT TCCCATTCA
 451  GAGGTTTCAA TTGTCTTTGT GGAAGAGAAG AAGATCTCTG AGTTGTTCAA
 501  GACATGCCCA AACTCGACAG AGTACATGAA ACTGTTGTG AGCtTcgGGG
 551  GTGTCTCACG TGAACAAAAA GAAGAAGCTG AAACTTTTGG GTTGGTTATA
 601  TATGCTTGGG ATGAATTTTT GAAGCTGGGT GAAGGAAAGC AATATGATCT
 651  CCCAATCAAA AAGAAAGCG ACATTTGCAC GATTATGTAT ACGAGTGGAA
 701  CCACTGGTGA CCCAAGGGA GTGATGATAT CTAACGAAAG CATTGTGACT
 751  CTAATCGCTG GAGTGATCCG TCTACTGAAA AGTGCTAACG AGGCTCTGAC
 801  TGTGAAAGAT GTGTATCTTT CTTATCTTCC TCTTGCCCAC ATCTTTGACC
 851  GAGTTATCGA GGAGTGTTTC ATTCAACATG GTGCTGCAAT TGGCTTCTGG
 901  CGAGGGGATG TAAAATTGTT GATCGAAGAC CTTGCTGAGC TTAAACCAAC
 951  TATTTTTTGT GCTGTACCTC GTGTCCTGGA TAGAGTATAC TCAGGTCTTC
1001  AGAAGAAGCT TTCTGATGGT GGATTCTTAA AAAAGTTCAT ATTTGATTCT
1051  GCATTTTCCT ATAAATTTGG TTATATGAAG AAGGGACAGT CTCATGTGGA
1101  GGCCTCTCCA CTTTTTGACA AACTTGTGTT CAGCAAGGTT AAACAAGGAC
1151  TCGGAGGCAA TGTGAGGATT ATTCTATCTG GAGCTGCTCC TCTTGCTAGT
1201  CACGTAGAGT CATTTCTAAG AGTGGTGGCA TGCTGTCATG TTCTCCAAGG
1251  ATACgGTCTT ACTGAAAGCT GTGCTGGAAC TTTTGTCTCG CTGCCAGATG
1301  AACTAGGTAT GCTCGGCACA GTTGGTCCAC CAGTGCCAAA CGTTGATATA
1351  CGCCTTGAAT CCGTCCCCGA GATGGAATAT GATGCTCTTG CGAGTACTGC
1401  ACGTGGTGAA ATCTGCATTC GGGGAAAGAC CCTTTTCTCT GGTTACTACA
1451  AACGTGAAGA TCTCACGAAA GAGGTTCTCA TTGATGGATG GCTGCACACA
1501  GGTGATGTTG GTGAGTGGCA ACCAGATGGA AGCATGAAGA TAATTGACAG
1551  GAAGAAGAAT ATCTTTAAAC TCTCACAAGG AGAGTATGTT GCGGTGGAGA
1601  ACATAGAAAA CATATACGGT GAAGTACAAG CTGTTGATTC CGTGTGGGTG
1651  TACGGTAACA GCTTTGAGTC CTTCCTAATA GCTATCGCCA ACCCAAACCA
1701  GCATATCCTT GAACGCTGGG CTGCAGAAAA CGGTGTGAGT GGTGACTATG
1751  ACGCTCTCTG TCAAAATGAA AAGGCAAAGG AATTCATTCT CGGAGAACTT
1801  GTTAAAATGG CCAAAGAGAA AAAGATGAAA GGGTTCGAGA TCATCAAGGC
1851  GATTCATCTT GACCCAGTGC CATTTGACAT GGAACGAGAT CTTCTTACGC
1901  CGACCTTCAA AAAGAAAGG CCTCAGTTGC TGAAATACTA CCAGAGTGTG
1951  ATCGACGAAA TGTACAAGAC CATAAATGCA AAATTTGCTT CCAGAGGGTA
2001  G
```

FIGURE 59

SEQ ID NO:122   AtACS1B Modified cDNA Nucleotide Sequence

```
   1  ATGACGTCGC AGAAAAGATT CATCTTTGAG GTGGAAGCCG CTAAGGAAGC
  51  CACAGATGGA AATCCCTCGG TTGGTCCTGT CTATCGTAGT ACTTTTGCTC
 101  AgAACGGATT CCCGAACCCG ATCGATGGTA TCCAAAGCTG CTGGGATATT
 151  TTCCGCACGG CTGTTGAGAA GTATCCAAAC AATCGAATGC TTGGTCGCCG
 201  TGAGATTTCG AACGGGAAGG CAGGAAAGTA CGTGTGGAAA ACATACAAAG
 251  AAGTATACGA CATTGTCATA AAACTTGGAA ATTCTCTACG TAGTTGCGGG
 301  ATTAAGGAGG GAGAAAAATG TGGTATATAT GGTATAAATT GTTGTGAGTG
 351  GATCATTAGC ATGGAGGCAT GTAATGCACA TGGCCTTTAT TGTGTCCCTT
 401  TATACGATAC GTTAGGCGCT GGTGCAGTGG AATTCATCAT TTCTCATGCA
 451  GAGGTTTCAA TTGCTTTCGT GGAGGAGAAG AAGATCCCTG AGCTTTTTAA
 501  GACTTGTCCA AACTCAACAA ATATATGAA GACTGTTGTG AGCTTTGGCG
 551  GTGTCAAACC GGAACAAAAA GAAGAAGCTG AAAAATTGGG ATTGGTAATA
 601  CATTCGTGGG ATGAGTTTTT GAAGCTGGGT GAGGGTAAGC AATATGAGCT
 651  TCCCATTAAA AAGCCAAGCG ACATATGCAC GATTATGTAT ACTAGCGGAA
 701  CAACTGGTGA CCCGAAGGGA GTTATGATTT CAAATGAAAG CATTGTTACT
 751  ATAACTACTG GAGTGATGCA TTTCCTAGGG AATGTGAATG CAAGCCTATC
 801  TGAGAAGGAT GTGTATATTT CTTATCTTCC TCTCGCGCAC GTCTTTGATC
 851  GGGCAATCGA GGAATGTATT ATTCAAGTAG GTGGTTCAAT TGGTTTCTGG
 901  CGCGGGGATG TCAAATTGTT GATTGAAGAC CTTGGTGAGC TAAAACCAAG
 951  TATCTTTTGC GCCGTTCCTC GTGTCCTAGA TCGAGTATAC ACAGGACTAC
1001  AGCAGAAACT ATCTGGTGGT GGTTTCTTCA AAAGAAGGT GTTTGATGTT
1051  GCTTTTTCCT ATAAATTTGG AAATATGAAG AAAGGACAGT CTCATGTGGC
1101  AGCTTCTCCA TTTTGTGACA AACTTGTATT CAACAAGGTT AAACAAGGAC
1151  TTGGAGGCAA TGTGAGGATT ATTCTGTCTG GAGCGGCTCC TCTCGCTAGT
1201  CACATAGAAT CTTTTCTAAG AGTTGTTGCA TGTTGTAATG TTCTACAAGG
1251  ATATGGTCTA ACTGAGAGTT GTGCTGGAAC TTTTGCAACG TTCCCAGACG
1301  AACTAGACAT GCTTGGGACT GTTGGTCCAC CCGTGCCAAA CGTCGATATA
1351  CGCCTTGAAT CTGTCCCGGA AATGAATTAT GATGCTCTTG AAGTACTCC
1401  GCGAGGCGAA ATATGCATAC GAGGAAAAAC TTTATTTTCA GGGTACTACA
1451  AACGTGAAGA CCTCACAAAA GAGGTTTTTA TCGACGgATG GTTGCACACA
1501  GGTGATGTTG GTGAGTGGCA aCCAAATGGA AGCATGAAGA TAATTGACCG
1551  GAAAAGAAC ATCTTCAAAC TCGCGCAAGg AGAGTATGTC GCTGTTGAGA
1601  ATTTAGAAAA TGTCTACAGT CAAGTAGAAG TTATTGAATC GATATGGGTA
1651  TATGGAAACA GCTTTGAGTC CTTCCTTGTC GCAATCGCTA ACCCGGCCCA
1701  ACAAACTCTT GAACGATGGG CTGTGGAGAA TGGAGTGAAT GGAGACTTCA
1751  ACTCCATCTG CCAAAACGCA AGGCAAAAG CATTCATACT TGGAGAACTC
1801  GTTAAAACAG CCAAAGAGAA CAAGTTGAAG GGTTTTGAGA TCATAAAAGA
1851  TGTTCATCTG GAACCAGTGG CGTTCGACAT GGAACGAGAC CTTCTTACTC
1901  CAACCTACAA AAAGAAGAGG CCTCAATTGC TCAAATACTA TCAGAATGTG
1951  ATCCATGAAA TGTACAAGAC AACAAAGGAA ACTCTAGCTT CCGGACAGTA
2001  A
```

FIGURE 60

SEQ ID NO:123    AtACS2 Modified cDNA Nucleotide Sequence

```
   1  ATGTCTTTAG CCGCGGATAA TGTGTTGTTG GTGGAAGAAG GAAGGCCAGC
  51  CACAGCGGAA CATCCATCGG CCGGACCGGT TTATCGATGT AAATACGCTA
 101  AAGATGGCCT CCTCGATCTC CCTACCGATA TTGATTCTCC TTGGCAGTTC
 151  TTTAGTGAGG CTGTGAAGAA ATATCCGAAT GAGCAAATGT GGGCCAACG
 201  CGTAACGACT GATTCTAAGG TCGGTCCATA CACGTGGATC ACATATAAGG
 251  AAGCGCACGA CGCTGCAATT CGGATTGGAT CAGCAATCAG AAGCCGAGGC
 301  GTTGATCCGG ACACTGTTG TGGTATTTAC GGAGCTAATT GTCCAGAATG
 351  GATTATTGCA ATGGAGGCCT GCATGAGCCA AGGGATCACC TACGTGCCTC
 401  TATAtGATTC TTTAGGCGTA AACGCAGTTG AATTCATCAT CAACCACGCC
 451  GAGGTTTCGC TAGTATTTGT TCAAGAGAAG ACAGTTTCAT CtATCTTATC
 501  GTGCCAAAAG GGATGTTCTT CGAATTTGAA GACTATTGTG AGCTTCGGGG
 551  AAGTCTCGAG TACACAAAAG GAAGAAGCTA AGAACCAATG TGTTTCTTTA
 601  TTTTCATGGA ATGAGTTCTC ACTAATGGGA AACTTAGATG AGGCAAATCT
 651  ACCTaGaAAG CGAAAGACAG ACATCTGCAC AATAATGTAC ACAAGCGGGA
 701  CGACTGGAGA ACCCAAAGGT GTAATCTTAA ACAACGCAGC AATTTCGGTC
 751  CAGGTTTTAT CCATAGACAA AATGCTTGAA GTCACTGATC GATCGTGTGA
 801  CACGAGCGAT GTGTTCTTCT CGTACTTGCC ATTAGCACAT GCTATGATC
 851  AAGTCATGGA GATTTACTTT TTATCTAGAG CTCCTCTGT TGGATACTGG
 901  CGTGGCGACA TTCGGTACCT GATGGATGAT GTTCAAGCTC TTAAACCTAC
 951  TGTGTTTTGC GGTGTTCCAC GAGTTTACGA CAAACTATAT GCCGGTATAA
1001  TGCAAAAAAT ATCAGCTAGT GGCTTGATAC GCAAGAAACT GTTTGATTTT
1051  GCTTATAACT ACAAATTGGG AAATATGAGA AAAGGATTCT CTCAAGAAGA
1101  AGCTTCTCCT CGTCTAGACA GACTTATGTT CGATAAGATA AAGAAGCAT
1151  TAGGAGGAAG AGCTCATATG TTGTTATCAG GAGCAGCGCC TCTACCTCGT
1201  CATGTAGAGG AGTTCTTGAG AATCATTCCT GCCTCTAATC TCTCTCAAGG
1251  TTATGGATTG ACTGAGAGTT GTGGGGGAAG CTTCACGACC TTAGCCGGAG
1301  TATTTCTAT GGTGGGGACA GTGGGTGTGC CAATGCCCAC GGTGGAGGCA
1351  AGGCTAGTGT CCGTACCAGA GATGGGTTAC GACGCCTTTT CCGCTGACGT
1401  GCCGAGAGGA GAGATTTGTC TTAGAGGAAA TTCAATGTTT TCTGGTTACC
1451  ATAAAAGACA AGATCTAACT GATCAAGTCC TAATCGATGG ATGGTTCCAC
1501  ACAGGAGATA TTGGAGAATG GCAAGAAGAT GGATCAATGA AGATCATCGA
1551  TAGGAAGAAG AACATCTTCA AGTTGTCTCA AGGTGAATAT GTTGCTGTTG
1601  AAAACCTCGA AAACACTTAC TCAAGATGTC CCCTCATTGC TCAGATATGG
1651  GTCTATGGCA ACAGCTTCGA GTCATTTTTG GTAGGTGTGG TTGTACCTGA
1701  TAGAAAGCT ATTGAAGATT GGGCTAAACT CAATTACCAA TCTCCCAATG
1751  ATTTCGAATC TCTATGTCAA AATCTCAAAG CTCAAAAATA CTTCTTGGAT
1801  GAGCTTAACT CTACCGCAAA GCAATATCAA CTTAAAGGAT TTGAAATGTT
1851  AAAAGCTATT CATTTAGAAC CAAACCCTTT TGATATTGAA AGAGATCTTA
1901  TTACTCCAAC TTTCAAGCTG AAAAGGCCAC AGCTCCTCCA ACATTACAAG
1951  GGCATAGTTG ATCAACTTTA TTCAGAAGCA AAGAGGTCCA TGGCATAG
```

FIGURE 61

SEQ ID NO:124  AtACS3B Modified cDNA Nucleotide Sequence

```
   1  ATGGAATTTG CTTCGCCGGA ACAACGTCGT CTCGAAACCA TTCGATCTCA
  51  CATCGATACT TCTCCGACCA ACGATCAATC ATCATCTCTA TTCCTCAACG
 101  CCACCGCTTC TTCTGCTTCA CCTTTCTTTA AAGAGGATAG CTACAGTGTT
 151  GTGCTTCCAG AAAAGCTTGA TACTGGAAAA TGGAATGTCT ACAGATCTAA
 201  AAGATCGCCT ACGAAACTCG TTAGTAGGTT CCCGGATCAT CCTGAAATCG
 251  GGACTTTACA TGACAATTTT GTACATGCTG TTGAAACATA TGCTGAAAAC
 301  AAGTATCTTG GTACACGAGT TCGGTCCGAT GGAACCATTG GAGAGTATTC
 351  ATGGATGACA TATGGAGAAG CAGCGTCTGA GCGACAAGCC ATTGGTTCAG
 401  GACTCTTGTT TCATGGAGTT AACCAAGGAG cTTGCGTTGG ACTCTATTTT
 451  ATTAACAGAC CAGAGTGGTT GGTTGTGGAT CATGCTTGTG CAGCATATTC
 501  ATTTGTCTCT GTTCCTTTAT ATGATACACT TGGTCCAGAC GCTGTTAAGT
 551  TTGTGGTGAA TCATGCTAAT CTGCAAGCTA TATTTGTGT ACCACAAACC
 601  TTGAATATTT TGCTAAGCTT CCTAGCGGAA ATCCCATCCA TTCGTCTCAT
 651  TGTGGTGGTG GGAGGGGCTG ATGAGCATTT GCCATCACTT CCTCGAGGAA
 701  CTGGAGTCAC AATTGTATCA TACCAAAAGC TATTGAGTCA GGGTCGAAGT
 751  AGCTTACATC CATTTTCGCC TCCAAAGCCA GAAGACATTG CAACCATATG
 801  CTACACAAGT GGAACCACAG GAACACCAAA GGGTGTTGTG TTGACTCATG
 851  GAAACTTGAT CGCGAATGTC GCTGGTTCCA GTGTGGAAGC AGAATTCTTT
 901  CCTTCAGATG TkTACATATC ATATCTTCCT TTGGCGCACA TATATGAACG
 951  TGCAAATCAG ATTATGGGGG TGTATGGTGG TGTTGCTGTC GGTTTCTATC
1001  AGGGGGATGT CTTCAAGCTG ATGGATGATT TTGCTGTGTT AAGACCAACA
1051  ATATTCTGTA GTGTCCCTCG CTTATATAAT CGAATATATG ATGGCATTAC
1101  AAGTGCCGTA AAATCATCTG GGGTTGTGAA AAAAGGCTT TTCGAAATTG
1151  CCTATAACTC AAAGAAGCAA GCGATCATTA ATGGGCGGAC TCCTTCTGCA
1201  TTTTGGACA AGCTGGTGTT CAACAAAATA AAGAAAAGC TTGGTGGACG
1251  GGTTCGGTTT ATGGGGTCTG GTGCTTCTCC TTTGTCACCT GATGTCATGG
1301  ATTTCTTGAG AATATGCTTT GGATGTTCGG TGCGTGAAGG GTATGGTATG
1351  ACCGAGACTT CTTGTGTCAT AAGTGCTATG GATGATGGTG ACAATTTATC
1401  TGGCCATGTC GGTTCCCCTA ATCCAGCTTG CGAGGTAAAA CTTGTGGATG
1451  TTCCCGAAAT GAATTACACA TCAGACGATC AACCATACCC ACGTGGTGAA
1501  ATCTGTGTAA GAGGACCAAT CATCTTCAAA GGCTACTACA AGATGAAGA
1551  ACAAACGAGA GAAATTCTTG ATGGAGATGG CTGGCTACAC ACAGGAGATA
1601  TCGGGTTGTG GTTACCTGGT GGTCGGCTCA AGATCATAGA CAGGAAGAAG
1651  AACATATTTA AGTTGGCGCA AGGAGAATAT ATAGCACCAG AGAAGATCGA
1701  AAATGTTTAT ACCAAATGTA GATTCGTTTC GCAGTGTTTC ATTCACGGTG
1751  ATAGCTTCAA TTCCTCTCTA GTAGCTATAG TTTCAGTCGA CCCCGAAGTT
1801  ATGAAAGATT GGGCTGCATC AGAAGGCATC AAGTATGAGC ATCTAGGACA
1851  GCTCTGTAAC GATCCAAGAG TGCGAAAGAC TGTTCTTGCT GAGATGGATG
1901  ACCTTGGAAG AGAAGCTCAG TTGAGAGGGT TTGAGTTTGC AAAGGCTGTG
1951  ACTTGGTGC CAGAACCATT gACCTTGGAG AATGGACTTC TCACACCAAC
2001  ATTCAAGATA AAGAGACCTC AAGCAAAGC CTACTTTGCA GAAGCAATTA
2051  GCAAAATGTA TGCGGAAATC GCAGCCTCGA ACCCCATTCC TTCTAAACTG
2101  TGA
```

Figure 62

SEQ ID NO:125   AtACS4A Modified cDNA Nucleotide Sequence

```
   1 ATGGCTTCGA CTTCTTCTTT GGGACCTTCT ACACTACTCT CTTACGGTTC
  51 TCCTTCTCGT CAGTTTCCTG ATTTTGGGTT CAGATTGATT TCGGGTCACG
 101 AAAGTGTTCG AATTCCATCA TTCCGGCGAT TTCGGGTTCA CTGCGAGTCA
 151 AAGGAAAAAG AAGTGAAGCC GTCTTCTCCA TTTCTTGAAA GCTCCTCGTT
 201 TTCGGGAGAT GCCGCTTTGC GCTCTAGTGA ATGGAAGGCT GTTCCTGATA
 251 TTTGGAGATC ATCTGCAGAA AAGTATGGTG ATAGAGTTGC ATTGGTGGAT
 301 CCTTATCATG ATCCTCCTTT GAAACTGACG TACAAGCAGT TGGAACAAGA
 351 AATTTTGGAC TTTGCTGAGG CTTACGAGT TCTTGGAGTG AAAGCAGATG
 401 AGAAGATTGC ACTTTTTGCT GATAACTCCT GCCGATGGCT TGTTTCAGAT
 451 CAAGGTATAA TGGCCACAGG GGCAGTCAAT GTTGTCAGAG GATCTAGGTC
 501 CTCTGTTGAA GAGTTACTGC AGATATACCG TCATTCTGAA AGCGTAGCCA
 551 TTGTTGTGGA TAATCCTGAG TTTTTCAACC GCATTGCTGA GTCATTTACG
 601 TCAAAGGCAT CTCTGAGATT TTGATACTT CTCTGGGGTG AGAAATCATC
 651 ACTGGTCACA CAGGGGATGC AGATTCCAGT TTACAGTTAT GCAGAAATTA
 701 TAAACCAAGG ACAGGAGAGT CGTGCAAAAT TATCAGCATC TAATGATACC
 751 AGGAGCTATA GAAATCAATT CATCGATTCA GATGATACAG CTGCAATTAT
 801 GTATACCAGT GGTACCACGG GAAATCCAAA AGGCGTTATG CTTACACATC
 851 GGAATCTCTT ACACCAGATA AACATTTAT CCAAATATGT ACCTGCTCTA
 901 GCTGGGGATA AATTTCTAAG CATGCTACCA TCATGGCATG CCTATGAACG
 951 TGCTAGTGAA TACTTCATAT TCACTTGTGG AGTTGAGCAA ATGTATACAT
1001 CTATAAGATA CTTAAAGGAT GATCTAAAGC GGTACCAACC GAACTATATT
1051 GTGTCCGTTC CTCTAGTATA TGAGACACTT TACAGTGGGA TTCAAAAGCA
1101 AATTTCTGCA AGTTCTGCTG GCCGTAAATT TCTAGCACTT ACATTGATCA
1151 AAGTCAGTAT GGCATATATG GAGATGAAAA GGATATATGA GGGTATGTGT
1201 CTGACAAAAG AGCAAAAGCC TCCAATGTAT ATTGTTGCTT TTGTGGATTG
1251 GTTGTGGGCG AGAGTAATTG CTGCCTTGTT GTGGCCATTA CATATGTTGG
1301 CCAAAAAGCT TATCTACAAG AAAATTCATT CGTCTATTGG GATATCGAAG
1351 GCTGGTATTA GCGGAGGTGG TAGTTTACCC ATTCATGTTG ACAAGTTTTT
1401 TGAGGCCATC GGTGTGATTC TACAAAATGG TTATGGTTTG ACAGAGACCT
1451 CACCTGTTGT CTGTGCACGG ACACTTAGCT GCAATGTTCT TGGCTCAGCT
1501 GGGCATCCAA TGCATGGTAC AGAATTCAAA ATTGTAGATC CTGAGACTAA
1551 TAATGTACTC CCTCCTGGTT CAAAGGGCAT TATCAAAGTC AGAGGTCCAC
1601 AGGTTATGAA GGGTTATTAT AAGAATCCAT CGACTACAAA GCAAGTTCTA
1651 AATGAGAGTG GATGGTTCAA TACAGGAGAC ACCGGTTGGA TTGCTCCTCA
1701 TCACTCAAAA GGGCGGAGTC GCCACTGTGC AGGTGTCATT GTTCTTGAAG
1751 GCCGTGCAAA AGACACAATT GTACTTCCA CAGGTGAAAA TGTGGAACCG
1801 TTGGAGATTG AAGAAGCCGC CATGAGAAGC AGGGTGATTG AACAAATTGT
1851 TGTTATTGGA CAGGACCGAC GTCGCCTTGG AGCTATCATT ATCCCAAACA
1901 AAGAGGAAGC ACAAAGAGTA GATCCTGAAA CATCCAAAGA AACACTAAAG
1951 AGCTTGGTCT ACCAAGAACT GAGAAAATGG ACATCAGAAT GTTCGTTTCA
2001 AGTCGGACCA GTCTTGATCG TCGACGACCC TTTCACGATA GACAACGGGT
2051 TAATGACACC AACTATGAAG ATTAGACGGG ACATGGTCGT GGCTAAATAC
2101 AAAGAGGAGA TTGATCAACT CTACAGTTAA
```

FIGURE 63

SEQ ID NO:126 AtACS6A Hypothetically Modified
cDNA Nucleotide Sequence

```
   1  ATGGAAGATT CTGGAGTGAA TCCAATGGAT TCACCATCTA AAGGCAGTGA
  51  CTTTGGAGTC TATGGAATCA TAGGAGGTGG AATCGTGGCT TTACTTGTGC
 101  CTGTGTTACT CTCTGTGGTG TTGAATGGAA CCAAAAAGGG GAAAAAGAGA
 151  GGTGTTCCCA TCAAAGTAGG TGGCGAGGAA GGTTACACAA TGCGTCATGC
 201  TCGAGCTCCT GAATTGGTTG ATGTACCTTG GAAGGAGCT GCTACTATGC
 251  CTGCTTTGTT TGAGCAGTCT TGTAAGAAGT ATTCGAAAGA TCGGTTACTA
 301  GGAACTAGAG AGTTTATAGA TAAGGAATTT ATTACTGCTA GTGATGGGAG
 351  GAAGTTTGAG AAGCTTCATT TAGGAGAGTA TAAATGGCAA AGTTATGGAG
 401  AGGTTTTTGA ACGTGTTTGT AACTTTGCGT CGGGGTTAGT TAATGTAGGA
 451  CATAATGTTG ATGATCGTGT TGCTATCTTT TCGGATACTC GTGCTGAGTG
 501  GTTTATCGCG TTTCAGGGAT GTTTCAGGCA GAGCATAACC GTTGTTACTA
 551  TTTATGCTTC TTTAGGAGAA GAGGCTTTGA TTTACTCACT CAATGAGACT
 601  CGAGTGTCAA CCTTAATATG TGACTCAAAA CAACTTAAGA AGTTGTCTGC
 651  GATACAATCA AGCTTGAAAA CTGTGAAGAA CATTATTTAC ATTGAAGAAG
 701  ATGGAGTAGA TGTTGCTTCT AGTGATGTCA ATAGTATGGG TGATATAACT
 751  GTTTCGTCGA TCTCTGAAGT TGAGAAACTT GGGCAGAAGA ACGCTGTTCA
 801  ACCGATCTTA CCTTCGAAGA ATGGAGTTGC TGTTATAATG TTTACCAGTG
 851  GTAGTACTGG TCTACCAAAG GGAGTTATGA TTACCCACGG AAATCTTGTC
 901  GCAACTGCTG CAGGAGTTAT GAAGGTGGTT CCAAAGTTGG ATAAAAATGA
 951  TACATATATT GCGTACTTAC CTTTGGCTCA TGTGTTTGAG CTGGAAGCTG
1001  AGATTGTGGT CTTTACCTCA GGTAGTGCCA TCGGTTACGG CTCAGCAATG
1051  ACTTTAACTG ACACTTCAAA TAAAGTTAAG AAAGGAACCA AGGAGATGT
1101  TTCAGCTCTG AAGCCAACTA TAATGACTGC AGTTCCAGCT ATTCTGGATC
1151  GTGTCCGAGA AGGAGTTCTT AAAAAGGTTG AGGAAAGGG AGGGATGGCG
1201  AAgACCCtTT TTGACTTTGC ATACAAGCGC CGGTTAGCAG CTGTGGATGG
1251  AAGTTGGTTT GGTGCCTGGG GTTTGgAGAA AATGTTATGG GATGCTCTTG
1301  TCTTCAAGAA AATACGCGCT GTGCTTGGAG GACACATCCG TTTTATGCTC
1351  GTTGGAGGAG CTCCTCTGTC TCCTGATTCG CAACGCTTCA TCAATATCTG
1401  CATGGGGTCT CCCATCGGCC AAGGATATGG ATTGACTGAA ACGTGTGCTG
1451  GAGCTACGTT TTCTGAGTGG GACGATCCTG CTGTTGGTCG TGTTGGACCT
1501  CCACTTCCAT GCGGCTACGT TAAGCTCGTT TCTTGGGAAG AAGGTGGCTA
1551  CAGAATTTCA GATAAACCAA TGCCTAGAGG GGAGATTGTG GTAGGTGGTA
1601  ACAGTGTAAC AGCAGGTTAC TTCAACAATC AAGAAAAAAC CGATGAGGTT
1651  TACAAGGTCG ATGAGAAGGG CACAAGGTGG TTTTACACCG AGATATTGG
1701  GAGATTCCAC CCTGATGGAT GTCTCGAAGT CATCGATAGA AAGAAAGATA
1751  TTGTTAAACT TCAACATGGG GAATACGTAT CCCTTGGAAA GGTGGAGGCA
1801  GCTTTGGGTT CGAGCAATTA CGTTGATAAC ATCATGGTCC ACGCAGACCC
1851  AATTAACAGC TACTGTGTAG CTCTTGTTGT TCCATCACGA GGAGCATTAG
1901  AGAAATGGGC AGAGGAAGCT GGAGTTAAAC ACAGCGAATT CGCTGAGCTA
1951  TGCGAGAAAG GTGAAGCAGT CAAGGAGGTT CAACAATCTC TTACCAAGGC
2001  CGGGAAGGCG GCAAAGCTCG AAAAGTTTGA GCTTCCAGCA AGATCAAGT
2051  TGCTGTCAGA GCCGTGGACA CCGGAGTCGG GATTGGTCAC TGCTGCTCTT
2101  AAGATAAAGA GAGAACAAAT AAAGTCCAAG TTCAAAGATG AACTCAGCAA
2151  GTTATATGCC TAA
```

FIGURE 64

SEQ ID NO:127  AtACS6B Modified cDNA Nucleotide Sequence

```
   1  ATGATTCCTT ATGCTGCTGG TGTTATTGTG CCATTGGCTT TGACGTTTCT
  51  GGTTCAGAAA TCTAAGAAAG AAAAGAAAAG AGGTGTTGTT GTTGATGTTG
 101  GTGGTGAACC AGGTTATGCT ATTAGGAATC ACAGGTTTAC TGAGCCTGTT
 151  AGTTCCCATT GGGAACATAT CTCAACGCTT CCAGAGCTCT TTGAGATATC
 201  GTGTAATGCT CACAGTGATA GGGTTTTCCT TGGCACCCGA AGCTGATCT
 251  CTAGAGAGAT TGAGACTAGT GAGGATGGAA AAACGTTCGA GAAACTGCAT
 301  TTAGGTGACT ACGAGTGGCT CACTTTTGGG AAGACTCTCG AAGCAGTGTG
 351  TGATTTTGCC TCTGGGTTAG TTCAGATTGG GCACAAGACG GAAGAGCGTG
 401  TCGCCATTTT TGCAGATACT AGAGAAGAAT GGTTCATCTC CCTACAGGGT
 451  TGCTTCAGGC GCAACGTCAC TGTGGTAACT ATCTATTCAT CTTTGGGAGA
 501  GGAAGCTCTT TGTCACTCGC TGAATGAGAC AGAGGTCACA ACCGTAATAT
 551  GTGGTAGCAA AGAACTCAAA AAGCTCATGG ACATAAGCCA ACAGCTTGAA
 601  ACTGTGAAAC GTGTGATATG CATGGATGAT GAATTCCCAT CTGATGTGAA
 651  CAGTAATTGG ATGGCGACTT CATTTACTGA TGTTCAGAAA CTTGGCCGCG
 701  AAAATCCTGT GGATCCTAAT TTCCCTCTCT CAGCAGATGT TGCTGTTATA
 751  ATGTACACCA GTGGAAGCAC TGGACTTCCC AAGGGTGTTA TGATGACGCA
 801  TGGTAATGTC CTAGCTACAG TTTCGGCAGT GATGACAATT GTTCCTGACC
 851  TTGGAAAGAG GGATATATAC ATGGCATATT TACCTTTGGC TCACATCCTT
 901  GAGTTAGCAG CTGAGAGCGT AATGGCTACT ATTGGGAGTG CTATTGGATA
 951  TGGGTCTCCC TTGACGCTAA CGGATACTTC AAACAAGATA AAAAAGGGTA
1001  CAAAAGGAGA TGTCACAGCA CTAAAGCCCA CTATAATGAC AGCTGTTCCA
1051  GCCATTCTTG ATCGTGTCAG GGATGGTGTC CGCAAAAAGG TTGATGCAAA
1101  GGGCGGATTG TCAAAGAAAT TGTTTGACTT TGCATATGCT CGGCGATTAT
1151  CTGCAATCAA TGGAAGTTGG TTTGGAGCCT GGGGATTGGA AAAGCTTTTG
1201  TGGGATGTGC TTGTGTTCAG GAAAATCCGT GCAGTTTTGG GAGGTCAAAT
1251  CCGCTATTTG CTCTCTGGTG GTGCCCCTCT TTCTGGTGAC ACTCAGAGAT
1301  TCATTAACAT CTGCGTTGGG GCTCCAATCG GTCAGGGATA TGGGCTCACA
1351  GAGACTTGTG CTGGTGGAAC CTTCTCGGAG TTTGAGGACA CATCCGTTGG
1401  CCGTGTTGGT GCTCCACTTC CTTGCTCCTT TGTAAAGCTA GTAGACTGGG
1451  CGGAAGGTGG GTATCTAACT AGTGATAAGC CGATGCCCCG TGGTGAAATT
1501  GTAATTGGTG GCTCAAATAT CACGCTTGGG TATTTCAAAA ATGAGGAGAA
1551  AACTAAAGAA GTGTACAAGG TTGATGAAAA GGGAATGAGG TGGTTCTACA
1601  CAGGAGACAT AGGACGATTT CACCCTGATG GCTGCCTCGA GATAATAGAC
1651  CGAAAAAAGG ATATCGTTAA ACTTCAGCAT GGAGAATATG TCTCCTTGGG
1701  CAAAGTTGAA GCTGCTCTAA GTATAAGTCC CTATGTTGAA AACATAATGG
1751  TTCATGCTGA TTCGTTCTAC AGTTACTGTG TGGCTCTTGT GGTCGCGTCC
1801  CAACATACAG TTGAAGGTTG GCTTCAAAG CAAGGAATAG ACTTTGCCAA
1851  CTTCGAAGAA CTGTGCACGA AGAGCAAGC CGTGAAAGAA GTGTATGCGT
1901  CCCTTGTGAA GGCGGCTAAA CAATCACGAT GGAGAAGTT TGAGATACCA
1951  GCAAAGATCA AATTATTGGC ATCTCCATGG ACGCCAGAGT CAGGATTAGT
2001  CACAGCAGCT CTAAAGCTGA AAAGAGATGT AATTAGGAGG GAATTCTCTG
2051  AAGATCTCAC CAAGTTATAT GCCTAA
```

FIGURE 65

SEQ ID NO:128  AtACS1A Second Amino Acid Sequence

```
  1  MSQQKKYIFQ  VEEGKEGSDG  RPSVGPVYRS  IFAKDGFPDP  IEGMDSCWDV
 51  FRMSVEKYPN  NPMLGRREIV  DGKPGKYVWQ  TYQEVYDIVM  KLGNSLRSVG
101  VKDEAKCGIY  GANSPEWIIS  MEACNAHGLY  CVPLYDTLGA  DAVEFIISHS
151  EVSIVFVEEK  KISELFKTCP  NSTEYMKTVV  SFGGVSREQK  EEAETFGLVI
201  YAWDEFLKLG  EGKQYDLPIK  KKSDICTIMY  TSGTTGDPKG  VMISNESIVT
251  LIAGVIRLLK  SANEALTVKD  VYLSYLPLAH  IFDRVIEECF  IQHGAAIGFW
301  RGDVKLLIED  LAELKPTIFC  AVPRVLDRVY  SGLQKKLSDG  GFLKKFIFDS
351  AFSYKFGYMK  KGQSHVEASP  LFDKLVFSKV  KQGLGGNVRI  ILSGAAPLAS
401  HVESFLRVVA  CCHVLQGYGL  TESCAGTFVS  LPDELGMLGT  VGPPVPNVDI
451  RLESVPEMEY  DALASTARGE  ICIRGKTLFS  GYYKREDLTK  EVLIDGWLHT
501  GDVGEWQPDG  SMKIIDRKKN  IFKLSQGEYV  AVENIENIYG  EVQAVDSVWV
551  YGNSFESFLI  AIANPNQHIL  ERWAAENGVS  GDYDALCQNE  KAKEFILGEL
601  VKMAKEKKMK  GFEIIKAIHL  DPVPFDMERD  LLTPTFKKKR  PQLLKYYQSV
651  IDEMYKTINA  KFASRG*
```

FIGURE 66

SEQ ID NO:129   AtACS1B Second Amino Acid Sequence

```
  1   MTSQKRFIFE  VEAAKEATDG  NPSVGPVYRS  TFAQNGFPNP  IDGIQSCWDI
 51   FRTAVEKYPN  NRMLGRREIS  NGKAGKYVWK  TYKEVYDIVI  KLGNSLRSCG
101   IKEGEKCGIY  GINCCEWIIS  MEACNAHGLY  CVPLYDTLGA  GAVEFIISHA
151   EVSIAFVEEK  KIPELFKTCP  NSTKYMKTVV  SFGGVKPEQK  EEAEKLGLVI
201   HSWDEFLKLG  EGKQYELPIK  KPSDICTIMY  TSGTTGDPKG  VMISNESIVT
251   ITTGVMHFLG  NVNASLSEKD  VYISYLPLAH  VFDRAIEECI  IQVGGSIGFW
301   RGDVKLLIED  LGELKPSIFC  AVPRVLDRVY  TGLQQKLSGG  GFFKKKVFDV
351   AFSYKFGNMK  KGQSHVAASP  FCDKLVFNKV  KQGLGGNVRI  ILSGAAPLAS
401   HIESFLRVVA  CCNVLQGYGL  TESCAGTFAT  FPDELDMLGT  VGPPVPNVDI
451   RLESVPEMNY  DALGSTPRGE  ICIRGKTLFS  GYYKREDLTK  EVFIDGWLHT
501   GDVGEWQPNG  SMKIIDRKKN  IFKLAQGEYV  AVENLENVYS  QVEVIESIWV
551   YGNSFESFLV  AIANPAQQTL  ERWAVENGVN  GDFNSICQNA  KAKAFILGEL
601   VKTAKENKLK  GFEIIKDVHL  EPVAFDMERD  LLTPTYKKKR  PQLLKYYQNV
651   IHEMYKTTKE  TLASGQ
```

FIGURE 67

SEQ ID NO:130  AtACS3B Second Amino Acid Sequence

```
  1  MEFASPEQRR  LETIRSHIDT  SPTNDQSSSL  FLNATASSAS  PFFKEDSYSV
 51  VLPEKLDTGK  WNVYRSKRSP  TKLVSRFPDH  PEIGTLHDNF  VHAVETYAEN
101  KYLGTRVRSD  GTIGEYSWMT  YGEAASERQA  IGSGLLFHGV  NQGDCVGLYF
151  INRPEWLVVD  HACAAYSFVS  VPLYDTLGPD  AVKFVVNHAN  LQAIFCVPQT
201  LNILLSFLAE  IPSIRLIVVV  GGADEHLPSL  PRGTGVTIVS  YQKLLSQGRS
251  SLHPFSPPKP  EDIATICYTS  GTTGTPKGVV  LTHGNLIANV  AGSSVEAEFF
301  PSDVYISYLP  LAHIYERANQ  IMGVYGGVAV  GFYQGDVFKL  MDDFAVLRPT
351  IFCSVPRLYN  RIYDGITSAV  KSSGVVKKRL  FEIAYNSKKQ  AIINGRTPSA
401  FWDKLVFNKI  KEKLGGRVRF  MGSGASPLSP  DVMDFLRICF  GCSVREGYGM
451  TETSCVISAM  DDGDNLSGHV  GSPNPACEVK  LVDVPEMNYT  SDDQPYPRGE
501  ICVRGPIIFK  GYYKDEEQTR  EILDGDGWLH  TGDIGLWLPG  GRLKIIDRKK
551  NIFKLAQGEY  IAPEKIENVY  TKCRFVSQCF  IHGDSFNSSL  VAIVSVDPEV
601  MKDWAASEGI  KYEHLGQLCN  DPRVRKTVLA  EMDDLGREAQ  LRGFEFAKAV
651  TLVPEPFTLE  NGLLTPTFKI  KRPQAKAYFA  EAISKMYAEI  AASNPIPSKL
```

FIGURE 68

SEQ ID NO:131    AtACS4A Second Amino Acid Sequence

```
  1  MASTSSLGPS TLLSYGSPSR QFPDFGFRLI SGHESVRIPS FRRFRVHCES
 51  KEKEVKPSSP FLESSSFSGD AALRSSEWKA VPDIWRSSAE KYGDRVALVD
101  PYHDPPLKLT YKQLEQEILD FAEGLRVLGV KADEKIALFA DNSCRWLVSD
151  QGIMATGAVN VVRGSRSSVE ELLQIYRHSE SVAIVVDNPE FFNRIAESFT
201  SKASLRFLIL LWGEKSSLVT QGMQIPVYSY AEIINQGQES RAKLSASNDT
251  RSYRNQFIDS DDTAAIMYTS GTTGNPKGVM LTHRNLLHQI KHLSKYVPAL
301  AGDKFLSMLP SWHAYERASE YFIFTCGVEQ MYTSIRYLKD DLKRYQPNYI
351  VSVPLVYETL YSGIQKQISA SSAGRKFLAL TLIKVSMAYM EMKRIYEGMC
401  LTKEQKPPMY IVAFVDWLWA RVIAALLWPL HMLAKKLIYK KIHSSIGISK
451  AGISGGGSLP IHVDKFFEAI GVILQNGYGL TETSPVVCAR TLSCNVLGSA
501  GHPMHGTEFK IVDPETNNVL PPGSKGIIKV RGPQVMKGYY KNPSTTKQVL
551  NESGWFNTGD TGWIAPHHSK GRSRHCAGVI VLEGRAKDTI VLSTGENVEP
601  LEIEEAAMRS RVIEQIVVIG QDRRRLGAII IPNKEEAQRV DPETSKETLK
651  SLVYQELRKW TSECSFQVGP VLIVDDPFTI DNGLMTPTMK IRRDMVVAKY
701  KEEIDQLYS
```

FIGURE 69

SEQ ID NO:132 AtACS6B Second Amino Acid Sequence

```
  1  MIPYAAGVIV  PLALTFLVQK  SKKEKKRGVV  VDVGGEPGYA  IRNHRFTEPV
 51  SSHWEHISTL  PELFEISCNA  HSDRVFLGTR  KLISREIETS  EDGKTFEKLH
101  LGDYEWLTFG  KTLEAVCDFA  SGLVQIGHKT  EERVAIFADT  REEWFISLQG
151  CFRRNVTVVT  IYSSLGEEAL  CHSLNETEVT  TVICGSKELK  KLMDISQQLE
201  TVKRVICMDD  EFPSDVNSNW  MATSFTDVQK  LGRENPVDPN  FPLSADVAVI
251  MYTSGSTGLP  KGVMMTHGNV  LATVSAVMTI  VPDLGKRDIY  MAYLPLAHIL
301  ELAAESVMAT  IGSAIGYGSP  LTLTDTSNKI  KKGTKGDVTA  LKPTIMTAVP
351  AILDRVRDGV  RKKVDAKGGL  SKKLFDFAYA  RRLSAINGSW  FGAWGLEKLL
401  WDVLVFRKIR  AVLGGQIRYL  LSGGAPLSGD  TQRFINICVG  APIGQGYGLT
451  ETCAGGTFSE  FEDTSVGRVG  APLPCSFVKL  VDWAEGGYLT  SDKPMPRGEI
501  VIGGSNITLG  YFKNEEKTKE  VYKVDEKGMR  WFYTGDIGRF  HPDGCLEIID
551  RKKDIVKLQH  GEYVSLGKVE  AALSISPYVE  NIMVHADSFY  SYCVALVVAS
601  QHTVEGWASK  QGIDFANFEE  LCTKEQAVKE  VYASLVKAAK  QSRLEKFEIP
651  AKIKLLASPW  TPESGLVTAA  LKLKRDVIRR  EFSEDLTKLY  A
```

PLANT ACYL-COA SYNTHETASES

This is a Continuation-In-Part of application Ser. No. 09/906,419, now abandoned, filed on Jul. 16, 2001, which claimed priority from provisional application 60/220,474 filed on Jul. 21, 2000, now abandoned.

FIELD OF THE INVENTION

The present invention relates to genes and proteins encoding plant acyl-CoA synthetases and methods of their use.

BACKGROUND

Plant metabolism has evolved the ability to produce a diverse range of structures, including more than 20,000 different terpenoids, flavonoids, alkaloids, and fatty acids. Fatty acids have been extensively exploited for industrial uses in products such as lubricants, plasticizers, and surfactants. In fact, approximately one-third of vegetable oils produced in the world are already used for non-food purposes (Ohlrogge, J (1994) Plant Physiol. 104:821–26).

In 1999, approximately 40 million hectares of transgenic crops were planted worldwide. Included in this figure is approximately 50% of the soybean acreage in the United States, over 70% of the Canola acreage in Canada, about 20% of the United States corn crop, and about 33% of the United States cotton crop (Ohlrogge, J (1999) Curr. Opin. Plant Biol. 2:121–22).

Various laboratories around the world have attempted to modify triacylglycerol (TAG) content in oilseed crops by manipulating the genes involved in TAG biosynthesis. The TAG biosynthetic pathway involves many enzymatic reactions. An increasing number of the genes that encode these enzymes have been cloned and studied in detail with respect to the quantitative and qualitative contributions they make to the TAG composition of a particular oilseed. There are still several genes in the TAG pathway, however, that have not been cloned and characterized in detail.

Most of the efforts to modify TAG content have focused on either increasing the nutritional characteristics and chemical stability of edible oils or on introducing new and unusual fatty acids into TAGs for use in various industrial applications. Progress has been achieved through overexpression and/or suppression of a modestly small number of genes in the TAG synthesis pathway. However, to date, the alterations in fatty acid content have not been substantial enough to create truly meaningful new oilseed lines.

Thus, there remains a need to identify and characterize additional genes in the TAG synthesis pathway, the manipulation of which can contribute to altered or increased fatty acid content in oilseeds.

SUMMARY OF THE INVENTION

The present invention relates to genes encoding plant acyl-CoA synthetases (ACS) and methods of their use. The present invention is not limited to any particular nucleic acid or amino acid sequence.

Accordingly, in some embodiments, the present invention provides compositions comprising an isolated nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:121, SEQ ID NO:122, SEQ ID NO:123, SEQ ID NO:124, SEQ ID NO:125, SEQ ID NO:126, and SEQ ID NO:127. The present invention is not limited to the nucleic acid sequences encoded by SEQ ID NOs:1–11 and 121–127. Indeed, it is contemplated that the present invention encompasses homologs, variants, and portions or fragments of the nucleic acids encoded by SEQ ID NOs:1–11 and 121–127. Accordingly, in some embodiments the present invention comprises sequences that hybridize to the nucleic acids encoded by SEQ ID NOs:1–11 and 121–127 under conditions of low to high stringency. In other embodiments, the present invention comprises nucleic acid sequences that compete with or inhibit the binding of the nucleic acid sequences encoded by SEQ ID NOs:1–11 and 121–127 to their complements. In some preferred embodiments, the nucleic acids encode a protein with Acyl-CoA synthetase activity. In some particularly preferred embodiments, the nucleic acid sequence encodes a protein that catalyzes the esterification of a fatty acid and coenzyme A. In other particularly preferred embodiments, the nucleic acid sequence encodes a protein comprising an amino acid sequence selected from the group consisting of SEQ ID NOs:12–22 and 128–132.

In some embodiments of the present invention, the nucleic acids described above are operably linked to a heterologous promoter. In further embodiments, the sequences described above are contained within a vector. In still further embodiments, the vectors are within a host cell. The present invention is not limited to any particular host cell. Indeed, a variety of host cells are contemplated, including, but not limited to, prokaryotic cells, eukaryotic cells, plant tissue cells, and cells in planta.

In some embodiments, the present invention provides methods for altering the phenotype of a plant comprising: providing i) a vector comprising a nucleic acid sequence encoding a protein, said nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:121, SEQ ID NO:122, SEQ ID NO:123, SEQ ID NO:124, SEQ ID NO:125, SEQ ID NO:126, and SEQ ID NO:127; and ii) plant tissue; and transfecting the plant tissue with the vector under conditions such that the protein is expressed. In other embodiments, the nucleic acid sequence encodes a protein comprising an amino acid sequence selected from the group consisting of SEQ ID NOs:12–22 and 128–132. In yet other embodiments, the nucleic acid sequence is selected from the group consisting of nucleic acid sequences that hybridize to SEQ ID NOs:1–11 and 121–127 under low to high stringency conditions.

In other embodiments, the present invention provides methods for assaying acyl-CoA synthetase activity comprising: providing a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:121, SEQ ID NO:122, SEQ ID NO:123, SEQ ID NO:124, SEQ ID NO:125, SEQ ID NO:126, and SEQ ID NO:127; expressing the nucleic acid sequence under conditions such that a protein is produced; and assaying the activity of the protein. In other embodiments, the nucleic acid sequence encodes a protein comprising an amino acid sequence selected from the group consisting of SEQ ID NOs:12–22 and 128–129. In yet other embodiments, the nucleic acid sequence is selected from the group consisting of nucleic acid sequences that hybridize to SEQ ID NOs:1–11 and 121–127 under low to high stringency conditions.

The present invention also provides methods for altering the phenotype of a plant comprising: providing: i) a vector comprising an antisense sequence corresponding to any of the nucleic acid sequences described above; and ii) plant tissue; and b) transfecting the plant tissue with the vector under conditions such that the antisense sequence is expressed and the activity of an acyl-CoA synthetase is down regulated as compared to wild-type plants. In particularly preferred embodiments, the nucleic acid sequence is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:121, SEQ ID NO:122, SEQ ID NO:123, SEQ ID NO:124, SEQ ID NO:125, SEQ ID NO:126, and SEQ ID NO:127. In different embodiments, an antisense sequence corresponds to any sequence which, when expressed, inhibits expression of an ACS gene; such sequences encompass expression products which include long as well as short RNA molecules.

The present invention also provides methods for producing variants of acyl-CoA synthetases comprising: providing any of the nucleic acid sequences described above; mutagenizing the nucleic acid sequence; and screening the variant for activity. In particularly preferred embodiments, the nucleic acid sequence is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:121, SEQ ID NO:122, SEQ ID NO:123, SEQ ID NO:124, SEQ ID NO:125, SEQ ID NO:126, and SEQ ID NO:127.

The present invention also provides methods for screening acyl-CoA synthetases comprising: providing a candidate acyl-CoA synthetase; and analyzing the candidate acyl-CoA synthetase for the presence of at least one of ACS motifs 1–9.

In additional embodiments, the present invention provides nucleic acids encoding a plant acyl-CoA synthetase, wherein the plant acyl-CoA synthetase competes for binding to a fatty acid substrate with a protein encoded by a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:121, SEQ ID NO:122, SEQ ID NO:123, SEQ ID NO:124, SEQ ID NO:125, SEQ ID NO:126, and SEQ ID NO:127.

In other embodiments, the present invention provides compositions comprising purified acyl-CoA synthetases comprising any of amino acid sequences SEQ ID NOs: 12–22 and 128–132, and portions thereof.

In some embodiments, the present invention provides compositions comprising an isolated nucleic acid sequence selected from the group consisting of SEQ ID NOs:23–32. The present invention is not limited to the nucleic acid sequences encoded by SEQ ID NOs:23–32. Indeed, it is contemplated that the present invention encompasses homologs, variants, and portions or fragments of the nucleic acids encoded by SEQ ID NOs:23–32. Accordingly, in some embodiments, the present invention comprises sequences that hybridize to the nucleic acids encoded by SEQ ID NOs:23–32 under conditions of low to high stringency. In other embodiments, the present invention comprises nucleic acid sequences that compete with or inhibit the binding of the nucleic acid sequences encoded by SEQ ID NOs:23–32 to their complements. In some preferred embodiments, the nucleic acids encode a protein with AMP binding activity. In some embodiments of the present invention, the nucleic acids described above are operably linked to a heterologous promoter. In further embodiments, the sequences described above are contained within a vector. In still further embodiments, the vectors are within a host cell. The present invention is not limited to any particular host cell. Indeed, a variety of host cells are contemplated, including, but not limited to, prokaryotic cells, eukaryotic cells, plant tissue cells, and cells in planta.

In some embodiments, the present invention provides methods for altering the phenotype of a plant comprising: providing i) a vector comprising a nucleic acid sequence encoding a protein, said nucleic acid sequence selected from the group consisting of SEQ ID NOs:23–32; and ii) plant tissue; and transfecting the plant tissue with the vector under conditions such that the protein is expressed.

In other embodiments, the present invention provides methods for altering the phenotype of a plant comprising: providing i) a vector comprising a nucleic acid sequence encoding a protein, said nucleic acid sequence selected from the group consisting of SEQ ID NOs:23–32; and ii) plant tissue; and transfecting the plant tissue with the vector under conditions such that the protein is expressed. In other embodiments, the nucleic acid sequence encodes a protein comprising an amino acid sequence selected from the group consisting of SEQ ID NOs:33–42. In yet other embodiments, the nucleic acid sequence is selected from the group consisting of nucleic acid sequences that hybridize to SEQ ID NOs:23–32 under low to high stringency conditions.

The present invention also provides methods for altering the phenotype of a plant comprising: providing: i) a vector comprising an antisense sequence corresponding to any of the nucleic acid sequences described above encoding an AMP-BP; and ii) plant tissue; and b) transfecting the plant tissue with the vector under conditions such that the antisense sequence is expressed and the activity of an AMP-BP is down regulated as compared to wild-type plants. In particularly preferred embodiments, the nucleic acid sequence is selected from the group consisting of SEQ ID NOs:23–32. In different embodiments, an antisense sequence corresponds to any sequence which, when expressed, inhibits expression of an AMP-BP gene; such sequences encompass expression products which include long as well as short RNA molecules.

The present invention also provides compositions comprising purified AMP-binding proteins comprising any of amino acid sequences SEQ ID NOs:33–42, and portions thereof.

BRIEF DESCRIPTION OF THE DRAWINGS

Figure 1A:
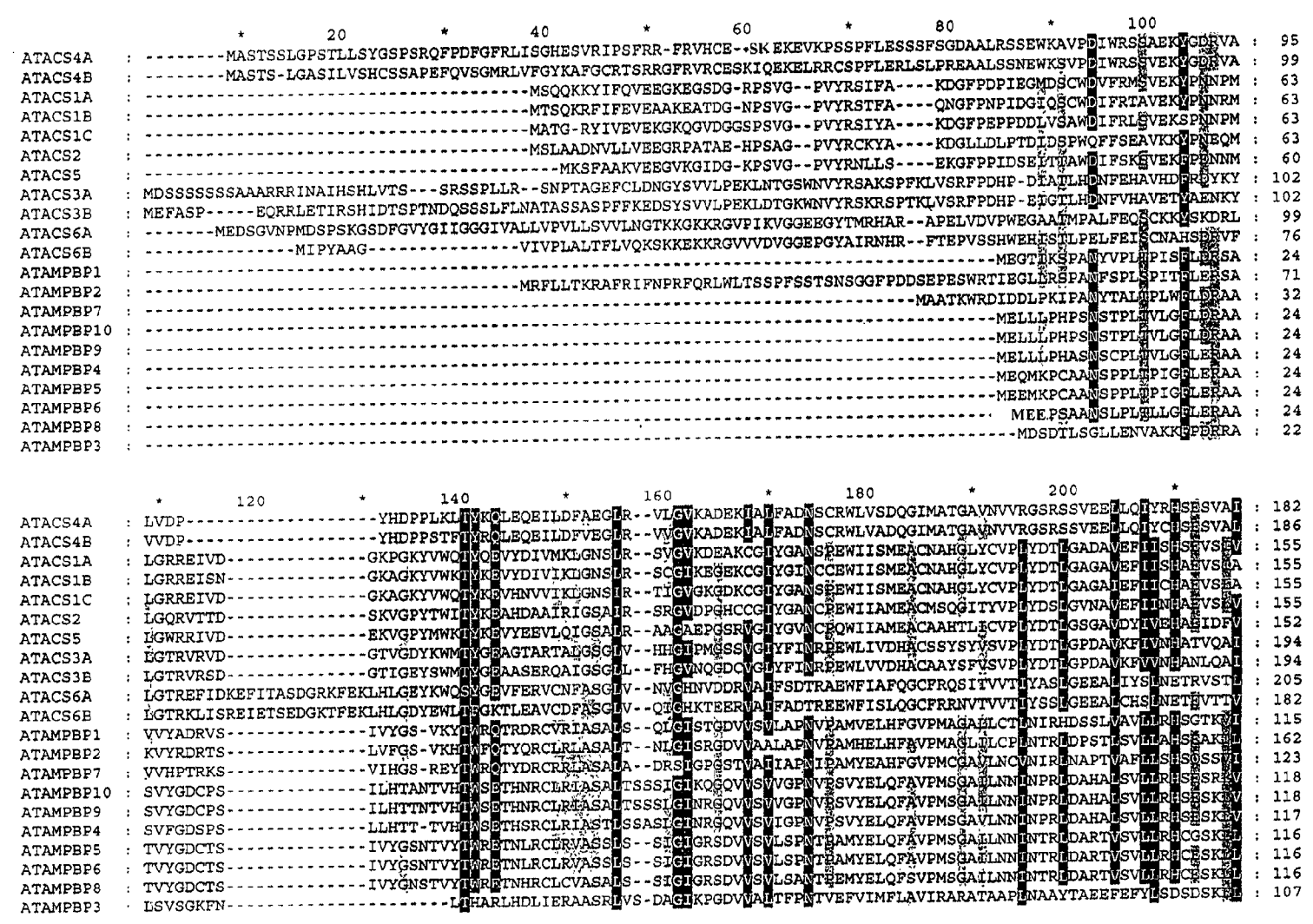
Figure 1B:
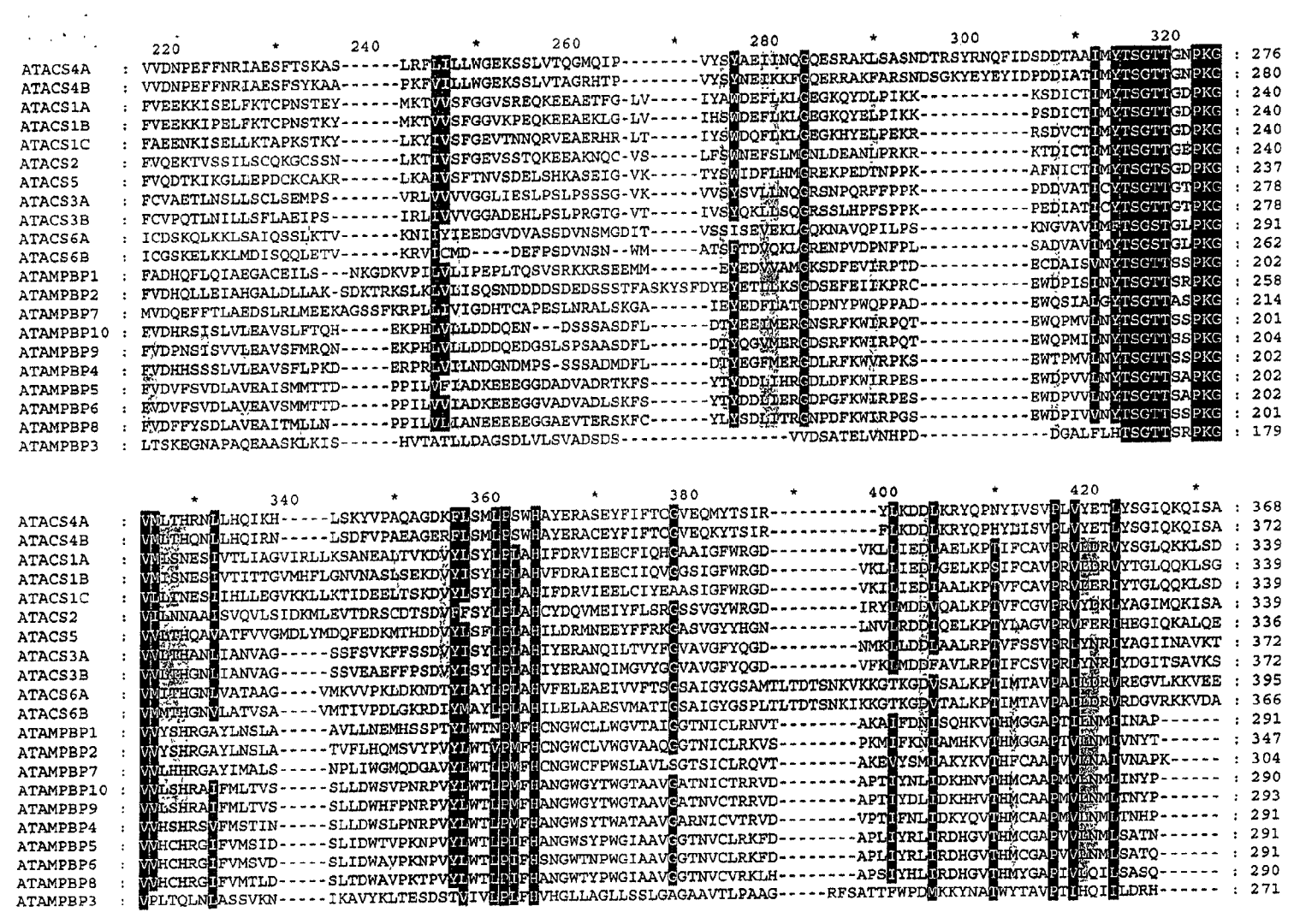
Figure 1C:
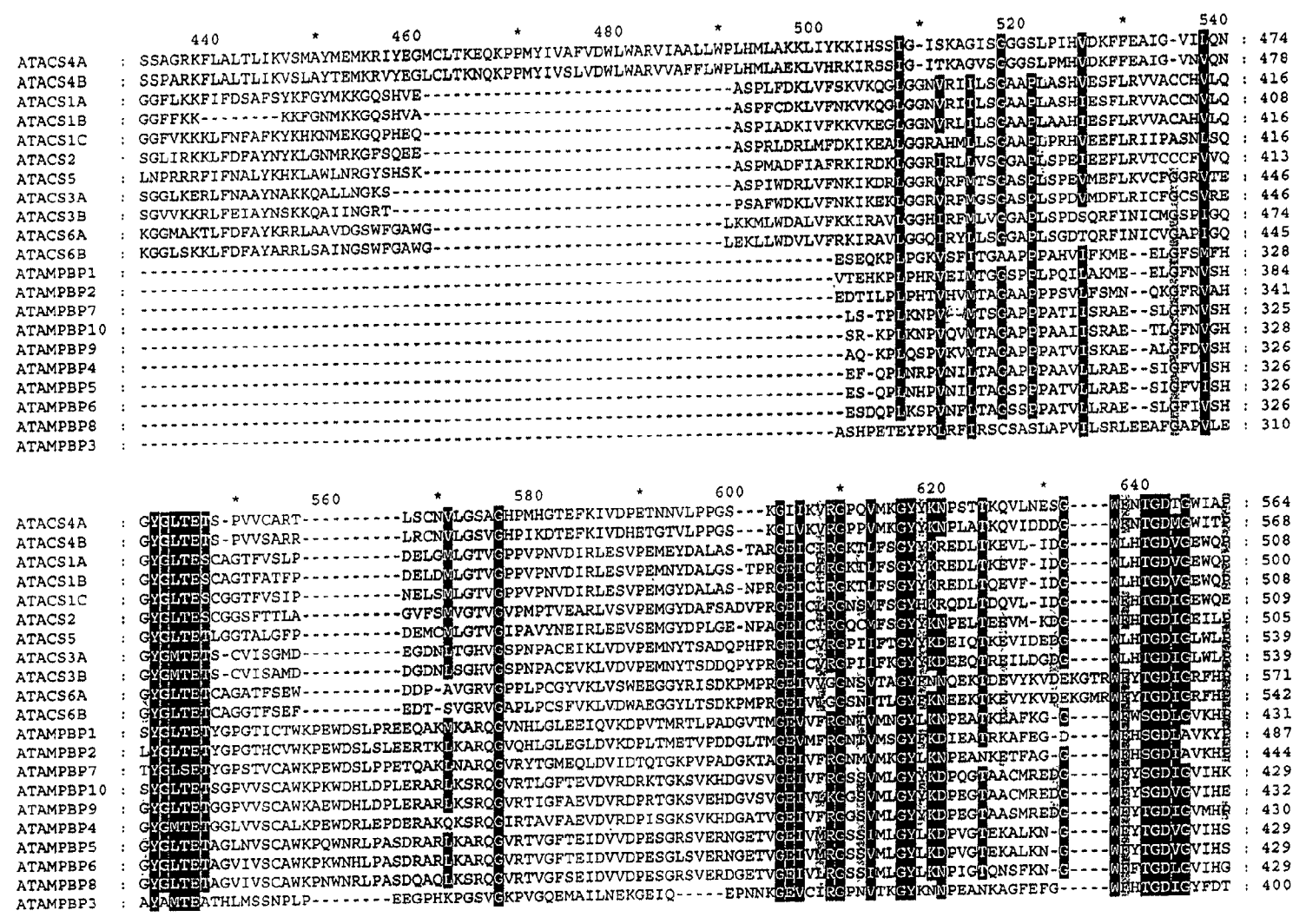
Figure 1D:
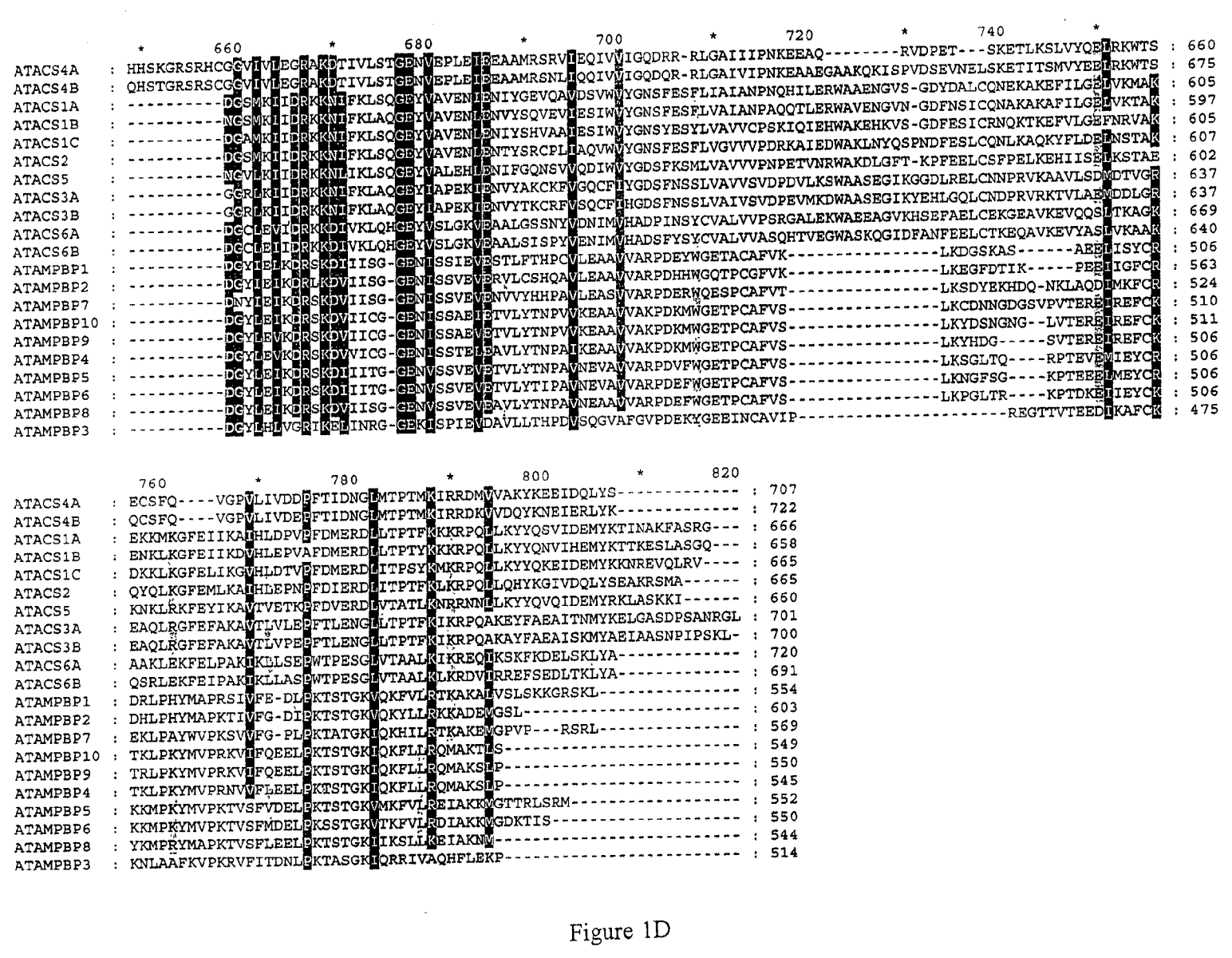

FIGS. 1A–1D present an amino acid sequence alignment for *Arabidopsis* ACS and AMP-binding protein sequences. These sequences are, from top to bottom, SEQ ID NOs: 18, 19, 12, 13, 14, 15, 20, 16, 17, 21, 22, 33, 34, 39, 42, 41, 36, 37, 38, 40, and 35.

FIG. 2 (SEQ ID NOS: 110 to 120) is a comparison of the degree of conservation of the deduced amino acid sequences of and around the insertional elements of each ACS. The residues corresponding to the predicted borders of the insertional element are numbered and denoted with arrows. These residues were determined by comparing the sequences of the candidate ACS genes to those of the other AMP-BP genes that were identified in the original data base screen and which lacked the insertional element. For clarity, FIG. 2 displays only the first few amino acid residues that flank the upstream and downstream borders of the insertional region.

FIG. 3 shows an AtACS1A original nucleic acid sequence (SEQ ID NO: 1).

FIG. 4 shows an AtACS1B original nucleic acid sequence (SEQ ID NO: 2).

FIG. 5 shows an AtACS1C original nucleic acid sequence (SEQ ID NO: 3).

FIG. 6 shows an AtACS2 original nucleic acid sequence (SEQ ID NO: 4).

FIG. 7 shows an AtACS3A original nucleic acid sequence (SEQ ID NO: 5).

FIG. 8 shows an AtACS3B original nucleic acid sequence (SEQ ID NO: 6).

FIG. 9 shows an AtACS4A original nucleic acid sequence (SEQ ID NO: 7).

FIG. 10 shows an AtACS4B original nucleic acid sequence (SEQ ID NO: 8).

FIG. 11 shows an AtACS5 original nucleic acid sequence (SEQ ID NO: 9).

FIG. 12 shows an AtACS6A original nucleic acid sequence (SEQ ID NO: 10).

FIG. 13 shows an AtACS6B original nucleic acid sequence (SEQ ID NO: 11).

FIG. 14 shows an AtACS 1A original amino acid sequence (SEQ ID NO: 12).

FIG. 15 shows an AtACS1B original amino acid sequence (SEQ ID NO: 13).

FIG. 16 shows an AtACS1C original amino acid sequence (SEQ ID NO: 14).

FIG. 17 shows an AtACS2 original amino acid sequence (SEQ ID NO: 15).

FIG. 18 shows an AtACS3A original amino acid sequence (SEQ ID NO: 16).

FIG. 19 shows an AtACS3B original amino acid sequence (SEQ ID NO: 17).

FIG. 20 shows an AtACS4A original amino acid sequence (SEQ ID NO: 18).

FIG. 21 shows an AtACS4B original amino acid sequence (SEQ ID NO: 19).

FIG. 22 shows an AtACS5 original amino acid sequence (SEQ ID NO: 20).

FIG. 23 shows an AtACS6A original amino acid sequence (SEQ ID NO: 21).

FIG. 24 shows an AtACS6B original amino acid sequence (SEQ ID NO: 22).

FIG. 25 shows an AMP-BP1 nucleic acid sequence (SEQ ID NO: 23).

FIG. 26 shows an AMP-BP2 nucleic acid sequence (SEQ ID NO: 24).

FIG. 27 shows an AMP-BP3 nucleic acid sequence (SEQ ID NO: 25).

FIG. 28 shows an AMP-BP4 nucleic acid sequence (SEQ ID NO: 26).

FIG. 29 shows an AMP-BP5 nucleic acid sequence (SEQ ID NO: 27).

FIG. 30 shows an AMP-BP6 nucleic acid sequence (SEQ ID NO: 28).

FIG. 31 shows an AMP-BP7 nucleic acid sequence (SEQ ID NO: 29).

FIG. 32 shows an AMP-BP8 nucleic acid sequence (SEQ ID NO: 30).

FIG. 33 shows an AMP-BP9 nucleic acid sequence (SEQ ID NO: 31).

FIG. 34 shows an AMP-BP10 nucleic acid sequence (SEQ ID NO: 32).

FIG. 35 shows an AMP-BP1 amino acid sequence (SEQ ID NO: 33).

FIG. 36 shows an AMP-BP2 amino acid sequence (SEQ ID NO: 34).

FIG. 37 shows an AMP-BP3 amino acid sequence (SEQ ID NO: 35).

FIG. 38 shows an AMP-BP4 amino acid sequence (SEQ ID NO: 36).

FIG. 39 shows an AMP-BP5 amino acid sequence (SEQ ID NO: 37).

FIG. 40 shows an AMP-BP6 amino acid sequence (SEQ ID NO: 38).

FIG. 41 shows an AMP-BP7 amino acid sequence (SEQ ID NO: 39).

FIG. 42 shows an AMP-BP8 amino acid sequence (SEQ ID NO: 40).

FIG. 43 shows an AMP-BP9 amino acid sequence (SEQ ID NO: 41).

FIG. 44 shows an AMP-BP10 amino acid sequence (SEQ ID NO: 42).

FIG. 45 shows an amino acid sequence alignment for ACS motif 1 (SEQ ID NO:43).

FIG. 46 shows an amino acid sequence alignment for ACS motif 2 (SEQ ID NO:44).

FIG. 47 shows an amino acid sequence alignment for ACS motif 3 (SEQ ID NO:45).

FIG. 48 shows an amino acid sequence alignment for ACS motif 4 (SEQ ID NO:46).

FIG. 49 shows an amino acid sequence alignment for ACS motif 5 (SEQ ID NO:47).

FIG. 50 shows an amino acid sequence alignment for ACS motif6 (SEQ ID NO:48).

FIG. 51 shows an amino acid sequence alignment for ACS motif 7 (SEQ ID NO:49).

FIG. 52 shows an amino acid sequence alignment for ACS motif 8 (SEQ ID NO:50).

FIG. 53 shows an amino acid sequence alignment for ACS motif 9 (SEQ ID NO:51).

FIG. 56 shows the results of the specificities of nine AtACS enzymes for eight fatty acid substrates.

FIG. 58 shows an AtACS1A modified nucleic acid sequence (SEQ ID NO: 121).

FIG. 59 shows an AtACS1B modified nucleic acid sequence (SEQ ID NO: 122).

FIG. 60 shows an AtACS2 modified nucleic acid sequence (SEQ ID NO: 123).

FIG. 61 shows an AtACS3B modified nucleic acid sequence (SEQ ID NO: 124).

FIG. 62 shows an AtACS4A modified nucleic acid sequence (SEQ ID NO: 125).

FIG. 63 shows an AtACS6A modified nucleic acid sequence (SEQ ID NO: 126).

FIG. 64 shows an AtACS6B modified nucleic acid sequence (SEQ ID NO: 127).

FIG. 65 shows an AtACS1A second amino acid sequence (SEQ ID NO: 128).

FIG. 66 shows an AtACS1B second amino acid sequence (SEQ ID NO: 129).

FIG. 67 shows an AtACS3B second amino acid sequence (SEQ ID NO: 130).

FIG. 68 shows an AtACS4A second amino acid sequence (SEQ ID NO: 131).

FIG. 69 shows an AtACS6B second amino acid sequence (SEQ ID NO: 132).

DESCRIPTION OF THE INVENTION

Figure 54:
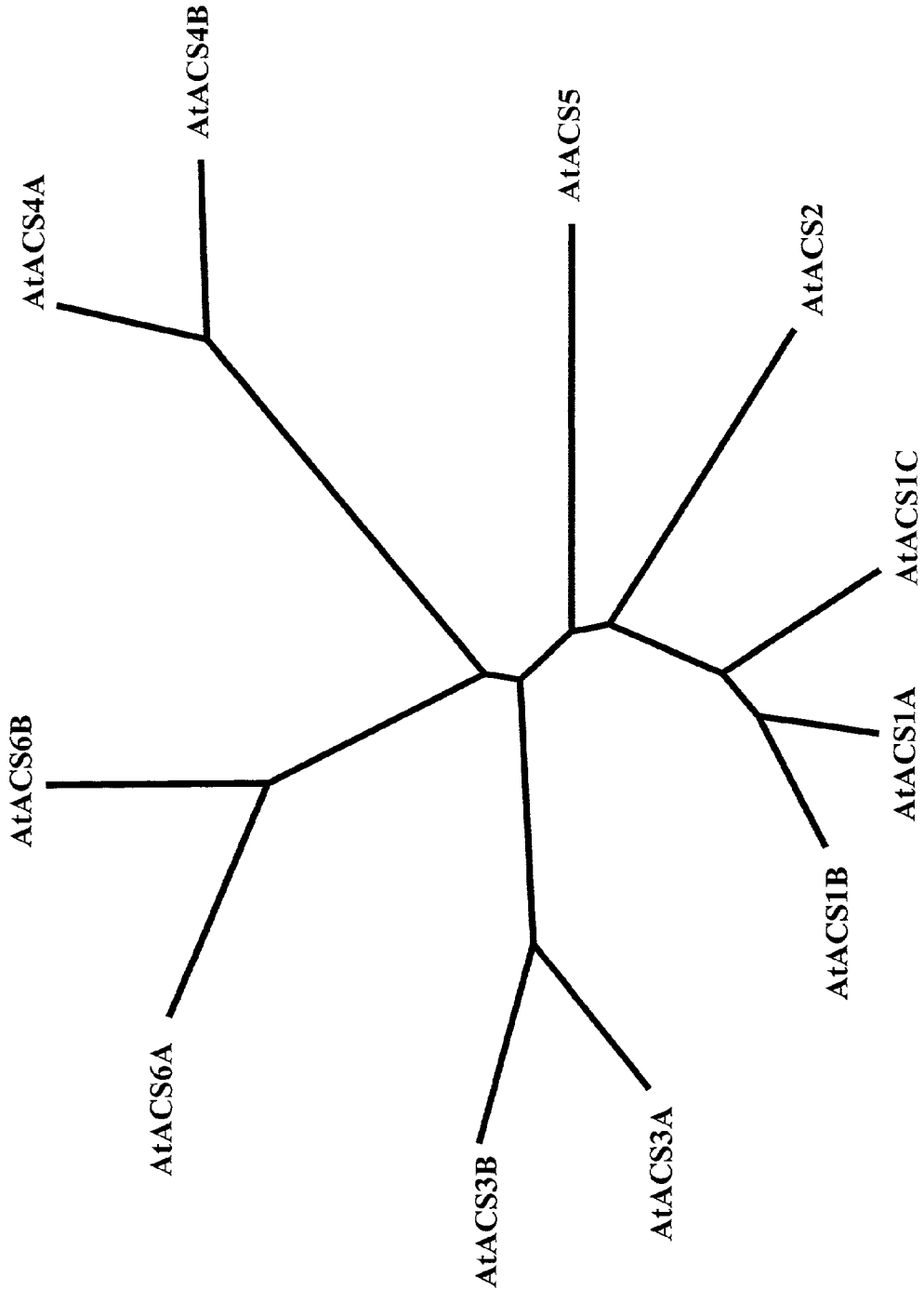
FIG. 54 shows a phylogenetic tree constructed to visually compare the relationship between each of the candidate ACS genes.

The present invention relates to genes encoding plant acyl-CoA synthetases (ACSs) and methods of their use. The present invention encompasses both native and recombinant wild-type forms of the enzyme, as well as mutant and variant forms, some of which possess altered characteristics relative to the wild-type enzyme. The present invention also relates to methods of using ACSs, including altered expression in transgenic plants and expression in prokaryotes and cell culture systems. After the "Definitions," the following description of the invention is divided into: I. Acyl-CoA Synthetases; II. Uses of Acyl-CoA Synthetase Nucleic Acids and Polypeptides; III. Identification of Other Acyl-CoA Synthetase Homologs; and IV. AMP Binding Proteins.

Definitions

To facilitate understanding of the invention, a number of terms are defined below.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, etc.). Plant tissue may be in planta, in organ culture, tissue culture, or cell culture. "Oil-producing species" as used herein refers to plant species which produce and store triacylglycerol in specific organs, primarily in seeds. Such species include soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

As used herein, the term "acyl-CoA synthetase (ACS)" refers to an enzymatic activity that catalyzes the formation of an acyl-CoA-fatty acid ester from a free fatty acid and coenzyme A (CoA). As used herein, the term "plastidial acyl-CoA synthetase" refers to an enzymatic activity that catalyzes the formation of an acyl-CoA-fatty acid ester from a free fatty acid and coenzyme A and that is localized to the chloroplast. As used herein, the term "plant acyl-CoA synthetase" refers to an acyl-CoA synthetase derived from a plant. The term plant acyl-CoA synthetases encompasses both acyl CoA synthetases that are identical to wild-type plant acyl CoA synthetases and those that are derived from wild type plant acyl-CoA synthetases (e.g., variants of plant acyl CoA synthetases or chimeric genes constructed with portions of plant acyl CoA synthetase coding regions).

As used herein, the term "AMP binding protein" ("AMP-BP") refers to a protein comprising an AMP-binding motif, which is found in all ACS genes. This motif is associated with the ability of a protein to bind ATP and to create an acyl- or acetyl-adenylate intermediate. However, not all AMP-BPs are ACSs; thus, in addition to ACS, the AMP-BP superfamily also contains several other classes of genes, at least some of which, such as 4-coumarate-CoA ligases and acetyl-CoA synthetases, are known to exist in plants.

As used herein, the term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides.

As used herein, the terms "protein" and "polypeptide" refer to compounds comprising amino acids joined via peptide bonds and are used interchangeably.

As used herein, where "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule; furthermore, an "amino acid sequence" can be deduced from the nucleic acid sequence encoding the protein.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

The term "portion" when used in reference to a protein (as in "a portion of a given protein") refers to fragments of that protein. The fragments may range in size from four amino acid residues to the entire amino sequence minus one amino acid.

As used herein, the term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

As used herein, the term "fusion protein" refers to a chimeric protein containing the protein of interest (e.g., ACSs and fragments thereof) joined to an exogenous protein fragment (e.g., the fusion partner which consists of a non-ACS protein). The fusion partner may enhance the solubility of ACS protein as expressed in a host cell, may provide an affinity tag to allow purification of the recombinant fusion protein from the host cell or culture supernatant, or both. If desired, the fusion protein may be removed from the protein of interest (e.g., ACS or fragments thereof) by a variety of enzymatic or chemical means know to the art.

As used herein, the term "transit peptide" refers to the N-terminal extension of a protein that serves as a signal for uptake and transport of that protein into an organelle such as a plastid or mitochondrion.

As used herein, the term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As used herein, the terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). "Nucleoside", as used herein, refers to a compound consisting of a purine [guanine (G) or adenine (A)] or pyrimidine [thymine (T), uridine (U), or cytidine (C)] base covalently linked to a pento se, whereas "nucleotide" refers to a nucleo side phosphorylated at one of its pentose hydroxyl groups.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a nucleic acid at which a new linkage would be to a 5' carbon is its 5' terminal nucleotide. The end of a nucleic acid at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein, the term "heterologous gene" refers to a gene encoding a factor that is not in its natural enviromnent (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" as used herein refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

As used herein, the term "over-expression" refers to the production of a gene product in transgenic organisms that exceeds levels of production in normal or non-transformed organisms. As used herein, the term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

A "complement" of a nucleic acid sequence as used herein refers to a nucleotide sequence whose nucleic acids show total complementarity to the nucleic acids of the nucleic acid sequence.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42_C in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 533 SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m-5°$ C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the terms "vector" and "vehicle" are used interchangeably in reference to nucleic acid molecules that transfer DNA segment(s) from one cell to another. Vectors may include plasmids, bacteriophages, viruses, cosmids, and the like.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "selectable marker" as used herein, refer to a gene which encodes an enzyme having an activity that confers resistance to an antibiotic or drug upon the cell in which the selectable marker is expressed. Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap (1994) Plant Mol. Biol. 24:119–127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

An enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al (1989) Molecular Cloning: A Laboratory Manual, 2nd ed. (Cold Spring Harbor Laboratory Press, New York) pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

As used herein, the term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208, GV3101) are referred to as "nopaline-type" *Agrobacteria; Agrobacterium* strains which cause production of octopine (e.g., strain LBA4404, Ach5, B6) are referred to as "octopine-type" Agrobacteria; and *Agrobacterium* strains which cause production of agropine (e.g., strain EHA105, EHA101, A281) are referred to as "agropine-type" *Agrobacteria*.

The terms "bombarding," "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., β-glucuronidase) encoded by the transgene. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

As used herein, the terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "amplification" is defined as the production of additional copies of a nucleic acid sequence and is generally carried out using polymerase chain reaction technologies well known in the art (Dieffenbach and GS Dvekler, (1995) PCR Primer, a Laboratory Manual, Cold Spring Harbor Press, Plainview N.Y.). As used herein, the term "polymerase chain reaction" ("PCR") refers to the methods disclosed in U.S. Pat. Nos. 4,683,195, 4,683,202 and 4,965,188, all of which are incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the term "sample template" refers to a nucleic acid originating from a sample which is analyzed for the presence of "target". In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other than those to be detected may be present as background in a test sample.

As used herein, the term "primer" refers to an oligonucleotide, whether occurring naturally (e.g., as in a purified restriction digest) or produced synthetically, which is capable of acting as a point of initiation of nucleic acid synthesis when placed under conditions in which synthesis of a primer extension product which is complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method.

As used herein, the term "probe" refers to an oligonucleotide (i.e., a sequence of nucleotides), whether occurring naturally (e.g., as in a purified restriction digest) or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used herein interchangeably. In addition to probes, primers and deoxynucleoside triphosphates may contain labels; these labels may comprise, but are not limited to, $^{32}$P, $^{33}$P, $^{SD}$, enzymes, or fluorescent molecules (e.g., fluorescent dyes).

As used herein, the terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31–9.58).

As used herein, the term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39–7.52).

As used herein, the terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "isolated" when used in relation to a nucleic acid, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising SEQ ID NO:1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i. e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

I. Acyl-CoA Synthetases

Acyl-CoA synthetases (ACSs) catalyze the following reaction:

Fatty acid+CoASH+ATP→acyl-CoA+AMP+PPi wherein free fatty acids are activated through ATP-dependent thioesterification to coenzyme A. This reaction is critical to most fatty acid metabolism, since all but a few fatty acid-utilizing enzymes require activated forms of these molecules as substrates. The ACSs are particularly important to plant fatty acid metabolism. The present invention is not limited to any particular mechanism. Indeed, an understanding of the mechanism is not required to practice the present invention. However, it is contemplated that free fatty acids synthesized in the chloroplasts undergo activation by ACS at the plastid outer envelope membrane before being incorporated into TAG in the endoplasmic reticulum. Therefore, modifications of fatty acid distribution in TAG pools within a seed are likely affected by the various isoforms of ACS.

In addition to their roles in TAG biosynthesis, ACSs are thought to perform other important functions within the plant cell. It is contemplated that altered expression of the ACSs of the present invention may be utilized to alter these functions. For example, ACS is necessary for activating fatty acids released from oil bodies in newly germinated seedlings. These acyl-CoAs serve as substrates for the beta-oxidation cycle, which supplies the plant with cellular energy until it becomes photosynthetically competent. ACS may also play a role in cuticle wax synthesis. The cuticle waxes are a mixture of hydrophobic lipid compounds found on the surfaces of the aerial tissues of most plants. These waxes retard water loss, protect the plants from pests, and provide signaling molecules needed for fertility.

ACS is also a necessary component of the process of protein acylation. Several essential proteins and enzymes characterized in other eukaryotic organisms undergo coupling between myristic and/or palmitic acids and specific amino acid residues near their N-termini. These fatty acid modifications are necessary for proper targeting and function of these proteins. Most of the acylated target proteins are involved in signal transduction or metabolic regulation. The fatty acids used for these modifications must be supplied as acyl-CoAs.

ACS also catalyzes the first step in the biosynthetic pathway of biotin, a vitamin cofactor necessary for many carboxylation/decarboxylation reactions. ACS may also play an important role in the synthesis of jasmonic acid, an important fatty acid-derived signaling compound involved in reproduction, plant defense, and a number of other plant response reactions.

One of the major goals of modern plant biotechnology is to manipulate lipid metabolism in oilseed crops to produce new and improved edible and industrial vegetable oils. Lipids constitute the structural components of cellular membranes and act as sources of energy for the germinating seed. Both de novo synthesis and modification of existing lipids are dependent on the activity of ACSs, as described above. To date, ACSs have been recalcitrant to traditional methods of purification due to their association with membranes.

Despite their crucial role in lipid metabolism, ACSs have not been well-characterized in plants. To date, the only molecular information regarding plant ACSs is provided by Fulda et al., Plant Molec. Biol. 33:911–22 (1997), who describe five cDNA clones from *Brassica napus*, only two of which had ACS activity when expressed in *E. coli*. The present inventors have identified and cloned over 20 different genes, eleven of which are identified as ACSs; the remaining genes are AMP-BPs. These results indicate that, surprisingly, ACS exists as a much larger gene family in plants than could have been predicted from the results of Fulda et al.

The ACS genes were discovered by a step-wise procedure. The first step was computer-assisted homology comparisons between amino acid sequences of known eukaryotic ACS sequences and EST sequences of *Arabidopsis* genome databases. Potential candidates, or ACS homologs, were then screened for the presence of a unique 40–50 position amino acid insertion near the middle of proteins encoded by ACS genes from *Bassica napus*; the results identified eleven genes as encoding ACSs. The sequences of the ACS genes were then compared by GAP analysis to establish that each gene was unique. The results of this analysis were also utilized to determine the relationships between the different genes; these relationships formed the basis on which to name the genes. The ACS homologs were also screened for activity by functional expression in *Saccharomyces cerevisiae* YB525 and for in vitro activity. Additional information about the identity and role of the ACS genes was obtained from analysis of their tissue-specific expression pattern, and chloroplast import assays.

Furthermore, T-DNA *Arabidopsis* mutants lacking an ACS gene have been identified and are described.

Eleven ACS genes have been identified. This family therefore represents the largest ACS gene family yet described in a single species, surpassing even that of humans, which family is known to contain at least six genes that encode ACS or VLCS (very long chain acyl-CoA synthetase) ((Steinberg, S. J et al. (2000) Journal of Biological Chemistry 275(45): 35162–35169).

Accordingly, the present invention describes the isolation of several isoforms of ACS genes from *Arabidopsis thaliana*. It is contemplated that these genes and their homologs and variants will find use in the development of plants containing specialized fatty acid compositions. Each of these genes is discussed in further detail below.

A. ACS Nucleic Acids

Nucleic acids encoding plant ACSs were identified in the following manner. BLAST searches of the *Arabidopsis* genome database were conducted for EST sequences encoding polypeptides having homology to amino acid sequences of *E. coli*, rat, and yeast ACSs. ESTs having homology to the ACS genes were then ordered from the *Arabidopsis* Biological Resource Center (ABRC, Ohio State University) and used to screen a 2–3 kb size selected library (also from the ABRC). Full-length cDNAs were cloned into pPCR-Script Cam vectors (Stratagene) or pYES2 vectors (Stratagene) and sequenced. The cloned sequences were verified by comparison to the corresponding nucleotide sequence in publicly available databases; discrepancies between the two sequences which resulted in an amino acid change in the encoded proteins were generally resolved by modifying the discrepant nucleotide in the cloned sequence to match that of the corresponding database nucleotide sequence.

Computer-assisted homology comparisons between known eukaryotic ACS sequences and the *Arabidopsis* sequences found either in library screens or in the public databases revealed more than 40 genes containing significant homology to known ACSs from other eukaryotic organisms. Each of these genes contained the AMP-binding protein signature motif, which is found in all ACS genes; therefore, these genes were considered "ACS homologs." However, the identification of ACS genes from this simple sequence analysis was not possible. This is because other groups of proteins also contain the AMP-binding protein signature motif; thus, while all ACSs are AMP-binding proteins, the reverse is not true. In addition to ACS, the AMP-BP superfamily also contains several other classes of genes, some of which, such as 4-coumarate-CoA ligases and acetyl-CoA synthetases, are known to exist in plants. Therefore, what was needed was a more definitive ACS-specific sequence determinate with which to identify more likely ACS candidate genes.

Previous studies identified a unique 40–50 amino acid insertion near the middle of ACS enzymes in *Brassica napus* ((Fulda, M et al. (1997) Plant Mol Biol 33(5): 911–22) and rat (Iijima, H. et al. (1996) Eur J Biochem 242(2): 186–90). Although the precise function of the insertion was unknown, evidence indicated that it might be a necessary component of eukaryotic ACS gene function. Moreover, both the length and the location of this insertion is quite closely conserved between the rapeseed and rat clones, spanning approximately amino acid residues 330 to 380 within proteins of about 660 amino acids total. This sequence insertion was also found in many other eukaryotic ACSs known to activate long-chain (C14–C20) fatty acids (Fujino and Yamamoto, 1992), (Johnson, DR et al. (1994) J Cell Biol 127(3): 751–62), (Kang, M J et al. (1997) Proc Natl Acad Sci USA 94(7): 2880–4), but it was not found in the VLCS genes (very long chain fatty acyl-CoA synthetases, acyl chains greater than C22) (Uchiyama, A et al. (1996) J Biol Chem 271(48): 30360–5), (Berger, J et al. (1998) FEBS Lett 425(2): 305–9), (Min, K T and Benzer, S (1999) Science 284(5422): 1985–8), (Choi, J Y and Martin, C E (1999) J Biol Chem 274(8): 4671–83), (Steinberg, S J et al. (1999) Biochem and Biophys Res Comm 257(2): 615–621). It was also not found in any of the acetyl-CoA synthetases ((Ke et al., 2000)) or 4-coumarate-CoA ligases ((Lee, M et al. (1995) Science 280(5365): 915–918), (Ehlting, J et al. (1999) Plant J 19(1): 9–20) that had been cloned from *Arabidopsis*. The maintenance of this sequence element in ACS genes from such evolutionarily distant species as *Brassica napus* and *Rattus norvegicus*, combined with its absence in genes that encode enzymes with specificity for short, or very long, but not long chain, fatty acids, suggested that this sequence element might be very useful as a long chain ACS-specific sequence "probe".

Therefore, the presence of this sequence element was used as a probe to analyze the entire set of *Arabidopsis* genes that contained the AMP-BP signature motif. Eleven of the forty uncharacterized genes, or ACS homologs, contained insertions near the predicted sites within the deduced amino acid sequences. These eleven genes were therefore tentatively identified as ACS genes.

The amino acid sequences of these genes were then compared by GAP analysis; the results (as shown in FIG. 1) established that each gene was unique. The results were also used as the basis for naming these genes. The genes are named AtACS for *Arabidopsis* thaliana acyl-CoA synthetase. The genes are numbered starting with the number 1. If a gene possesses greater than 66% amino acid identity to any other gene(s), the number is maintained between the genes and each is lettered progressively (1A, 1B, 1C etc.). A phylogenetic tree was constructed to visually compare the relationship between each of the candidate ACS genes. This tree is shown in FIG. 54. A summary of the information pertaining to each of the AtACS genes, including the corresponding EST sequences, is shown in Table 1.

TABLE 1

AtACS Gene Information Summary

| Gene Name | Genbank Accession # | Chromosome/Genomic clone/MIPS protein entry | Corresponding Ests (Genbank Accession #s) |
|---|---|---|---|
| AtACS1A | | Chromosome 4 BAC clone T32A16 At4g23850 | AV564087, AV554986, N38362, T45466, AA597813, N65639, T20845 |
| AtACS1B | | Chromosome 4 BAC clone T22B4 At4g11030 | * |
| AtACS1C | | Chromosome 1 BAC clone F15H21 At1g64400 | AI992650, AI999263, AV536372, T43231, AA395246, H77181, H76835 |
| AtACS2 | | Chromosome 1 BAC clone F13F21 At1g49430 | AV524574, AV527146, AV563196, |

TABLE 1-continued

AtACS Gene Information Summary

| Gene Name | Genbank Accession # | Chromosome/Genomic clone/MIPS protein entry | Corresponding Ests (Genbank Accession #s) |
|---|---|---|---|
| AtACS3A | | Chromosome 3<br>BAC clone F2O10<br>At3g05970 | AV518034,<br>AV542593,<br>AV560461,<br>AV522512,<br>N65171,<br>AV520714,<br>AV558696,<br>AV559865,<br>AV527730,<br>BE526116,<br>AV531977,<br>AV521092<br>AV551395,<br>AV563566,<br>H76931 |
| AtACS3B | | Chromosome 5<br>BAC clone F15A18<br>At5g227600 | AV548579,<br>AI994483,<br>AA586273,<br>T20754,<br>T44244,<br>BG459477,<br>BG459383 |
| AtACS4A | | Chromosome 4<br>BAC clone ATFCA0<br>At4g14070 | AI999282 |
| AtACS4B | | Chromosome 3<br>BAC clone MYM9<br>At3g23790 | * |
| AtACS5 | | Chromosome 2<br>BAC clone T813<br>At2g47240 | AV559619,<br>AV565921,<br>AI995760,<br>AV563860,<br>AV560369,<br>AV558313,<br>AV563291,<br>BE522084,<br>AV556901,<br>AV538317,<br>AV550568,<br>BE529524,<br>AV529145,<br>Z26001,<br>BE522229,<br>BE525438,<br>BE524235,<br>BE529120,<br>BE530866,<br>BE530784 |
| AtACS6A | | Chromosome 2<br>BAC clone T103<br>At2g04350 | AV526744,<br>AV552610,<br>N96529,<br>T13791 |
| AtACS6B | | Chromosome 1<br>BAC clone T5M16<br>At1g77590 | AI992417,<br>AV556982,<br>AV539306,<br>AV541829,<br>BE525296,<br>AV567096,<br>H76796,<br>AV551722,<br>H76865,<br>BE522855 |

The ACS genes were isolated generally as follows (greater detail is provided in Example 1):

AtAMP-BP3 (SEQ ID NO: 25), AtACS3A (SEQ ID NO: 5), and AtACS 6A (SEQ ID NO: 10) were isolated from the library based on homology to ESTs FAFM13, 205M6T7, and G2B10T7, respectively.

cDNAs corresponding to AtACS2 (SEQ ID NO: 4), AtACS6B (SEQ ID NO:11), AtACS5 (SEQ ID NO: 9) were cloned from the library based on homology to ESTs 229E14T7, 203J11T7, and GbGe115a, respectively. The 5' ends of the cDNAs were not present in the isolated clones and were cloned by 5' RACE amplifications with total phage DNA isolated from the cDNA library.

cDNAs corresponding to AtACS3B (SEQ ID NO:6), AtACS1A (SEQ ID NO:1), and AtACS1C (SEQ ID NO: 3) were cloned from the genomic library based on homology to ESTs 123N12T7, 240K22T7, and 119E14T7, respectively. Full length cDNAs were amplified using primers designed from the genomic sequences. Corresponding cDNA clones were apparently not present in the cDNA library.

AtACS1B (SEQ ID NO:2) was identified by a BLAST search from the *Arabidopsis* Genome Initiative database as a homologous sequence to AtACS 1A and 1C. Primers designed to the putative start and stop codons amplify an appropriately sized product from genomic DNA and also amplify a cDNA clone when utilized for RT-PCR. The amplified clone was longer than the predicted cDNA.

AtACS4A (SEQ ID NO:7), which was originally named AMP-BP3 and later correctly identified as AtACS4A, was identified from the *Arabidopsis* databases using the sequence of the *Brassica* AMP-BP clone pMF28P (Genbank Accession #Z72151).

AtACS4B (SEQ ID NO:8) was found in the *Arabidopsis* database by homology to AtACS4A.

The sequences obtained for the cloned ACS genes were subsequently compared to sequences contained in the public databases by BLAST searches. This comparison was a control step, undertaken because it had been commonly observed that many commercial brands of Taq polymerase used for the amplification step in PCR appear to introduce errors at a significantly high frequency. The frequency of errors introduced by PCR was considered greater than what would be expected to occur in the public database sequences, which are considered to be highly accurate, though probably not completely error-free. Discrepancies between the sequence of any particular clone and its corresponding sequence in a public database were generally assumed to be an error in the clone sequence. If the discrepancy resulted in a silent change, or in other words correcting the cloned sequence to match the sequence in the public database resulted in a nucleotide change that did not result in a change in the encoded amino acid sequence of the clone, no repairs were generally deemed necessary or usually made to the cloned sequence. If the discrepancy did result in a change in the encoded amino acid sequence of the clone, in most cases the sequence of the clone was modified to match that of the sequence in the public database. When a particular ACS cDNA sequence was modified to encode an amino sequence which matched that encoded by the corresponding nucleotide sequence in a public database, it is contemplated that both the original cDNA sequence and the modified cDNA sequence encode ACS. When a particular ACS cDNA sequence differed from its corresponding nucleotide sequence in a public database and where both sequences encode the same amino acid sequence, it is contemplated that both cDNA sequences are equivalent.

As described above, ACSs bear strong homology to other AMP-binding proteins. Therefore, it was necessary to screen candidate ACS genes to determine if they did indeed encode ACS activity. The screens were conducted by screening for complementation of the mutant *Saccharomyces cerevisiae* strain YB525 (Johnson et al., (1994) J. Cell. Biol. 127: 751–762), which is deficient in two ACS genes. In some cases, cDNAs originally suspected of encoding ACS activity were found not to be true ACSs (e.g., AtAMP-BP 1, SEQ ID NO:23, and AtAMP-BP3, SEQ ID NO: 25).

Accordingly, the present invention provides nucleic acids encoding plant ACSs (e.g., such as the nucleic acid sequences SEQ ID NOs: 1–11 and 121–127, as shown in FIGS. 3–13 and 58–64, or which encode amino acid sequences SEQ ID NOS: 12–22 and 128–132, as shown in FIGS. 14–24 and 65–69). Other embodiments of the present invention provide nucleic acid sequences that are capable of hybridizing to SEQ ID NOs: 1–11 and 121–127 under conditions of high to low stringency. In some embodiments, the hybridizing nucleic acid sequence encodes a protein that retains at least one biological activity of the naturally occurring ACS it is derived from. In preferred embodiments, hybridization conditions are based on the melting temperature ($T_m$) of the nucleic acid binding complex and confer a defined "stringency" as explained above.

In other embodiments of the present invention, variants of the disclosed ACSs are provided. In preferred embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence. Non-limiting examples of variants are given in Table 2.

It is contemplated that is possible to modify the structure of a peptide having an activity (e.g., ACS activity) for such purposes as increasing synthetic activity or altering the affinity of the ACS for a particular fatty acid substrate. Such modified peptides are considered functional equivalents of peptides having an activity of an ACS as defined herein. A modified peptide can be produced in which the nucleotide sequence encoding the polypeptide has been altered, such as by substitution, deletion, or addition. In some preferred embodiments of the present invention, the alteration increases synthetic activity or alters the affinity of the ACS for a particular fatty acid substrate. In particularly preferred embodiments, these modifications do not significantly reduce the synthetic activity of the modified enzyme. In other words, construct "X" can be evaluated in order to determine whether it is a member of the genus of modified or variant ACSs of the present invention as defined functionally, rather than structurally. In preferred embodiments, the activity of variant ACSs is evaluated by the methods described in Examples 4 and 5. Accordingly, in some embodiments the present invention provides nucleic acids encoding plant acyl-CoA synthetases that complement yeast strain YB525. In other embodiments, the present invention provides nucleic acids encoding plant acyl-CoA synthetases that compete for the binding of fatty acid substrates with the proteins encoded by SEQ ID NOs: 1–11 and 121–127.

Moreover, as described above, variant forms of ACSs are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ACSs disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur -containing (cysteine and methionine) (e.g., Stryer ed., *Biochemistry*, pg. 17–21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter an ACS coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

B. ACS Polypeptides

The family of ACS genes provided by the present invention represents a very diverse group of genes, as indicated by the results of the ACS amino acid sequence analysis summarized in FIG. 1 and Table 1. While half of the gene family members are nearly identical in length (approximately 665 amino acids) (AtACS1A, 1B, 1C, 2, and 5), the other half all contain N-terminal extensions of between about 30 and 60 amino acid residues (AtACS3A, 3B, 4A, 4B, 6A, and 6B). As a group, the family of genes share only 30% identical amino acids and is clearly delineated into several distinct subgroupings. The number of ESTs associated with each of the ACS genes also varied considerably, with some genes represented by numerous ESTs and others not represented at all. Collectively, these observations support the biochemical evidence tabulated from previous reports that the ACS gene family is responsible for providing acyl-CoA substrates for a number of distinct metabolic pathways that are carried out under conditions that vary considerably with respect to tissue type, cell type, and organelle, with varied levels of demand upon particular isoforms compared to others. It is interesting to note that all of the ACS amino acid sequences appear to lack a typical plastidial targeting consensus sequence, yet subsequent analysis has demonstrated that at least some of these ACSs can be imported into the chloroplast, and at least one ACS may be associated with the chloroplast envelope membranes (see Example 8).

The degree of conservation of the deduced amino acid sequences of and around the insertional elements of each ACS gene of the present invention were also compared. The results of this comparison are shown in FIG. 2. The residues corresponding to the predicted borders of the insertional element are numbered and denoted with arrows. These residues were determined by comparing the sequences of the candidate ACS genes to those of the other AMP-BP genes that were identified in the original data base screen and which lacked the insertional element. For clarity, FIG. 2 displays only the first few amino acid residues that flank the upstream and downstream borders of the insertional region. Taking into account the N-terminal extensions present in some of the ACS genes, the comparison of the insertional element sequences confirmed the conservation of location of this element within the open reading frames of all members of this set of genes. The homology between the entire set of full-length insertional elements is quite weak, displaying approximately 30% identical amino acids between all eleven genes, which closely matches the degree of conservation between the eleven full-length proteins. Surprisingly, the regions immediately flanking the insertional element are highly conserved across the whole family of eleven candidate ACS genes (see FIG. 2). These data suggest that amino acid residues encoded by the insertional element are necessary for proper ACS function in the plant, with the residues in the middle of the element evolving with the rest of the gene to diversify and specialize the enzymatic function of each gene, while the residues near the borders of the element constitute a more invariable region of the enzyme that is essential to the core reaction.

Accordingly, the present invention also provides ACS polypeptides (e.g., SEQ ID NOs: 12–22 and 128–132 as shown in FIGS. 14–24 and 65–69), and compositions comprising purified ACS polypeptides. Still further embodiments of the present invention provide fragments, fusion proteins or functional equivalents of ACSs. Functional equivalents of ACSs may be screened in assays, such as are described in Examples 4 and 5. In still other embodiments of the present invention, nucleic acid sequences corresponding to a selected ACS may be used to generate recombinant DNA molecules that direct the expression of an ACS and variants in appropriate host cells. In some embodiments of the present invention, the polypeptide may be a naturally purified product, while in other embodiments it may be a product of chemical synthetic procedures, and in still other embodiments it may be produced by recombinant techniques using a prokaryotic or eukaryotic host cell (e.g., by bacterial cells in culture). In other embodiments, the polypeptides of the invention may also include an initial methionine amino acid residue.

In some embodiments of the present invention, due to the inherent degeneracy of the genetic code, DNA sequences other than SEQ ID NOs: 1–11 and 121–127 encoding substantially the same or a functionally equivalent amino acid sequence, may be used to clone and express an ACS. In general, such nucleic acid sequences hybridize to SEQ ID NOs: 1–11 and 121–127 under conditions of high to low stringency as described above. As will be understood by those of skill in the art, it may be advantageous to produce ACS-encoding nucleotide sequences possessing non-naturally occurring codons. Therefore, in some preferred embodiments, codons preferred by a particular prokaryotic or eukaryotic host are selected, for example, to increase the rate of ACS expression or to produce recombinant RNA transcripts having desirable properties, such as increased synthetic activity or altered affinity of the ACS for a particular fatty acid substrate.

II. Uses of ACS Polynucleotides and Polypeptides

1. Vectors for Expression of ACSs

In some embodiments of the present invention, the ACS nucleic acids are used to construct vectors for the expression of ACS polypeptides. Accordingly, the nucleic acids of the present invention may be employed for producing polypeptides by recombinant techniques. Thus, for example, the nucleic acid may be included in any one of a variety of expression vectors for expressing a polypeptide.

In some embodiments of the present invention, vectors are provided for the transfection of plant hosts to create transgenic plants. In general, these vectors comprise an ACS nucleic acid (e.g., SEQ ID NOs: 1–11 and 121–127) operably linked to a promoter and other regulatory sequences (e.g., enhancers, polyadenylation signals, etc.) required for expression in a plant. The ACS nucleic acid can be oriented to produce sense or antisense transcripts, depending on the desired use. In some embodiments, the promoter is a constitutive promoter (e.g., superpromoter or SD promoter). In other embodiments, the promoter is a seed specific promoter (e.g., phaseolin promoter [See e.g., U.S. Pat. No. 5,589,616, incorporated herein by reference], napin promoter [See e.g., U.S. Pat. No. 5,608,152, incorporated herein by reference], or acyl-CoA carrier protein promoter [See e.g., U.S. Pat. No. 5,767,363, incorporated herein by reference]).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

It may be desirable to target the nucleic acid sequence of interest to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

The nucleic acids of the present invention may also be utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted ACS polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

Alternatively, vectors can be constructed for expression in hosts other plants (e.g., prokaryotic cells such as *E. coli*, yeast cells, *C. elegans*, and mammalian cell culture cells). In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). Large numbers of suitable vectors that are replicable and viable in the host are known to those of skill in the art, and are commercially available. Any other plasmid or vector may be used as long as they are replicable and viable in the host.

In some preferred embodiments of the present invention, bacterial expression vectors comprise an origin of replication, a suitable promoter and optionally an enhancer, and also any necessary ribosome binding sites, polyadenylation sites, transcriptional termination sequences, and 5' flanking nontranscribed sequences. Promoters useful in the present invention include, but are not limited to, retroviral LTRs, SV40 promoter, CMV promoter, RSV promoter, *E. coli* lac or trp promoters, phage lambda $P_L$ and $P_R$ promoters, T3, SP6 and T7 promoters. In other embodiments of the present invention, recombinant expression vectors include origins of replication and selectable markers, (e.g., tetracycline or ampicillin resistance in *E. coli*, or neomycin phosphotransferase gene for selection in eukaryotic cells).

2. Expression of ACSs in Transgenic Plants

Vectors described above can be utilized to express the ACSs of the present invention in transgenic plants. A variety of methods are known for producing transgenic plants.

In some embodiments, *Agrobacterium* mediated transfection is utilized to create transgenic plants. Since most dicotyledonous plant are natural hosts for *Agrobacterium*, almost every dicotyledonous plant may be transformed by *Agrobacterium* in vitro. Although monocotyledonous plants, and in particular, cereals and grasses, are not natural hosts to *Agrobacterium*, work to transform them using *Agrobacterium* has also been carried out (Hooykas-Van Slogteren et al. (1984) Nature 311:763–764). Plant genera that may be transformed by *Agrobacterium* include *Arabidopsis, Chrysanthemum, Dianthus, Gerbera, Euphorbia, Pelaronium,* *Ipomoea, Passiflora, Cyclamen, Malus, Prunus, Rosa, Rubus, Populus, Santalum, Allium, Lilium, Narcissus, Ananas, Arachis, Phaseolus* and *Pisum*.

For transformation with *Agrobacterium*, disarmed *Agrobacterium* cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference). The nucleic acid sequence of interest is then stably integrated into the plant genome by infection with the transformed *Agrobacterium* strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467–486).

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be transformed by *Agrobacterium* and (b) that the transformed cells or tissues can be induced to regenerate into whole plants. The third method is transformation of seeds, apices or meristems with *Agrobacterium*. This method requires micropropagation.

One of skill in the art knows that the efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., (1987) Plant Molec. Biol. 8:291–298). Alternatively, transformation efficiency may be enhanced by wounding the target tissue to be transformed. Wounding of plant tissue may be achieved, for example, by punching, maceration, bombardment with microprojectiles, etc. (See e.g., Bidney et al., (1992) Plant Molec. Biol. 18:301–313).

In still further embodiments, the plant cells are transfected with vectors via particle bombardment (i. e., with a gene gun). Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Plants, plant cells and tissues transformed with a heterologous nucleic acid sequence of interest are readily detected using methods known in the art including, but not limited to, restriction mapping of the genomic DNA, PCR-analysis, DNA-DNA hybridization, DNA-RNA hybridization, DNA sequence analysis and the like.

Additionally, selection of transformed plant cells may be accomplished using a selection marker gene. It is preferred, though not necessary, that a selection marker gene be used to select transformed plant cells. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methothrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the Ti-plasmid of *Agrobacterium*, the tk-gene from SV40, cytochrome P450 from *Streptomyces griseolus*, the Adh-gene from Maize or *Arabidopsis*, etc. Any gene encoding an enzyme capable of converting a substance which is otherwise harmless to plant cells into a substance which is harmful to plant cells may be used.

It is contemplated that the ACS polynucleotides of the present invention may be utilized to either increase or decrease the level of ACS mRNA and/or protein in transfected cells as compared to the levels in wild-type cells. Accordingly, in some embodiments, expression in plants by the methods described above leads to the over-expression of ACS in transgenic plants, plant tissues, or plant cells. The present invention is not limited to any particular mechanism. Indeed, an understanding of a mechanism is not required to practice the present invention. However, it is contemplated that over-expression of the ACS polynucleotides of the present invention will overcome limitations in the accumulation of fatty acids in oilseeds.

In other embodiments of the present invention, the ACS polynucleotides are utilized to decrease the level of ACS protein or mRNA in transgenic plants, plant tissues, or plant cells as compared to wild-type plants, plant tissues, or plant cells. One method of reducing ACS expression utilizes expression of antisense transcripts. Antisense RNA has been used to inhibit plant target genes in a tissue-specific manner (e.g., van der Krol et al (1988) Biotechniques 6:958–976). Antisense inhibition has been shown using the entire cDNA sequence as well as a partial cDNA sequence (e.g., Sheehy et al (1988) Proc. Natl. Acad. Sci. USA 85:8805–8809; Cannon et al. (1990) Plant Mol. Biol. 15:39–47). There is also evidence that 3' non-coding sequence fragment and 5' coding sequence fragments, containing as few as 41 base-pairs of a 1.87 kb cDNA, can play important roles in antisense inhibition (Ch'ng et al. (1989)Proc. Natl. Acad. Sci. USA 86:10006–10010).

Accordingly, in some embodiments, the ACS nucleic acids of the present invention (e.g., SEQ ID NOs: 1–11 and 121–127, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes is described in Haseloff, et al., Nature 334:585–591 (1988).

Another method of reducing ACS expression utilizes the phenomenon of cosuppression or gene silencing (See e.g., U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al. (1990) Plant Cell 2:279–289; van der Krol et al. (1990) Plant Cell 2:291–299; Smith et al., (1990) Mol. Gen. Genetics 224: 477–481). Accordingly, in some embodiments the *Arabidopsis* ACS nucleic acids (e.g., SEQ ID NOs: 1–11 and 121–127, and fragments and variants thereof) are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are over-expressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

3. Other Host Cells and Systems for Production of ACSs

The present invention also contemplates that the vectors described above can be utilized to express plant ACS genes and variants in prokaryotic and eukaryotic cells. In some embodiments of the present invention, the host cell can be a prokaryotic cell (e.g., a bacterial cell). Specific examples of host cells include, but are not limited to, *E. coli, Salmonella typhimurium, Bacillus subtilis*, and various species within the genera *Pseudomonas, Streptomyces*, and *Staphylococcus*. The constructs in host cells can be used in a conventional manner to produce the gene product encoded by the recombinant sequence. In some embodiments, introduction of the construct into the host cell can be accomplished by any suitable method known in the art (e.g., calcium phosphate transfection, DEAE-Dextran mediated transfection, or electroporation (e.g., Davis et al. (1986) Basic Methods in Molecular Biology). Alternatively, in some embodiments of the present invention, the polypeptides of the invention can be synthetically produced by conventional peptide synthesizers.

In some embodiments of the present invention, following transformation of a suitable host strain and growth of the host strain to an appropriate cell density, the selected promoter is induced by appropriate means (e.g., temperature shift or chemical induction), and the host cells are cultured for an additional period. In other embodiments of the present invention, the host cells are harvested (e.g., by centrifugation), disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega; this cell-free system is described in U.S. Pat. No. 5,324,637, hereby incorporated by reference).

4. Purification of ACSs

The present invention also provides methods for recovering and purifying ACSs from native and recombinant cell cultures including, but not limited to, ammonium sulfate precipitation, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed as one or more purification steps.

In other embodiments of the present invention, the nucleic acid construct containing DNA encoding the wild-type or a variant ACS further comprises the addition of exogenous sequences (i.e., sequences not encoded by the ACS coding region) to either the 5' or 3' end of the ACS coding region to allow for ease in purification of the resulting polymerase protein (the resulting protein containing such an affinity tag is termed a "fusion protein"). Several commercially available expression vectors are available for attaching affinity tags (e.g., an exogenous sequence) to either the amino or carboxy-termini of a coding region. In general these affinity tags are short stretches of amino acids that do not alter the characteristics of the protein to be expressed (i.e., no change to enzymatic activities results).

For example, the pET expression system (Novagen) utilizes a vector containing the T7 promoter operably linked to a fusion protein with a short stretch of histidine residues at either end of the protein and a host cell that can be induced to express the T7 DNA polymerase (i.e., a DE3 host strain). The production of fusion proteins containing a histidine tract is not limited to the use of a particular expression vector and host strain. Several commercially available expression vectors and host strains can be used to express protein sequences as a fusion protein containing a histidine tract (e.g., the pQE series [pQE-8, 12, 16, 17, 18, 30, 31, 32, 40, 41, 42, 50, 51, 52, 60 and 70] of expression vectors (Qiagen) used with host strains M15[pREP4] [Qiagen] and SG13009 [pREP4] [Qiagen]) can be used to express fusion proteins containing six histidine residues at the amino-terminus of the fusion protein). Additional expression systems which utilize other affinity tags are known to the art.

Once a suitable nucleic acid construct has been made, the ACS may be produced from the construct. The examples below and standard molecular biological teachings known in the art enable one to manipulate the construct by a variety of suitable methods. Once the desired ACS has been expressed, the enzyme may be tested for activity as described Examples 4 and 5.

5. Deletion Mutants of ACSs

The present invention further provides fragments of ACSs. In some embodiments of the present invention, when expression of a portion of an ACS is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751–757) and *S. typhimurium*, and its in vitro activity has been demonstrated on recombinant proteins (Miller et al. (1990) PNAS 84:2718–1722). Therefore, removal of an N-terminal methionine, if desired, can be achieved either in vivo by expressing such recombinant polypeptides in a host producing MAP (e.g., *E. coli* or CM89 or *S. cerevisiae*), or in vitro by use of purified MAP. It is contemplated that deletion mutants of ACSs can be screened for activity as described above.

6. Use of ACS Nucleic Acids in Directed Evolution

It is contemplated that the ACS nucleic acids (e.g., SEQ ID NOs: 1–11 and 121–127, and fragments and variants thereof) can be utilized as starting nucleic acids for directed evolution. These techniques can be utilized to develop ACS variants having desirable properties such as increased synthetic activity or altered affinity for a particular fatty acid substrate.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458–67; Leung et al. (1998)Technique, 1:11–15; Eckert and Kunkel (1991) PCR Methods Appl., 1:17–24; Caldwell and Joyce (1992) PCR Methods Appl., 2:28–33; and Zhao and Arnold (1997) Nuc. Acids. Res., 25:1307–08). After mutagenesis, the resulting clones are selected for desirable activity (e.g., screened for ACS activity as described above). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370:324–25; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNAse treatment, the staggered extension process (STEP), and random priming in vitro recombination. In the DNAse mediated method, DNA segments isolated from a pool of positive mutants are cleaved into random fragments with DNAseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398–91; Stemmer, (1994) Proc. Natl. Acad. Sci. USA, 91, 10747–51; Crameri et al (1996) Nat. Biotech., 14:315–19; Zhang et al. (1997) Proc. Natl. Acad. Sci. USA, 94:4504–09; and Crameri et al. (1997) Nat. Biotech., 15:436–38). Variants produced by directed evolution can be screened for ACS activity by the methods described in Examples 4 and 5.

In further embodiments of the present invention, other combinatorial mutagenesis approaches are applied. For example, the amino acid sequences for a population of ACS homologs or other related proteins can be aligned, preferably to promote the highest homology possible. Such a population of variants can include, for example, ACS homologs from one or more species, or ACS homologs from the same species but which differ due to mutation. Amino acids appearing at each position of the aligned sequences are selected to create a degenerate set of combinatorial sequences.

In a preferred embodiment of the present invention, the combinatorial ACS library is produced by way of a degenerate library of genes encoding a library of polypeptides including at least a portion of potential ACS-protein sequences. For example, a mixture of synthetic oligonucleotides are enzymatically ligated into gene sequences such that the degenerate set of potential ACS sequences are expressible as individual polypeptides, or alternatively, as a set of larger fusion proteins (e.g., for phage display) containing the set of ACS sequences therein.

There are many ways in which the library of potential ACS homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ACS sequences. The synthesis of degenerate oligonucleotides is well known in the art (e.g., Narang, Tetrahedron 39:39, 1983; Itakura et al. (1981) Recombinant DNA, Proc 3rd Cleveland Sympos. Macromol., Walton, ed., Elsevier, Amsterdam, pp 273–289; Itakura et al. (1984) Annu. Rev. Biochem. 53:323; Itakura et al. (1984) Science 198:1056; and Ike et al. (1983) Nucleic Acid Res. 11:477). Such techniques have been employed in the directed evolution of other proteins (e.g., Scott et al. (1980) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815, each of which is incorporated herein by reference).

A wide range of techniques are known in the art for screening gene products of combinatorial libraries generated by point mutations, and for screening cDNA libraries for gene products having a particular property of interest. Such techniques are generally adaptable for rapid screening of gene libraries generated by the combinatorial mutagenesis of ACS homologs. The most widely used techniques for screening large gene libraries typically comprise cloning the gene library into replicable expression vectors, transforming appropriate cells with the resulting library of vectors, and expressing the combinatorial genes under conditions such that detection of a desired activity facilitates relatively easy isolation of the vector encoding the gene whose product was detected. The illustrative assays described below are amenable to high through-put analysis as necessary to screen large numbers of degenerate sequences created by combinatorial mutagenesis techniques.

In some embodiments of the present invention, the gene library is expressed as a fusion protein on the surface of a viral particle. For example, foreign peptide sequences can be expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of viral replication. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (e.g., WO 90/02909; WO 92/09690; Marks et al. (1992) J. Biol. Chem., 267:16007–16010; Griffths et al. (1993) EMBO J., 12:725–734; Clackson et al. (1991) Nature, 352:624–628; and Barbas et al. (1992) PNAS 89:4457–4461).

In another embodiment of the present invention, the recombinant phage antibody system (e.g., RPAS, Pharmacia Catalog number 27-9400-01) is modified for use in expressing and screening ACS combinatorial libraries. The pCANTAB 5 phagemid of the RPAS kit contains the gene encoding the phage gIII coat protein. In some embodiments of the present invention, the ACS combinatorial gene library is cloned into the phagemid adjacent to the gIII signal sequence such that it will be expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate ACS gene insert. The resulting recombinant phage contain phagemid DNA encoding a specific candidate ACS-protein and display one or more copies of the corresponding fusion coat protein. In some embodiments of the present invention, the phage-displayed candidate proteins that are capable of, for example, binding a particular acyl-CoA, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning greatly enriches for ACS homologs, which are then screened for further biological activities.

In light of the present disclosure, other forms of mutagenesis generally applicable will be apparent to those skilled in the art in addition to the aforementioned rational mutagenesis based on conserved versus non-conserved residues. For example, ACS homologs can be generated and screened using, for example, alanine scanning mutagenesis, linker scanning mutagenesis, or saturation mutagenesis.

7. Chemical Synthesis of ACS Polypeptides

In an alternate embodiment of the invention, the coding sequence of an ACS is synthesized, whole or in part, using chemical methods well known in the art (e.g., Caruthers et al. (1980) Nuc. Acids Res. Symp. Ser., 7:215–233; Crea and Horn (1980) Nuc. Acids Res., 9:2331; Matteucci and Caruthers (1980) Tetrahedron Lett., 21:719; and Chow and Kempe (1981) Nuc. Acids Res., 9:2807–2817). In other embodiments of the present invention, the protein itself is produced using chemical methods to synthesize either a full-length ACS amino acid sequence or a portion thereof. For example, peptides can be synthesized by solid phase techniques, cleaved from the resin, and purified by preparative high performance liquid chromatography (e.g., Creighton, *Proteins Structures and Molecular Principles*, W H Freeman and Co, New York N.Y., 1983). In other embodiments of the present invention, the composition of the synthetic peptides is confirmed by amino acid analysis or sequencing (e.g., Creighton, supra).

Direct peptide synthesis can be performed using various solid-phase techniques (Roberge et al., Science 269:202–204, 1995) and automated synthesis may be achieved, for example, using ABI 431 A Peptide Synthesizer (Perkin Elmer) in accordance with the instructions provided by the manufacturer. Additionally, the amino acid sequence of an ACS, or any part thereof, may be altered during direct synthesis and/or combined using chemical methods with other sequences to produce a variant polypeptide.

III. Identification of Other Acyl-CoA Synthetase Homologs

As described above, plant ACSs are members of a larger family of AMP-binding proteins (AMP-BPs). Therefore, methods for discriminating between AMP-BPs and true ACSs are desirable. FIG. 1 provides an amino acid comparison of the ACSs of the present invention (SEQ ID NOs:12–22) and ten putative *Arabidopsis* AMP-binding proteins (SEQ ID NOs: 33–42). The AMP-BP sequences were determined by BLAST searches of the TAIR database (The *Arabidopsis* Information Resource; http://www.arabidopsis1.org/blast/) with ACS sequences. Most of the AMP-BP sequences were identified as BAC hits. The presumed cDNA sequences for these were deduced by homology comparisons to the ACSs and other AMP-BPs using GCG (Genetic Computer Group, Madison, Wis.). The sequences were then aligned using Pileup (Genetic Computer Group, Madison, Wis.) and shaded using the Boxshade server. The AMP-BP genes have also been isolated and sequenced, as described below (see Example 2).

This comparison led to the identification of at least nine conserved motifs in ACS, which are described in more detail below. Of these nine motifs, some are conserved between ACSs and AMBPS, while others are conserved only in ACSs; other motifs are conserved only in AMP-BPs, but these are not included in the nine motifs. The motifs are numbered from 1 to 9, in going from the amino to the carboxy terminal of the proteins. Where more than one amino acid occurs at a particular position in a motif, the most common amino acid is listed first, followed by less common amino acids, separated by a slash, which indicates that these amino acids occupy the same position in the motif. If more than four different amino acids occupy the same position, the position is indicated by an "X", with the amino acids which occur at that position listed at the end of the sequence. Accordingly, in some embodiments, the present invention provides plant ACSs comprising at least one of ACS motifs 1–9, or nucleic acid sequences encoding such plant ACSs.

ACS motif 1 (FIG. 45; SEQ ID NO:43, V-P/T-L/I-Y-D/A/S-T/S-L-G) is present in ACSs and absent in AMP-BPs. A second motif, ACS motif 2 (FIG. 46; SEQ ID NO:44, I-MIC-Y/F/K-T-S-G-T/S-T/S-G-$X_1$-P-K-G-V, where $X_1$ is D, L, T, N, or E) is similar in both ACSs and AMP-BPs. A motif found in both ACSs and AMP-BPs is well known (PROSITE PS00455=[LIVMFY]-X2-[STG]-[STAG]-G-[ST]-[STEI]-[SG]-X-[PASLIVM]-[KR]) SEQ ID NO:133, is very highly conserved, and acts as the unifying feature of the AMP-binding protein (AMP-BP) superfamily (Babbitt PC et al. (1992) Biochemistry 31(24): 5594–604; Fulda M et al. (1994) Mol Gen Genet 242(3): 241–9) to which ACS belongs. However, the sequence shown, SEQ ID NO:44, is specific to ACSs alone, as the similar motif in ACSs differs slightly from that in AMP-BPs, particularly in amino positions 1, 2, 9, and 10 of motif 2. ACS motif 3 (FIG. 47; SEQ ID NO:45, S/A-Y/M/F-L-P-L/S-A/W-H) is present in ACSs and absent in AMP-BPs. ACS motif 4 (FIG. 48; SEQ ID NO:46; L/Q-K/R-P-T/P/S) is present in ACSs and absent in AMP-BPs. ACS motif 5 (FIG. 49; SEQ ID NO:47, S/G/V-G-A/G/S-A/L/S-P-L/I/M) is present in ACSs and absent in AMP-BPs. ACS motif 6 (FIG. 50; SEQ ID NO:48, G-Y-G-L/M-T-E-T/S) is present in both ACSs and AMP-BPs. Note that only G occupies the first position in ACSs, while several different amino acids occupy this position in AMP-BPs. ACS motif 7 (FIG. 51; SEQ ID NO:49, P/S/A-R/K-G/A-E/I-I/V-C/K/V-I/V/L-R/G-G) is present in ACSs and is absent in AMP-BPs. ACS motif 8 (FIG. 52; SEQ ID NO:50, I-I-D-R-K-K) is present in ACSs, except AtACS4A and AtACS4B, and absent in AMP-BPs. The 25 amino acid consensus sequence (SEQ ID NO:109) shown at the top of FIG. 52 is a consensus sequence derived from several genes (for example, from *E. coli*, yeast, and human) which are known to bind fatty acids; this 25 amino acid sequence is implicated in fatty acid binding in *E. coli* genes, based upon experiments in which mutagenesis of 15 of the 25 amino acids resulted in absent or different specificity fatty acid binding (Black, PN (1997) J Biol Chem 272: 4896–4903). ACS motif 9 (FIG. 53; SEQ ID NO:51, L-L/V/M/I-T-P/A-T/A/S-F/L/M/Y-K-$X_1$-K/R-R, where $X_1$=I, K, M, N, or L) is present in ACSs and absent in AMP-BPs.

It is contemplated that the sequences described herein can be utilized to clone and characterize ACS homologs from other species of plants. Accordingly, in some embodiments, the ACS nucleic acids or fragments thereof are utilized to screen cDNA or genomic libraries prepared from the RNA or DNA of another plant species. In other embodiments, primers that are completely or partially complementary to portions of SEQ ID NOs:1–11 and 121–127 are utilized to amplify ACS homologs from nucleic acid isolated from other plant species. For example, degenerate primers may be utilized to amplify ACS homologs for genomic DNA samples or cDNA samples from other species. Alternatively, RT-PCR may be utilized to directly amplify homologs from RNA isolated from other species.

It is also contemplated that the sequences described herein (e.g., both nucleic acid and polypeptide sequences, SEQ ID NOs: 1–22 and 121–132), may be utilized to search computer databases for homologous sequences from other species. For example, BLAST searches (Altshul et al. (1997) Nucleic Acids Res. 25:3389–3402; http://www.ncbi.nlm.nih.gov/blast) may be utilized to search for nucleic acids and proteins having homology (e.g., greater than 60%, 70%, 80%, or 90%) to SEQ ID NOs:1–22 and 121–132.

In some embodiments, nucleic acids suspected of being ACS homologs are screened by comparing motifs. In some embodiments, the protein sequence can be analyzed for the presence or absence of one or more of ACS motifs 1–9 (SEQ ID NOs: 43–51, respectively). The presence or absence of these motifs indicates that the candidate ACS is a true ACS. In still further embodiments, the nucleic acids can be utilized in genetic screens for ACS activity. For example, the nucleic acids can be analyzed for complementation of the mutant *S. cerevisiae* strain YB525. In other embodiments, the nucleic acids can be expressed and analyzed for complementation or biochemical activity as described in Example 4 and 5.

Within the ACS group, AtACS4A and AtACS4B are somewhat divergent from the other ACS genes. This conclusion is based upon the observation that in motifs 3, 4, 5 and 7, the amino acids for AtACS4A and AtACS4B are likely to be different from those of the other ACSs, yet these different amino acids are generally identical to each other in AtACS4A and AtACS4B. This conclusion is also supported by the observation that AtACS4A and AtACS4B do not contain motif 8. Moreover, this conclusion is also supported by the inability to observe ACS enzyme activity, either by complementation or by an in vitro assay, with these two clones (see Examples 4 and 5). Yet these two genes are more closely related to the ACSs than to any of the other genes in the superfamily. It is possible that these genes encode ACSs that activate specialized substrates, or are inactive under the conditions used in these experiments due to special requirements, such as folding or multimer formation requirements, or the need for post-translational modifications not met by the cellular machinery of *Saccharomyces cerevisiae*. Alternatively, these genes may encode a different type of enzyme related to ACS. For example, in yet another possibility, it is contemplated that these two enzymes are acyl-ACP synthetases. This function can be examined by over-expressing the ACS4A and ACS4B in yeast, and then assaying yeast extract for acyl ACP synthase activity, in a manner similar to that described in Examples 4 and 5, in which ACP is used as a substrate instead of CoA.

IV. AMP Binding Proteins

A construction of the phylogenetic relationship between all 44 members of the *Arabidopsis* AMP-BP superfamily revealed several interesting phenomenon. Only three genes (At3g16170, At3g48990, and At1g30520) align independently, while the other 41 members of the superfamily separate into three main groups: The ACS subfamily; a subfamily containing the three known 4-coumarate-CoA ligases plus ten other related genes; and a subfamily of fourteen previously unknown genes.

The discovery of the third subfamily was unexpected. This subfamily as a whole was more closely related than the other two groups, containing at least 42% amino acid identity, while bearing weak and roughly equal homology (approximately 20–25% amino acid identity) to the ACS, acetyl-CoA synthetase, and 4-coumarate-CoA ligase genes. Searches of all public databases revealed that higher plants (including rice and *Brassica* sp.) are the only organisms that contain genes highly homologous to those of this third subfamily. This subfamily thus represents a unique class of enzymes that may play a specialized role in a plant-specific aspect of carboxylic acid activation. It is also possible that this subfamily represents a functionally equivalent but structurally unrelated counterpart to the ACS subfamily.

In order to characterize this subfamily of genes, full-length cDNAs for ten of the fourteen members of this subfamily were cloned into pYES2 and transformed into *Saccharomyces cerevisiae* YB525, as described in the following examples (see particularly Examples 1–5). These constructs were used in the complementation and in vitro enzyme activity analyses, exactly as described for the ACS genes in the following examples. In the complementation assays, the genes of the AtAMP-BP subfamily were unable to activate exogenous myristic acid, and all ten genes were therefore unable to complement the YB525 phenotype. In the in vitro enzyme assays, cell-free lysates prepared from these transformed yeast lines containing one of these ten genes were also inactive against oleic acid in the in vitro enzyme assays.

These data do not rule out the possibility that the genes of this group are ACSs. In fact, the phylogenetic analysis of the AMP-BP superfamily as a whole supports the hypothesis that these genes catalyze the coenzyme A-dependent activation of some type of carboxylic acid, given the fact that each of the other classes in the phylogenetic tree contain representative genes that do exactly that. It is contemplated that AMP-BPs are very long chain ACSs. Medium chain- or very long chain-CoA synthetases have been characterized in other organisms ((Min and Benzer (1999) Science 284 (5422): 1985–8). While medium-chain fatty acids are very rare in *Arabidopsis* ((Ohlrogge and Browse (1995) Plant Cell 7(7): 957–70), a critical role for very long chain acyl groups is obvious. Very long chain fatty acids (longer than C24) are the substrates for the biosynthesis of the complex mixture of esters, alcohols, ketones, aldehydes, and alkanes that make the cuticular wax layer present on the surface of plants. Cuticular waxes also play essential roles in plant fertility and insect defense ((Preuss, D et al. (1993) Genes Dev 7(6): 974–85). This function can be examined by over-expressing the AMP-BPs in yeast, and then assaying yeast extract for very long chain ACS activity, in a manner similar to that described in Examples 4 and 5.

EXAMPLES

The following examples serve to illustrate certain preferred embodiments and aspects of the present invention and are not to be construed as limiting the scope thereof.

In the disclosure which follows, the following abbreviations apply: M (molar); mM (millimolar); µM (micromolar); nM (nanomolar); mol (moles); mmol (millimoles); µmol (micromoles); nmol (nanomoles); grn (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade); ATP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (National Institutes of Health, Besthesda, MD); RNA (ribonucleic acid); PBS (phosphate buffered saline); g (gravity); OD (optical density); HEPES (N-[2-Hydroxyethyl]piperazine-N-[2-ethanesulfonic acid]); SDS (sodium dodecylsulfate); Tris-HCl (tris[Hydroxymethyl] aminomethane-hydrochloride); rpm (revolutions per minute); EDTA (ethylenediaminetetracetic acid); bla (β-lactamase or ampicillin-resistance gene); ORI (plasmid origin of replication); and Sigma (Sigma Chemical Company, St. Louis, Mo.); GC (gas chromatography); fames (fatty acid methyl esters).

Example 1

This Example describes the procedures utilized to identify and clone the ACS genes of the present invention.

Sequencing and Homology Analysis

All DNA sequencing was conducted in the Macromolecular Analysis Laboratory at Washington State University using automated sequencing equipment (Applied Biosystems, Foster City, Calif.). Sequences were assembled and modified using the GCG suite of programs (Wisconsin Package Version 10.0, Genetics Computer Group, Madison, Wis.). Database searches were conducted against the AtDB Illustra database (genome-www.standford.edu/*Arabidopsis*), its successor at The *Arabidopsis* Information Resource (TAIR) (www.*arabidopsis*.org), and the Munich Information Center for Protein Sequences *Arabidopsis thaliana* database (MATDB) (mips.gsf.de/proj/thal/db/search/search-_frame.html).

Identification and Cloning of Genes

Full-length ACS clones were isolated by first screening the EST databases ((Newman et al. (1994) Plant Physiol 106(4): 1241–55) to identify partial cDNA clones with homology to known ACSs. The inserts from these clones were used to screen for full length clones present in any of various cDNA libraries available from the *Arabidopsis* Biological Resource Center ((Weigel, D et al. (1992) Cell 69(5): 843–59; and Kieber, J J et al. (1993) Cell 72(3): 427–41). When full-length clones could not be identified using this approach, the missing portions of the genes were identified by isolation of genomic clones from an *Arabidopsis thaliana* genomic DNA library ((Voytas, D F et al. (990) Genetics 126(3): 713–21).

Once the initiator codon of each gene had been determined, a new gene-specific oligonucleotide primer pair was used to amplify RT-PCR products spanning the full-length open reading frame. Briefly, 2 ug of total RNA from mature seeds, tissue-culture-grown roots, stems, young rosette leaves, flowers, and siliques were used as template for a scaled-up first-strand cDNA synthesis, using an equimolar mixture of capped oligo-dT primers ($T_{20}C$, $T_{20}A$, and $T_{20}G$) and Superscript II reverse transcriptase as described in the Hieroglyph differential display manual (Genomyx Corp.). Aliquots of these reactions were used as template in amplifications using Pfu Turbo polymerase (Stratagene, La Jolla, Calif.), or with ExTaq polymerase (PanVera, Madison, Wis.), as described in the respective manufacturer's protocol. The Pfu Turbo-generated products were cloned into the pCR-ScriptCam vector supplied in the blunt cloning kit (Stratagene). The ExTaq-generated products were cloned into the pCR2.1 vector supplied in the TOPO-TA cloning kit (Invitrogen). These clones were sequenced to verify the fidelity of amplification.

Cloning of *Arabidopsis* ACS genes in *E. coli* and *Saccharomyces cerevisiae*

The cloned ACS sequences, which include the modified sequences as described above for AtACS1A, AtACS1B, AtACS2, AtACS3B, AtACS4A, and AtACS6B (SEQ ID NOS: 121–127, respectively, as shown in FIGS. 58–64, respectively), and the unmodified original sequences as described above for AtACS1C, AtACS3A, AtACS4B, AtACS5, and AtACS6A (SEQ ID NOS: 3, 5, 8, 9, and 10, respectively, as shown in FIGS. 5, 7, 10, 11, and 12, respectively) were subsequently cloned in *E. coli* and then used for transfection and expression in yeast.

For expression in yeast, one of two methods was used to reamplify the open reading frames of the *Arabidopsis* cDNAs for re-cloning. Some genes were amplified from the original plasmids using new oligonucleotide primer pairs that introduced restriction sites compatible for insertion into the multiple cloning site of the *Saccharomyces cerevisiae* inducible expression vector pYES2 (Invitrogen). The PCR products were restricted with appropriate enzymes then gel-purified. Concentrated solutions of the insert DNAs were ligated to appropriately digested pYES2 DNA and transformed into competent *E. coli*. Plasmid DNA from the resulting bacterial colonies was resequenced to ensure accurate reamplification then transformed into *S. cerevisiae* YB525 cells (provided by Prof. J I Gordon, Washington University, St. Louis, Mo.) ((Knoll, L J et al. (1995) Genetics 126(3): 713–21) that had been made competent for chemical transformation using the S. c. EasyComp kit (Invitrogen). Alternatively, PCR products for some of the ACS cDNAs were generated using the sticky end PCR technique ((Zeng, G (1998) Biotechniques 25(2): 206–8). These products were ligated, transformed, and sequenced as described above.

Acyl CoA Synthetase cDNA Identification and Cloning

AtACS1A

The cDNA clone corresponding to 240K22T7 was ordered from ABRC and unsuccessfully used to screen the Lambda PRL2 cDNA library. The remaining sequence was determined by isolation of a genomic clone from the genomic library using 240K22T7 insert as probe. The full-length cDNA was amplified using the new sequence information and cloned into a pPCR-Script Amp vector (Stratagene) and sequenced. Due to problems encountered when recloning this construct, the cDNA was reamplified from pooled RT reactions. The primers used for this amplification added KpnI and SphI sites to the 5' and 3' ends of the gene, respectively. The resulting PCR product was then cut with these two enzymes and cloned into the same sites in the yeast expression vector pYES2 (Invitrogen) and sequenced.

AtACs1B

AtACS1B was found by searching the AGI database for sequences homologous to AtACS 1A and 1C. Primers were designed based on the putative start and stop codons. The primers successfully amplified an appropriately sized product from genomic DNA. The genomic product itself has not yet been cloned. ATACS1B has been cloned by RT-PCR and sequenced.

AtACs1C

The cDNA clone corresponding to 119E14T7 and unsuccessfully used to screen the Lambda PRL2 cDNA library. The remaining sequence was determined by isolation of a genomic clone from a genomic library using the 119E14T7 insert as probe. The sequence determined from the genomic clone was used to design primers for amplification of the full-length cDNA from DNA prepared from the cDNA libraries. This cDNA was cloned into pYES2 in a fashion similar to that described for AtACS7.

AtACs2

The cDNA clone corresponding to EST 229E14T7 was ordered from ABRC. The insert DNA was excised and used as probe for screening the Lambda PRL2 cDNA library. A clone was isolated with an approximately 2 kb insert and excised from the plasmid DNA. Sequencing revealed that the 5' end of the cDNA was missing based on homology to *Brassica* sequences. Five prime RACE amplifications were performed with total phage DNA isolated from the cDNA library. This led to the cloning and sequencing of the 5' sequence.

AtACs3A

The cDNA clone corresponding to EST 205M6T7 from ABRC represents a full length clone from the Lambda PRL2 cDNA library. The plasmid was sequenced to determine that it was full-length, and then new primers were used to re-amplify the open reading frame, thereby adding appropriate restriction sties on the ends for cloning into pYES2.

AtACs3B

The cDNA clone corresponding to EST 123N12T7 was ordered from ABRC and unsuccessfully used to screen the Lambda PRL2 cDNA library. The remaining sequence was determined by isolation of a genomic clone from the genomic library using the 123N12T7 insert as probe. The full-length cDNA was amplified using the new sequence information, cloned into the pPCR-Script Cam vector (Stratagene), and sequenced.

AtACs4A

This gene, originally named AMP-BP3 and later renamed AtACS4A, was identified from the *Arabidopsis* databases using the sequence of the *Brassica* AMP-BP clone pMF28P (Genbank Accession #Z72151). The presumed start codon and stop codon were identified by homology. The full-length cDNA was amplified by RT-PCR using the primers AMP-BP35SacICut (5'-TGCATGGAGCTCATGGCTTCGACT-TCTTCTTTG GGAC-3') (SEQ ID NO: 73) and AMP-BP33XhoICut (5'-ACGATCCTCGAGTTAACTGT AGAGTTGATCAATCTC-3') (SEQ ID NO: 74). The resulting PCR product was cut with SacI and XhoI and ligated into the same sites in the yeast expression vector pYES2 (Invitrogen) and sequenced.

The initial cDNA nucleic acid sequence and deduced amino acid sequence for AtACS4A were initially predicted from the genomic sequence; this prediction involved a calculation of where one of the exons would splice. However, the actual sequence indicated that an additional six nucleotides were included at this spot; these six nucleotides, which appeared between nucleotides 145 and 146 in the originally predicted sequence, are AGTCAA, and were then assigned nucleic acid positions 146 to 151, with the remaining nucleic acid sequence renumbered accordingly. As a result of the "changed" nucleic acid sequence, the deduced amino acid sequence also changed. The nucleic acid sequence of the AtACS4A cDNA, as determined by sequencing, encoded two more amino acids than were originally predicted; these two amino acids were S and K, and occurred between amino acid positions 49 and 50 in the original sequence. Thus, S and K were assigned to amino acid positions 50 and 51, with the remaining amino acid sequence renumbered accordingly.

AtACs4B

The presence of this gene was found in the *Arabidopsis* database by homology to AtACS4A. The start and stop codons were deduced and primers designed according to them. The primers 4B-KpnI (5'-CGAATGGTACCAATG-GCTTCAACGTCTCTCG GAGCTTCG-3') (SEQ ID NO:75) and 4B-3SphI (5'-ATACTGCATGCCTACTTGTA-GAGTCTTTCTATTTCA-3') (SEQ ID NO: 76) were used to amplify the full-length cDNA by RT-PCR. The resulting PCR product was cloned directly into the blunt-end vector pCRScript-Cam (Stratagene) and sequenced. The insert was cut using KpnI and SphI. Unfortunately, this cut the gene into two pieces. The 5' Kpn-Sph fragment was cloned into pYES2 first. The resulting construct was cut with SphI and the 3' Sph-Sph fragment of AtACS4B was ligated into it.

AtACs5

The cDNA clone corresponding to EST GbGe115a was ordered from ABRC. The insert DNA was excised and used as probe for screening the Lambda PRL2 cDNA library. A clone was isolated and again found to be missing sequence from the 5' end of the OR, which was determined by 5' RACE. The full-length cDNA was cloned into pPCR-Script Cam vector (Stratagene) and sequenced.

AtACs6A

The cDNA clone corresponding to EST G2B10T7 from ABRC represents a full length clone from the Lambda PRL2 cDNA library. The plasmid was sequenced to determine that it was full-length, and then new primers were used to re-amplify the open reading frame, thereby adding appropriate restriction sties on the ends for cloning into pYES2.

AtACs6B

The cDNA clone corresponding to EST 203J11T7 was ordered from ABRC. The insert DNA was excised and used as probe for screening the Lambda PRL2 cDNA library. A almost full-length clone was isolated. Sequence missing from the 5' end of the open reading frame was determined by isolating a genomic clone from a genomic DNA library (ABRC) using the 203J11T7 insert as a probe. The full-length cDNA open reading frame was amplified with new primers designed from sequence from the 3' end of the partial cDNA clone and the 5' sequence of genomic clone. The cDNA was cloned into pPCR-Script Cam vector (Stratagene) and sequenced.

Acyl CoA Synthetase cDNA Clones: Verification and Modification

Each of the sequences obtained for the cloned ACS genes as described above was then compared to its corresponding sequence contained in the public databases by BLAST searches. This comparison was made because it is well known that many commercial brands of Taq polymerase used for the amplification step in PCR seem to introduce errors at a much greater frequency than would be expected to occur in the public database sequences. Moreover, the sequences in the public databases are considered to be highly accurate, though probably not completely error-free. Discrepancies between the sequence of any particular clone and its corresponding sequence in a public database were generally assumed to be an error in the clone sequence. If the discrepancy resulted in a silent change, or in other words modifying the cloned sequence to match the sequence in the public database resulted in a nucleotide change that did not result in a change in the encoded amino acid sequence of the clone, no repairs were deemed necessary or made to the cloned sequence. If the discrepancy did result in a change in the encoded amino acid sequence of the clone, in most cases the sequence of the clone was modified to match that of the sequence in the public database.

The databases which were searched included the *Arabidopsis* database (genome-www.Stanford.edu/ *Arabidopsis*) This database was later updated to the TAIR (www.arabidopsis.org). The searches were conducted throughout the cloning of the ACS genes. These databases contain several different subsets of sequences (one nucleotide set for ESTs, one nucleotide set for BAC genomic sequences, one or more amino acid sets and so on). Each could be searched using either nucleotide or amino acid sequence queries.

The results of the comparisons are listed in Table 2, where only those cloned ACS sequences for which a discrepancy was observed are included.

TABLE 2

Discrepancies between initially cloned ACS cDNA genes and corresponding sequences in public databases.

| | Changes: Nucleic Acid Sequence[2] | Changes: Amino Acid sequence[3] |
|---|---|---|
| AtACS 1A | 4: A/T | 2: T/S* |
| | 108: R/A | – – – |
| | 991: C/T | 331: P/S* |
| | 1384: A/G | 462: T/A |
| | 1755: C/T | – – – |
| AtACS 1B | 1038: G | 346: K |
| | Insert between 1038 + 1039: | Insert between 346 + 347: |
| | GTGTTTGATGTT (SEQ ID NO:134) | VFDV (SEQ ID NO:136) |
| | GCTTTTTCCTAT (SEQ ID NO:135) | AFSY (SEQ ID NO:137) |
| | 1039: A | 347: K |
| | 1958: G/C | 653: S/T* |
| AtACS 1C | No Discrepancies | – – – |
| AtACS 2 | 405: C/T | – – – |
| | 492: G/T | – – – |
| | 655: C/A | – – – |
| | 657: T/A | – – – |
| AtACS 3A peroxisomal enzyme | No Discrepancies | – – – |
| AtACS 3B peroxisomal enzyme | 88: A/C | 30: I/L* |
| | 431: C/A | 144: A/D |
| | 1014: G/C | 338: L/F* |
| | 1074: R/A | – – – |
| | 1374: C/T | – – – |
| | 1407: C/T | – – – |
| | 1413: A/T | – – – |
| | 1440: G/A | – – – |
| | 1473: G/A | – – – |
| | 1476: A/C | 492: E/D* |
| | 1536: Y/C | – – – |
| AtACS 4A acyl-ACP synthase | 899: A/T | 300: Q/L |
| | 1730: G/C | 577: G/A* |
| AtACS 4B acyl-ACP synthase | No Discrepancies | – – – |
| AtACS 5 | No Discrepancies | – – – |
| AtACS 6A | 1276: A/G | – – – |
| AtACS 6B | 1188: A/G | – – – |
| | 2021: G/A | 674: R/K* |

[1]The numbering of the nucleic acid sequence is relative to the A of the start codon ATG, where this A is position 1. The numbering of the amino acid sequence is relative to the start methionine M1.
[2]Each cloned cDNA sequence was compared to the corresponding sequence present in a public database, and any discrepancies between the two sequences noted. The position at which a nucleotide discrepancy occurred is indicated by a number, followed by the discrepant nucleotides, which is indicated by two letters separated by a slash; the first letter is the nucleotide present in the original cloned cDNA sequence, and the second is the nucleotide present in the database sequence. If the #discrepancy in the cloned sequence was generally modified to match that of the corresponding sequence present in a public database. The nucleotides present in the final cloned cDNA sequence are indicated by bold type. The letters "R" and "Y" in the nucleic acid sequences represent degenerate bases.
[3]The position at which a different amino acid was encoded by discrepant nucleotides is indicated by a number, followed by the different amino acid residue, which is indicated by two letters separated by a slash; the first letter is the amino acid residue encoded by the original cloned cDNA sequence, and the second is the amino acid residue encoded by the corresponding sequence in a public database. A "– – –" indicates that the original amino acid residue was unaffected by a #nucleotide discrepancy.
*Conservative amino acid changes are represented by an asterisk next to the amino acid changes. Non-conservative changes contain no marks. The determination of which changes were conservative was based on whether or not the two amino acids fell into the same family of amino acids: acidic, basic, uncharged polar, or nonpolar. If the change created a "jump" from one class to another, it was considered non-conservative.

Typically, modification of a cloned ACS sequence to match a corresponding sequence in a public database utilized one of two main methods. One method was site-directed mutagenesis using the QuikChange site-directed mutagenesis kit from Stratagene (catalog number 200519). The other method was to simply re-clone a new copy of the cDNA by performing new RT-PCR reactions, digesting the PCR product with the appropriate restriction endonucleases, ligating the product to the yeast expression vector plasmid and retransforming chemically competent *E. coli* cells. Transformed colonies were grown in liquid culture, plasmid DNA purified, and the cDNA inserts were resequenced.

The cloned ACS sequences which were modified are described below.

AtACs1A

Several discrepancies were observed in the original cloned sequence; however, repeated attempts to modify the nucleotide at position 991 by QuikChange mutagenesis failed. Therefore, a new copy of the AtACS 1 A cDNA was obtained by RT-PCR using the ProSTAR Ultra HF RT-PCR System (Stratagene, catalog number 600164), using *Arabidopsis* flower mRNA as the template for the RT reaction. The RT reaction was primed using an equimolar mixture of capped oligodT primers (5'-TTTTTTTTTTTTTTTTTTTC-3'(SEQ ID NO:138), 5'-TTTTTTTTTTTTTTTTTTTA-3'(SEQ ID NO:139), 5'-TTTTTTTTTTTTTTTTTTTG-3'(SEQ ID NO:140)). One transformed *E. coli* colony was obtained, and its plasmid contained a copy of the AtACS1A cDNA which was sequenced and determined to be identical to the public database sequence. The resulting sequence (SEQ ID NO: 121) is shown in FIG. 58, and the encoded amino acid sequence (SEQ ID NO:128) is shown in FIG. 65.

AtACs1B

The original sequence was a predicted sequence based upon a comparison of the AtACS1B genomic sequence to the cDNA sequences of AtACS1C and AtACS1A. When the AtACS1B cDNA was cloned by RT-PCR, it was shown to contain the inserted 24 nucleotide sequence GTGTTTGAT-GTTGCTTTTTCCTAT (SEQ ID NO:141) between nucleotides G1038 and A1039. The discrepancy at nucleotide 1958, which in the new sequence is nucleotide 1982 (after the addition of the 24 nucleotides), was modified to a C. The resulting sequence (SEQ ID NO: 122) is shown in FIG. 59, and the encoded amino acid sequence (SEQ ID NO:129) is shown in FIG. 66.

AtACs2

An apparent nucleotide discrepancy at position 1645 occurs very near an intron/exon junction in the database genomic sequence for LACS2. Subsequent examination led to the conclusion that this apparent discrepancy was in fact a misinterpretation of the alignment of the sequences in the original BLAST comparisons. Therefore, this nucleotide was not modified. Because the remaining nucleotide discrepancies did not result in different encoded amino acids, the original cloned sequence was not modified. The genomic sequence (SEQ ID NO:123) is shown in FIG. 60.

AtACs3B

The original copy of this cDNA contained many discrepancies when compared to the sequence in the public databases, and was therefore recloned by RT-PCR. The new copy still did not match the database at nucleotide position 431. This nucleotide was modified by site-directed mutagenesis using the QuikChange site-directed mutagenesis kit. The resulting sequence (SEQ ID NO: 124) is shown in FIG. 61, and the encoded amino acid sequence (SEQ ID NO:130) is shown in FIG. 67.

AtACs4A

Two nucleotide discrepancies were observed, and each nucleotide was modified by site-directed mutagenesis using the QuikChange Site-directed mutagenesis kit. The resulting sequence (SEQ ID NO: 125) is shown in FIG. 62, and the encoded amino acid sequence (SEQ ID NO:131) is shown in FIG. 68.

AtACs6A

One nucleotide discrepancy was observed; however, because the nucleotide discrepancy did not result in a different encoded amino acid, the original cloned sequence was not modified. The genomic sequence (SEQ ID NO:126) is shown in FIG. 63.

AtACs6B

A nucleotide discrepancy was observed at position 2021, and this nucleotide was modified by site-directed mutagenesis using the QuikChange Site-directed mutagenesis kit. The resulting sequence (SEQ ID NO: 127) is shown in FIG. 64, and the encoded amino acid sequence (SEQ ID NO: 132) is shown in FIG. 69.

Example 2

This Example describes the cloning of ten AMP-BPs. These ten AMP-BPs were selected from a total of fourteen members of AMP-BPs discovered through the grouping of the original 44 genes into subfamilies as determined by phylogenetic relationships among the 44 genes as described above. The methods of sequencing and homology analysis, identification and cloning of genes, and cloning of *Arabidopsis* genes in *E. coli* and *Saccharomyces cerevisiae* are described in Example 1, with additional details provided below.

Total RNA was isolated from *Arabidopsis* dry seeds, roots, old stems, young stems, young leaves, old leaves, young stems, old stems, flowers, new siliques, and old siliques. First strand cDNA was prepared from each of these RNA preps with Superscript II reverse transcriptase (Gibco-BRL) as described in the Hieroglyph mRNA Profile Kit (Genomyx). Using gene specific primers designed from the expected start codon and stop codon of each gene (Example 3), the open reading frame for each gene was amplified from a pool of all of the RT reaction.

The PCR reactions were carried out on an MJ Research PTC 100 thermal cycler. The polymerase was ExTAQ (Panvera Corp.). The reactions (50 μl) contained 5 μl of the 10XTaq buffer, 4μl of the 10 mM dNTP mix (Panvera) 5 μl each of 5 μM stocks of the 5' and 3' primers and 2 μl of the pooled RT reactions. The conditions were: 95° C. for 3 minutes, followed by 30 cycles of 95° C. for 20 sec, 58° C. for 30 sec, 72° C. for 1 minute. A final 72° C. incubation of 2 minutes was followed by an indefinite 4° C. hold until samples were removed.

A small amount of each reaction was analyzed by agarose gel electrophoresis to ascertain successful amplification. The remainder of each successful amplification was electrophoresed and the band cut out followed by purification of the DNA from the gel slice using Qiagen gel extraction columns. A 4 μl aliquot of each DNA was ligated to TOPO-activated pCR2.1 vector (Invitrogen), using their standard conditions and transformed into TOP10F' competent cells supplied with the kit. Positive transformants were selected by growth on agar plates containing either 100 (g/ml carbenicillin or 50 μg/ml kanamycin plus X-GAL and IPTG for blue/white screening. Colonies containing plasmids with AMP-BP inserts were identified by colony PCR screening several white colonies, using the same PCR conditions as described above. Representative positive colonies for each gene were grown in 50 ml of liquid L-broth plus appropriate antibiotic overnight at 37° C., followed by isolation of plasmid DNA using Promega's Wizard MidiPrep kit.

Plasmid DNA was quantified spectrophotometrically and sequenced with several vector- and gene-specific primers.

AtAMP-BP1

The full length gene was isolated from 2–3 Kb size-selected cDNA library (Kieber et al. (1993) Cell 72(3): 427–441) obtained from the *Arabidopsis* Biological Resource Center (ABRC) at Ohio State University. The insert from the partial cDNA clone 99N9T7 (Genbank Accession #T22607) was used as the probe. After sequencing, the full-length open reading frame was amplified from this plasmid with Pfu Turbo Polymerase (Stratagene) with primers containing restriction sites compatible for cloning into the yeast expression vector pYES2 (Invitrogen). The product was cut out and ligated into pYES2 using standard procedures.

AtAMP-BP3

The cDNA clone corresponding to EST FAFM13 was ordered from the *Arabidopsis* Biological Resource Center (ABRC, Ohio State University). The insert DNA was excised and used as probe for screening a Lambda PRL2 cDNA library (also obtained from the ARBC). A clone was identified and isolated. The insert DNA from the lambda phage clone was excised by in vivo excision as described in library instructions resulting in the gene fused in pBlue-Script SK+.

All other AMP-BPs

All other AMP-BP genes were cloned by identification in the databases by homology to cloned *Arabidopsis* ACS genes. The start codon and stop codon were identified and primers designed to these spots. These primers may or may not have contained restriction sites to facilitate cloning. The full-length open reading frames were amplified by RT-PCR from total RNA. These PCR reactions were carried out with one of two different DNA polymerases: ExTaq (Panvera) or Pfu Turbo (Stratagene). Those products (AtAMP-BPs 2, 4, 5, 6, and 7) generated with ExTaq were cloned directly into the A-overhand vector pCR2.1 (Invitrogen). These genes were later cut out of pCR2.1 and ligated into pYES2. The Pfu Turbo generated AtAMP-BP8 product was cloned into the blunt-end vector pCRScript-CAM (Stratagene), then cut out of this vector and ligated into pYES2. The Pfu Turbo products for AtAMP-BP9 and 10 were cut with Kpn1 and SphI and cloned directly into pYES2.

Example 3

This Example describes primers useful for amplifying full-length ACSs and AMP-BPs and for use in RNAse protection assays.

AtACs1A
(SEQ ID NO: 52) AAGGCGATTCATCTTGAC-AtACS1A gene specific RPA primer
(SEQ ID NO: 53) CTGGTACCATGACGCAGCAGAA-GAAATAC-5' yeast vector cloning primer+KpnI restriction site.
(SEQ ID NO: 54) CTCTCGAGCTACCCTCTGGAAG-CAAATT AtACs1B
(SEQ ID NO: 55) ATGACGTCGCAGAAAAGAT-TCATCTTTG-5' start codon cloning primer
(SEQ ID NO:56) TTACTGTCCGGAAGCTAGACTTTC-CTTTC-3' stop codon cloning primer AtACs1C
(SEQ ID NO: 57) GAGTCTATCTGCCGAAACC-AtACS1C gene specific RPA primer
(SEQ ID NO: 58) ATGGCGACTGGTCGATACATCGT-TGAGGTTG-5' start codon cloning primer
(SEQ ID NO: 59) TTACACTCGTAGCTGCACTTCTC-3' stop codon cloning primer AtACs2
(SEQ ID NO: 60) 6RPA-AACTCAATTACCAATCTCCC
(SEQ ID NO: 61) CGCCATGAACACCGAGTCAG-5' Start codon cloning primer
(SEQ ID NO: 62) GAGCCATTCAGAGCTTCGACG-3' Stop codon cloning primer AtACs3A
(SEQ ID NO: 63) ATCCGAGAGTGAAAGCAG-AtACS3A gene specific RPA primer
(SEQ ID NO: 64) CTGGTACCATGGATTCTTCTTCT-TCGTC-5' start codon for cloning into yeast expression vector pYES2, KpnI restriction site included.
(SEQ ID NO: 65) AGCTCGAGTTCACAAACCTCTATT-AGCAG-3' stop codon for cloning into pYES2, XhoI restriction site included.

AtACs3B
(SEQ ID NO: 66) CTTGCTGAGATGGATGAC-AtACS3B gene specific RPA primer
(SEQ ID NO: 67) CATGGAATTTGCTTCGCCGGAAC
(SEQ ID NO: 68) GTACCATGGAATTTGCTTCGCCG-GAAC-5' KpnI overhang sticky-end primers for cloning into yeast expression vector pYES2 (Invitrogen).
(SEQ ID NO: 69) CTCACAGTTTAGAAGGAATGGGG
(SEQ ID NO: 70) CATGCTCACAGTTTAGAAG-GAATGGGG-3' SphI overhang sticky end cloning primers for cloning into pYES2.

AtACs4A
(SEQ ID NO: 71) ATGGCTTCGACTTCTTCTTTGGGA
(SEQ ID NO: 72) CAAATGTCTTAACTGTAGAGT-TGATCA
(SEQ ID NO: 73) TGCATGGAGCTCATGGCTTCGACT-TCTTCTTTGGGAC AMP-BP35SacICut
(SEQ ID NO: 74) ACGATCCTCGAGTTAACTGTA-GAGTTGATCAATCTC-3') AMP-BP33XhoICut

AtACs4B
(SEQ ID NO: 75) CGAATGGTACCAATGGCT-TCAACGTCTCTCGGAGCTTCG-4B-KpnI
(SEQ ID NO: 76) ATACTGCATGCCTACTTGTA-GAGTCTTTCTATTTCA-4B-3SphI

AtACs5
(SEQ ID NO: 77) ACGGCAGAAAAGAACAAG-AtACS5 gene specific RPA primer
(SEQ ID NO: 78) CTGGTACCATGAAGTCTTTTGCG-GCTAAG-5' start codon primer for cloning into pYES2, KpnI restriction site included.
(SEQ ID NO: 79) ACTCTAGATTATTGATA-CATATAACGTAC-3' stop codon primer for cloning into pYES2, XbaI restriction site included.

AtACs6A
(SEQ ID NO: 80) ATGGAAGATTCTGGAGTGAATC-CAATG-5' start codon cloning primer (SEQ ID NO: 81) TTAGGCATATAACTTGCTGAGT-TCATC-3' stop codon cloning primer AtACs6B (SEQ ID NO: 82) CTTCAAAGCAAGGAATAGAC-AtACS6B gene specific RPA primer
(SEQ ID NO: 83) ATGATTCCTTATGCTGCTGGTG-AtACS6B 5' Start codon cloning primer
(SEQ ID NO: 84) TTAGGCATATAACTTGGTGAGATC-3' stop codon cloning primer AtAMP-BP1

(SEQ ID NO: 85) ATGGAGGGAACTATCAAATCTC-5' start codon cloning primer
(SEQ ID NO: 86) TCATAACTTGCTTCTGCCTTTC-3' stop codon cloning primer AtAMP-BP2

(SEQ ID NO: 87) ATGAGATTCT TGTTAACCAA AAG-5' start codon cloning primer
(SEQ ID NO: 88) TTACAAGCTA CCCATTTCAT CAG-3' stop codon cloning primer AtAMP-BP3

(SEQ ID NO: 89) TGAGAAATATGGGGAAGAG-AtAAMP-BP gene specific RPA primer
(SEQ ID NO: 90) ATGGATAGCGATACTCTCTCAG-5' Start codon cloning primer
(SEQ ID NO: 91) TCAGGGCTTCTCAAGGAAATG-3' Stop codon cloning primer AtAMP-BP4

(SEQ ID NO: 92) ATGGAACTTT TACTCCCACA CG-5' start codon cloning primer
(SEQ ID NO: 93) TCATCAAGGCAAGGACTTAG C-3' stop codon cloning primer AtAMP-BP5

(SEQ ID NO: 94) GAAAACAATACATTGACCACTCAA-GATG-5' gene specific cloning primer
(SEQ ID NO: 95)TCGCAAGTTCTAATTTTACATC-CGACTC-3' gene specific cloning primer.

AMP-BP5 and AMP-BP6 are very similar, therefore the gene-specific cloning primers were moved "outward" from the start and stop codons a bit, to ensure gene-specificity.

AtAMP-BP6

(SEQ ID NO: 96) TTTGATTACCACTAGGAGGAA-GAGATG-5' gene specific cloning primer
(SEQ ID NO: 97) CGGTGAAAGAAAGACGTTTAA-GAAATTG-3' gene specific cloning primer AtAMP-BP7

(SEQ ID NO: 98) ATGGCGGCAACGAAGTGGCGTG-5' start codon cloning primer
(SEQ ID NO: 99) CTATAACCTGCTTCTTGGTACTG-GTCCC-3' stop codon cloning primer AtAMP-BP8

(SEQ ID NO: 100) ATGGAAGATTTGAAGCCAAG TGCC-5' start codon cloning primer
(SEQ ID NO: 101) TTACATGTTTTTGGCAATCT CTT-TAAGC-3' stop codon cloning primer AtAMP-BP9

(SEQ ID NO: 102) TACAAAACATTAACAAAAAT-CAAAGTATGG
(SEQ ID NO: 103) ATAACTCAAGCGAATCTTTAAG-GCAGAGA

AtAMP-BP10

(SEQ ID NO: 104) ACGATACTATAGTTTCTTG-CAGCTAACTAA
(SEQ ID NO: 105) TTATTTAATGGACTTGTTCAAGA-CAGGGT

AMP-BP9 and 10 are so similar that primers upstream of the start codon and downstream of the stop codon had to be used to ensure gene-specific amplifications.

Example 4

This Example describes the detection of ACS enzyme activity by complementation. Eleven candidate ACS genes were cloned into the galactose-inducible *Saccharomyces cerevisiae* expression vector pYES2. These constructs were tested for their ability to complement the phenotype of *Saccharomyces cerevisiae* strain YB525. This yeast strain contains insertional disruptions in two of its ACS genes, FAA1 and FAA4 ((Knoll, L J et al. (1995) J Biol Chem 270(18): 10861–7), which are responsible for the majority of ACS enzyme activity in *S. cerevisiae*. Thus, these cells are completely dependent on complementation by an active ACS when grown on media containing fatty acids as a sole carbon source and cerulenin to inhibit endogenous fatty acid synthesis by the fatty acid synthase complex.

A culture of YB525 was grown in YBD liquid media until approximately mid-log phase. Cells were harvested and made competent for transformation using the S.c. Easy-Comp kit (Invitrogen). *Arabidopsis* cDNAs were ligated into the pYES2 vector (Invitrogen), then checked for proper orientation and sequence. Any base pairs that did not match the AGI database sequence were corrected using the Quick-change site-directed mutagenesis kit (Stratagene). The expression constructs were transformed into chemically competent YB525 cells and uracil auxotrophs selected on DOBA-ura plates (DOBA: 2% yeast nitrogen base, 2% dextrose, 0.1% complete supplement mixture lacking uracil, 17g/L agar) (BIO101). Representative colonies were chosen at random and grown until mid- to late-log phase in DOB liquid media (DOBA minus agar). Galactose was added to a concentration of 2% to induce high-level expression of the transgenes from the GAL1 promoter of the vector. The cultures were then grown for an additional 2 to 4 hours. Aliquots of each culture were diluted 1:1 (vol/vol) with 2 M sorbitol and 5 ul aliquots plated on DOBA plates containing galactose plus 500 uM myristic acid and 25 uM cerulenin, followed by incubation at 30° C. for 3–4 days.

The results of the complementation experiment show that after four days at 30° C., seven of the eleven candidate ACS genes had complemented the mutant phenotype and restored growth rates to wild-type levels, as compared to the wild-type strain Invisc (Invitrogen) that was used as a positive control. Only AtACS3A, 3B, 4A, and 4B did not complement the mutant phenotype.

The explanation for the inability of some of the genes to restore cerulenin-insensitive growth to this strain was obvious. The AtACS3A and AtACS3B genes contain PTS2 and PTS1 peroxisome targeting sequences, respectively. Targeting of an ACS to the peroxisome renders the enzyme inaccessible to the pool of exogenous fatty acid, as evidenced by the inability of Faa2p, the endogenous peroxisomal Saccharomyces ACS ((Johnson, D R et al. (1994) J Cell Biol 127(3): 751–62; and Knoll, L J et al. (1995) J Biol Chem 270(18): 10861–7), to support growth under the conditions used in this experiment.

The inability of the AtACS4A and AtACS4B genes to complement the YB525 strain was less easily explained. The deduced amino acid sequences for these two proteins did not contain recognizable peroxisome targeting sequences. AtACS4A and 4B do contain N-terminal extensions, however, that may target the encoded enzymes to other sites within the yeast cell that are separated from the pool of exogenous fatty acids. These two genes also contain abnormally long insertional elements, as seen in FIG. 2. This difference in length was also observed in bnapmf28, the *Brassica napus* homolog of AtACS4A, which was also inactive in ACS assays when over-expressed in *E. coli* ((Fulda, M et al. (1997) Plant Mol Biol 33(5): 911–22).

In general, the results of the complementation experiment indicate that most of the candidate genes are in fact ACSs, and that the insertional element described above is a reliable tool for distinguishing ACS genes from other related AMP-binding protein genes.

Example 5

This Example describes a biochemical assay for ACS activity. The results of the yeast complementation experiment clearly demonstrated that many of the candidate genes chosen from the initial library screens and database searches did encode ACS enzymes. However, additional analysis was necessary to address the inability of the AtACS3A, 3B, 4A, and 4B genes to complement the ACS deficiency in the *S. cerevisiae* YB525. In order to directly test the ability of this family of genes to produce active ACS enzymes, cell-free lysates were prepared from *S. cerevisiae* YB525 cells over-expressing each of the eleven candidate ACS genes, as described below. These lysates served as enzyme sources in ACS enzyme activity assays, using $^{14}$C-labeled oleic acid as a substrate.

Enzyme Overproduction in *Saccharomyces cerevisiae*

Transformed YB525 cells were selected on solid selective media lacking uracil. Several colonies from each transformation were restreaked on a new selective media plate. Representative colonies were randomly chosen to inoculate liquid media cultures. This media lacked uracil and contained dextrose as the carbon source, which suppressed the GAL1 promoter of the pYES2 vector. These cultures were grown at 30° C. with vigorous shaking to an optical density at 600 nm of about 0.7–1.0. Galactose (20% w/v) was added to a final concentration of 2% to induce gene expression. The cultures were shaken at 30° C. for an additional 2–4 hours and the cells harvested by centrifugation. The yeast cells were washed once with distilled water and harvested again for spheroplast production. Spheroplasts were generated from intact cells using lytic enzyme (ICN) following the manufacturers protocol. The spheroplasts were lysed by sonication on ice (2×1 min) followed by removal of solid debris by centrifugation at 8,000×g for 15 min at 4° C. The resulting supernatants were used as enzyme sources for the ACS assay.

ACS Enzyme Assay

The assay conditions were similar to those described previously (Fulda, M et al. (1997) Plant Mol Biol 33(5): 911–22. The assay was conducted in 1.5 ml Eppendorf tubes in a volume of 100 ul. The assay mixture contained 100 mM Bis-Tris-propane (pH 7.6), 10 mM MgCl$_2$, 5 mM ATP, 2.5 mM dithiothreitol, 1 mM CoA, 10 uM 1-$^{14}$C-labeled oleic acid (specific activity 50–57 mCi/mmol, DuPont-NEN), and 20 ug of crude yeast cell lysate protein. The assay was initiated by addition of the fatty acid and incubated at room temperature for 15 minutes. The reactions were stopped by addition of 100 ul of 10% acetic acid in isopropanol and extracted twice with 900 ul of hexane (previously saturated with 50% isopropanol). Enzyme activity was measured by analyzing aliquots of the aqueous phase by liquid scintillation counting. Lysates from yeast cells bearing the empty pYES2 vector served as a negative control, while commercial ACS enzyme from *Pseudomonas* sp. (Sigma) served as the positive control.

Results

Figure 55:
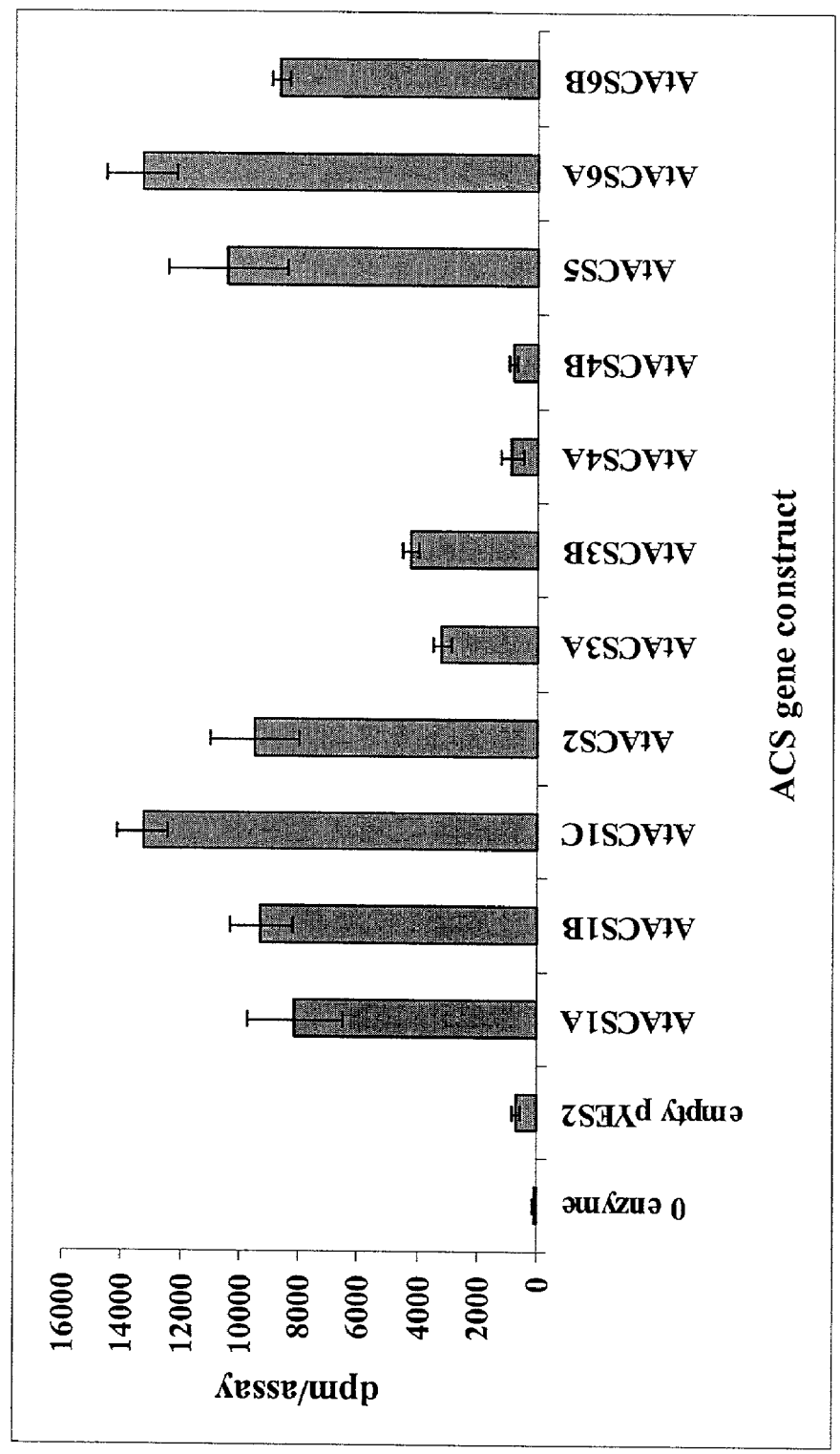
FIG. 55 shows the results of acyl-CoA synthetase activity from in vitro assays.

The results of these assays are shown in FIG. 55, and demonstrate that all cell lines except those containing the AtACS4A and AtACS4B constructs produced significant levels of ACS activity. The results for these two genes was consistent with those observed in the yeast complementation experiment and in the *E. coli* expression studies ((Fulda, M et al. (1997) Plant Mol Biol 33(5): 911–22). Thus, in contrast to the complementation study, cells containing constructs AtACS3A and AtACS3B produced active enzymes. The levels of activity produced by these two constructs was somewhat lower than that produced by the other active genes; thus, the activity of AtACS3A and 3B was approximately 5-6-fold higher than that of the empty pYES2 negative control, compared to 12- and 20-fold higher activity for AtACS1A and AtACS6A, respectively. These levels of activity demonstrate that the AtACS3A and AtACS3B genes encode ACS. These results also further demonstrate that the other seven members of this family are ACSs as well.

The lack of enzyme activity for cells containing AtACS4A and 4B constructs provide further support to the hypothesis that the enzymes encoded by these genes are unique with respect to the other nine ACS genes. These genes may encode ACSs that activate specialized substrates, or the may encode a different type of enzyme related to ACS. It is also possible that these enzymes are indeed ACSs, but are inactive under the conditions used in these experiments due to special folding or multimer formation requirements, or the need for post-translational modifications not met by the cellular machinery of *Saccharomyces cerevisiae*.

Alternatively, it is contemplated that these two genes encode acyl ACP synthetases, as described previously.

Example 6

This example describes the fatty acid substrate specificities for the AtACS enzymes. The enzymes were obtained from K27 *E. coli* mutants transformed with the AtACS genes. The K27 mutant was selected because it is unlike the YB525 strain of yeast, which still contains at least two active long chain acyl-CoA synthetases. Instead, the mutation in the K27 strain disables the only acyl-CoA synthetase gene in

*E. coli*, thus providing an *E. coli* strain with an ideal genetic background in which to analyze the substrate specificity of each *Arabidopsis* ACS at a high level of sensitivity.

Materials and Methods

The substrate specificity of each *Arabidopsis* ACS enzyme was analyzed by cloning each of the AtACS genes in prokaryotic expression vectors (pET24c or d, Novagen) and overexpressing the enzymes in K27 mutant *E. coli* (which can be obtained from the American Type Culture Collection). In order to make the cells of the *E. coli* K27 mutant compatible with T7 RNA polymerase-driven expression, the λDE3 prophage carrying the T7 RNA polymerase gene was integrated into the *E. coli* chromosome, using the DE3 Lysogenization kit (Novagen). After induction with IPTG, the cells of each ACS-expressing line were harvested, lysed by sonication, and the membrane fraction isolated by ultracentrifugation.

Results

Essentially all of the ACS enzyme activity was recovered in the membrane fraction. The membranes were used in in vitro enzyme assays (as described in Example 5) using eight different 1-[$^{14}$C] or 9,10-[$^{3}$H]fatty acid substrates, ranging in length from 14 carbons to 20 carbons, and spanning a range of desaturation, from 0 to 3 double bonds. A summary of the specificities of the enzymes toward eight of the fatty acids is shown in FIG. 56.

The enzymes AtACS3A and AtACS3B activated all the fatty acids tested at relatively high rates. Especially noteworthy was the strong activity by AtACS3A and AtACS3B toward eicosenoic acid, a 20-carbon fatty acid found only in the seed storage lipids of *Arabidopsis*. Peroxisomal ACSs participate in β-oxidation, and therefore would be expected to effectively utilize all fatty acids stored in the seed triacylglycerols. Thus, the substrate specificities of AtACS3A and AtACS3B further support the hypothesis that these enzymes are peroxisomal.

The other seven ACS enzymes showed very similar patterns of substrate preference, as shown in FIG. 56. Each enzyme activated all of the substrates tested, with highest levels of activity observed with both the saturated and monounsaturated 16-carbon fatty acids and the monounsaturated and polyunsaturated 18-carbon fatty acids. AtACS6B preferred oleic acid slightly more than any of the other fatty acids. This enzyme is believed to be the major plastidial isoform (as described in Examples 8 and 9), and as such should effectively activate oleate, the most abundant fatty acid produced by the plastid fatty acid synthase complex in *Arabidopsis*. For most of the ACS enzymes, stearate (18:0) and eiconsenoate (20:1) were poor substrates. These data correlate very strongly with the fatty acid profiles seen in *Arabidopsis* leaf lipids, which consist mostly of monounsaturated and polyunsaturated 16- and 18-carbon acyl groups (Ohlrogge and Browse (1995) Plant Cell 7(7): 957–70).

Thus, in general, the fatty acid preferences for these enzymes correlate very well with the observed fatty acid compositions of *Arabidopsis* membrane and seed storage lipids, which are made up primarily of 16:0, 18:0, 18:1, 18:2, 18:3, and 20:1. The lack of striking substrate specificity differences between the different isoforms suggests that the specific roles fulfilled by each enzyme are not determined by substrate preference but by other factors such as subcellular targeting, or differences in temporal-, tissue-, or cell-type expression.

Example 7

This Example describes the cellular location of ACS transcription as assayed by RNAse protection assays and by RNA expression profiles.

RNAse Protection Assays

In vitro transcription and RNAse protection assays were performed basically as described in the Maxiscript and RPA II manuals (Ambion), respectively. Briefly, several different tissues (e.g., seed, cultured roots, stem, young leaves [post-bolting], silique, flowers and buds, green rosette [pre-bolting], and older leaves [post-bolting]) were harvested from wild-type *Arabidopsis* ecotype Columbia plants. Tissues were frozen in liquid nitrogen and stored at −80° C. until use.

Total RNA was isolated from the tissues using standard methods. The RNA pellets were dissolved in DEPC-treated water and quantified spectrophotometrically. Gene specific RPA probes templates were produced by PCR amplifying small (200–500 bp) fragments of each ACS gene from the full-length or partial cDNA clones obtained from ABRC. Primer sequences are provided in Example 3. The PCR products were electrophoresed through TAE-agarose gels and gel-purified using Qiaquick spin columns (Qiagen).

The PCR products were transcribed in vitro in 20 μl reactions containing: 2 μl 10 X transcription buffer, approximately 1 μg of template DNA, 1 μl each ATP, CTP, and GTP, 5 μl 12.5 μM$^{32}$P labeled UTP, and 2μl either SP6, T3, or T7 RNA polymerase. The contents were mixed and incubated at 37° C. for 1 hour. DNAse I was added to stop the reaction and remove template DNA.

The radiolabeled RNA probe was then gel-purified on 5% TBE, 8 M Urea acrylamide gels. The RNA was eluted in elution buffer (0.5 M ammonium acetate, 1 mM EDTA, 0.1% SDS) overnight. An aliquot of the eluted probe was quantified by scintillation counting and, according to the manufacturer's calculation methods, the number of counts corresponding to 2 femptomoles of probe was determined. Twenty micrograms of total RNA from each tissue was co-precipitated with 2 femptomoles of probe and resuspended in 20 μl hybridization buffer (Solution A from the kit). After heating at 95° C. for 3–4 minutes, the RNA/probe mixture was incubated overnight at 45° C.

Unprotected RNA was digested by adding to the RNA/probe mixture 200 ml RNAse solution ($\frac{1}{100}$ dilution of stock RNAse A/RNAse T1 mixture) and incubating the mix at 37° C. for 30 minutes. Three hundred microliters of solution Dx was then added to each tube to stop the reaction. Two microliters of carrier yeast RNA was added to increase pellet visibility. The mixture was chilled at −20° C. for at least 15 minutes, and then centrifuged at maximum speed for minutes in a cold room. The pellets were dissolved in nondenaturing gel sample buffer and electrophoresed through a nondenaturing 5% TBE acrylamide gel. After running, the gel was dried in a gel drier and the images were developed in a Bio-Rad Phosphorimager.

The results are summarized in Table 3 below. A relatively strong signal for a given tissue is designated by (+++), a relatively weak signal is designated by (+), and the apparent absence of a signal is indicated by (−). As can be seen, the RNAs for the different ACSs localize to a variety of tissues.

TABLE 3

RNAse Protection Assay Results

| ACS | dry, mature seed | cultured roots | stem | young leaves | silique | flowers and buds | green rosette | older leaves |
|---|---|---|---|---|---|---|---|---|
| AtACS1A | − | ++ | + | + | − | +++ | + | − |
| AtACS1C | − | + | + | − | + | + | + | + |
| AtACS2 | − | +++ | + | ++ | + | ++ | +++ | + |
| AtACS3A | + | − | + | + | − | + | na | na |
| AtACS3B | ++ | + | + | + | − | ++ | na | na |
| AtACS5 | + | − | + | − | − | +++ | na | na |
| AtACS6B | − | ++ | − | − | − | +++ | na | na |

RNA Expression Profiles

The tissue-specific RNA expression profiles of each of the ACS genes was also examined by semi-quantitative RT-PCR ((Kong, SE et al. (1999) Anal Biochem 271(1): 111–4). This technique was chosen because careful control of the PCR conditions allows for easy and sensitive comparisons of the expression levels for each of the different genes while eliminating the risk of cross-hybridization between related genes on a Northern blot. Each gene was analyzed using RNA from mature seeds, tissue culture-grown roots, leaves, stems, flowers, and siliques.

RNA preparations from mature seed, roots, young leaves, stems, siliques, and flowers were quantified spectrophotometrically and 1 ug aliquots of each used as template for reverse transcription, as described above. One ul of each RT reaction was used as template in a 50 ul PCR reaction containing gene-specific primers. The amplification conditions were as follows: 95° C. 3 min, and 30 cycles of 94° C. 15 sec, 55° C. 30 sec, 72° C. 1 min. One-third of each reaction was analyzed by TAE-agarose gel electrophoresis and the degree of gene expression correlated to the relative intensity of each band as determined by visual comparison of the ethidium bromide staining intensity when the gels were visualized under UV illumination. The actin gene ACT8 ((An et al., 1996)) was used as a control to insure that equal amounts of RNA were used in both the RT and PCR portions of the experiments.

The results are summarized in Table 4 below. The relative strength of the signal is scored from 3 plusses ("+++"), denoting the strongest signal, to a negative sign ("−"), denoting the apparent absence of a signal.

TABLE 4

Tissue Specific RNA Expression Assay Results

| ACS | dry, mature seed | cultured roots | stem | Leaves | flowers | siliques |
|---|---|---|---|---|---|---|
| AtACS1A | − | ++ | + | + | ++ | + |
| AtACS1B | − | − | − | − | ++ | − |
| AtACS1C | − | + | − | + | + | + |
| AtACS2 | − | + | ++ | + | +++ | − |
| AtACS3A | ++ | ++ | + | + | ++ | + |
| AtACS3B | + | + | − | + | ++ | − |
| AtACS4A | ++ | ++ | ++ | + | +++ | + |
| AtACS4B | +++ | + | + | + | ++ | − |
| AtACS5 | − | ++ | + | + | ++ | + |
| AtACS6A | ++ | + | + | + | ++ | + |
| AtACS6B | + | + | − | + | ++ | + |

The relative intensities of the bands for the positive control, the *Arabidopsis* actin ACT8 gene, were almost equivalent, with slight reductions in mature seed and siliques. This profile closely parallels the relative Northern blot signal intensities for this gene ((An, YQ et al. (1996) Anal Biochem 271(1): 111–4), thus validating the accuracy of this technique. As seen in Table 4, most of the ACS genes are expressed in a variety of tissues at widely varying levels.

Close inspection of Table 4 reveals several interesting phenomena. First, several ACS genes are expressed in the mature seed of the plant. The deposition of transcripts for these genes in the mature seed indicates that the ACS enzymes encoded by them are needed during the very early stages of germination. This is consistent with a strong demand for the enzymes of beta-oxidation and membrane lipid biosynthesis in the emerging seedling. The second interesting pattern observed is the strength of expression of all eleven ACS genes in flowers. These data are consistent with the high level of metabolic activity in flowers. The overall complexity of expression for the genes in this group suggests that at least some of the ACSs may have overlapping functions within the plant. Only AtACS1B seems to be highly specific, showing extremely high expression in flowers, but no expression in any of the other tissues tested. Nearly all the ACS genes, with the exception of AtACS1B and possibly AtACS2, are expressed in siliques.

In other experiments, the RNA expression pattern of AtACS6A (the closest paralog of AtACS6B) is similar to 6B in that highest levels of expression were observed in young, developing leaves and seeds; this is consistent with the belief that de novo FAS is most active in these tissues. This observation suggests that many genes in this gene family may participate in glycerolipid synthesis in the developing seed.

Example 8

This Example describes the analysis of the subcellular localization of ACSs by a chloroplast import assay. Briefly, intact chloroplasts were isolated from young pea seedling extracts by centrifugation through Percoll gradients, and incubated with labeled expression products from an in vitro transcription/translation reaction mixture with an ACS encoding sequence. The chloroplasts were then separated from the labeled expression products by centrifugation through a Percoll cushion, lysed, and the different fractions of the chloroplast separated. The import of the labeled ACS was determined by the presence of label in chloroplast lysates, the location was determined by the presence of label in different fractions, and the identification of labeled ACS was confirmed by gel electrophoresis.

Chloroplasts are isolated from nine to ten day old pea seedlings by first removing the seedlings from a growth chamber and placing them in lab light for at least one hour to allow for starch degradation before grinding the tissue (this minimizes disruption of intact chloroplasts).

Next, a standard Percoll gradient was formed by adding 1 mg glutathione to a 50 ml open top centrifuge tubes, followed by the addition of 17.5 ml 2×GR buffer (1×GR buffer is 50 mM HEPES/KOH pH 8.0, 10 mM EDTA, 0.33 M sorbitol, 5 mM Na$^+$ ascorbate, pH 7.5, and 0.05% BSA) and 17.5 ml Percoll. The mixture was then covered with parafilm and mixed. Next, the tubes were centrifuged in SS34 rotors at 4° C. min at 19,000 rpm (no brake).

When the gradient was almost complete, the aerial portions of the plants were cut and placed in a pre-weighed flask (about 40 g of tissue from a flat planted with ~200 ml peas). The tissue was placed in a chilled blender containing 250 ml 1×GR and pulsed three times for one second each. The extract was filtered through a funnel lined with cheesecloth and Miracloth. The process was then repeated with a second 40 g batch. The pooled extracts were placed in chilled 250 ml bottles and pelleted in a swinging bucket rotor for 3 min at 3200 rpm. The supernatant was decanted, and the pellet resuspended in 5 ml 1×GR. The pellets (containing chloroplasts) were then layered onto the gradients with a glass pipette and centrifuged in a swinging bucket rotor at 2600 rpm for 15 min. The lower intact chloroplast band was removed and placed into two 50 ml tubes. The tubes were filled to top with 1×IB (1×IB buffer is 50 mM HEPES/KOH, pH 8.0, 0.33 M sorbitol) and centrifuged in a swinging bucket rotor at 2600 rpm for 5 min. The supernatant was removed and the pellet resuspended in 10 ml of IB.

The concentration of chloroplasts was determined by placing 1 ml acetone in each of three 1.5 ml tubes. Water (250 µl) was added to the first tube, 225 µl water and 25 µl chloroplasts were added to the second tube, and 200 µl water and 50 µl chloroplasts were added to the third tube. The tubes were mixed well and centrifuged to pellet the proteins. The OD at 652 nm was determined and the concentration of chloroplasts calculated by the following formula: (OD652/34.5)×1.25)/sample amount×10 ml=mg total. The chloroplasts samples were then repelleted and resuspended to 1 mg/ml in 1×IB.

Labeled ACS gene products were prepared by in vitro transcription and translation of ACS cDNAs using a TNT kit (Promega) according to the manufacturer's instructions. Labeled control proteins for the import assay were also prepared in the same manner; these control proteins included luciferase, which is not imported into chloroplasts, the small subunit of RiBisCO, which is imported and is localized to the stroma, with concomitant cleavage of the signal peptide (Froelich, J E et al. (2001) Plant Physiol 125: 306–317), and LeHPL, a tomato hydroperoxide lyase which is associated with the chloroplast envelopes, despite its lack of a typical signal peptide (Froelich, J E et al. (2001) Plant Physiol 125: 306–317).

Import assays were performed in following reaction mixtures: 75µl 1×IB, 5 µl 2×IB, 15 µl 50 mM Mg-ATP (in IB), 50 µl 2×chloroplasts (1 mg/ml), and 5 µl translation product. The reaction mixtures were incubated in water bath at 25° C. for 15–30 min in the presence of light. The import reaction mixtures were then loaded onto 1 ml of 40% Percoll and centrifuged at 3,000×g for 8 min. The supernatant was removed, the pellet resuspended, and centrifuged again. Next, 600 µl lysis buffer (25 mM HEPES+5 mM MgCl$_2$) was added to the pellet. This mixture was incubated on ice, in the dark, for about 20 min. The mixture was then divided into 3 equal parts in microfuge tubes and centrifuged in an Airfuge at 100,000×g for 40 min at 4° C. The pellets were then resuspended in either 200 µl lysis buffer, 200 µl 2M NaCl, or 100 mM Na$_2$CO$_3$. The mixtures were then centrifuged in an Airfuge at 100,000×g for 30 min at 4° C. The supernatant was removed and 100% TCA added to 10%. The mixtures were stored overnight.

The next day, the mixtures were centrifuged at 20,000×g for 10 min, washed with cold acetone, and resuspended in 30 µl 5×SDS Loading dye. Ten microliters of the chloroplast import assays were then loaded onto 10% nondenaturing gels and electrophoresed. Following electrophoresis, the gels were dried and exposed to film.

The results indicate that despite the lack of a typical chloroplast targeting signal, labeled AtACS6B was targeted to intact chloroplast, and was only present in the membrane fractions. Treatment of the lysed membranes with lysis buffer and NaCl did not dissociate AtACS6B from the membranes, whereas treatment with Na$_2$CO$_3$ extracted a portion of it from the membranes. This pattern was similar to that observed with a control protein, LeHPL, a hydroperoxide lyase from tomato which has been shown to associate with chloroplast outer envelope, even though it too lacks a signal peptide (Froelich, J E et al. (2001) Plant Physiol 125: 306–317). Thus, the results suggest that AtACS6B is associated with the chloroplast envelope membranes. Moreover, ATACS6B does not appear to be proteolytically processed during plastidial targeting, because the gel mobility of the AtACS6B associated with the chloroplast was identical to that of the starting product, produced by in vitro translation.

Additional results indicated that AtACS2 is also imported into chloroplasts.

Example 9

This Example describes identification and analyses of ACS knock-out mutant *Arabidopsis* plants. Two different mutants were found in two different lines of T-DNA *Arabidopsis* plants.

The first population, a T-DNA tagged population, available through the *Arabidopsis* Biological Resource Center (http://aims.cps.msu.edu/aims/), represents 6,000 individual transformants, each containing one or more T-DNA insertions. The T-DNA is a 17.0 kb DNA fragment that contains the nptII gene, which confers resistance to kanamycin.

Insertions of the large T-DNA fragment in a gene of interest effectively prevents transcription of that gene.

This population was searched using a P1/KFLB primer combination (primers listed below), and resulted in the identification of a mutant line in the CD5–7 population (Feldmann lines) that contains a T-DNA interrupted AtACS6B coding region. The T-DNA insertional event occurs in the third exon, 1120 bp downstream from the start codon in the genomic sequence. From a sample of pooled seeds, two mutants were identified by using P1/KFLB and the P1/P2 gene specific primer combinations in PCR analysis first on pooled and later on individual plants: a heterozygous mutant containing one copy of a T-DNA interrupted AtACS6B gene, and a homozygous mutant lacking both native copies of AtACS6B (both designated the $T_1$ generation). The seeds were germinated after surface sterilization in 20% bleach +0.1% SDS for 20 minutes, followed by rinsing 3 times in sterile water. The sterilized seeds suspended in 0.1% agarose were plated on germination medium (MS salts, 1% sucrose, 3.5 g/L Phytagel, 75 mg/L kanamycin, pH 5.7). PCR analysis and protocols were performed according to the protocols at http://www.biotech.wisc.edu/Arabidopsis/ using PanVera ExTaq.

```
P1 primer
(GAAAGTTAAACTCAATTCCTCCGTCGATCA)    (SEQ ID NO:106)

P2 primer
(GCATATAACTTGGTGAGATCTTCAGAGAATT)   (SEQ ID NO:107)

KFLB primer
(TGCACTCGAAATCAGCCAATTTTAGACAA).    (SEQ ID NO:108)
```

In order to screen for the presence of multiple T-DNA insertions, progeny from the heterozygous $T_1$ plants were subjected to segregation analysis. The kanamycin segregation ratios of the $T_2$ seed of the heterozygous mutant indicated that only one T-DNA insertional event was present. Of 471 seed, 121 were kanamycin-sensitive, while 370 were resistant to kanamycin. This ratio represents a 3:1 hypothesis for a single insertion ($\chi^2=0.033$; $P>0.8$). Southern blot analysis of 5 $T_2$ plants from homozygous mutant showed identical restriction patterns to the heterozygous plants when probed with a LB fragment, confirming that the homozygous $T_1$ individual also contained only one insert.

Results from a Northern blot analysis showed the lack of full-length AtACS6B transcript in the acs6b/acs6b mutant. Total RNA was isolated from floral and bud tissues of wild type, heterozygous, and homozygous AtACS6B plants. As expected, transcripts of full-length AtACS6B were present only in wild-type and heterozygous mutant plants. A truncated transcript corresponding to the length of transcript preceding the T-DNA insertion was present in the heterozygous and homozygous mutants.

A comparison of the phenotypes of the homozygous mutant and the wild-type plants showed that at all stages of the life cycle, the homozygous mutant was indistinguishable from wild type plants grown under the same conditions. Quantitative measurements of growth rate also showed no difference between the homozygous mutant and wild-type plants.

Fatty acid analysis of above-ground portions of wild type and homozygous mutant plants at 19 days of age revealed no significant differences between any of the fatty acid species typically found in Arabidopsis leaves (fatty acids were analyzed as methyl esters of total extracted lipids).

Figure 57:
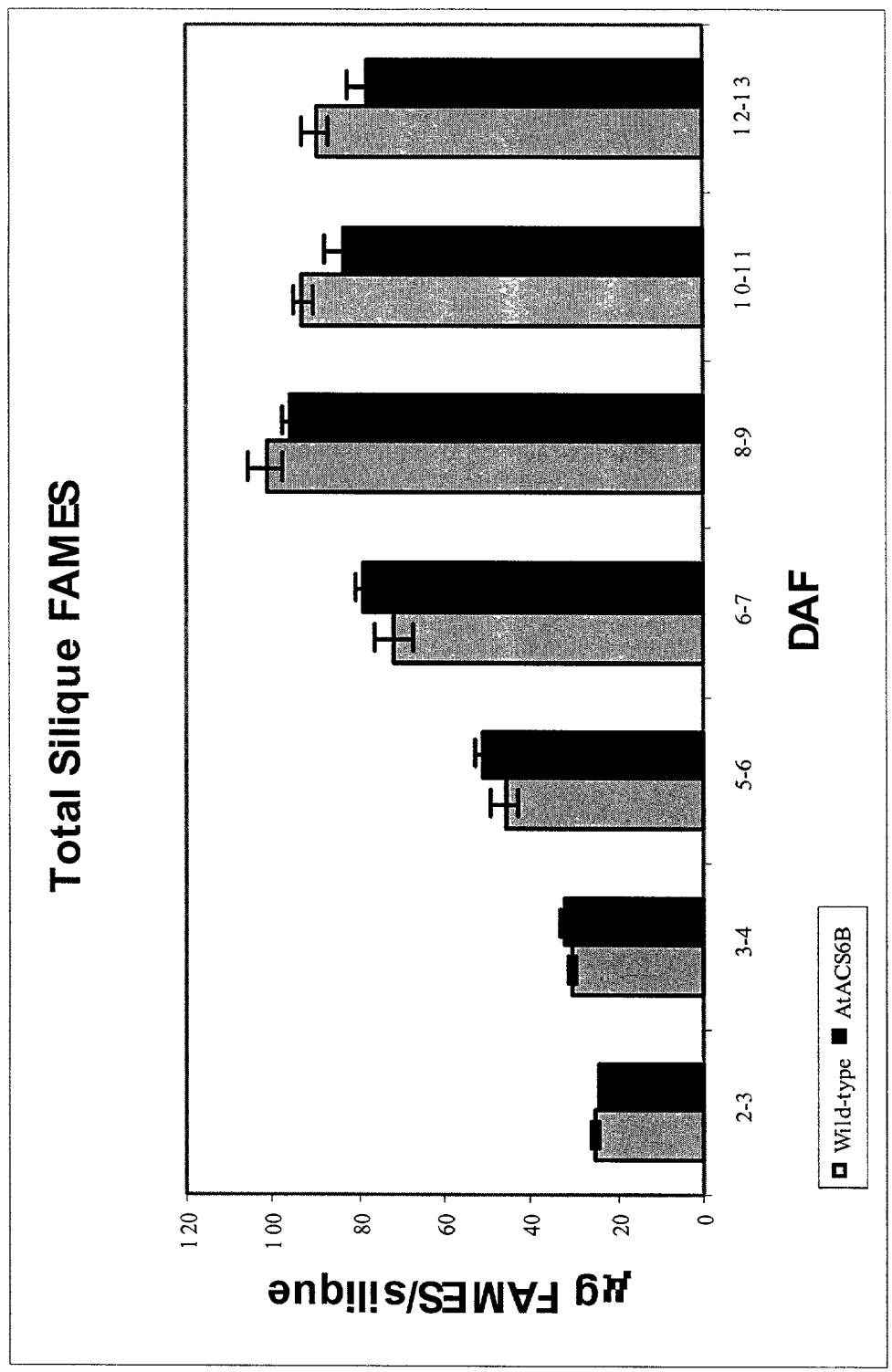
FIG. 57 shows the results of a fatty acid analysis of the siliques from wild-type and AtACS6B knockout mutant *Arabidopsis* 42 day old plants grown under 14: 10 photoperiod. The total lipids were derivatized with an internal standard using 2.5% $H_2SO_4$ in methanol and the fatty acid methyl esters were analyzed by gas chromatography. Values are means +/−SE (n=12).

Northern analysis showed that the AtACS6B transcript was more abundant in developing seeds than in leaves. Therefore, lipids of developing seeds from homozygous and wild-type plants were analyzed. The plants were grown under 14 hour photoperiod, and secondary and axillary floral stems were removed as they appeared in order to facilitate the cataloging and collection of siliques. At 42 days, intact siliques of varying developmental stages were removed and the total fatty acids analyzed. The lipid content of the homozygous mutant from 2 to 13 DAF did not differ significantly from that of wild type plants (see FIG. 57). The peak of lipid accumulation (8–9 days after flowering, or DAF) corresponds to the highest level of AtACS6B transcripts at 6 to 11 DAF developing siliques.

ACS activity was measured in chloroplasts isolated from wild type and homozygous mutant plants. Intact chloroplasts were isolated from 19 day old leaf tissue as described in Example 8. ACS was assayed as described in Example 5; the assay included isolated chloroplasts, CoenzymeA, ATP, and 1-$^{14}$C-oleic acid (18:1). When compared with wild type, the homozygous mutant chloroplasts exhibited a 13.75-fold decrease in ACS activity in this assay.

In summary, these results indicate that in the AtACS6B knock-out mutant, there were no visible phenotypic differences or measurable changes in fatty acid quantity or species between wild type and homozygous mutant plants, yet the homozygous mutant chloroplasts exhibited significantly less ACS activity than did the wild-type plants.

Another mutant, an ACS2 T-DNA knockout mutant, was also discovered, but in a different population of T-DNA mutant plants. This population of T-DNA mutant plants was prepared in a glabrous plant line, which is a Columbia mutant which is missing the gene responsible for developing trichomes. Thus, the wild-type plant for this mutant is a glabrous plant, or one which does not have trichomes.

The phenotype of the ACS2 mutant is quite different from that of the wild-type, in that the mutant has smaller, curled leaves and flowers slightly later. Segregation analysis indicated that the homozygous ACS2 knockout plant (11-4) contained multiple T-DNA insertions. To obtain a plant line which contained only insertions in the ACS2 genes, the plants were backcrossed with Columbia pollen. After several generations of selfing, plant lines which contained only insertions (homozygous) in ACS2 were obtained. These plants exhibited the small, puckered leaf phenotype of the original mutant, indicating that the absence of functional ACS2 transcript was responsible for the phenotype. On the other hand, even though phenotypically this mutant is quite different, the leaf fatty acids of this mutant do not appear to differ significantly from those of the wild-type plant.

Leaf fatty acids were analyzed by removing leaves from each of a wild-type plant (glabrous, "glb"), progeny of the original mutant plant with the same phenotype (homozygous, "11-4"), and progeny of the original mutant plant crossed with wild-type phenotype which exhibits a wild type phenotype (which is therefore believed to be hemizygous, "wt"), and placing them in individual glass screw-cap tubes. One and a half milliliters 2.5% $H_2SO_4$ in methanol were added to each tube and the tubes were incubated at 80° C. for 1.5 hours. Next, 1.5 ml water and 500 µl hexane were added to each tube. The tubes were vortexed and centrifuged to separate the phases. The hexane phases were then transferred to GC vials for GC analysis according to the following program: 150° C. for 1 min, then ramp at 15 degrees/min to 240° C., then hold for 2 min.

The fatty acid profiles of the mutants did not differ significantly from those of wild-type plants (See Table 5).

TABLE 5

Fatty acid profiles of leaves obtained from wild-type plants ("glb"; five different leaves from one plant were analyzed), progeny of the original ACS2 mutant plant crossed with the same phenotype (homozygous, "11-4"; five different plants were analyzed), and progeny of the original mutant ACS2 plant with wild-type phenotype (hemizygous, "wt"; five different plants were analyzed).

| Fatty acid | 16:0 | 16:1c | 16:1t | 16:2 | 16:3 | 18:0 | 18:1 | 18:2 | 18:3 |
|---|---|---|---|---|---|---|---|---|---|
| Retention time | 4.39 | | 4.69 | 4.80 | 5.19 | 5.51 | 5.64 | 5.92 | 6.29 |
| glb-#1 | 11.76 | | 1.33 | 0.36 | 10.99 | 0.88 | 0.88 | 9.18 | 41.41 |
| glb-#1 | 13.72 | | 3.23 | 0.69 | 12.49 | 0.94 | 1.20 | 9.88 | 41.68 |
| glb-#1 | 13.50 | 0.63 | 2.54 | 0.41 | 11.27 | 1.18 | 1.53 | 10.27 | 44.84 |
| glb-#1 | 12.51 | 0.36 | 2.85 | 0.39 | 11.36 | 0.71 | 0.74 | 9.09 | 45.62 |
| glb-#1 | 13.47 | | 2.81 | 0.41 | 11.52 | 0.95 | 0.82 | 9.69 | 48.62 |
| Average | 12.99 | 0.50 | 2.55 | 0.45 | 11.53 | 0.93 | 1.03 | 9.62 | 44.43 |
| 11-4 #1 | 12.18 | 0.52 | 2.28 | 0.62 | 11.48 | | 1.62 | 12.15 | 40.69 |
| 11-4 #2 | 11.82 | 0.47 | 2.15 | 0.62 | 10.96 | 0.96 | 2.34 | 13.14 | 36.96 |
| 11-4 #3 | 11.83 | 0.63 | 2.47 | 0.86 | 11.90 | 0.54 | 1.82 | 10.23 | 41.17 |
| 11-4 #4 | 12.74 | 0.57 | 2.13 | 0.62 | 12.14 | | 2.21 | 13.01 | 40.60 |
| 11-4 #5 | 12.20 | 0.49 | 1.99 | 0.54 | 11.10 | 0.59 | 1.66 | 12.79 | 41.27 |
| Average | 12.15 | 0.54 | 2.20 | 0.65 | 11.52 | 0.70 | 1.93 | 12.26 | 40.14 |
| wt #1 | 11.61 | 0.67 | 2.78 | 0.89 | 13.77 | 0.86 | 2.60 | 11.08 | 42.79 |
| wt #2 | 11.79 | 0.74 | 2.61 | 0.93 | 12.76 | 0.92 | 3.46 | 12.75 | 41.84 |
| wt #3 | 11.62 | 0.89 | 2.44 | 1.06 | 12.64 | 0.99 | 4.00 | 12.82 | 40.45 |
| wt #4 | 11.57 | 0.79 | 2.57 | 0.92 | 12.47 | 0.88 | 3.56 | 11.69 | 41.60 |
| wt #5 | 11.63 | 0.85 | 2.55 | 1.07 | 11.46 | 1.07 | 4.15 | 13.66 | 39.67 |
| Average | 11.644 | 0.788 | 2.59 | 0.974 | 12.62 | 0.944 | 3.554 | 12.4 | 41.27 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. An isolated nucleic acid sequence comprising SEQ ID NO:4.

2. The nucleic acid sequence of claim 1, wherein said sequence is operably linked to a heterologous promoter.

3. The nucleic acid sequence of claim 1, wherein said sequence is contained within a vector.

4. The nucleic acid sequence of claim 2, wherein said nucleic acid sequence is within a host cell.

5. A method for altering the phenotype of a plant comprising:
 a) providing:
  i) a vector comprising a nucleic acid sequence encoding a protein, said nucleic acid sequence comprising SEQ ID NO:4; and
  ii) plant tissue; and
 b) transfecting said plant tissue with said vector under conditions such that said protein is expressed.

6. A method for assaying acyl-CoA synthetase activity comprising:
 a) providing a nucleic acid comprising SEQ ID NO:4;
 b) expressing said nucleic acid sequence under conditions such that a protein is produced; and
 c) assaying the activity of said protein.

* * * * *

SEQUENCE LISTING

<160> NUMBER OF SEQ ID NOS: 141

<210> SEQ ID NO 1
<211> LENGTH: 2001
<212> TYPE: DNA
<213> ORGANISM: Arabidopsis thaliana

<400> SEQUENCE: 1

```
atgacgcagc agaagaaata catcttccaa gttgaagaag gcaaagaagg tagcgatgga      60
agaccatcag ttggtccagt gtaccggagt atctttgcca aggacggrtt tcccgacccg     120
atcgaaggaa tggatagttg ttgggatgtt ttccgcatgt ctgttgagaa gtatccaaac     180
aatccaatgc tgggacgccg cgagattgta gatggaaagc cgggtaagta tgtctggcaa     240
acataccaag aagtctacga cattgtcatg aaacttggaa attctctcag aagtgttgga     300
gttaaggacg aagcaaaatg tggtatctat ggtgcaaatt ctcctgagtg gattatcagc     360
atggaggctt gtaatgcaca tggactctat tgtgtaccgt tatatgatac actaggtgct     420
gatgctgtgg aattcatcat ttcccattca gaggtttcaa ttgtctttgt ggaagagaag     480
aagatctctg agttgttcaa gacatgccca aactcgacag agtacatgaa aactgttgtg     540
agcttcgggg gtgtctcacg tgaacaaaaa gaagaagctg aaactttggg gttggttata     600
tatgcttggg atgaattttt gaagctgggt gaaggaaagc aatatgatct cccaatcaaa     660
```

```
aagaaaagcg acatttgcac gattatgtat acgagtggaa ccactggtga cccaaaggga    720
gtgatgatat ctaacgaaag cattgtgact ctaatcgctg gagtgatccg tctactgaaa    780
agtgctaacg aggctctgac tgtgaaagat gtgtatcttt cttatcttcc tcttgcccac    840
atctttgacc gagttatcga ggagtgtttc attcaacatg gtgctgcaat tggcttctgg    900
cgagggatg taaaattgtt gatcgaagac cttgctgagc ttaaaccaac tattttttgt    960
gctgtacctc gtgtcctgga tagagtatac ccaggtcttc agaagaagct ttctgatggt   1020
ggattcttaa aaagttcat atttgattct gcattttcct ataaatttgg ttatatgaag    1080
aagggacagt ctcatgtgga ggcctctcca cttttttgaca aacttgtgtt cagcaaggtt   1140
aaacaaggac tcggaggcaa tgtgaggatt attctatctg gagctgctcc tcttgctagt   1200
cacgtagagt catttctaag agtggtggca tgctgtcatg ttctccaagg atacggtctt   1260
actgaaagct gtgctggaac ttttgtctcg ctgccagatg aactaggtat gctcggcaca   1320
gttggtccac cagtgccaaa cgttgatata cgccttgaat ccgtccccga gatggaatat   1380
gatactcttg cgagtactgc acgtggtgaa atctgcattc ggggaaagac cctttttctct  1440
ggttactaca aacgtgaaga tctcacgaaa gaggttctca ttgatggatg gctgcacaca   1500
ggtgatgttg gtgagtggca accagatgga agcatgaaga taattgacag gaagaagaat   1560
atctttaaac tctcacaagg agagtatgtt gcggtggaga catagaaaa catatacggt    1620
gaagtacaag ctgttgattc cgtgtgggtg tacggtaaca gctttgagtc cttcctaata   1680
gctatcgcca acccaaacca gcatatcctt gaacgctggg ctgcagaaaa cggtgtgagt   1740
ggtgactatg acgccctctg tcaaaatgaa aaggcaaagg aattcattct cggagaactt   1800
gttaaaatgg ccaaagagaa aaagatgaaa gggttcgaga tcatcaaggc gattcatctt   1860
gacccagtgc catttgacat ggaacgagat cttcttacgc cgaccttcaa aaagaaaagg   1920
cctcagttgc tgaaatacta ccagagtgtg atcgacgaaa tgtacaagac cataaatgca   1980
aaatttgctt ccagagggta g                                              2001

<210> SEQ ID NO 2
<211> LENGTH: 1977
<212> TYPE: DNA
<213> ORGANISM: Arabidopsis thaliana

<400> SEQUENCE: 2
atgacgtcgc agaaaagatt catctttgag gtggaagccg ctaaggaagc cacagatgga     60
aatccctcgg ttggtcctgt ctatcgtagt acttttgctc agaacggatt cccgaacccg    120
atcgatggta tccaaagctg ctgggatatt ttccgcacgg ctgttgagaa gtatccaaac    180
aatcgaatgc ttggtcgccg tgagatttcg aacgggaagg caggaaagta cgtgtggaaa    240
acatacaaag aagtatacga cattgtcata aaacttggaa attctctacg tagttgcggg    300
attaaggagg gagaaaaatg tggtatatat ggtataaatt gttgtgagtg gatcattagc    360
atggaggcat gtaatgcaca tggccttat tgtgtcccctt tatacgatac gttaggcgct    420
ggtgcagtgg aattcatcat ttctcatgca gaggttcaa ttgctttcgt ggaggagaag    480
aagatccctg agcttttta gacttgtcca aactcaacaa aatatatgaa gactgttgtg    540
agctttggcg gtgtcaaacc ggaacaaaaa gaagaagctg aaaaattggg attggtaata   600
cattcgtggg atgagttttt gaagctgggt gagggtaagc aatatgagct tcccattaaa    660
aagccaagcg acatatgcac gattatgtat actagcggaa caactggtga cccgaaggga    720
```

```
gttatgattt caaatgaaag cattgttact ataactactg gagtgatgca tttcctaggg      780
aatgtgaatg caagcctatc tgagaaggat gtgtatattt cttatcttcc tctcgcgcac      840
gtctttgatc gggcaatcga ggaatgtatt attcaagtag gtggttcaat tggtttctgg      900
cgcggggatg tcaaattgtt gattgaagac cttggtgagc taaaaccaag tatcttttgc      960
gccgttcctc gtgtcctaga tcgagtatac acaggactac agcagaaact atctggtggt     1020
ggtttcttca aaagaagaa atttggaaat atgaagaaag gacagtctca tgtggcagct      1080
tctccatttt gtgacaaact tgtattcaac aaggttaaac aaggacttgg aggcaatgtg     1140
aggattattc tgtctggagc ggctcctctc gctagtcaca tagaatcttt tctaagagtt     1200
gttgcatgtt gtaatgttct acaaggatat ggtctaactg agagttgtgc tggaactttt     1260
gcaacgttcc cagacgaact agacatgctt gggactgttg gtccacccgt gccaaacgtc     1320
gatatacgcc ttgaatctgt cccggaaatg aattatgatg ctcttggaag tactccgcga     1380
ggcgaaatat gcatacgagg aaaaacttta ttttcagggt actacaaacg tgaagacctc     1440
acaaaagagg tttttatcga cggatggttg cacacaggtg atgttggtga gtggcaacca     1500
aatggaagca tgaagataat tgaccggaaa agaacatct tcaaactcgc gcaaggagag      1560
tatgtcgctg ttgagaattt agaaaatgtc tacagtcaag tagaagttat tgaatcgata     1620
tgggtatatg gaaacagctt tgagtccttc cttgtcgcaa tcgctaaccc ggcccaacaa     1680
actcttgaac gatgggctgt ggagaatgga gtgaatggag acttcaactc catctgccaa     1740
aacgcaaagg caaagcatt catacttgga gaactcgtta aaacagccaa agagaacaag      1800
ttgaagggtt ttgagatcat aaaagatgtt catctggaac cagtggcgtt cgacatggaa     1860
cgagaccttc ttactccaac ctacaaaaag aagaggcctc aattgctcaa atactatcag     1920
aatgtgatcc atgaaatgta caagacaaca aaggaaagtc tagcttccgg acagtaa        1977
```

<210> SEQ ID NO 3
<211> LENGTH: 1998
<212> TYPE: DNA
<213> ORGANISM: Arabidopsis thaliana

<400> SEQUENCE: 3

```
atggcgactg gtcgatacat cgttgaggtt gagaagggaa agcaaggcgt tgatggagga       60
agtccatcgg tcggtccagt ttaccggagt atctatgcta aagacggttt tcctgaaccg      120
cctgatgatc tcgtcagtgc atgggatatt ttccgtttat ctgtggagaa atctccaaat      180
aatcctatgc ttggtcgtag agaaatagtt gatggaaaag ctgggaaata tgtatggcaa      240
acttacaaag aagtacataa tgtagtgatt aagcttggaa actctatcag aactattgga      300
gttggaaaag gagataaatg cggtatttat ggcgccaata gtcctgaatg gattataagc      360
atggaggctt gcaatgctca tggactctac tgtgtacctt tatatgacac tctaggtgct      420
ggagcaatag aattcatcat ttgtcatgct gaggtctcac ttgcttttgc tgaggagaac      480
aaaatctctg agttattgaa gacagctcct aaatcaacta atatttgaa gtatattgtg       540 agctttggtg aggttacaaa taatcagaga gtagaagctg agaggcacag attaacaata     600
tattcatggg accaattctt gaagctaggc gagggtaaac attatgaatt accagagaag      660
agaagaagcg atgtttgcac cataatgtat acaagtggca caactggtga tcctaaagga     720
gtattgctta caaatgagag cattattcat ctccttgaag gtgttaaaaa attgcttaaa     780
actattgacg aagagttaac cagtaaagat gtatatctct catatctacc tctggctcat    840
atcttcgatc gtgtgattga ggagctgtgt atttatgaag cagcctctat cggattctgg    900
```

-continued

```
cgaggggatg ttaagatatt gatagaagac attgctgcat tgaaacctac tgttttctgc    960
gctgttcctc gcgtgctaga gagaatatac accggtcttc agcagaaact ttctgatggt   1020
ggttttgtaa agaagaaatt attcaacttt gcattcaaat acaaacataa aaacatggag   1080
aaagggcagc tcatgaaca agcatctcca atagctgaca aaattgtatt taaaaaggta    1140
aaagaagggt tgggaggaaa cgtgcgtctt atcctctcag gagcagctcc tcttgcagct   1200
cacatcgaat cttttccttcg agttgtcgcg tgtgctcatg ttttgcaagg atacggtcta  1260
acagagagtt gtggtgggac ttttgtgtcc attccaaacg agctttcaat gcttggaacg   1320
gttggtccac cggttccaaa cgttgacata aggctagagt cagttccaga gatgggttat   1380
gacgctcttg caagcaatcc acgtggagag atttgcatca ggggaaagac tttgttctct   1440
ggatactaca aacgtgaaga tctcactcaa gaagtcttca ttgatggatg gcttcacact   1500
ggtgatgtcg gtgagtggca accagatgga gccatgaaga tcatcgaccg taagaagaac   1560
atctttaaac tgtctcaagg agaatacgtt gccgttgaga acttggagaa catatacagt   1620
catgtcgccg ccattgaatc gatatgggta tatggaaaca gctatgagtc ttacttagtg   1680
gctgtggtat gtccaagcaa gatccagatc gagcattggg ccaaagaaca caaagtttca   1740
ggagactttg agtctatctg ccgaaaccaa aagactaaag agtttgtcct tggagagttc   1800
aacagagtag ccaaagacaa aaagctgaag ggatttgagc tgatcaaagg tgttcatttg   1860
gacacagtcc cgttcgacat ggaaagagat ctcatcactc cttcttacaa gatgaaaaga   1920
cctcagcttc tcaagtacta tcagaaagag attgatgaaa tgtataagaa aaacagagaa   1980
gtgcagctac gagtgtaa                                                 1998
```

<210> SEQ ID NO 4
<211> LENGTH: 1998
<212> TYPE: DNA
<213> ORGANISM: Arabidopsis thaliana

<400> SEQUENCE: 4

```
atgtctttag ccgcggataa tgtgttgttg gtggaagaag gaaggccagc cacagcggaa     60
catccatcgg ccggaccggt ttatcgatgt aaatacgcta agatggccct cctcgatctc    120
cctaccgata ttgattctcc ttggcagttc tttagtgagg ctgtgaagaa atatccgaat    180
gagcaaatgt tgggccaacg cgtaacgact gattctaagg tcggtccata cacgtggatc    240
acatataagg aagcgcacga cgctgcaatt cggattggat cagcaatcag aagccgaggc    300
gttgatccgg gacactgttg tggtatttac ggagctaatt gtccagaatg gattattgca    360
atggaggcct gcatgagcca aggatcacc tacgtgcctc tatacgattc tttaggcgta    420
aacgcagttg aattcatcat caaccacgcc gaggtttcgc tagtatttgt tcaagagaag    480
acagtttcat cgatcttatc gtgccaaaag ggatgttctt cgaatttgaa gactattgtg    540
agcttcgggg aagtctcgag tacacaaaag gaagaagcta agaaccaatg tgtttcttta    600
ttttcatgga atgagttctc actaatggga aacttagatg aggcaaatct acctcgtaag    660
cgaaagacag acatctgcac aataatgtac acaagcggga cgactggaga acccaaaggt    720
gtaatcttaa acaacgcagc aatttcggtc caggttttat ccatagacaa aatgcttgaa    780
gtcactgatc gatcgtgtga cacgagcgat gtgttcttct cgtacttgcc attagcacat    840
tgctatgatc aagtcatgga gatttacttt ttatctagag ctcctctgt tggatactgg    900
cgtggcgaca ttcggtacct gatggatgat gttcaagctc ttaaacctac tgtgttttgc   960
```

| | |
|---|---:|
| ggtgttccac gagtttacga caaactatat gccggtataa tgcaaaaaat atcagctagt | 1020 |
| ggcttgatac gcaagaaact gtttgatttt gcttataact acaaattggg aaatatgaga | 1080 |
| aaaggattct ctcaagaaga agcttctcct cgtctagaca gacttatgtt cgataagata | 1140 |
| aaagaagcat taggaggaag agctcatatg ttgttatcag gagcagcgcc tctacctcgt | 1200 |
| catgtagagg agttcttgag aatcattcct gcctctaatc tctctcaagg ttatggattg | 1260 |
| actgagagtt gtgggggaag cttcacgacc ttagccggag tattttctat ggtggggaca | 1320 |
| gtgggtgtgc caatgccac ggtggaggca aggctagtgt ccgtaccaga gatgggttac | 1380 |
| gacgcctttt ccgctgacgt gccgagagga gagatttgtc ttagaggaaa ttcaatgttt | 1440 |
| tctggttacc ataaaagaca agatctaact gatcaagtcc taatcgatgg atggttccac | 1500 |
| acaggagata ttggagaatg gcaagaagat ggatcaatga agatcatcga taggaagaag | 1560 |
| aacatcttca gttgtctca aggtgaatat gttgctgttg aaaacctcga aaacacttac | 1620 |
| tcaagatgtc ccctcattgc tcaggtatgg gtctatggca acagcttcga gtcattttg | 1680 |
| gtaggtgtgg ttgtacctga tagaaaagct attgaagatt gggctaaact caattaccaa | 1740 |
| tctcccaatg atttcgaatc tctatgtcaa aatctcaaag ctcaaaaata cttcttggat | 1800 |
| gagcttaact ctaccgcaaa gcaatatcaa cttaaaggat ttgaaatgtt aaaagctatt | 1860 |
| catttagaac caaaccettt tgatattgaa agagatctta ttactccaac tttcaagctg | 1920 |
| aaaaggccac agctcctcca acattacaag ggcatagttg atcaacttta ttcagaagca | 1980 |
| aagaggtcca tggcatag | 1998 |

<210> SEQ ID NO 5
<211> LENGTH: 2257
<212> TYPE: DNA
<213> ORGANISM: Arabidopsis thaliana

<400> SEQUENCE: 5

| | |
|---|---:|
| atggattctt cttcttcgtc ttcctccgcc gccgcacgcc gccgtatcaa cgctatccac | 60 |
| tctcacctcg tcacctcttc tcgctcttcc cctctcctcc gctccaatcc caccgccggc | 120 |
| gagttctgtc ttgataatgg ctatagtgtt gttcttcccg agaaactgaa tactggcagt | 180 |
| tggaacgtct acagatctgc aaaatccccg ttcaagctcg ttagcagatt cccagatcat | 240 |
| cctgacatcg ctactctcca tgacaatttt gagcatgctg ttcatgattt tcgagattac | 300 |
| aagtatttag gaactcgtgt tcgtgtcgac ggaactgttg gagactacaa atggatgaca | 360 |
| tatgagaag ctggtacagc aagaactgct ttaggttctg gtttggttca tcacgtaatc | 420 |
| cccatgggat cttctgttgg aatttacttc atcaatcgcc cagagtggct cattgttgat | 480 |
| catgcttgtt cttcttattc ttatgtgtct gttcctttgt atgatactct tggtcctgat | 540 |
| gctgtgaaat ttattgtcaa tcatgcaact gtgcaagcca tattttgtgt ggcagagact | 600 |
| ttaaactctt tacttagctg tttgtctgag atgccaagtg tacgcctggt ggtggttgtt | 660 |
| ggagggttaa ttgaatcttt accctcgctt ccctcatcat caggagtgaa agttgtatcc | 720 |
| tattcggtgt tactgaatca gggtcgtagt aaccctcagc gatttttcc accaaaaccc | 780 |
| gatgatgttg caaccatatg ctatacaagc ggaacaactg ggacacccaa gggagtcgta | 840 |
| ttaactcatg caaacttgat tgccaatgtt gctggctcca gctttagtgt gaagtttttc | 900 |
| tcttcagatg tttacatttc gtatcttcca cttgctcaca tttacgaacg agctaatcag | 960 |
| atcctaacag tgtactttgg agttgctgtt ggattctacc aaggggacaa tatgaaacta | 1020 |
| ctggatgatt tggctgctct gagacctact gtatttagca gtgtccctcg attatacaat | 1080 |

```
agaatatatg ctggtatcat taatgcagta aaaacctctg gtggtctgaa agagagactc    1140
ttcaatgctg cctataatgc aaagaagcag gctctcttga atggaaagag tgcttctccc    1200
atatgggaca ggttggtatt taataaaata aaggacagac ttggagggcg ggttcgtttt    1260
atgacgtctg gtgcttcacc tctctctcct gaagtgatgg aattttttgaa agtatgcttt    1320 ggaggaaggg taacagaggg atatggaatg actgaaacat cttgtgttat aagtggaatg    1380
gacgagggtg ataacctcac tggacatgtt ggctctccta atccagcttg tgaaataaag    1440
cttgtggatg tcccagaaat gaactataca tcagcggatc agccccatcc ccgtggcgaa    1500
atatgtgtta ggggtcctat cattttttaca ggctattaca aagatgaaat tcaaacgaaa    1560
gaggtgattg atgaagatgg atggcttcac actggagata taggtctgtg gctgccggga    1620
ggacgtctaa aaattattga cagaaagaag aacatcttca aattggcgca ggggagtat    1680 atagctccag agaaaattga aaacgtctat gccaaatgca aatttgtggg ccagtgcttc    1740
atatatggtg atagctttaa ttcatcattg gtagctgttg tatcggttga tccagatgtg    1800
ctgaaaagct gggcagcttc agaaggcatt aagggaggag atctgagaga attgtgtaat    1860
aatccgagag tgaaagcagc agtactatct gacatggaca ctgttggaag agaagctcag    1920
ttgagaggct tcgagtttgc aaaggctgtg acattggtgc tggaaccatt tactctggaa    1980
aatggcttgt tgactccgac gttcaagatt aagagaccac aagcaaagga atatttcgca    2040
gaagcaataa caaacatgta caaggagctt ggtgcttctg atccctctgc taatagaggt    2100 tgtgtgagcgg ccgcactcga gcaccaccac caccaccact gagatccggc tgctaacaaa    2160
gcccgaaagg aagctgagtt ggctgctgcc accgctgagc aataactagc ataaccccttt    2220 ggggcctcta acgggtcttt gaggggtttt ttgctga                              2257

<210> SEQ ID NO 6
<211> LENGTH: 2103
<212> TYPE: DNA
<213> ORGANISM: Arabidopsis thaliana

<400> SEQUENCE: 6
atggaatttg cttcgccgga caacgtcgt ctcgaaacca ttcgatctca catcgatact      60
tctccgacca acgatcaatc atcatctata ttcctcaacg ccaccgcttc ttctgcttca    120 ccttttcttta aagaggatag ctacagtgtt gtgcttccag aaaagcttga tactggaaaa    180
tggaatgtct acagatctaa aagatcgcct acgaaactcg ttagtaggtt cccggatcat    240
cctgaaatcg ggactttaca tgacaatttt gtacatgctg ttgaaacata tgctgaaaac    300
aagtatcttg gtacacgagt tcggtccgat ggaaccattg gagagtattc atggatgaca    360
tatggagaag cagcgtctga gcgacaagcc attggttcag gactcttgtt tcatggagtt    420
aaccaaggag cttgcgttgg actctatttt attaacagac cagagtggtt ggttgtggat    480
catgcttgtg cagcatattc atttgtctct gttccttttat atgatacact tggtccagac    540
gctgttaagt ttgtggtgaa tcatgctaat ctgcaagcta tattttgtgt accacaaaacc    600 ttgaatatttt tgctaagctt cctagcggaa atcccatcca ttcgtctcat tgtggtggtg    660
ggaggggctg atgagcattt gccatcactt cctcgaggaa ctggagtcac aattgtatca    720
taccaaaagc tattgagtca gggtcgaagt agcttacatc cattttcgcc tccaaagcca    780
gaagacattg caaccatatg ctacacaagt ggaaccacag gaacaccaaa gggtgttgtg    840
ttgactcatg gaaacttgat cgcgaatgtc gctggttcca gtgtggaagc agaattcttt    900
```

```
ccttcagatg tttacatatc atatcttcct ttggcgcaca tatatgaacg tgcaaatcag    960
attatggggg tgtatggtgg tgttgctgtc ggtttctatc aggggatgt cttgaagctg   1020 atggatgatt ttgctgtgtt aagaccaaca atattctgta gtgtccctcg cttrtataat   1080
cgaatatatg atggcattac aagtgccgta aaatcatctg gggttgtgaa aaaaaggctt   1140
ttcgaaattg cctataactc aaagaagcaa gcgatcatta atgggcggac tccttctgca   1200
ttttgggaca agctggtgtt caacaaaata aaagaaaagc ttggtggacg ggttcggttt   1260
atggggtctg gtgcttctcc tttgtcacct gatgtcatgg atttcttgag aatatgcttt   1320
ggatgttcgg tgcgtgaagg gtatggtatg accgagactt cttgtgtcat aagcgctatg   1380
gatgatggtg acaatttatc tggccacgtc ggatcccta atccagcttg cgaggtaaag   1440
cttgtggatg ttcccgaaat gaattacaca tcggaagatc aaccataccc acgtggtgaa   1500
atctgtgtaa gaggaccaat catcttcaaa ggctaytaca agatgaaga caaacgaga   1560 gaaattcttg atggagatgg ctggctacac acaggagata tcgggttgtg gttacctggt   1620
ggtcggctca agatcataga caggaagaag aacatattta gttggcgca aggagaatat   1680 atagcaccag agaagatcga aaatgtttat accaaatgta gattcgtttc gcagtgtttc   1740
attcacggtg atagcttcaa ttcctctcta gtagctatag tttcagtcga ccccgaagtt   1800
atgaaagatt gggctgcatc agaaggcatc aagtatgagc atctaggaca gctctgtaac   1860
gatccaagag tgcgaaagac tgttcttgct gagatggatg accttggaag agaagctcag   1920
ttgagagggt ttgagtttgc aaaggctgtg actttggtgc cagaaccatt caccttggag   1980
aatggacttc tcacaccaac attcaagata aagagacctc aagcaaaagc ctactttgca   2040
gaagcaatta gcaaaatgta tgcggaaatc gcagcctcga accccattcc ttctaaactg   2100
tga                                                                  2103

<210> SEQ ID NO 7
<211> LENGTH: 2130
<212> TYPE: DNA
<213> ORGANISM: Arabidopsis thaliana

<400> SEQUENCE: 7
atggcttcga cttcttcttt gggaccttct acactactct cttacggttc tccttctcgt     60
cagtttcctg attttgggtt cagattgatt tcgggtcacg aaagtgttcg aattccatca    120
ttccggcgat ttcgggttca ctgcgagtca aaggaaaaag aagtgaagcc gtcttctcca    180
tttcttgaaa gctcctcgtt ttcgggagat gccgctttgc gctctagtga atggaaggct    240
gttcctgata tttggagatc atctgcagaa aagtatggtg atagagttgc attggtggat    300
ccttatcatg atcctccttt gaaactgacg tacaagcagt tggaacaaga aattttggac    360
tttgctgagg gcttacgagt tcttggagtg aaagcagatg agaagattgc acttttttgct   420 gataactcct gccgatggct tgtttcagat caaggtataa tggccacagg ggcagtcaat    480
gttgtcagag gatctaggtc ctctgttgaa gagttactgc agatataccg tcattctgaa    540
agcgtagcca ttgttgtgga taatcctgag tttttcaacc gcattgctga gtcatttacg    600
tcaaaggcat ctctgagatt tttgatactt ctctggggtg agaaatcatc actggtcaca    660
caggggatgc agattccagt ttacagttat gcagaaatta taaaccaagg acaggagagt    720
cgtgcaaaat tatcagcatc taatgatacc aggagctata gaaatcaatt catcgattca    780
gatgatacag ctgcaattat gtataccagt ggtaccacgg gaaatccaaa aggcgttatg    840
cttacacatc ggaatctctt acaccagata aaacatttat ccaaatatgt acctgctcaa    900
```

-continued

```
gctggggata aatttctaag catgctacca tcatggcatg cctatgaacg tgctagtgaa      960
tacttcatat tcacttgtgg agttgagcaa atgtatacat ctataagata cttaaaggat     1020
gatctaaagc ggtaccaacc gaactatatt gtgtccgttc ctctagtata tgagacactt     1080
tacagtggga ttcaaaagca aatttctgca agttctgctg gccgtaaatt tctagcactt     1140
acattgatca aagtcagtat ggcatatatg gagatgaaaa ggatatatga gggtatgtgt     1200
ctgacaaaag agcaaaagcc tccaatgtat attgttgctt ttgtggattg gttgtgggcg     1260
agagtaattg ctgccttgtt gtggccatta catatgttgg ccaaaaagct tatctacaag     1320
aaaattcatt cgtctattgg gatatcgaag ctggtatta gcggaggtgg tagtttaccc      1380
attcatgttg acaagttttt tgaggccatc ggtgtgattc tacaaaatgg ttatggtttg     1440
acagagacct cacctgttgt ctgtgcacgg acacttagct gcaatgttct tggctcagct     1500
gggcatccaa tgcatggtac agaattcaaa attgtagatc ctgagactaa taatgtactc     1560
cctcctggtt caagggcat tatcaaagtc agaggtccac aggttatgaa gggttattat      1620
aagaatccat cgactacaaa gcaagttcta aatgagagtg atggttcaa tacaggagac      1680 accggttgga ttgctcctca tcactcaaaa gggcggagtc gccactgtgg aggtgtcatt     1740
gttcttgaag gccgtgcaaa agacacaatt gtactttcca caggtgaaaa tgtgaaccg      1800 ttggagattg aagaagccgc catgagaagc agggtgattg aacaaattgt tgttattgga     1860
caggaccgac gtcgccttgg agctatcatt atcccaaaca aagaggaagc acaaagagta     1920
gatcctgaaa catccaaaga aacactaaag agcttggtct accaagaact gagaaaatgg     1980
acatcagaat gttcgtttca agtcggacca gtcttgatcg tcgacgaccc tttcacgata     2040
gacaacgggt taatgacacc aactatgaag attagacggg acatggtcgt ggctaaatac     2100
aaagaggaga ttgatcaact ctacagttaa                                       2130
```

<210> SEQ ID NO 8
<211> LENGTH: 2169
<212> TYPE: DNA
<213> ORGANISM: Arabidopsis thaliana

<400> SEQUENCE: 8

```
atggcttcaa cgtctctcgg agcttcgatt ctcgtttctc actgctgctc agctcctgaa       60
tttcaagttt ctgggatgag attggtgttt ggttacaagg cttttggctg cagaacttca     120 cgcagggat ttcgagttcg ctgcgaatcc aagattcagg agaaggagtt aaggcggtgt       180
tcgccattct tagaacgctt atcattgcca agggaggctg ctttgagctc taatgaatgg     240
aagtctgttc ctgatatttg gagatcatct gtggagaagt acggtgacag agttgcggtg     300
gtagatccgt atcatgaccc gccttctaca ttcacgtaca gacagttgga acaagaaatc     360
ttggactttg ttgagggttt acgagtcgtt ggagtgaaag cagacgagaa gattgcactt     420
tttgctgata actcctgtcg atggcttgtt gcggatcaag gtataatggc cacaggagca     480
gtcaatgttg ttagaggatc cagatcgtct gttgaagagt tattgcagat atactgtcat     540
tcggaaagtg tagcccttgt tgtggataac cctgagtttt caatcgcat gcggagtca       600 ttttcttaca aggcagctcc aaaatttgtg attcttctct gggggaaaa atcgtcgttg      660 gttacagcgg gtaggcacac accagtctat agttacaacg aaattaaaaa gtttggacaa     720
gagagacgtg caaaatttgc aagatctaat gattctggga agtatgaata tgaatacatc     780
gatccagatg atatagccac aattatgtat accagtggaa ccacaggaaa tccaaaaggt     840
```

-continued

```
gttatgctca cacatcagaa tttgttacac cagataagaa acttgtccga ttttgtgcct      900
gcggaagctg gggaaagatt tctgagtatg ttgccatcat ggcatgctta tgaacgggct      960
tgtgaatact tcatatttac atgtggagtt gagcaaaagt atacgtctat aagattctta     1020
aaggatgatc tcaagcgtta tcaaccacac tatcttattt cagttccttt agtatatgag     1080
acactctaca gcgggattca aaagcaaatt tctgcaagct cccctgctcg taaatttttg     1140
gcacttacat tgatcaaagt cagcctggca tatacggaaa tgaaaagagt ttatgagggt     1200
ctttgtttga caaaaaatca aaagcctcca atgtatattg tttcgttggt ggattggttg     1260
tgggcgagag tagttgcatt tttcctatgg ccattgcata tgttggctga aaagcttgta     1320
cacagaaaaa ttcgttcgtc tattgggata caaaggctg tgttagtgg aggtggtagt       1380 ttacctatgc atgttgacaa gttttttgag gccatcggtg tgaatgtaca aaatgggtat     1440
ggtttgacag aaacctcacc ggttgtctct gcgcgaaggc ttaggtgtaa cgttcttggc     1500
tcagttgggc atcctattaa agatacgag ttcaaaattg tagatcatga gactggtact      1560
gttcttccac ctggttcaaa gggcattgtc aaagtcagag gcccaccggt gatgaaaggt     1620
tactacaaga atccactggc caccaagcag gttatagatg acgatggatg gttcaatact     1680
ggagatatgg gttggattac tcctcagcac tcaacaggac ggagtcgtag ctgtggaggt     1740
gtcatcgttc ttgaagggcg tgccaaggac actatcgtgc tttccacagg tgaaaatgtg     1800
gaaccattgg agattgaaga agcggccatg agaagcaatt tgattcaaca aatagtggtt     1860
attggacagg atcaacgccg ccttggagct attgttatcc caaacaaaga agcagcagaa     1920
ggagcagcaa agcagaaaat ttcacctgta gattctgaag tcaatgaact tagcaaggag     1980
acgataacaa gcatggtcta tgaagaacta aggaaatgga cgtcacaatg ctcgttccaa     2040
gtgggaccag ttctgatcgt ggatgaacca ttcacgatag acaacggttt aatgacaccg     2100
acaatgaaaa taagacggga caaggtggtt gatcaataca agaatgaaat agaaagactc     2160
tacaagtag                                                            2169
```

<210> SEQ ID NO 9
<211> LENGTH: 1983
<212> TYPE: DNA
<213> ORGANISM: Arabidopsis thaliana

<400> SEQUENCE: 9

```
atgaagtctt ttgcggctaa ggtagaagag ggagttaaag gaatagacgg aaagccgtcg      60
gtaggtccgg tgtaccggaa tcttctgtcg gaaaaaggtt ttcctccgat tgattcygag     120
atcaccactg cttgggacat tttcagtaaa tcagtggaga aattccctga caataatatg     180
cttggatggc gtcgaattgt tgatgagaag gttggaccat atatgtggaa aacgtacaag     240
gaagtatacg aagaagtttt gcagattggc tctgcactac gagccgccgg agctgaacct     300
gggagtcgag tgggatcta cggtgttaat tgtcctcagt ggatcatagc aatggaggct     360
tgtgcagctc acactctaat ctgtgtacct ctatatgata cattgggttc aggagcagtc     420
gattacattg tagagcatgc ggaaatcgac tttgtgtttg tccaagacac caaaattaaa     480
ggacttcttg agccagattg caaatgtgct aaacggctaa agctatagt ttccttcact      540 aacgtgagcg acgagcttag ccacaaggct tcagaaattg gagtcaaaac atactcctgg     600
atcgattttc tccatatggg acgtgagaaa ccggaagaca cgaacccgcc taaggcgttt     660
aacatatgca cctataatgta caccagcggc acaagcggtg atcctaaagg tgtggttttg     720
actcaccaag cggtcgcgac ttttgttgtt gggatggatc tctatatgga ccagtttgaa     780
```

-continued

```
gataagatga cacatgatga tgtgtatctc tccttcttgc ccttggctca tattcttgac    840
cgtatgaacg aggaatactt ctttcgcaaa ggcgcttccg tcggctatta ccatggaaat    900
ttgaacgtgt tacgtgacga tattcaagaa ctgaaaccga cttatctagc tggagtacca    960
agagtgtttg agagaatcca tgagggatt  caaaaggctc ttcaagaact aacccaaga   1020
aggagattca tcttcaatgc tctctacaaa cacaagcttg cgtggttgaa tcgtgggtac   1080
tctcatagta aagcttcacc catggctgat tcattgctt  tcagaaagat tagagacaaa   1140
ttgggaggtc gcatccggtt gctagtatct ggaggagcac ctttgagccc cgagattgaa   1200
gagttttga  gagttacttg ttgttgcttt gtcgttcaag gctacggtct aacggagaca   1260
cttggaggaa cggctttggg tttcccggac gagatgtgta tgctagggac agtcggtatt   1320
ccagcggttt acaacgagat acggcttgaa gaggtgtctg aaatgggcta tgaccccgctc  1380
ggagaaaatc cggcaggaga gatctgtata agaggacaat gtatgttttc agggtattac   1440
aagaaccctg aactcactga agaagtcatg aaagatggat ggttccacac aggagatata   1500
ggtgagattc ttccaaacgg agtactcaag atcatcgatc gtaaaaagaa tctgatcaaa   1560
ctttctcaag gagaatatgt tgctctcgag catttggaaa acatcttcgg gcaaaactct   1620
gttgtccaag atatatgggt ttatggagac agcttcaaat ctatgcttgt cgcggtggtt   1680
gttcccaacc cagaaaccgt caacaggtgg gctaaagatc tcggttttac taaaccattc   1740
gaagaactct gttctttccc ggaactaaaa gaacacatca tttcagaact gaagtccacg   1800
gcagaaaaga acaagctaag aaagtttgag tacatcaaag cggtgacagt ggagacaaaa   1860
cctttcgacg tagagagaga cttagtgact gcgacgctca agaatcggag gaacaatctt   1920
ctcaaatatt atcaggtgca aatcgacgaa atgtaccgca aattggcctc aagaaaaatc   1980
tga                                                                1983
```

<210> SEQ ID NO 10
<211> LENGTH: 2163
<212> TYPE: DNA
<213> ORGANISM: Arabidopsis thaliana

<400> SEQUENCE: 10

```
atggaagatt ctggagtgaa tccaatggat tcaccatcta aaggcagtga ctttggagtc     60
tatggaatca taggaggtgg aatcgtggct ttacttgtgc ctgtgttact ctctgtggtg    120
ttgaatggaa ccaaaaaggg gaaaaagaga ggtgttccca tcaaagtagg tggcgaggaa    180
ggttacacaa tgcgtcatgc tcgagctcct gaattggttg atgtaccttg ggaaggagct    240
gctactatgc ctgctttgtt tgagcagtct tgtaagaagt attcgaaaga tcggttacta    300
ggaactagag agtttataga taaggaattt attactgcta gtgatgggag gaagtttgag    360
aagcttcatt taggagagta taatggcaa  agttatggag aggttttga  acgtgtttgt    420
aactttgcgt cggggttagt taatgtagga cataatgttg atgatcgtgt tgctatcttt    480
tcggatactc gtgctgagtg gtttatcgcg tttcagggat gtttcaggca gagcataacc    540
gttgttacta tttatgcttc tttaggagaa gaggctttga tttactcact caatgagact    600
cgagtgtcaa ccttaatatg tgactcaaaa caacttaaga agttgtctgc gatacaatca    660
agcttgaaaa ctgtgaagaa cattatttac attgaagaag atggagtaga tgttgcttct    720
agtgatgtca atagtatggg tgatataact gtttcgtcga tctctgaagt tgagaaactt    780
gggcagaaga acgctgttca accgatctta ccttcgaaga atggagttgc tgttataatg    840
```

-continued

| | |
|---|---|
| tttaccagtg gtagtactgg tctaccaaag ggagttatga ttacccacgg aaatcttgtc | 900 |
| gcaactgctg caggagttat gaaggtggtt ccaaagttgg ataaaaatga tacatatatt | 960 |
| gcgtacttac ctttggctca tgtgtttgag ctggaagctg agattgtggt ctttacctca | 1020 |
| ggtagtgcca tcggttacgg ctcagcaatg actttaactg acacttcaaa taaagttaag | 1080 |
| aaaggaacca aaggagatgt ttcagctctg aagccaacta taatgactgc agttccagct | 1140 |
| attctggatc gtgtccgaga aggagttctt aaaaaggttg aggaaaaggg agggatggcg | 1200 |
| aagacccttt ttgactttgc atacaagcgc cggttagcag ctgtggatgg aagttggttt | 1260 |
| ggtgcctggg gtttggagaa aatgttatgg gatgctcttg tcttcaagaa atacgcgct | 1320 |
| gtgcttggag gacacatccg tttttatgctc gttggaggag ctcctctgtc tcctgattcg | 1380 |
| caacgcttca tcaatatctg catggggtct cccatcggcc aaggatatgg attgactgaa | 1440 |
| acgtgtgctg gagctacgtt ttctgagtgg gacgatcctg ctgttggtcg tgttggacct | 1500 |
| ccacttccat gcggctacgt taagctcgtt tcttgggaag aaggtggcta cagaatttca | 1560 |
| gataaaccaa tgcctagagg ggagattgtg gtaggtggta acagtgtaac agcaggttac | 1620 |
| ttcaacaatc aagaaaaaac cgatgaggtt tacaaggtcg atgagaaggg cacaaggtgg | 1680 |
| ttttacaccg gagatattgg gagattccac cctgatggat gtctcgaagt catcgataga | 1740 |
| aagaaagata ttgttaaact tcaacatggg gaatacgtat cccttggaaa ggtggaggca | 1800 |
| gctttgggtt cgagcaatta cgttgataac atcatggtcc acgcagaccc aattaacagc | 1860 |
| tactgtgtag ctcttgttgt tccatcacga ggagcattag agaaatgggc agaggaagct | 1920 |
| ggagttaaac acagcgaatt cgctgagcta tgcgagaaag gtgaagcagt caaggaggtt | 1980 |
| caacaatctc ttaccaaggc cgggaaggcg gcaaagctcg aaaagtttga gcttccagca | 2040 |
| aagatcaagt tgctgtcaga gccgtggaca ccggagtcgg gattggtcac tgctgctctt | 2100 |
| aagataaaga gagaacaaat aaagtccaag ttcaaagatg aactcagcaa gttatatgcc | 2160 |
| taa | 2163 |

<210> SEQ ID NO 11
<211> LENGTH: 2076
<212> TYPE: DNA
<213> ORGANISM: Arabidopsis thaliana

<400> SEQUENCE: 11

| | |
|---|---|
| atgattcctt atgctgctgg tgttattgtg ccattggctt tgacgtttct ggttcagaaa | 60 |
| tctaagaaag aaaagaaaag aggtgttgtt gttgatgttg tggtgaacc aggttatgct | 120 |
| attaggaatc acaggtttac tgagcctgtt agttcccatt gggaacatat ctcaacgctt | 180 |
| ccagagctct ttgagatatc gtgtaatgct cacagtgata gggttttcct ggcacccga | 240 |
| aagctgatct ctagagagat tgagactagt gaggatggaa aaacgttcga gaaactgcat | 300 |
| ttaggtgact acgagtggct cacttttggg aagactctcg aagcagtgtg tgattttgcc | 360 |
| tctgggttag ttcagattgg gcacaagacg gaagagcgtg tcgccatttt tgcagatact | 420 |
| agagaagaat ggttcatctc cctacaggt tgcttcaggc gcaacgtcac tgtggtaact | 480 |
| atctattcat ctttgggaga ggaagctctt tgtcactcgc tgaatgagac agaggtcaca | 540 |
| accgtaatat gtggtagcaa agaactcaaa aagctcatgg acataagcca acagcttgaa | 600 |
| actgtgaaac gtgtgatatg catggatgat gaattcccat ctgatgtgaa cagtaattgg | 660 |
| atggcgactt catttactga tgttcagaaa cttggccgcg aaaatcctgt ggatcctaat | 720 |
| ttccctctct cagcagatgt tgctgttata atgtacacca gtggaagcac tggacttccc | 780 |

```
aagggtgtta tgatgacgca tggtaatgtc ctagctacag tttcggcagt gatgacaatt    840
gttcctgacc ttggaaagag ggatatatac atggcatatt tacctttggc tcacatcctt    900
gagttagcag ctgagagcgt aatggctact attgggagtg ctattggata tgggtctccc    960
ttgacgctaa cggatacttc aaacaagata aaaagggta caaaggaga tgtcacagca     1020 ctaaagccca ctataatgac agctgttcca gccattcttg atcgtgtcag ggatggtgtc   1080
cgcaaaaagg ttgatgcaaa gggcggattg tcaaagaaat tgtttgactt tgcatatgct   1140
cggcgattat ctgcaatcaa tggaagttgg tttggagcct ggggattaga aaagcttttg   1200
tgggatgtgc ttgtgttcag gaaaatccgt gcagttttgg gaggtcaaat ccgctatttg   1260
ctctctggtg gtgcccctct ttctggtgac actcagagat tcattaacat ctgcgttggg   1320
gctccaatcg gtcagggata tgggctcaca gagacttgtg ctggtggaac cttctcggag   1380
tttgaggaca catccgttgg ccgtgttggt gctccacttc cttgctccct tgtaaagcta   1440
gtagactggg cggaaggtgg gtatctaact agtgataagc cgatgccccg tggtgaaatt   1500
gtaattggtg gctcaaatat cacgcttggg tatttcaaaa atgaggagaa actaaagaa    1560 gtgtacaagg ttgatgaaaa gggaatgagg tggttctaca caggagacat aggacgattt   1620
caccctgatg gctgcctcga gataatagac cgaaaaaagg atatcgttaa acttcagcat   1680
ggagaatatg tctccttggg caaagttgaa gctgctctaa gtataagtcc ctatgttgaa   1740
aacataatgg ttcatgctga ttcgttctac agttactgtg tggctcttgt ggtcgcgtcc   1800
caacatacag ttgaaggttg ggcttcaaag caaggaatag actttgccaa cttcgaagaa   1860
ctgtgcacga aagagcaagc cgtgaaagaa gtgtatgcgt cccttgtgaa ggcggctaaa   1920
caatcacgat tggagaagtt tgagatacca gcaaagatca aattattggc atctccatgg   1980
acgccagagt caggattagt cacagcagct ctaaagctga agagatgt aattaggagg     2040 gaattctctg aagatctcac caagttatat gcctaa                             2076
```

<210> SEQ ID NO 12
<211> LENGTH: 666
<212> TYPE: PRT
<213> ORGANISM: Arabidopsis thaliana

<400> SEQUENCE: 12

```
Met Ser Gln Gln Lys Lys Tyr Ile Phe Gln Val Glu Glu Gly Lys Glu
1               5                   10                  15

Gly Ser Asp Gly Arg Pro Ser Val Gly Pro Val Tyr Arg Ser Ile Phe
            20                  25                  30

Ala Lys Asp Gly Phe Pro Asp Pro Ile Glu Gly Met Asp Ser Cys Trp
        35                  40                  45

Asp Val Phe Arg Met Ser Val Glu Lys Tyr Pro Asn Asn Pro Met Leu
    50                  55                  60

Gly Arg Arg Glu Ile Val Asp Gly Lys Pro Gly Lys Tyr Val Trp Gln
65                  70                  75                  80

Thr Tyr Gln Glu Val Tyr Asp Ile Val Met Lys Leu Gly Asn Ser Leu
                85                  90                  95

Arg Ser Val Gly Val Lys Asp Glu Ala Lys Cys Gly Ile Tyr Gly Ala
            100                 105                 110

Asn Ser Pro Glu Trp Ile Ile Ser Met Glu Ala Cys Asn Ala His Gly
        115                 120                 125

Leu Tyr Cys Val Pro Leu Tyr Asp Thr Leu Gly Ala Asp Ala Val Glu
    130                 135                 140
```

```
Phe Ile Ile Ser His Ser Glu Val Ser Ile Val Phe Val Glu Glu Lys
145                 150                 155                 160

Lys Ile Ser Glu Leu Phe Lys Thr Cys Pro Asn Ser Thr Glu Tyr Met
            165                 170                 175

Lys Thr Val Val Ser Phe Gly Val Ser Arg Glu Gln Lys Glu Glu
        180                 185                 190

Ala Glu Thr Phe Gly Leu Val Ile Tyr Ala Trp Asp Glu Phe Leu Lys
        195                 200                 205

Leu Gly Glu Gly Lys Gln Tyr Asp Leu Pro Ile Lys Lys Lys Ser Asp
    210                 215                 220

Ile Cys Thr Ile Met Tyr Thr Ser Gly Thr Thr Gly Asp Pro Lys Gly
225                 230                 235                 240

Val Met Ile Ser Asn Glu Ser Ile Val Thr Leu Ile Ala Gly Val Ile
                245                 250                 255

Arg Leu Leu Lys Ser Ala Asn Glu Ala Leu Thr Val Lys Asp Val Tyr
                260                 265                 270

Leu Ser Tyr Leu Pro Leu Ala His Ile Phe Asp Arg Val Ile Glu Glu
        275                 280                 285

Cys Phe Ile Gln His Gly Ala Ala Ile Gly Phe Trp Arg Gly Asp Val
    290                 295                 300

Lys Leu Leu Ile Glu Asp Leu Ala Glu Leu Lys Pro Thr Ile Phe Cys
305                 310                 315                 320

Ala Val Pro Arg Val Leu Asp Arg Val Tyr Pro Gly Leu Gln Lys Lys
                325                 330                 335

Leu Ser Asp Gly Gly Phe Leu Lys Lys Phe Ile Phe Asp Ser Ala Phe
                340                 345                 350

Ser Tyr Lys Phe Gly Tyr Met Lys Lys Gly Gln Ser His Val Glu Ala
            355                 360                 365

Ser Pro Leu Phe Asp Lys Leu Val Phe Ser Lys Val Lys Gln Gly Leu
        370                 375                 380

Gly Gly Asn Val Arg Ile Ile Leu Ser Gly Ala Ala Pro Leu Ala Ser
385                 390                 395                 400

His Val Glu Ser Phe Leu Arg Val Val Ala Cys Cys His Val Leu Gln
                405                 410                 415

Gly Tyr Gly Leu Thr Glu Ser Cys Ala Gly Thr Phe Val Ser Leu Pro
            420                 425                 430

Asp Glu Leu Gly Met Leu Gly Thr Val Gly Pro Pro Val Pro Asn Val
        435                 440                 445

Asp Ile Arg Leu Glu Ser Val Pro Glu Met Glu Tyr Asp Thr Leu Ala
450                 455                 460

Ser Thr Ala Arg Gly Glu Ile Cys Ile Arg Gly Lys Thr Leu Phe Ser
465                 470                 475                 480

Gly Tyr Tyr Lys Arg Glu Asp Leu Thr Lys Glu Val Leu Ile Asp Gly
            485                 490                 495

Trp Leu His Thr Gly Asp Val Gly Glu Trp Gln Pro Asp Gly Ser Met
                500                 505                 510

Lys Ile Ile Asp Arg Lys Lys Asn Ile Phe Lys Leu Ser Gln Gly Glu
            515                 520                 525

Tyr Val Ala Val Glu Asn Ile Glu Asn Ile Tyr Gly Glu Val Gln Ala
        530                 535                 540

Val Asp Ser Val Trp Val Tyr Gly Asn Ser Phe Glu Ser Phe Leu Ile
545                 550                 555                 560
```

```
Ala Ile Ala Asn Pro Asn Gln His Ile Leu Glu Arg Trp Ala Ala Glu
                565                 570                 575

Asn Gly Val Ser Gly Asp Tyr Asp Ala Leu Cys Gln Asn Glu Lys Ala
            580                 585                 590

Lys Glu Phe Ile Leu Gly Glu Leu Val Lys Met Ala Lys Glu Lys Lys
        595                 600                 605

Met Lys Gly Phe Glu Ile Ile Lys Ala Ile His Leu Asp Pro Val Pro
    610                 615                 620

Phe Asp Met Glu Arg Asp Leu Leu Thr Pro Thr Phe Lys Lys Lys Arg
625                 630                 635                 640

Pro Gln Leu Leu Lys Tyr Tyr Gln Ser Val Ile Asp Glu Met Tyr Lys
                645                 650                 655

Thr Ile Asn Ala Lys Phe Ala Ser Arg Gly
                660                 665

<210> SEQ ID NO 13
<211> LENGTH: 658
<212> TYPE: PRT
<213> ORGANISM: Arabidopsis thaliana

<400> SEQUENCE: 13

Met Thr Ser Gln Lys Arg Phe Ile Phe Glu Val Glu Ala Ala Lys Glu
1               5                   10                  15

Ala Thr Asp Gly Asn Pro Ser Val Gly Pro Val Tyr Arg Ser Thr Phe
                20                  25                  30

Ala Gln Asn Gly Phe Pro Asn Pro Ile Asp Gly Ile Gln Ser Cys Trp
            35                  40                  45

Asp Ile Phe Arg Thr Ala Val Glu Lys Tyr Pro Asn Asn Arg Met Leu
        50                  55                  60

Gly Arg Arg Glu Ile Ser Asn Gly Lys Ala Gly Lys Tyr Val Trp Lys
65                  70                  75                  80

Thr Tyr Lys Glu Val Tyr Asp Ile Val Ile Lys Leu Gly Asn Ser Leu
                85                  90                  95

Arg Ser Cys Gly Ile Lys Glu Gly Glu Lys Cys Gly Ile Tyr Gly Ile
                100                 105                 110

Asn Cys Cys Glu Trp Ile Ile Ser Met Glu Ala Cys Asn Ala His Gly
            115                 120                 125

Leu Tyr Cys Val Pro Leu Tyr Asp Thr Leu Gly Ala Gly Ala Val Glu
    130                 135                 140

Phe Ile Ile Ser His Ala Glu Val Ser Ile Ala Phe Val Glu Glu Lys
145                 150                 155                 160

Lys Ile Pro Glu Leu Phe Lys Thr Cys Pro Asn Ser Thr Lys Tyr Met
                165                 170                 175

Lys Thr Val Val Ser Phe Gly Val Lys Pro Glu Gln Lys Glu Glu
                180                 185                 190

Ala Glu Lys Leu Gly Leu Val Ile His Ser Trp Asp Glu Phe Leu Lys
            195                 200                 205

Leu Gly Glu Gly Lys Gln Tyr Glu Leu Pro Ile Lys Lys Pro Ser Asp
    210                 215                 220

Ile Cys Thr Ile Met Tyr Thr Ser Gly Thr Thr Gly Asp Pro Lys Gly
225                 230                 235                 240

Val Met Ile Ser Asn Glu Ser Ile Val Thr Ile Thr Gly Val Met
                245                 250                 255

His Phe Leu Gly Asn Val Asn Ala Ser Leu Ser Glu Lys Asp Val Tyr
                260                 265                 270
```

```
Ile Ser Tyr Leu Pro Leu Ala His Val Phe Asp Arg Ala Ile Glu Glu
        275                 280                 285

Cys Ile Ile Gln Val Gly Gly Ser Ile Gly Phe Trp Arg Gly Asp Val
    290                 295                 300

Lys Leu Leu Ile Glu Asp Leu Gly Glu Leu Lys Pro Ser Ile Phe Cys
305                 310                 315                 320

Ala Val Pro Arg Val Leu Asp Arg Val Tyr Thr Gly Leu Gln Gln Lys
                325                 330                 335

Leu Ser Gly Gly Phe Phe Lys Lys Lys Phe Gly Asn Met Lys
            340                 345                 350

Lys Gly Gln Ser His Val Ala Ala Ser Pro Phe Cys Asp Lys Leu Val
        355                 360                 365

Phe Asn Lys Val Lys Gln Gly Leu Gly Gly Asn Val Arg Ile Ile Leu
    370                 375                 380

Ser Gly Ala Ala Pro Leu Ala Ser His Ile Glu Ser Phe Leu Arg Val
385                 390                 395                 400

Val Ala Cys Cys Asn Val Leu Gln Gly Tyr Gly Leu Thr Glu Ser Cys
                405                 410                 415

Ala Gly Thr Phe Ala Thr Phe Pro Asp Glu Leu Asp Met Leu Gly Thr
            420                 425                 430

Val Gly Pro Pro Val Pro Asn Val Asp Ile Arg Leu Glu Ser Val Pro
        435                 440                 445

Glu Met Asn Tyr Asp Ala Leu Gly Ser Thr Pro Arg Gly Glu Ile Cys
    450                 455                 460

Ile Arg Gly Lys Thr Leu Phe Ser Gly Tyr Tyr Lys Arg Glu Asp Leu
465                 470                 475                 480

Thr Lys Glu Val Phe Ile Asp Gly Trp Leu His Thr Gly Asp Val Gly
                485                 490                 495

Glu Trp Gln Pro Asn Gly Ser Met Lys Ile Ile Asp Arg Lys Lys Asn
            500                 505                 510

Ile Phe Lys Leu Ala Gln Gly Glu Tyr Val Ala Val Glu Asn Leu Glu
        515                 520                 525

Asn Val Tyr Ser Gln Val Glu Val Ile Glu Ser Ile Trp Val Tyr Gly
    530                 535                 540

Asn Ser Phe Glu Ser Phe Leu Val Ala Ile Ala Asn Pro Ala Gln Gln
545                 550                 555                 560

Thr Leu Glu Arg Trp Ala Val Glu Asn Gly Val Asn Gly Asp Phe Asn
                565                 570                 575

Ser Ile Cys Gln Asn Ala Lys Ala Lys Ala Phe Ile Leu Gly Glu Leu
            580                 585                 590

Val Lys Thr Ala Lys Glu Asn Lys Leu Lys Gly Phe Glu Ile Ile Lys
        595                 600                 605

Asp Val His Leu Glu Pro Val Ala Phe Asp Met Glu Arg Asp Leu Leu
    610                 615                 620

Thr Pro Thr Tyr Lys Lys Arg Pro Gln Leu Leu Lys Tyr Tyr Gln
625                 630                 635                 640

Asn Val Ile His Glu Met Tyr Lys Thr Thr Lys Glu Ser Leu Ala Ser
                645                 650                 655

Gly Gln

<210> SEQ ID NO 14
<211> LENGTH: 665
<212> TYPE: PRT
```

<213> ORGANISM: Arabidopsis thaliana

<400> SEQUENCE: 14

```
Met Ala Thr Gly Arg Tyr Ile Val Glu Val Glu Lys Gly Lys Gln Gly
1               5                   10                  15
Val Asp Gly Gly Ser Pro Ser Val Gly Pro Val Tyr Arg Ser Ile Tyr
            20                  25                  30
Ala Lys Asp Gly Phe Pro Glu Pro Pro Asp Asp Leu Val Ser Ala Trp
        35                  40                  45
Asp Ile Phe Arg Leu Ser Val Glu Lys Ser Pro Asn Asn Pro Met Leu
    50                  55                  60
Gly Arg Arg Glu Ile Val Asp Gly Lys Ala Gly Lys Tyr Val Trp Gln
65                  70                  75                  80
Thr Tyr Lys Glu Val His Asn Val Val Ile Lys Leu Gly Asn Ser Ile
                85                  90                  95
Arg Thr Ile Gly Val Gly Lys Gly Asp Lys Cys Gly Ile Tyr Gly Ala
            100                 105                 110
Asn Ser Pro Glu Trp Ile Ile Ser Met Glu Ala Cys Asn Ala His Gly
        115                 120                 125
Leu Tyr Cys Val Pro Leu Tyr Asp Thr Leu Gly Ala Gly Ala Ile Glu
    130                 135                 140
Phe Ile Ile Cys His Ala Glu Val Ser Leu Ala Phe Ala Glu Glu Asn
145                 150                 155                 160
Lys Ile Ser Glu Leu Leu Lys Thr Ala Pro Lys Ser Thr Lys Tyr Leu
                165                 170                 175
Lys Tyr Ile Val Ser Phe Gly Glu Val Thr Asn Asn Gln Arg Val Glu
            180                 185                 190
Ala Glu Arg His Arg Leu Thr Ile Tyr Ser Trp Asp Gln Phe Leu Lys
        195                 200                 205
Leu Gly Glu Gly Lys His Tyr Glu Leu Pro Glu Lys Arg Arg Ser Asp
    210                 215                 220
Val Cys Thr Ile Met Tyr Thr Ser Gly Thr Thr Gly Asp Pro Lys Gly
225                 230                 235                 240
Val Leu Leu Thr Asn Glu Ser Ile Ile His Leu Leu Glu Gly Val Lys
                245                 250                 255
Lys Leu Leu Lys Thr Ile Asp Glu Glu Leu Thr Ser Lys Asp Val Tyr
            260                 265                 270
Leu Ser Tyr Leu Pro Leu Ala His Ile Phe Asp Arg Val Ile Glu Glu
        275                 280                 285
Leu Cys Ile Tyr Glu Ala Ala Ser Ile Gly Phe Trp Arg Gly Asp Val
    290                 295                 300
Lys Ile Leu Ile Glu Asp Ile Ala Ala Leu Lys Pro Thr Val Phe Cys
305                 310                 315                 320
Ala Val Pro Arg Val Leu Glu Arg Ile Tyr Thr Gly Leu Gln Gln Lys
                325                 330                 335
Leu Ser Asp Gly Gly Phe Val Lys Lys Lys Leu Phe Asn Phe Ala Phe
            340                 345                 350
Lys Tyr Lys His Lys Asn Met Glu Lys Gly Gln Pro His Glu Gln Ala
        355                 360                 365
Ser Pro Ile Ala Asp Lys Ile Val Phe Lys Val Lys Glu Gly Leu
    370                 375                 380
Gly Gly Asn Val Arg Leu Ile Leu Ser Gly Ala Ala Pro Leu Ala Ala
385                 390                 395                 400
```

```
His Ile Glu Ser Phe Leu Arg Val Val Ala Cys Ala His Val Leu Gln
                405                 410                 415

Gly Tyr Gly Leu Thr Glu Ser Cys Gly Gly Thr Phe Val Ser Ile Pro
            420                 425                 430

Asn Glu Leu Ser Met Leu Gly Thr Val Gly Pro Pro Val Pro Asn Val
        435                 440                 445

Asp Ile Arg Leu Glu Ser Val Pro Glu Met Gly Tyr Asp Ala Leu Ala
    450                 455                 460

Ser Asn Pro Arg Gly Glu Ile Cys Ile Arg Gly Lys Thr Leu Phe Ser
465                 470                 475                 480

Gly Tyr Tyr Lys Arg Glu Asp Leu Thr Gln Glu Val Phe Ile Asp Gly
                485                 490                 495

Trp Leu His Thr Gly Asp Val Gly Glu Trp Gln Pro Asp Gly Ala Met
            500                 505                 510

Lys Ile Ile Asp Arg Lys Lys Asn Ile Phe Lys Leu Ser Gln Gly Glu
        515                 520                 525

Tyr Val Ala Val Glu Asn Leu Glu Asn Ile Tyr Ser His Val Ala Ala
    530                 535                 540

Ile Glu Ser Ile Trp Val Tyr Gly Asn Ser Tyr Glu Ser Tyr Leu Val
545                 550                 555                 560

Ala Val Val Cys Pro Ser Lys Ile Gln Ile Glu His Trp Ala Lys Glu
                565                 570                 575

His Lys Val Ser Gly Asp Phe Glu Ser Ile Cys Arg Asn Gln Lys Thr
            580                 585                 590

Lys Glu Phe Val Leu Gly Glu Phe Asn Arg Val Ala Lys Asp Lys Lys
        595                 600                 605

Leu Lys Gly Phe Glu Leu Ile Lys Gly Val His Leu Asp Thr Val Pro
    610                 615                 620

Phe Asp Met Glu Arg Asp Leu Ile Thr Pro Ser Tyr Lys Met Lys Arg
625                 630                 635                 640

Pro Gln Leu Leu Lys Tyr Tyr Gln Lys Glu Ile Asp Glu Met Tyr Lys
                645                 650                 655

Lys Asn Arg Glu Val Gln Leu Arg Val
            660                 665

<210> SEQ ID NO 15
<211> LENGTH: 665
<212> TYPE: PRT
<213> ORGANISM: Arabidopsis thaliana

<400> SEQUENCE: 15

Met Ser Leu Ala Ala Asp Asn Val Leu Leu Val Glu Glu Gly Arg Pro
1               5                   10                  15

Ala Thr Ala Glu His Pro Ser Ala Gly Pro Val Tyr Arg Cys Lys Tyr
            20                  25                  30

Ala Lys Asp Gly Leu Leu Asp Leu Pro Thr Asp Ile Asp Ser Pro Trp
        35                  40                  45

Gln Phe Phe Ser Glu Ala Val Lys Lys Tyr Pro Asn Glu Gln Met Leu
    50                  55                  60

Gly Gln Arg Val Thr Thr Asp Ser Lys Val Gly Pro Tyr Thr Trp Ile
65                  70                  75                  80

Thr Tyr Lys Glu Ala His Asp Ala Ala Ile Arg Ile Gly Ser Ala Ile
                85                  90                  95

Arg Ser Arg Gly Val Asp Pro Gly His Cys Cys Gly Ile Tyr Gly Ala
            100                 105                 110
```

-continued

```
Asn Cys Pro Glu Trp Ile Ile Ala Met Glu Ala Cys Met Ser Gln Gly
            115                 120                 125
Ile Thr Tyr Val Pro Leu Tyr Asp Ser Leu Gly Val Asn Ala Val Glu
        130                 135                 140
Phe Ile Ile Asn His Ala Glu Val Ser Leu Val Phe Val Gln Glu Lys
145                 150                 155                 160
Thr Val Ser Ser Ile Leu Ser Cys Gln Lys Gly Cys Ser Ser Asn Leu
                165                 170                 175
Lys Thr Ile Val Ser Phe Gly Glu Val Ser Ser Thr Gln Lys Glu Glu
            180                 185                 190
Ala Lys Asn Gln Cys Val Ser Leu Phe Ser Trp Asn Glu Phe Ser Leu
        195                 200                 205
Met Gly Asn Leu Asp Glu Ala Asn Leu Pro Arg Lys Arg Lys Thr Asp
    210                 215                 220
Ile Cys Thr Ile Met Tyr Thr Ser Gly Thr Thr Gly Glu Pro Lys Gly
225                 230                 235                 240
Val Ile Leu Asn Asn Ala Ala Ile Ser Val Gln Val Leu Ser Ile Asp
                245                 250                 255
Lys Met Leu Glu Val Thr Asp Arg Ser Cys Asp Thr Ser Asp Val Phe
            260                 265                 270
Phe Ser Tyr Leu Pro Leu Ala His Cys Tyr Asp Gln Val Met Glu Ile
        275                 280                 285
Tyr Phe Leu Ser Arg Gly Ser Ser Val Gly Tyr Trp Arg Gly Asp Ile
    290                 295                 300
Arg Tyr Leu Met Asp Asp Val Gln Ala Leu Lys Pro Thr Val Phe Cys
305                 310                 315                 320
Gly Val Pro Arg Val Tyr Asp Lys Leu Tyr Ala Gly Ile Met Gln Lys
                325                 330                 335
Ile Ser Ala Ser Gly Leu Ile Arg Lys Lys Leu Phe Asp Phe Ala Tyr
            340                 345                 350
Asn Tyr Lys Leu Gly Asn Met Arg Lys Gly Phe Ser Gln Glu Glu Ala
        355                 360                 365
Ser Pro Arg Leu Asp Arg Leu Met Phe Asp Lys Ile Lys Glu Ala Leu
    370                 375                 380
Gly Gly Arg Ala His Met Leu Leu Ser Gly Ala Ala Pro Leu Pro Arg
385                 390                 395                 400
His Val Glu Glu Phe Leu Arg Ile Ile Pro Ala Ser Asn Leu Ser Gln
                405                 410                 415
Gly Tyr Gly Leu Thr Glu Ser Cys Gly Gly Ser Phe Thr Thr Leu Ala
            420                 425                 430
Gly Val Phe Ser Met Val Gly Thr Val Gly Val Pro Met Pro Thr Val
        435                 440                 445
Glu Ala Arg Leu Val Ser Val Pro Glu Met Gly Tyr Asp Ala Phe Ser
    450                 455                 460
Ala Asp Val Pro Arg Gly Glu Ile Cys Leu Arg Gly Asn Ser Met Phe
465                 470                 475                 480
Ser Gly Tyr His Lys Arg Gln Asp Leu Thr Asp Gln Val Leu Ile Asp
                485                 490                 495
Gly Trp Phe His Thr Gly Asp Ile Gly Glu Trp Gln Glu Asp Gly Ser
            500                 505                 510
Met Lys Ile Ile Asp Arg Lys Lys Asn Ile Phe Lys Leu Ser Gln Gly
        515                 520                 525
```

```
Glu Tyr Val Ala Val Glu Asn Leu Glu Asn Thr Tyr Ser Arg Cys Pro
    530                 535                 540

Leu Ile Ala Gln Val Trp Val Tyr Gly Asn Ser Phe Glu Ser Phe Leu
545                 550                 555                 560

Val Gly Val Val Val Pro Asp Arg Lys Ala Ile Glu Asp Trp Ala Lys
                565                 570                 575

Leu Asn Tyr Gln Ser Pro Asn Asp Phe Glu Ser Leu Cys Gln Asn Leu
            580                 585                 590

Lys Ala Gln Lys Tyr Phe Leu Asp Glu Leu Asn Ser Thr Ala Lys Gln
        595                 600                 605

Tyr Gln Leu Lys Gly Phe Glu Met Leu Lys Ala Ile His Leu Glu Pro
    610                 615                 620

Asn Pro Phe Asp Ile Glu Arg Asp Leu Ile Thr Pro Thr Phe Lys Leu
625                 630                 635                 640

Lys Arg Pro Gln Leu Leu Gln His Tyr Lys Gly Ile Val Asp Gln Leu
                645                 650                 655

Tyr Ser Glu Ala Lys Arg Ser Met Ala
            660                 665

<210> SEQ ID NO 16
<211> LENGTH: 701
<212> TYPE: PRT
<213> ORGANISM: Arabidopsis thaliana

<400> SEQUENCE: 16

Met Asp Ser Ser Ser Ser Ser Ala Ala Arg Arg Ile
1               5                   10              15

Asn Ala Ile His Ser His Leu Val Thr Ser Ser Arg Ser Ser Pro Leu
                20                  25                  30

Leu Arg Ser Asn Pro Thr Ala Gly Glu Phe Cys Leu Asp Asn Gly Tyr
            35                  40                  45

Ser Val Val Leu Pro Glu Lys Leu Asn Thr Gly Ser Trp Asn Val Tyr
    50                  55                  60

Arg Ser Ala Lys Ser Pro Phe Lys Leu Val Ser Arg Phe Pro Asp His
65                  70                  75                  80

Pro Asp Ile Ala Thr Leu His Asp Asn Phe Glu His Ala Val His Asp
                85                  90                  95

Phe Arg Asp Tyr Lys Tyr Leu Gly Thr Arg Val Arg Val Asp Gly Thr
            100                 105                 110

Val Gly Asp Tyr Lys Trp Met Thr Tyr Gly Glu Ala Gly Thr Ala Arg
        115                 120                 125

Thr Ala Leu Gly Ser Gly Leu Val His His Gly Ile Pro Met Gly Ser
    130                 135                 140

Ser Val Gly Ile Tyr Phe Ile Asn Arg Pro Glu Trp Leu Ile Val Asp
145                 150                 155                 160

His Ala Cys Ser Ser Tyr Ser Tyr Val Ser Val Pro Leu Tyr Asp Thr
                165                 170                 175

Leu Gly Pro Asp Ala Val Lys Phe Ile Val Asn His Ala Thr Val Gln
            180                 185                 190

Ala Ile Phe Cys Val Ala Glu Thr Leu Asn Ser Leu Leu Ser Cys Leu
        195                 200                 205

Ser Glu Met Pro Ser Val Arg Leu Val Val Val Gly Gly Leu Ile
    210                 215                 220

Glu Ser Leu Pro Ser Leu Pro Ser Ser Gly Val Lys Val Val Ser
225                 230                 235                 240
```

-continued

```
Tyr Ser Val Leu Leu Asn Gln Gly Arg Ser Asn Pro Gln Arg Phe Phe
            245                 250                 255
Pro Pro Lys Pro Asp Asp Val Ala Thr Ile Cys Tyr Thr Ser Gly Thr
        260                 265                 270
Thr Gly Thr Pro Lys Gly Val Leu Thr His Ala Asn Leu Ile Ala
    275                 280                 285
Asn Val Ala Gly Ser Ser Phe Ser Val Lys Phe Phe Ser Ser Asp Val
290                 295                 300
Tyr Ile Ser Tyr Leu Pro Leu Ala His Ile Tyr Glu Arg Ala Asn Gln
305                 310                 315                 320
Ile Leu Thr Val Tyr Phe Gly Val Ala Val Gly Phe Tyr Gln Gly Asp
                325                 330                 335
Asn Met Lys Leu Leu Asp Asp Leu Ala Ala Leu Arg Pro Thr Val Phe
            340                 345                 350
Ser Ser Val Pro Arg Leu Tyr Asn Arg Ile Tyr Ala Gly Ile Ile Asn
        355                 360                 365
Ala Val Lys Thr Ser Gly Gly Leu Lys Glu Arg Leu Phe Asn Ala Ala
    370                 375                 380
Tyr Asn Ala Lys Lys Gln Ala Leu Leu Asn Gly Lys Ser Ala Ser Pro
385                 390                 395                 400
Ile Trp Asp Arg Leu Val Phe Asn Lys Ile Lys Asp Arg Leu Gly Gly
                405                 410                 415
Arg Val Arg Phe Met Thr Ser Gly Ala Ser Pro Leu Ser Pro Glu Val
            420                 425                 430
Met Glu Phe Leu Lys Val Cys Phe Gly Gly Arg Val Thr Glu Gly Tyr
        435                 440                 445
Gly Met Thr Glu Thr Ser Cys Val Ile Ser Gly Met Asp Glu Gly Asp
    450                 455                 460
Asn Leu Thr Gly His Val Gly Ser Pro Asn Pro Ala Cys Glu Ile Lys
465                 470                 475                 480
Leu Val Asp Val Pro Glu Met Asn Tyr Thr Ser Ala Asp Gln Pro His
                485                 490                 495
Pro Arg Gly Glu Ile Cys Val Arg Gly Pro Ile Ile Phe Thr Gly Tyr
            500                 505                 510
Tyr Lys Asp Glu Ile Gln Thr Lys Glu Val Ile Asp Glu Asp Gly Trp
        515                 520                 525
Leu His Thr Gly Asp Ile Gly Leu Trp Leu Pro Gly Gly Arg Leu Lys
    530                 535                 540
Ile Ile Asp Arg Lys Lys Asn Ile Phe Lys Leu Ala Gln Gly Glu Tyr
545                 550                 555                 560
Ile Ala Pro Glu Lys Ile Glu Asn Val Tyr Ala Lys Cys Lys Phe Val
                565                 570                 575
Gly Gln Cys Phe Ile Tyr Gly Asp Ser Phe Asn Ser Ser Leu Val Ala
            580                 585                 590
Val Val Ser Val Asp Pro Asp Val Leu Lys Ser Trp Ala Ala Ser Glu
        595                 600                 605
Gly Ile Lys Gly Gly Asp Leu Arg Glu Leu Cys Asn Asn Pro Arg Val
    610                 615                 620
Lys Ala Ala Val Leu Ser Asp Met Asp Thr Val Gly Arg Glu Ala Gln
625                 630                 635                 640
Leu Arg Gly Phe Glu Phe Ala Lys Ala Val Thr Leu Val Leu Glu Pro
                645                 650                 655
```

```
Phe Thr Leu Glu Asn Gly Leu Leu Thr Pro Thr Phe Lys Ile Lys Arg
            660                 665                 670

Pro Gln Ala Lys Glu Tyr Phe Ala Glu Ala Ile Thr Asn Met Tyr Lys
        675                 680                 685

Glu Leu Gly Ala Ser Asp Pro Ser Ala Asn Arg Gly Leu
    690                 695                 700

<210> SEQ ID NO 17
<211> LENGTH: 700
<212> TYPE: PRT
<213> ORGANISM: Arabidopsis thaliana

<400> SEQUENCE: 17

Met Glu Phe Ala Ser Pro Glu Gln Arg Arg Leu Glu Thr Ile Arg Ser
1               5                   10                  15

His Ile Asp Thr Ser Pro Thr Asn Asp Gln Ser Ser Ile Phe Leu
            20                  25                  30

Asn Ala Thr Ala Ser Ser Ala Ser Pro Phe Phe Lys Glu Asp Ser Tyr
        35                  40                  45

Ser Val Val Leu Pro Glu Lys Leu Asp Thr Gly Lys Trp Asn Val Tyr
    50                  55                  60

Arg Ser Lys Arg Ser Pro Thr Lys Leu Val Ser Arg Phe Pro Asp His
65                  70                  75                  80

Pro Glu Ile Gly Thr Leu His Asp Asn Phe Val His Ala Val Glu Thr
                85                  90                  95

Tyr Ala Glu Asn Lys Tyr Leu Gly Thr Arg Val Arg Ser Asp Gly Thr
            100                 105                 110

Ile Gly Glu Tyr Ser Trp Met Thr Tyr Gly Glu Ala Ala Ser Glu Arg
        115                 120                 125

Gln Ala Ile Gly Ser Gly Leu Leu Phe His Gly Val Asn Gln Gly Ala
    130                 135                 140

Cys Val Gly Leu Tyr Phe Ile Asn Arg Pro Glu Trp Leu Val Val Asp
145                 150                 155                 160

His Ala Cys Ala Ala Tyr Ser Phe Val Ser Val Pro Leu Tyr Asp Thr
                165                 170                 175

Leu Gly Pro Asp Ala Val Lys Phe Val Val Asn His Ala Asn Leu Gln
            180                 185                 190

Ala Ile Phe Cys Val Pro Gln Thr Leu Asn Ile Leu Leu Ser Phe Leu
        195                 200                 205

Ala Glu Ile Pro Ser Ile Arg Leu Ile Val Val Gly Gly Ala Asp
    210                 215                 220

Glu His Leu Pro Ser Leu Pro Arg Gly Thr Gly Val Thr Ile Val Ser
225                 230                 235                 240

Tyr Gln Lys Leu Leu Ser Gln Gly Arg Ser Ser Leu His Pro Phe Ser
                245                 250                 255

Pro Pro Lys Pro Glu Asp Ile Ala Thr Ile Cys Tyr Thr Ser Gly Thr
            260                 265                 270

Thr Gly Thr Pro Lys Gly Val Val Leu Thr His Gly Asn Leu Ile Ala
        275                 280                 285

Asn Val Ala Gly Ser Ser Val Glu Ala Glu Phe Phe Pro Ser Asp Val
    290                 295                 300

Tyr Ile Ser Tyr Leu Pro Leu Ala His Ile Tyr Glu Arg Ala Asn Gln
305                 310                 315                 320

Ile Met Gly Val Tyr Gly Val Ala Val Gly Phe Tyr Gln Gly Asp
                325                 330                 335
```

Val Leu Lys Leu Met Asp Asp Phe Ala Val Leu Arg Pro Thr Ile Phe
        340                 345                 350

Cys Ser Val Pro Arg Leu Tyr Asn Arg Ile Tyr Asp Gly Ile Thr Ser
        355                 360                 365

Ala Val Lys Ser Ser Gly Val Val Lys Lys Arg Leu Phe Glu Ile Ala
        370                 375                 380

Tyr Asn Ser Lys Lys Gln Ala Ile Ile Asn Gly Arg Thr Pro Ser Ala
385                 390                 395                 400

Phe Trp Asp Lys Leu Val Phe Asn Lys Ile Lys Glu Lys Leu Gly Gly
                405                 410                 415

Arg Val Arg Phe Met Gly Ser Gly Ala Ser Pro Leu Ser Pro Asp Val
                420                 425                 430

Met Asp Phe Leu Arg Ile Cys Phe Gly Cys Ser Val Arg Glu Gly Tyr
        435                 440                 445

Gly Met Thr Glu Thr Ser Cys Val Ile Ser Ala Met Asp Asp Gly Asp
        450                 455                 460

Asn Leu Ser Gly His Val Gly Ser Pro Asn Pro Ala Cys Glu Val Lys
465                 470                 475                 480

Leu Val Asp Val Pro Glu Met Asn Tyr Thr Ser Glu Asp Gln Pro Tyr
                485                 490                 495

Pro Arg Gly Glu Ile Cys Val Arg Gly Pro Ile Ile Phe Lys Gly Tyr
                500                 505                 510

Tyr Lys Asp Glu Glu Gln Thr Arg Glu Ile Leu Asp Gly Asp Gly Trp
        515                 520                 525

Leu His Thr Gly Asp Ile Gly Leu Trp Leu Pro Gly Gly Arg Leu Lys
        530                 535                 540

Ile Ile Asp Arg Lys Lys Asn Ile Phe Lys Leu Ala Gln Gly Glu Tyr
545                 550                 555                 560

Ile Ala Pro Glu Lys Ile Glu Asn Val Tyr Thr Lys Cys Arg Phe Val
                565                 570                 575

Ser Gln Cys Phe Ile His Gly Asp Ser Phe Asn Ser Ser Leu Val Ala
                580                 585                 590

Ile Val Ser Val Asp Pro Glu Val Met Lys Asp Trp Ala Ala Ser Glu
        595                 600                 605

Gly Ile Lys Tyr Glu His Leu Gly Gln Leu Cys Asn Asp Pro Arg Val
        610                 615                 620

Arg Lys Thr Val Leu Ala Glu Met Asp Asp Leu Gly Arg Glu Ala Gln
625                 630                 635                 640

Leu Arg Gly Phe Glu Phe Ala Lys Ala Val Thr Leu Val Pro Glu Pro
                645                 650                 655

Phe Thr Leu Glu Asn Gly Leu Leu Thr Pro Thr Phe Lys Ile Lys Arg
                660                 665                 670

Pro Gln Ala Lys Ala Tyr Phe Ala Glu Ala Ile Ser Lys Met Tyr Ala
        675                 680                 685

Glu Ile Ala Ala Ser Asn Pro Ile Pro Ser Lys Leu
        690                 695                 700

<210> SEQ ID NO 18
<211> LENGTH: 709
<212> TYPE: PRT
<213> ORGANISM: Arabidopsis thaliana

<400> SEQUENCE: 18

Met Ala Ser Thr Ser Ser Leu Gly Pro Ser Thr Leu Leu Ser Tyr Gly

-continued

```
                1               5                       10                      15
Ser Pro Ser Arg Gln Phe Pro Asp Phe Gly Phe Arg Leu Ile Ser Gly
                20                      25                      30

His Glu Ser Val Arg Ile Pro Ser Phe Arg Arg Phe Arg Val His Cys
            35                      40                      45

Glu Ser Lys Glu Lys Glu Val Lys Pro Ser Ser Pro Phe Leu Glu Ser
            50                      55                      60

Ser Ser Phe Ser Gly Asp Ala Ala Leu Arg Ser Ser Glu Trp Lys Ala
 65                     70                      75                      80

Val Pro Asp Ile Trp Arg Ser Ser Ala Glu Lys Tyr Gly Asp Arg Val
                85                      90                      95

Ala Leu Val Asp Pro Tyr His Asp Pro Pro Leu Lys Leu Thr Tyr Lys
                100                     105                     110

Gln Leu Glu Gln Glu Ile Leu Asp Phe Ala Glu Gly Leu Arg Val Leu
                115                     120                     125

Gly Val Lys Ala Asp Glu Lys Ile Ala Leu Phe Ala Asp Asn Ser Cys
                130                     135                     140

Arg Trp Leu Val Ser Asp Gln Gly Ile Met Ala Thr Gly Ala Val Asn
145                     150                     155                     160

Val Val Arg Gly Ser Arg Ser Val Glu Glu Leu Leu Gln Ile Tyr
                165                     170                     175

Arg His Ser Glu Ser Val Ala Ile Val Val Asp Asn Pro Glu Phe Phe
                180                     185                     190

Asn Arg Ile Ala Glu Ser Phe Thr Ser Lys Ala Ser Leu Arg Phe Leu
            195                     200                     205

Ile Leu Leu Trp Gly Glu Lys Ser Ser Leu Val Thr Gln Gly Met Gln
210                     215                     220

Ile Pro Val Tyr Ser Tyr Ala Glu Ile Ile Asn Gln Gly Gln Glu Ser
225                     230                     235                     240

Arg Ala Lys Leu Ser Ala Ser Asn Asp Thr Arg Ser Tyr Arg Asn Gln
                245                     250                     255

Phe Ile Asp Ser Asp Asp Thr Ala Ala Ile Met Tyr Thr Ser Gly Thr
                260                     265                     270

Thr Gly Asn Pro Lys Gly Val Met Leu Thr His Arg Asn Leu Leu His
            275                     280                     285

Gln Ile Lys His Leu Ser Lys Tyr Val Pro Ala Gln Ala Gly Asp Lys
            290                     295                     300

Phe Leu Ser Met Leu Pro Ser Trp His Ala Tyr Glu Arg Ala Ser Glu
305                     310                     315                     320

Tyr Phe Ile Phe Thr Cys Gly Val Glu Gln Met Tyr Thr Ser Ile Arg
                325                     330                     335

Tyr Leu Lys Asp Asp Leu Lys Arg Tyr Gln Pro Asn Tyr Ile Val Ser
                340                     345                     350

Val Pro Leu Val Tyr Glu Thr Leu Tyr Ser Gly Ile Gln Lys Gln Ile
            355                     360                     365

Ser Ala Ser Ser Ala Gly Arg Lys Phe Leu Ala Leu Thr Leu Ile Lys
            370                     375                     380

Val Ser Met Ala Tyr Met Glu Met Lys Arg Ile Tyr Glu Gly Met Cys
385                     390                     395                     400

Leu Thr Lys Glu Gln Lys Pro Pro Met Tyr Ile Val Ala Phe Val Asp
                405                     410                     415

Trp Leu Trp Ala Arg Val Ile Ala Ala Leu Leu Trp Pro Leu His Met
                420                     425                     430
```

```
Leu Ala Lys Lys Leu Ile Tyr Lys Lys Ile His Ser Ser Ile Gly Ile
            435                 440                 445

Ser Lys Ala Gly Ile Ser Gly Gly Ser Leu Pro Ile His Val Asp
        450                 455                 460

Lys Phe Phe Glu Ala Ile Gly Val Ile Leu Gln Asn Gly Tyr Gly Leu
465                 470                 475                 480

Thr Glu Thr Ser Pro Val Val Cys Ala Arg Thr Leu Ser Cys Asn Val
                485                 490                 495

Leu Gly Ser Ala Gly His Pro Met His Gly Thr Glu Phe Lys Ile Val
            500                 505                 510

Asp Pro Glu Thr Asn Asn Val Leu Pro Pro Gly Ser Lys Gly Ile Ile
            515                 520                 525

Lys Val Arg Gly Pro Gln Val Met Lys Gly Tyr Tyr Lys Asn Pro Ser
            530                 535                 540

Thr Thr Lys Gln Val Leu Asn Glu Ser Gly Trp Phe Asn Thr Gly Asp
545                 550                 555                 560

Thr Gly Trp Ile Ala Pro His His Ser Lys Gly Arg Ser Arg His Cys
            565                 570                 575

Gly Gly Val Ile Val Leu Glu Gly Arg Ala Lys Asp Thr Ile Val Leu
            580                 585                 590

Ser Thr Gly Glu Asn Val Glu Pro Leu Glu Ile Glu Glu Ala Ala Met
            595                 600                 605

Arg Ser Arg Val Ile Glu Gln Ile Val Val Ile Gly Gln Asp Arg Arg
        610                 615                 620

Arg Leu Gly Ala Ile Ile Ile Pro Asn Lys Glu Glu Ala Gln Arg Val
625                 630                 635                 640

Asp Pro Glu Thr Ser Lys Glu Thr Leu Lys Ser Leu Val Tyr Gln Glu
                645                 650                 655

Leu Arg Lys Trp Thr Ser Glu Cys Ser Phe Gln Val Gly Pro Val Leu
            660                 665                 670

Ile Val Asp Asp Pro Phe Thr Ile Asp Asn Gly Leu Met Thr Pro Thr
            675                 680                 685

Met Lys Ile Arg Arg Asp Met Val Val Ala Lys Tyr Lys Glu Glu Ile
            690                 695                 700

Asp Gln Leu Tyr Ser
705

<210> SEQ ID NO 19
<211> LENGTH: 722
<212> TYPE: PRT
<213> ORGANISM: Arabidopsis thaliana

<400> SEQUENCE: 19

Met Ala Ser Thr Ser Leu Gly Ala Ser Ile Leu Val Ser His Cys Ser
1               5                   10                  15

Ser Ala Pro Glu Phe Gln Val Ser Gly Met Arg Leu Val Phe Gly Tyr
            20                  25                  30

Lys Ala Phe Gly Cys Arg Thr Ser Arg Arg Gly Phe Val Arg Cys
            35                  40                  45

Glu Ser Lys Ile Gln Glu Lys Glu Leu Arg Arg Cys Ser Pro Phe Leu
        50                  55                  60

Glu Arg Leu Ser Leu Pro Arg Glu Ala Ala Leu Ser Ser Asn Glu Trp
65                  70                  75                  80

Lys Ser Val Pro Asp Ile Trp Arg Ser Ser Val Glu Lys Tyr Gly Asp
```

-continued

```
                 85                   90                   95
Arg Val Ala Val Val Asp Pro Tyr His Asp Pro Ser Thr Phe Thr
            100                 105                 110
Tyr Arg Gln Leu Glu Gln Glu Ile Leu Asp Phe Val Glu Gly Leu Arg
            115                 120                 125
Val Val Gly Val Lys Ala Asp Glu Lys Ile Ala Leu Phe Ala Asp Asn
130                 135                 140
Ser Cys Arg Trp Leu Val Ala Asp Gln Gly Ile Met Ala Thr Gly Ala
145                 150                 155                 160
Val Asn Val Val Arg Gly Ser Arg Ser Ser Val Glu Glu Leu Leu Gln
                165                 170                 175
Ile Tyr Cys His Ser Glu Ser Val Ala Leu Val Val Asp Asn Pro Glu
                180                 185                 190
Phe Phe Asn Arg Ile Ala Glu Ser Phe Ser Tyr Lys Ala Ala Pro Lys
                195                 200                 205
Phe Val Ile Leu Leu Trp Gly Glu Lys Ser Ser Leu Val Thr Ala Gly
            210                 215                 220
Arg His Thr Pro Val Tyr Ser Tyr Asn Glu Ile Lys Lys Phe Gly Gln
225                 230                 235                 240
Glu Arg Arg Ala Lys Phe Ala Arg Ser Asn Asp Ser Gly Lys Tyr Glu
                245                 250                 255
Tyr Glu Tyr Ile Asp Pro Asp Ile Ala Thr Ile Met Tyr Thr Ser
            260                 265                 270
Gly Thr Thr Gly Asn Pro Lys Gly Val Met Leu Thr His Gln Asn Leu
            275                 280                 285
Leu His Gln Ile Arg Asn Leu Ser Asp Phe Val Pro Ala Glu Ala Gly
            290                 295                 300
Glu Arg Phe Leu Ser Met Leu Pro Ser Trp His Ala Tyr Glu Arg Ala
305                 310                 315                 320
Cys Glu Tyr Phe Ile Phe Thr Cys Gly Val Glu Gln Lys Tyr Thr Ser
                325                 330                 335
Ile Arg Phe Leu Lys Asp Asp Leu Lys Arg Tyr Gln Pro His Tyr Leu
                340                 345                 350
Ile Ser Val Pro Leu Val Tyr Glu Thr Leu Tyr Ser Gly Ile Gln Lys
                355                 360                 365
Gln Ile Ser Ala Ser Ser Pro Ala Arg Lys Phe Leu Ala Leu Thr Leu
            370                 375                 380
Ile Lys Val Ser Leu Ala Tyr Thr Glu Met Lys Arg Val Tyr Glu Gly
385                 390                 395                 400
Leu Cys Leu Thr Lys Asn Gln Lys Pro Pro Met Tyr Ile Val Ser Leu
                405                 410                 415
Val Asp Trp Leu Trp Ala Arg Val Val Ala Phe Phe Leu Trp Pro Leu
            420                 425                 430
His Met Leu Ala Glu Lys Leu Val His Arg Lys Ile Arg Ser Ser Ile
            435                 440                 445
Gly Ile Thr Lys Ala Gly Val Ser Gly Gly Ser Leu Pro Met His
            450                 455                 460
Val Asp Lys Phe Phe Glu Ala Ile Gly Val Asn Val Gln Asn Gly Tyr
465                 470                 475                 480
Gly Leu Thr Glu Thr Ser Pro Val Val Ser Ala Arg Arg Leu Arg Cys
                485                 490                 495
Asn Val Leu Gly Ser Val Gly His Pro Ile Lys Asp Thr Glu Phe Lys
            500                 505                 510
```

```
Ile Val Asp His Glu Thr Gly Thr Val Leu Pro Pro Gly Ser Lys Gly
            515                 520                 525
Ile Val Lys Val Arg Gly Pro Pro Val Met Lys Gly Tyr Tyr Lys Asn
        530                 535                 540
Pro Leu Ala Thr Lys Gln Val Ile Asp Asp Gly Trp Phe Asn Thr
545                 550                 555                 560
Gly Asp Met Gly Trp Ile Thr Pro Gln His Ser Thr Gly Arg Ser Arg
                565                 570                 575
Ser Cys Gly Gly Val Ile Val Leu Glu Gly Arg Ala Lys Asp Thr Ile
            580                 585                 590
Val Leu Ser Thr Gly Glu Asn Val Glu Pro Leu Glu Ile Glu Glu Ala
        595                 600                 605
Ala Met Arg Ser Asn Leu Ile Gln Gln Ile Val Val Ile Gly Gln Asp
        610                 615                 620
Gln Arg Arg Leu Gly Ala Ile Val Ile Pro Asn Lys Glu Ala Ala Glu
625                 630                 635                 640
Gly Ala Ala Lys Gln Lys Ile Ser Pro Val Asp Ser Glu Val Asn Glu
                645                 650                 655
Leu Ser Lys Glu Thr Ile Thr Ser Met Val Tyr Glu Leu Arg Lys
            660                 665                 670
Trp Thr Ser Gln Cys Ser Phe Gln Val Gly Pro Val Leu Ile Val Asp
        675                 680                 685
Glu Pro Phe Thr Ile Asp Asn Gly Leu Met Thr Pro Thr Met Lys Ile
        690                 695                 700
Arg Arg Asp Lys Val Val Asp Gln Tyr Lys Asn Glu Ile Glu Arg Leu
705                 710                 715                 720
Tyr Lys

<210> SEQ ID NO 20
<211> LENGTH: 660
<212> TYPE: PRT
<213> ORGANISM: Arabidopsis thaliana

<400> SEQUENCE: 20

Met Lys Ser Phe Ala Ala Lys Val Glu Glu Gly Val Lys Gly Ile Asp
1               5                  10                  15
Gly Lys Pro Ser Val Gly Pro Val Tyr Arg Asn Leu Leu Ser Glu Lys
            20                  25                  30
Gly Phe Pro Pro Ile Asp Ser Glu Ile Thr Thr Ala Trp Asp Ile Phe
        35                  40                  45
Ser Lys Ser Val Glu Lys Phe Pro Asp Asn Asn Met Leu Gly Trp Arg
    50                  55                  60
Arg Ile Val Asp Glu Lys Val Gly Pro Tyr Met Trp Lys Thr Tyr Lys
65                  70                  75                  80
Glu Val Tyr Glu Glu Val Leu Gln Ile Gly Ser Ala Leu Arg Ala Ala
                85                  90                  95
Gly Ala Glu Pro Gly Ser Arg Val Gly Ile Tyr Gly Val Asn Cys Pro
            100                 105                 110
Gln Trp Ile Ile Ala Met Glu Ala Cys Ala Ala His Thr Leu Ile Cys
        115                 120                 125
Val Pro Leu Tyr Asp Thr Leu Gly Ser Gly Ala Val Asp Tyr Ile Val
    130                 135                 140
Glu His Ala Glu Ile Asp Phe Val Phe Val Gln Asp Thr Lys Ile Lys
145                 150                 155                 160
```

```
Gly Leu Leu Glu Pro Asp Cys Lys Cys Ala Lys Arg Leu Lys Ala Ile
                165                 170                 175

Val Ser Phe Thr Asn Val Ser Asp Glu Leu Ser His Lys Ala Ser Glu
            180                 185                 190

Ile Gly Val Lys Thr Tyr Ser Trp Ile Asp Phe Leu His Met Gly Arg
        195                 200                 205

Glu Lys Pro Glu Asp Thr Asn Pro Pro Lys Ala Phe Asn Ile Cys Thr
    210                 215                 220

Ile Met Tyr Thr Ser Gly Thr Ser Gly Asp Pro Lys Gly Val Val Leu
225                 230                 235                 240

Thr His Gln Ala Val Ala Thr Phe Val Val Gly Met Asp Leu Tyr Met
                245                 250                 255

Asp Gln Phe Glu Asp Lys Met Thr His Asp Asp Val Tyr Leu Ser Phe
            260                 265                 270

Leu Pro Leu Ala His Ile Leu Asp Arg Met Asn Glu Glu Tyr Phe Phe
        275                 280                 285

Arg Lys Gly Ala Ser Val Gly Tyr Tyr His Gly Asn Leu Asn Val Leu
    290                 295                 300

Arg Asp Asp Ile Gln Glu Leu Lys Pro Thr Tyr Leu Ala Gly Val Pro
305                 310                 315                 320

Arg Val Phe Glu Arg Ile His Glu Gly Ile Gln Lys Ala Leu Gln Glu
                325                 330                 335

Leu Asn Pro Arg Arg Phe Ile Phe Asn Ala Leu Tyr Lys His Lys Lys
            340                 345                 350

Leu Ala Trp Leu Asn Arg Gly Tyr Ser His Ser Lys Ala Ser Pro Met
        355                 360                 365

Ala Asp Phe Ile Ala Phe Arg Lys Ile Arg Asp Lys Leu Gly Gly Arg
    370                 375                 380

Ile Arg Leu Leu Val Ser Gly Gly Ala Pro Leu Ser Pro Glu Ile Glu
385                 390                 395                 400

Glu Phe Leu Arg Val Thr Cys Cys Cys Phe Val Val Gln Gly Tyr Gly
                405                 410                 415

Leu Thr Glu Thr Leu Gly Gly Thr Ala Leu Gly Phe Pro Asp Glu Met
            420                 425                 430

Cys Met Leu Gly Thr Val Gly Ile Pro Ala Val Tyr Asn Glu Ile Arg
        435                 440                 445

Leu Glu Glu Val Ser Glu Met Gly Tyr Asp Pro Leu Gly Glu Asn Pro
    450                 455                 460

Ala Gly Glu Ile Cys Ile Arg Gly Gln Cys Met Phe Ser Gly Tyr Tyr
465                 470                 475                 480

Lys Asn Pro Glu Leu Thr Glu Val Met Lys Asp Gly Trp Phe His
                485                 490                 495

Thr Gly Asp Ile Gly Glu Ile Leu Pro Asn Gly Val Leu Lys Ile Ile
            500                 505                 510

Asp Arg Lys Lys Asn Leu Ile Lys Leu Ser Gln Gly Glu Tyr Val Ala
        515                 520                 525

Leu Glu His Leu Glu Asn Ile Phe Gly Gln Asn Ser Val Val Gln Asp
    530                 535                 540

Ile Trp Val Tyr Gly Asp Ser Phe Lys Ser Met Leu Val Ala Val Val
545                 550                 555                 560

Val Pro Asn Pro Glu Thr Val Asn Arg Trp Ala Lys Asp Leu Gly Phe
                565                 570                 575
```

```
Thr Lys Pro Phe Glu Glu Leu Cys Ser Phe Pro Glu Leu Lys Glu His
            580                 585                 590

Ile Ile Ser Glu Leu Lys Ser Thr Ala Glu Lys Asn Lys Leu Arg Lys
            595                 600                 605

Phe Glu Tyr Ile Lys Ala Val Thr Val Glu Thr Lys Pro Phe Asp Val
            610                 615                 620

Glu Arg Asp Leu Val Thr Ala Thr Leu Lys Asn Arg Arg Asn Asn Leu
625                 630                 635                 640

Leu Lys Tyr Tyr Gln Val Gln Ile Asp Glu Met Tyr Arg Lys Leu Ala
            645                 650                 655

Ser Lys Lys Ile
            660

<210> SEQ ID NO 21
<211> LENGTH: 720
<212> TYPE: PRT
<213> ORGANISM: Arabidopsis thaliana

<400> SEQUENCE: 21

Met Glu Asp Ser Gly Val Asn Pro Met Asp Ser Pro Ser Lys Gly Ser
1               5                   10                  15

Asp Phe Gly Val Tyr Gly Ile Ile Gly Gly Ile Val Ala Leu Leu
            20                  25                  30

Val Pro Val Leu Leu Ser Val Leu Asn Gly Thr Lys Lys Gly Lys
            35                  40                  45

Lys Arg Gly Val Pro Ile Lys Val Gly Gly Glu Gly Tyr Thr Met
50                  55                  60

Arg His Ala Arg Ala Pro Glu Leu Val Asp Val Pro Trp Glu Gly Ala
65                  70                  75                  80

Ala Thr Met Pro Ala Leu Phe Glu Gln Ser Cys Lys Lys Tyr Ser Lys
            85                  90                  95

Asp Arg Leu Leu Gly Thr Arg Glu Phe Ile Asp Lys Glu Phe Ile Thr
            100                 105                 110

Ala Ser Asp Gly Arg Lys Phe Glu Lys Leu His Leu Gly Glu Tyr Lys
            115                 120                 125

Trp Gln Ser Tyr Gly Glu Val Phe Glu Arg Val Cys Asn Phe Ala Ser
            130                 135                 140

Gly Leu Val Asn Val Gly His Asn Val Asp Asp Arg Val Ala Ile Phe
145                 150                 155                 160

Ser Asp Thr Arg Ala Glu Trp Phe Ile Ala Phe Gln Gly Cys Phe Arg
            165                 170                 175

Gln Ser Ile Thr Val Val Thr Ile Tyr Ala Ser Leu Gly Glu Glu Ala
            180                 185                 190

Leu Ile Tyr Ser Leu Asn Glu Thr Arg Val Ser Thr Leu Ile Cys Asp
            195                 200                 205

Ser Lys Gln Leu Lys Lys Leu Ser Ala Ile Gln Ser Ser Leu Lys Thr
            210                 215                 220

Val Lys Asn Ile Ile Tyr Ile Glu Glu Asp Gly Val Asp Val Ala Ser
225                 230                 235                 240

Ser Asp Val Asn Ser Met Gly Asp Ile Thr Val Ser Ser Ile Ser Glu
            245                 250                 255

Val Glu Lys Leu Gly Gln Lys Asn Ala Val Gln Pro Ile Leu Pro Ser
            260                 265                 270

Lys Asn Gly Val Ala Val Ile Met Phe Thr Ser Gly Ser Thr Gly Leu
            275                 280                 285
```

```
Pro Lys Gly Val Met Ile Thr His Gly Asn Leu Val Ala Thr Ala Ala
    290                 295                 300

Gly Val Met Lys Val Val Pro Lys Leu Asp Lys Asn Asp Thr Tyr Ile
305                 310                 315                 320

Ala Tyr Leu Pro Leu Ala His Val Phe Glu Leu Ala Glu Ile Val
                325                 330                 335

Val Phe Thr Ser Gly Ser Ala Ile Gly Tyr Gly Ser Ala Met Thr Leu
            340                 345                 350

Thr Asp Thr Ser Asn Lys Val Lys Lys Gly Thr Lys Gly Asp Val Ser
            355                 360                 365

Ala Leu Lys Pro Thr Ile Met Thr Ala Val Pro Ala Ile Leu Asp Arg
    370                 375                 380

Val Arg Glu Gly Val Leu Lys Lys Val Glu Glu Lys Gly Gly Met Ala
385                 390                 395                 400

Lys Thr Leu Phe Asp Phe Ala Tyr Lys Arg Arg Leu Ala Ala Val Asp
                405                 410                 415

Gly Ser Trp Phe Gly Ala Trp Gly Leu Lys Lys Met Leu Trp Asp Ala
            420                 425                 430

Leu Val Phe Lys Lys Ile Arg Ala Val Leu Gly Gly His Ile Arg Phe
            435                 440                 445

Met Leu Val Gly Gly Ala Pro Leu Ser Pro Asp Ser Gln Arg Phe Ile
    450                 455                 460

Asn Ile Cys Met Gly Ser Pro Ile Gly Gln Gly Tyr Gly Leu Thr Glu
465                 470                 475                 480

Thr Cys Ala Gly Ala Thr Phe Ser Glu Trp Asp Asp Pro Ala Val Gly
            485                 490                 495

Arg Val Gly Pro Pro Leu Pro Cys Gly Tyr Val Lys Leu Val Ser Trp
            500                 505                 510

Glu Glu Gly Gly Tyr Arg Ile Ser Asp Lys Pro Met Pro Arg Gly Glu
            515                 520                 525

Ile Val Val Gly Gly Asn Ser Val Thr Ala Gly Tyr Phe Asn Asn Gln
    530                 535                 540

Glu Lys Thr Asp Glu Val Tyr Lys Val Asp Glu Lys Gly Thr Arg Trp
545                 550                 555                 560

Phe Tyr Thr Gly Asp Ile Gly Arg Phe His Pro Asp Gly Cys Leu Glu
                565                 570                 575

Val Ile Asp Arg Lys Lys Asp Ile Val Lys Leu Gln His Gly Glu Tyr
            580                 585                 590

Val Ser Leu Gly Lys Val Glu Ala Ala Leu Gly Ser Ser Asn Tyr Val
            595                 600                 605

Asp Asn Ile Met Val His Ala Asp Pro Ile Asn Ser Tyr Cys Val Ala
    610                 615                 620

Leu Val Val Pro Ser Arg Gly Ala Leu Glu Lys Trp Ala Glu Glu Ala
625                 630                 635                 640

Gly Val Lys His Ser Glu Phe Ala Glu Leu Cys Glu Lys Gly Glu Ala
                645                 650                 655

Val Lys Glu Val Gln Gln Ser Leu Thr Lys Ala Gly Lys Ala Ala Lys
            660                 665                 670

Leu Glu Lys Phe Glu Leu Pro Ala Lys Ile Lys Leu Leu Ser Glu Pro
            675                 680                 685

Trp Thr Pro Glu Ser Gly Leu Val Thr Ala Ala Leu Lys Ile Lys Arg
    690                 695                 700
```

```
Glu Gln Ile Lys Ser Lys Phe Lys Asp Glu Leu Ser Lys Leu Tyr Ala
705                 710                 715                 720

<210> SEQ ID NO 22
<211> LENGTH: 691
<212> TYPE: PRT
<213> ORGANISM: Arabidopsis thaliana

<400> SEQUENCE: 22

Met Ile Pro Tyr Ala Ala Gly Val Ile Val Pro Leu Ala Leu Thr Phe
1               5                   10                  15

Leu Val Gln Lys Ser Lys Glu Lys Lys Arg Gly Val Val Asp
            20                  25                  30

Val Gly Gly Glu Pro Gly Tyr Ala Ile Arg Asn His Arg Phe Thr Glu
                35                  40                  45

Pro Val Ser Ser His Trp Glu His Ile Ser Thr Leu Pro Glu Leu Phe
            50                  55                  60

Glu Ile Ser Cys Asn Ala His Ser Asp Arg Val Phe Leu Gly Thr Arg
65                  70                  75                  80

Lys Leu Ile Ser Arg Glu Ile Glu Thr Ser Glu Asp Gly Lys Thr Phe
                85                  90                  95

Glu Lys Leu His Leu Gly Asp Tyr Glu Trp Leu Thr Phe Gly Lys Thr
                100                 105                 110

Leu Glu Ala Val Cys Asp Phe Ala Ser Gly Leu Val Gln Ile Gly His
            115                 120                 125

Lys Thr Glu Glu Arg Val Ala Ile Phe Ala Asp Thr Arg Glu Glu Trp
            130                 135                 140

Phe Ile Ser Leu Gln Gly Cys Phe Arg Arg Asn Val Thr Val Val Thr
145                 150                 155                 160

Ile Tyr Ser Ser Leu Gly Glu Glu Ala Leu Cys His Ser Leu Asn Glu
                165                 170                 175

Thr Glu Val Thr Thr Val Ile Cys Gly Ser Lys Glu Leu Lys Lys Leu
            180                 185                 190

Met Asp Ile Ser Gln Gln Leu Glu Thr Val Lys Arg Val Ile Cys Met
        195                 200                 205

Asp Asp Glu Phe Pro Ser Asp Val Asn Ser Asn Trp Met Ala Thr Ser
210                 215                 220

Phe Thr Asp Val Gln Lys Leu Gly Arg Glu Asn Pro Val Asp Pro Asn
225                 230                 235                 240

Phe Pro Leu Ser Ala Asp Val Ala Val Ile Met Tyr Thr Ser Gly Ser
                245                 250                 255

Thr Gly Leu Pro Lys Gly Val Met Met Thr His Gly Asn Val Leu Ala
            260                 265                 270

Thr Val Ser Ala Val Met Thr Ile Val Pro Asp Leu Gly Lys Arg Asp
        275                 280                 285

Ile Tyr Met Ala Tyr Leu Pro Leu Ala His Ile Leu Glu Leu Ala Ala
            290                 295                 300

Glu Ser Val Met Ala Thr Ile Gly Ser Ala Ile Gly Tyr Gly Ser Pro
305                 310                 315                 320

Leu Thr Leu Thr Asp Thr Ser Asn Lys Ile Lys Lys Gly Thr Lys Gly
                325                 330                 335

Asp Val Thr Ala Leu Lys Pro Thr Ile Met Thr Ala Val Pro Ala Ile
            340                 345                 350

Leu Asp Arg Val Arg Asp Gly Val Arg Lys Lys Val Asp Ala Lys Gly
            355                 360                 365
```

```
Gly Leu Ser Lys Lys Leu Phe Asp Phe Ala Tyr Ala Arg Arg Leu Ser
    370                 375                 380

Ala Ile Asn Gly Ser Trp Phe Gly Ala Trp Gly Leu Glu Lys Leu Leu
385                 390                 395                 400

Trp Asp Val Leu Val Phe Arg Lys Ile Arg Ala Val Leu Gly Gly Gln
                405                 410                 415

Ile Arg Tyr Leu Leu Ser Gly Ala Pro Leu Ser Gly Asp Thr Gln
                420                 425                 430

Arg Phe Ile Asn Ile Cys Val Gly Ala Pro Ile Gly Gln Gly Tyr Gly
                435                 440                 445

Leu Thr Glu Thr Cys Ala Gly Gly Thr Phe Ser Glu Phe Glu Asp Thr
    450                 455                 460

Ser Val Gly Arg Val Gly Ala Pro Leu Pro Cys Ser Phe Val Lys Leu
465                 470                 475                 480

Val Asp Trp Ala Glu Gly Gly Tyr Leu Thr Ser Asp Lys Pro Met Pro
                485                 490                 495

Arg Gly Glu Ile Val Ile Gly Gly Ser Asn Ile Thr Leu Gly Tyr Phe
                500                 505                 510

Lys Asn Glu Glu Lys Thr Lys Glu Val Tyr Lys Val Asp Glu Lys Gly
                515                 520                 525

Met Arg Trp Phe Tyr Thr Gly Asp Ile Gly Arg Phe His Pro Asp Gly
    530                 535                 540

Cys Leu Glu Ile Ile Asp Arg Lys Lys Asp Ile Val Lys Leu Gln His
545                 550                 555                 560

Gly Glu Tyr Val Ser Leu Gly Lys Val Glu Ala Ala Leu Ser Ile Ser
                565                 570                 575

Pro Tyr Val Glu Asn Ile Met Val His Ala Asp Ser Phe Tyr Ser Tyr
                580                 585                 590

Cys Val Ala Leu Val Val Ala Ser Gln His Thr Val Glu Gly Trp Ala
    595                 600                 605

Ser Lys Gln Gly Ile Asp Phe Ala Asn Phe Glu Glu Leu Cys Thr Lys
610                 615                 620

Glu Gln Ala Val Lys Glu Val Tyr Ala Ser Leu Val Lys Ala Ala Lys
625                 630                 635                 640

Gln Ser Arg Leu Glu Lys Phe Glu Ile Pro Ala Lys Ile Lys Leu Leu
                645                 650                 655

Ala Ser Pro Trp Thr Pro Glu Ser Gly Leu Val Thr Ala Ala Leu Lys
                660                 665                 670

Leu Arg Arg Asp Val Ile Arg Arg Glu Phe Ser Glu Asp Leu Thr Lys
                675                 680                 685

Leu Tyr Ala
    690

<210> SEQ ID NO 23
<211> LENGTH: 1665
<212> TYPE: DNA
<213> ORGANISM: Arabidopsis thaliana

<400> SEQUENCE: 23 atggaggga a ctatcaaatc tccggccaac tacgttcctc tcactccgat cagcttcctc      60
gatagatctg ctgtcgtcta cgctgacaga gtctccatcg tttatggctc cgtcaagtac     120
acgtggcgcc agactcgtga ccgctgcgtc agaatcgcct ccgctctctc ccagctcgga     180
atctctaccg gagatgtggt ttcagtgttg ctccaaacg ttccagctat ggttgaattg     240
```

```
cattttggtg ttcctatggc tggagctttg ctctgtacac tcaacattcg tcatgattca      300
tcacttgttg ctgtcttgct tagacattca gggacaaaag tgattttttgc agatcatcag     360 tttctccaaa tagctgaagg agcttgtgaa atcctctcaa ataaaggtga caaggtcccg      420
attttggtct tgatcccaga gcctcttact caatctgttt caaggaagaa gagatctgag      480
gaaatgatgg aatacgaaga tgttgtagcg atggggaaat cggacttcga ggttatacga      540
ccaacagatg agtgtgatgc tatatctgtt aattacacaa gcggtaccac ttcaagcccc      600
aaaggtgttt tttatagtca cagaggtgct tatttgaatt ctctggctgc ggttttactc      660
aacgaaatgc actcctcgcc tacttatcta tggactaatc ccatgtttca ctgcaatggc      720
tggtgcttat tgtggggtgt tactgctatt ggtgggacta atatatgttt gaggaatgtt      780
acggccaagg ctatatttga taatatttcc cagcataagg tgactcatat gggaggtgcg      840
ccgacgatat tgaatatgat catcaatgcg cctgaatctg agcagaaacc gcttcccggg      900
aaggtgtctt ttataaccgg tgctgcaccg ccaccagctc atgtgatttt caagatggaa      960
gagttggggt tttctatgtt tcattcctat gggttaactg aaacttatgg accaggcaca     1020
atctgtacat ggaagcctga gtgggactct ttgcctagag aagaacaggc gaaaatgaaa     1080
gctcgacaag gcgtgaatca tttagggctc gaggaaatac aagttaaaga ccctgtaacc     1140
atgagaactt tgccagctga tggtgtgact atgggtgaag ttgtcttcag aggaaacacg     1200
gtgatgaatg gttacttaaa gaaccctgaa gcaaccaagg aagcttttaa aggaggttgg     1260
ttttggagtg gcgacttagg tgttaaacac cctgacggat acatagagct gaaagacaga     1320
tcgaaagaca tttataatctc tggaggagaa acattagct cgattgaagt cgagtctact    1380
ctgttcactc acccttgtgt tcttgaagca gctgtagttg cgaggcctga tgagtattgg     1440
ggtgagactg cttgtgcatt tgtgaaactt aaagacgggt ctaaggccag tgcggaggag     1500
cttattagct attgcaggga ccggcttcca cattatatgg ctccgaggag tattgtgttt     1560
gaggatcttc ctaaaacatc gactggaaaa gtccagaagt tgttctgag gaccaaggct      1620 aaggctttgg taagcttatc aaagaaaggc agaagcaagt tatga                     1665
```

<210> SEQ ID NO 24
<211> LENGTH: 1812
<212> TYPE: DNA
<213> ORGANISM: Arabidopsis thaliana

<400> SEQUENCE: 24

```
atgagattct tgttaaccaa aagagcattc agaatcttca acccacgttt ccagagactg       60
tggttaactt cttctccctt ctcctcaacc tcaaattccg gcggatttcc cgacgattcc      120
gagccggaat catggagaac tatagagggt cttctccgtt cccctgcaaa tttctctcct      180
ttatctccaa tcacgttctt ggagcgatcc gctaaggttt acagagacag aacctctctt      240
gtgtttggtt ccgttaaaca cacttggttc caaacttatc aacgttgtct ccgtcttgcc      300
tctgctctta ccaatctcgg aatctctcgt ggcgatgtgg ttgcagcttt agctccgaat      360
gttccagcta tgcatgagct tcatttcgct gttcctatgc ctggtttgat tctttgtccg      420
cttaatactc gacttgatcc ttccacattg tcggttttgt tagcacactc cgaggccaaa      480
atcctctttg ttgatcatca gttacttgag attgctcatg gagctcttga tcttcttgct      540
aaatcagata aaactagaaa aagtctgaag cttgtgttga tctctcagtc taatgatgat      600
gatgatagtg atgaagatag ctcatctacc tttgcctcaa agtactcttt tgattacgaa      660
```

| | |
|---|---:|
| tatgaaactc tgcttaaatc cggagatagc gagtttgaga taatcaaacc gagatgcgaa | 720 |
| tgggatccta ttagtataaa ctacacttca gggacgactt cgagacctaa gggtgtagtg | 780 |
| tatagccata gaggagctta tctcaattct cttgctacag tctttcttca ccagatgtct | 840 |
| gtttatccgg tgtatttatg gacagtgccg atgtttcact gtaacggatg gtgtcttgtt | 900 |
| tggggagtag cagctcaagg tggtactaat atctgtctca ggaaagtctc tcctaagatg | 960 |
| atctttaaga acattgctat gcataaagtg actcacatgg gaggagcccc aactgtgttg | 1020 |
| aatatgattg tgaactatac tgtgactgaa cataaaccgc ttcctcacag ggttgagatc | 1080 |
| atgacaggtg ggtcaccgcc tctaccgcag atcctggcta agatggaaga attaggtttc | 1140 |
| aatgtgtctc atctttatgg tttgacagag acatacggtc cagggacaca ttgcgtgtgg | 1200 |
| aaacctgaat gggattcact ttcgttggag gagagaacta agttgaaggc tagacaagga | 1260 |
| gtgcagcatt tgggtctaga agggctcgat gtgaaagatc cgctgacaat ggagactgtc | 1320 |
| cctgatgatg gtttaaccat gggtgaggtt atgttcagag aaacactgt gatgagtgga | 1380 |
| tatttcaagg acatagaggc aacacgaaaa gctttcgagg gagattggtt ccacagtggt | 1440 |
| gatctcgctg ttaagtatcc agacgggtac atagagataa agaccggtt aaaagatgtg | 1500 |
| atcatctcag gaggagaaaa cataagctca gtggaggttg agagagtttt gtgcagccat | 1560 |
| caagcggttc ttgaagctgc tgttgtagca cgtccagatc atcactgggg acagactcct | 1620 |
| tgcggttttg taaagctgaa agaaggattt gataccatca acccgagga gattatcggg | 1680 |
| ttctgtcgag atcatttgcc gcattacatg gctccaaaga ctatagtttt cggggacata | 1740 |
| cctaaaacct cgacggggaa agtacaaaag tatcttctga ggaagaaagc tgatgaaatg | 1800 |
| ggtagcttgt aa | 1812 |

<210> SEQ ID NO 25
<211> LENGTH: 1545
<212> TYPE: DNA
<213> ORGANISM: Arabidopsis thaliana

<400> SEQUENCE: 25

| | |
|---|---:|
| atggatagcg atactctctc aggattattg gaaaacgtcg ccaaaaaatt ccccgatcgc | 60 |
| cgagctctct ccgtttctgg aaaattcaat ctcactcacg cgcgtcttca cgatctaatc | 120 |
| gaacgcgccg cttcacgcct tgtctccgac gctggaatca aacccggcga tgtcgttgct | 180 |
| ctcaccttcc ctaacaccgt cgagtttgtt ataatgtttt tagcggtgat aagagctaga | 240 |
| gccacggcgg cgccgttgaa cgcagcgtac acggcggagg aatttgagtt ttacctctcc | 300 |
| gattcagatt caaagctatt gttaacctct aaagaaggaa acgcaccggc tcaagaagca | 360 |
| gcttcaaagc tgaaaatctc tcacgtcacc gctacgctgc ttgacgctgg ctcggacctt | 420 |
| gtactatccg ttgcggattc agattccgtc gttgactcag cgacggaact cgttaatcac | 480 |
| ccggacgacg gtgctctctt cctccacact tctggcacta cgagccgtcc aaagggtgta | 540 |
| ccgcttacgc agctcaatct agcttcatcc gtcaagaaca ttaaagctgt gtacaagctt | 600 |
| actgagtctg attctacggt gattgttctc cctctgttcc atgttcatgg attgttagct | 660 |
| gggttgctta gctcgcttgg agctggtgct gctgtaactc ttccagctgc tggtagattc | 720 |
| tcagcaacaa cattttggcc agatatgaag aagtataacg ctacatggta tactgctgtg | 780 |
| ccgaccattc atcagatcat attggaccgc cacgcgagcc accctgagac ggaatatcct | 840 |
| aaactccggt tcatcaggag ttgcagtgct tcttttggctc cggtgatatt gtccaggctt | 900 |
| gaggaagcgt ttggagcacc ggtgctcgag gcctatgcaa tgacagaggc aacacatttg | 960 |

-continued

```
atgagctcaa accccttacc agaggaaggt ccacacaagc ctgggtctgt tgggaaaccg    1020
gtaggtcaag aaatggcgat ccttaatgag aaaggcgaga tccaagagcc aaataacaaa    1080
ggagaggttt gtataagagg tccaaatgtg accaagggtt acaagaataa cccagaagcc    1140
aacaaggcag gtttcgagtt tgggtggttc cacactggtg atatcggtta ctttgatacc    1200
gatgggtatt tgcatctggt gggtcggatc aaagagctta ttaaccgtgg aggtgagaag    1260
atatctccaa ttgaagtgga tgcagtactc ttaacgcatc ctgacgtttc tcagggtgtt    1320
gcattcggtg ttcctgatga gaaatatggg gaagagatta ctgtgcggt gattccaaga     1380 gaaggaacta ctgtaaccga gaggacatt aaagcgtttt gtaagaagaa tttggcagct     1440
ttcaaggtgc caaagagagt gttcatcact gataacctcc ccaaaactgc ctctggtaag    1500
attcagcgcc gtatcgtcgc acaacatttc cttgagaagc cctga                    1545
```

<210> SEQ ID NO 26
<211> LENGTH: 1638
<212> TYPE: DNA
<213> ORGANISM: Arabidopsis thaliana

<400> SEQUENCE: 26

```
atggaacttt tactcccaca cgcttcaaac tcatgtcctc tcactgttct tggcttctta     60
gaacgagccg cctctgtctt cggcgactct ccttcactcc tccacacaac cactgttcat    120
acttggtctg aaactcattc tcgatgtctc cgtatagctt caactctctc ttccgcttcc    180
ctcggaatca accgcggcca agttgtctct gttattggtc aaacgtccc atctgtctac     240 gagcttcagt tcgcagttcc gatgtcaggc gcagtcctca acaacatcaa cccacgttta    300
gacgctcatg cactctccgt ccttctacgt cacagcgaat ccaagctcgt gtttgttgac    360
catcacttaa gctctttagt cctcgaagct gtctcgtttt tgcccaagga tgagagacct    420
cgtctcgtca tactcaacga cggaaacgac atgccatcat cttcatcagc tgatatggat    480
tttcttgaca cgtacgaagg gtttatggag agaggagacc tgaggttcaa gtgggtacgt    540
cctaaaagcg agtggactcc aatggtgctt aactacacct caggaactac gtcgtcccca    600
aagggagtgg tgcatagcca cagatcggtt ttcatgagca ctattaactc tttgctagac    660
tggtctttgc ctaaccgtcc ggtatacctg tggacactgc cgatgttcca tgccaatggt    720
tggagctaca catgggccac agcagctgtg ggagccagaa acatctgtgt cacaagagtt    780
gatgtgccga ctattttcaa cttgatcgac aagtatcaag tgacccacat gtgcgctgcg    840
ccaatggttc tcaacatgtt gactaatcac ccagcccaga aaccgcttca gagcccagtt    900
aaggttatga ctgctggagc tccaccacca gctacagtca tctccaaggc tgaggcgctt    960
ggtttcgacg tgagtcacgg ttacgggatg acagaaacag gcggtctggt tgtctcgtgc    1020
gcattgaagc tgagtgggga tcgtctagaa ccagacgaga gagcaaaaca gaaatcaagg    1080
caaggaatta gaactgcagt attcgcggaa gtcgatgtta gagacccaat atccgggaag    1140
agcgtgaagc atgatggagc aactgtggga gagatcgtct tcagaggcgg ttcggtcatg    1200
ctaggttatt acaaagaccc agaaggcacc gcagcaagta tgagagaaga cggatggttc    1260
tacaccggag acattggagt aatgcaccca gacggttact tggaagtcaa agacagatca    1320
aaggatgtgg tcatttgcgg aggagagaac atcagcagca cggaactcga ggcagttctg    1380
tacacaaacc ccgcaattaa ggaagcagct gtggtagcta agccagacaa gatgtgggga    1440
gaaactccat gtgcatttgt cagcctgaag tatcatgacg ggtctgtgac tgagagagag    1500
```

```
atacgggagt tttgtaaaac caagctgcca aagtatatgg ttccaaggaa tgtggttttc    1560
ctggaagagc ttccaaagac ttctactgga aagattcaaa agtttcttct cagacaaatg    1620
gctaagtcct tgccttga                                                 1638

<210> SEQ ID NO 27
<211> LENGTH: 1659
<212> TYPE: DNA
<213> ORGANISM: Arabidopsis thaliana

<400> SEQUENCE: 27
atggagcaaa tgaagccatg cgccgcaaac tcgccgccgt tgacgccgat aggtttctta     60
gagagagccg ccaccgttta cggtgactgt acctccatcg tttatggcag caacaccgtt    120
tacacgtggc gtgaaacaaa cctccgttgt ctccgcgtgg cgtcttctct gtcttcaatc    180
ggaatcggca ggtctgacgt agtctctgtt ctctctccca atactccggc tatgtacgag    240
ctccagtttg ctgttcccat gtccggcgca atcctcaaca acatcaacac tcgcctcgac    300
gcacgcaccg tctctgttct tctccgtcac tgtggatcta agcttctctt cgtcgacgtc    360
ttctccgttg atcttgccgt tgaagcgatc tcgatgatga cgactgatcc gccgattctt    420
gtcttcatcg ccgataaaga agaagaagga ggagatgctg acgtggcgga tcgtaccaaa    480
ttcagttaca cttacgatga tctgatccat agaggtgatc tggattttaa atggatccga    540
cccgaaagcg aatgggatcc ggttgtgctt aattacactt ccggtacgac ttcggctcct    600
aaaggagtcg tacactgcca cagaggaatt ttcgtaatgt caattgattc tttaatcgat    660
tggaccgtac cgaaaaatcc ggtttactta tggactctac cgatatttca cgctaacggc    720
tggagctatc catggggaat cgccgccgtc ggaggaacta acgtctgttt gcgtaaattc    780
gacgcgccgt taatctaccg tttgatccgt gatcacggcg tcacacacat gtgtggagct    840
ccggtagtgc tcaacatgtt gtcggcgact aacgaatttc agccgttaaa tcgtcctgtc    900
aacatcttaa ccgccggtgc tccgcctcca gcagccgtac tcctccgagc agaatcaatt    960
ggattcgtga taagtcacgg atacgggtta acggaaaccg ccggattaaa cgtgtcatgc   1020
gcgtggaagc cacagtggaa tcgtttaccg gcgagcgatc gagcgaggtt gaaagcacgg   1080
caaggagtga gaaccgtcgg atttactgaa atcgacgtgg tggatcctga atcaggtagg   1140
agcgttgaga gaaacggaga aaccgtcgga gaaatagtga tgagaggaag ctcgatcatg   1200
ctcggttact aaaagatcc ggtcggaaca gagaaagctt taaagaacgg gtggttttac    1260
accggagatg ttggtgtgat tcattccgat ggttatctag agattaaaga tagatcgaaa   1320
gatataatta aacgggaggg tgaaaatgtg agtagtgttg aggttgaaac ggttttgtat   1380
acgaatccgg cggtgaatga agtggcggtg gtggcgagac ctgatgtgtt ttggggagag   1440
acgccgtgtg cgtttgttag tttgaaaagt gggttgactc aaagaccgac ggaggtggaa   1500
atgatagagt attgtaggaa gaagatgccg aaatatatgg ttcctaaaac ggtgtccttt    1560
gtggatgagc tgcctaaaac ttcgacgggg aaggttatga agtttgtact tagagagatt   1620
gcgaagaaga tgggtacgac gaggttgagt cggatgtaa                          1659

<210> SEQ ID NO 28
<211> LENGTH: 1653
<212> TYPE: DNA
<213> ORGANISM: Arabidopsis thaliana

<400> SEQUENCE: 28
atggaggaaa tgaagccatg cgccgcaaac tcgccgccgt tgacgccgat aggttttta     60
```

-continued

```
gagagagccg ccaccgttta cggtgactgt acctccatcg tttatggcag caacaccgtt    120
tacacgtggc gtgaaacaaa cctccgttgt ctccgcgtgg cgtcttctct gtcttcaatc    180
ggaatcggca ggtctgacgt agtctctgtt ctctctccca atactccggc tatgtacgag    240
ctccagtttg ctgttcccat gtccggcgca atcctcaaca acatcaacac acgcctcgac    300
gcacgcaccg tctctgttct tctccgtcac tgtgaatcta agcttctttt cgtcgacgtc    360
ttctccgttg atctcgccgt tgaagcggtc tcgatgatga cgactgatcc gccgattctc    420
gtcgtcatcg ccgataaaga agaggaagga ggagttgctg acgtggctga tctttcaaaa    480
ttcagttaca cttacgatga tcttatcgaa agaggtgatc cgggttttaa atggatccga    540
cccgaaagcg aatgggatcc ggttgtgctt aattacactt ccggtacgac ttcagctcct    600
aaaggagtgg tacactgcca cagaggaatt tcgtaatgt cagttgattc actaattgat     660
tgggccgtac cgaaaaatcc ggtttactta tggactctac cgatatttca ctctaacggt    720
tggaccaatc catgggggaat cgccgccgtc ggaggaacta acgtctgttt gcgtaaattt    780
gacgcgccgt taatctaccg tctgatccgt gatcacggcg tcacacacat gtgtggagct    840
ccggtggtgc tcaacatgtt atccgcgact caggaatctc agcctcttaa ccatcccgtc    900
aacatcttaa ccgccggttc tccgcctcca gctaccgtcc tcctccgagc cgaatcaatt    960
ggtttcgtta tcagtcacgg ttacggatta acggaaaccg ccggtgtaat cgtctcgtgc   1020
gcgtggaagc caaaatggaa tcatttaccg gcaagcgatc gagcgagatt gaaggcacgg   1080
caaggagtga gaaccgtcgg gtttactgaa attgacgtgg tggatcctga atcgggtttg   1140
agcgttgaga gaaatggaga aactgtcgga gaaattgtga tgagaggaag ctcggtcatg   1200
ctcggttact aaaagatcc ggtcggaaca gagaaagctt taaagaacgg gtggttttac    1260
accggagatg ttggtgtgat tcattccgat ggttatctag agattaaaga tagatcgaaa   1320
gatataatta taacgggagg tgagaatgtg agtagtgttg aggttgaaac ggtgttgtac   1380
acgattccgg cggtgaatga agtggcggtg gtggctagac ctgatgagtt ttggggagag   1440
acaccgtgtg cgtttgtgag tttgaaaaat gggtttagtg ggaaacctac ggaggaggaa   1500
ttgatggagt attgtagaaa gaagatgccc aagtatatgg ttcctaaaac ggtgtcgttt   1560
atggatgagt tgcctaagag ttcgacggga aaggttacga agtttgtgct tagggacatt   1620
gcaaagaaga tgggtgataa gacaatttct taa                                1653
```

<210> SEQ ID NO 29
<211> LENGTH: 1710
<212> TYPE: DNA
<213> ORGANISM: Arabidopsis thaliana

<400> SEQUENCE: 29

```
atggcggcaa cgaagtggcg tgacatcgat gatcttccca agattccggc caactacacg     60
gcgttgactc cgctttggtt ccttgatagg gctgccgtgg ttcatccgac cagaaaatct    120
gtgattcacg gatcgcgaga gtacacgtgg cgccagactt atgaccggtg tcgccgactc    180
gcctccgctc tcgccgatcg atcaatcggt cccggttcaa cggtggctat tattgcacct    240
aacatcccag caatgtacga agctcatttc ggagtaccaa tgtgtggagc tgttctgaat    300
tgtgtcaaca tccgtctcaa tgccccaaca gtcgcttttc ttcttagtca ctcgcagagc    360
tctgttataa tggtggatca ggagttcttt actctggctg aggattcttt gagacttatg    420
gaggagaaag ctggaagtag cttcaaacgc ccgcttttaa tcgtcattgg tgatcacacc    480
```

```
tgtgctcctg agtcacttaa ccgggctttg tcgaagggag ctatagaata tgaggatttt      540
cttgcaaccg gagatccaaa ttatccgtgg cagccaccga ctgatgagtg cagagcatc      600 gctcttggtt atacctcggg aacaactgct agtccgaaag gagtggtgct tcatcatcga     660
ggtgcgtata taatggcttt gagcaatcct ctcatttggg ggatgcaaga tggtgctgtt    720
tacttgtgga ctctccctat gtttcattgc aacggttggt gtttcccttg gtcccttgct    780
gtgctctctg gtacaagcat ctgtctccgt caggttacgg cgaaggaagt gtattcaatg    840
atagccaaat acaaggtaac tcatttctgt gcagctcctg tggtcctcaa cgctattgtc    900
aatgctccta aagaagacac tatccttcct cttccccata cagtccatgt catgacagca    960
ggagctgctc ctccaccttc tgttctcttc tccatgaacc agaagggctt ccgagtcgct   1020
cacacctatg gctttccga gacttatggt ccttccaccg tatgcgcttg aaacccgag    1080 tgggattccc tccctcctga cgcaggcc aagctcaatg ctcgccaagg tgtccgctat   1140
actggcatgg agcagcttga tgtcattgac actcagaccg gaaaacctgt tcctgcagat  1200
ggaaaaaccg caggagaaat tgttttccga gggaatatgg tgatgaaagg ctatctaaag  1260
aatccggaag cgaacaaaga gacatttgct ggtgggtggt tccactcggg ggatattgca  1320
gtgaaacacc cagacaacta tatcgagatc aaggacaggt caaaggacgt tataatctct  1380
gggggcgaga atatcagcag tgtcgaagtc gaaaacgtag tgtaccatca ccccgcggtt  1440
cttgaagcct ctgttgtggc caggccagac gagcggtggc aagaatctcc gtgtgcgttt  1500
gtgacactta agagcgatta cgagaagcat gaccagaata agttggctca ggatataatg  1560
aaattctgcc gggagaagct tccggcatat tgggtcccaa agtcagtggt gtttgggccg  1620
ttaccaaaga cagcaactgg aaaaattcag aagcatattc tgaggaccaa ggccaaagag  1680
atgggaccag taccaagaag caggttatag                                    1710

<210> SEQ ID NO 30
<211> LENGTH: 1629
<212> TYPE: DNA
<213> ORGANISM: Arabidopsis thaliana

<400> SEQUENCE: 30
atggaagagc caagtgccgc taactcgtta ccattgacac tgttaggctt tcttgagaga      60
gcagccaccg tgtatggaga ctgtacctcc atcgtttacg gcaattccac cgtgtacaca    120
tggcgagaaa cgaatcaccg ttgcctctgc gtcgcgtctg ctctgtcttc cattggaata    180
ggaagatccg acgttgtctc tgtcctatct gctaatactc cggaaatgta cgagctccag    240 tttccgttc cgatgtctgg cgcgatcctt aacaacatca taccgcct cgacgcgcga      300 accgtctctg ttcttctccg ccattgcgag tctaagctgc tcttcgtcga cttcttttac    360
tccgatctcg ctgtcgaagc gatcacgatg ttgctcaatc cgccgattct cgtcctaatc    420
gccaatgagg aggaggaaga aggaggagct gaagtaacgg agcgttcaaa attctgttac    480
ttgtacagtg atctaatcac tagagggaat ccggatttta atggatccg acccggaagt     540 gaatgggacc cgattgtggt caattacaca tcaggtacga cgtcgtctcc taaaggagtg    600
gttcattgcc acagggtat attcgtcatg acgcttgatt ccctaaccga ttgggccgta    660
ccgaaaaccc cggtttactt atggacctta ccgatatttc acgccaacgg ttggacctat    720
ccatggggaa tcgccgccgt cggaggaact aacgtctgtg tgcgtaaact ccacgcgccg   780
tcaatatacc atctaatccg tgatcacggc gtgactcaca tgtacggcgc accaatagtg   840
cttcagattc tatcggcgag tcaagaatct gatcagcctc ttaagagtcc ggtcaatttc    900
```

| | |
|---|---|
| ttaaccgccg gttcttctcc gccagctacg gtgcttctcc gcgccgagtc tctaggtttc | 960 |
| atcgtcagtc acggttacgg attaacggag acagccggtg tgatcgtctc ctgcgcgtgg | 1020 |
| aagccaaact ggaatcggtt accggcgagt gatcaagcgc aattgaaatc acggcaagga | 1080 |
| gtgagaaccg tcggatttag cgaaatcgat gtagtggatc cagaatcagg tcggagcgtg | 1140 |
| gagagagacg gagaaacagt cggagaaata gtgttgagag ggagttcaat catgctcgga | 1200 |
| tacttaaaaa atccgatcgg aactcaaaat tcgtttaaaa acgggtggtt cttcaccgga | 1260 |
| gacctcggtg tgattcacgg ggatggttac ttagagatta agatagatc gaaagatgtg | 1320 |
| attatttcag gaggagagaa tgtgagtagt gtggaagtgg aggcggtgtt gtacacgaat | 1380 |
| ccggcggtga atgaagcggc ggtggtggct agacctgacg agttttgggg agagacgccg | 1440 |
| tgtgcttttg ttagtttaaa acccggggttg acccggaaac caacggataa ggagattata | 1500 |
| gagtattgca aatataaaat gccacgttac atggctccta aaacggtctc gtttcttgaa | 1560 |
| gagttaccaa agacttccac tgggaagatt ataaagtcat tgcttaaaga gattgccaaa | 1620 |
| aacatgtaa | 1629 |

<210> SEQ ID NO 31
<211> LENGTH: 1653
<212> TYPE: DNA
<213> ORGANISM: Arabidopsis thaliana

<400> SEQUENCE: 31

| | |
|---|---|
| atggaactct tacttccaca cccttcgaac tcaacacctc tcaccgtcct cggcttctta | 60 |
| gaccgagccg cctctgtcta cggcgactgt ccgtccatcc tccacaccac taacaccgtc | 120 |
| cacacttggt ccgaaaccca caaccgctgt cttcgaatcg cctcggctct cacttcttcc | 180 |
| tctctcggca taaaccgagg ccaagttgtc tccgtcgtag gtcccaacgt cccgtccgtc | 240 |
| tacgagcttc agtttgctgt cccaatgtcc ggagccatct taaacaacat caaccctcgt | 300 |
| ttggacgcac atgcactctc tgtcctcctg cgtcacagtg aatctaagct cgttttcgtc | 360 |
| gatcccaatt caatctccgt agtcctcgaa gcagtctcgt tcatgaggca aaacgagaaa | 420 |
| cctcaccttg tcctcctaga cgacgaccaa gaggacggtt cttttgtctcc ttcggccgca | 480 |
| tcagattttc ttgacacata ccaaggagtt atggagagag gagattcaag attcaagtgg | 540 |
| atccgtcctc aaaccgagtg gcagcctatg attctcaact atacttctgg aacaacgtca | 600 |
| tctcccaaag gagtagtgtt gagccacaga gcaatttttca tgctaaccgt aagctcattg | 660 |
| cttgactggc attttccgaa caggccggtt tacttgtgga ctctaccaat gttccacgcc | 720 |
| aatggttggg gtatacatg gggcactgcg gcggttggag ccaccaacgt ctgcacccgt | 780 |
| agagtcgacg cgccgactat ctatgacttg atcgataagc atcacgtaac tcacatgtgt | 840 |
| gccgcaccaa tggttctcaa catgctaacc aactacccgt ctcgtaaacc gctaaagaac | 900 |
| ccggttcagg ttatgaccgc cggagctcca cctccagcag ccatcatctc aagagcagaa | 960 |
| accctaggtt tcaacgtcgg tcatgggtac ggtttaacgg aaaccggagg cccggttgtg | 1020 |
| tcatgtgctt ggaaggctga gtgggatcat cttgatccat tggaaagagc aagactgaaa | 1080 |
| tcaagacaag gagtaagaac catcggattc gcggaagttg atgttaggga cccgagaacc | 1140 |
| gggaagagtg tggaacacga cggtgtttcc gttggagaga tcgttttaaa aggcggttcg | 1200 |
| gttatgcttg gttactacaa agaccctgaa ggaaccgcag cgtgtatgag agaggacgga | 1260 |
| tggttctaca gcggagacgt aggagttata catgaagacg gttacttgga agttaaagac | 1320 |

-continued

| | |
|---|---|
| cggtcaaagg atgtgatcat atgcggagga gagaacataa gtagtgccga ggttgagacg | 1380 |
| gttctgtata caaatccagt agttaaagaa gccgcggtgg tggctaaacc ggataagatg | 1440 |
| tggggagaga caccgtgtgc ttttgtgagc ttgaagtatg attcgaatgg taatgggttg | 1500 |
| gtgactgaga gggaaataag ggagttttgt aagacgaggt tacctaagta tatggttcca | 1560 |
| aggaaagtaa tttttcagga ggagcttcca aagacttcta ctggaaagat acagaagttt | 1620 |
| cttctaagac aaatggctaa gtctctgcct taa | 1653 |

<210> SEQ ID NO 32
<211> LENGTH: 1644
<212> TYPE: DNA
<213> ORGANISM: Arabidopsis thaliana

<400> SEQUENCE: 32

| | |
|---|---|
| atggaactct tacttccaca cccatcaaac tcaactccac tcaccgtcct cggcttctta | 60 |
| gaccgagccg cttccgtcta tggtgactgt ccgtccatcc tccacactgc aaacaccgtt | 120 |
| catacttggt ccgaaacaca taaccgctgt ctccgtatcg catcggctct aacttcctcc | 180 |
| tctatcggaa ttaaacaagg ccaagtcgtc tctgtcgtgg gtcccaacgt cccgtccgtc | 240 |
| tatgagcttc agtttgctgt cccaatgtcc ggagccatct taaacaacat caaccctcgc | 300 |
| ttagacgcac acgcactctc tgtcctcctg cgtcacagcg aatccagact cgttttcgtc | 360 |
| gaccaccgtt ctatatcctt agtccttgaa gcagtttcat tattcacaca acacgagaaa | 420 |
| cctcacctcg tcctcctgga cgatgaccaa gagaacgatt cttcatccgc atcagatttt | 480 |
| cttgacacgt acgaagaaat tatggagaga ggaaattcaa gattcaagtg gatccgtcct | 540 |
| caaaccgaat ggcaaccaat ggttcttaac tatacttccg gaacgacgtc gtctcccaag | 600 |
| ggagtggtac ttagccacag agcgattttc atgctcactg ttagctcctt gcttgattgg | 660 |
| tcagtaccaa accggccagt ttacttgtgg actctaccga tgtttcacgc caatggttgg | 720 |
| ggttacactt ggggcaccgc agcggttgga gccaccaaca tctgcacgcg tagagtcgac | 780 |
| gcaccgacta tttacaactt gatcgataag cacaatgtga cccacatgtg tgctgcacct | 840 |
| atggttctca acatgctaat taactatcca ttaagtacgc cgctcaagaa cccggttatg | 900 |
| acctctggag ctcccccacc agcaaccatt atctcccgag cggagtcact tggtttcaac | 960 |
| gtcagccact catacggttt aacagagact agcggtccgg ttgtgtcatg tgcttggaag | 1020 |
| cctaagtggg accatcttga tccattggag agagctaggc tgaagtcaag gcaaggagta | 1080 |
| agaacactcg gattcacgga agtcgatgta agggatcgaa aaacaggaaa gagtgtgaaa | 1140 |
| cacgacggag tttcggttgg agagattgtt tcagaggca gctcagtcat gttgggatac | 1200 |
| tacaaagacc ctcaaggaac tgcggcttgt atgagagagg acgggtggtt ctactctgga | 1260 |
| gacatcgggg ttatacacaa agatggttac ttggagatca agatcggtc aaaagatgtg | 1320 |
| atcatatgcg gaggagaaaa tataagcagc gcagagatta gacggttct gtatacaaat | 1380 |
| ccggtggtga aggaagctgc ggtggtggct aaaccggata gatgtgggg agagacacca | 1440 |
| tgtgcttttg tgagcttgaa gtgtgataac aatggtgatg gttcggttcc cgtgaccgag | 1500 |
| agagagataa gggagttttg taagacgaag ttacctaagt acatggttcc gaggaaagtg | 1560 |
| atctttcagg aggaacttcc caagacttcc acaggaaaaa ttcagaagtt tttgctaaga | 1620 |
| caaatggcta agaccctgtc ttga | 1644 |

<210> SEQ ID NO 33
<211> LENGTH: 554

```
<212> TYPE: PRT
<213> ORGANISM: Arabidopsis thaliana

<400> SEQUENCE: 33

Met Glu Gly Thr Ile Lys Ser Pro Ala Asn Tyr Val Pro Leu Thr Pro
1               5                   10                  15

Ile Ser Phe Leu Asp Arg Ser Ala Val Val Tyr Ala Asp Arg Val Ser
            20                  25                  30

Ile Val Tyr Gly Ser Val Lys Tyr Thr Trp Arg Gln Thr Arg Asp Arg
        35                  40                  45

Cys Val Arg Ile Ala Ser Ala Leu Ser Gln Leu Gly Ile Ser Thr Gly
50                  55                  60

Asp Val Ser Val Leu Ala Pro Asn Val Pro Ala Met Val Glu Leu
65                  70                  75                  80

His Phe Gly Val Pro Met Ala Gly Ala Leu Leu Cys Thr Leu Asn Ile
                85                  90                  95

Arg His Asp Ser Ser Leu Val Ala Val Leu Leu Arg His Ser Gly Thr
            100                 105                 110

Lys Val Ile Phe Ala Asp His Gln Phe Leu Gln Ile Ala Glu Gly Ala
        115                 120                 125

Cys Glu Ile Leu Ser Asn Lys Gly Asp Lys Val Pro Ile Leu Val Leu
130                 135                 140

Ile Pro Glu Pro Leu Thr Gln Ser Val Ser Arg Lys Lys Arg Ser Glu
145                 150                 155                 160

Glu Met Met Glu Tyr Glu Asp Val Val Ala Met Gly Lys Ser Asp Phe
                165                 170                 175

Glu Val Ile Arg Pro Thr Asp Glu Cys Asp Ala Ile Ser Val Asn Tyr
            180                 185                 190

Thr Ser Gly Thr Thr Ser Ser Pro Lys Gly Val Val Tyr Ser His Arg
        195                 200                 205

Gly Ala Tyr Leu Asn Ser Leu Ala Ala Val Leu Leu Asn Glu Met His
        210                 215                 220

Ser Ser Pro Thr Tyr Leu Trp Thr Asn Pro Met Phe His Cys Asn Gly
225                 230                 235                 240

Trp Cys Leu Leu Trp Gly Val Thr Ala Ile Gly Gly Thr Asn Ile Cys
                245                 250                 255

Leu Arg Asn Val Thr Ala Lys Ala Ile Phe Asp Asn Ile Ser Gln His
            260                 265                 270

Lys Val Thr His Met Gly Gly Ala Pro Thr Ile Leu Asn Met Ile Ile
        275                 280                 285

Asn Ala Pro Glu Ser Glu Gln Lys Pro Leu Pro Gly Lys Val Ser Phe
    290                 295                 300

Ile Thr Gly Ala Ala Pro Pro Ala His Val Ile Phe Lys Met Glu
305                 310                 315                 320

Glu Leu Gly Phe Ser Met Phe His Ser Tyr Gly Leu Thr Glu Thr Tyr
                325                 330                 335

Gly Pro Gly Thr Ile Cys Thr Trp Lys Pro Glu Trp Asp Ser Leu Pro
            340                 345                 350

Arg Glu Glu Gln Ala Lys Met Lys Ala Arg Gln Gly Val Asn His Leu
        355                 360                 365

Gly Leu Glu Glu Ile Gln Val Lys Asp Pro Val Thr Met Arg Thr Leu
    370                 375                 380

Pro Ala Asp Gly Val Thr Met Gly Glu Val Val Phe Arg Gly Asn Thr
385                 390                 395                 400
```

Val Met Asn Gly Tyr Leu Lys Asn Pro Glu Ala Thr Lys Glu Ala Phe
            405                 410                 415

Lys Gly Gly Trp Phe Trp Ser Gly Asp Leu Gly Val Lys His Pro Asp
        420                 425                 430

Gly Tyr Ile Glu Leu Lys Asp Arg Ser Lys Asp Ile Ile Ser Gly
        435                 440                 445

Gly Glu Asn Ile Ser Ser Ile Glu Val Glu Ser Thr Leu Phe Thr His
    450                 455                 460

Pro Cys Val Leu Glu Ala Ala Val Val Ala Arg Pro Asp Glu Tyr Trp
465                 470                 475                 480

Gly Glu Thr Ala Cys Ala Phe Val Lys Leu Lys Asp Gly Ser Lys Ala
                485                 490                 495

Ser Ala Glu Glu Leu Ile Ser Tyr Cys Arg Asp Arg Leu Pro His Tyr
            500                 505                 510

Met Ala Pro Arg Ser Ile Val Phe Glu Asp Leu Pro Lys Thr Ser Thr
        515                 520                 525

Gly Lys Val Gln Lys Phe Val Leu Arg Thr Lys Ala Lys Ala Leu Val
    530                 535                 540

Ser Leu Ser Lys Lys Gly Arg Ser Lys Leu
545                 550

<210> SEQ ID NO 34
<211> LENGTH: 603
<212> TYPE: PRT
<213> ORGANISM: Arabidopsis thaliana

<400> SEQUENCE: 34

Met Arg Phe Leu Leu Thr Lys Arg Ala Phe Arg Ile Phe Asn Pro Arg
1               5                   10                  15

Phe Gln Arg Leu Trp Leu Thr Ser Ser Pro Phe Ser Ser Thr Ser Asn
            20                  25                  30

Ser Gly Gly Phe Pro Asp Asp Ser Glu Pro Glu Ser Trp Arg Thr Ile
        35                  40                  45

Glu Gly Leu Leu Arg Ser Pro Ala Asn Phe Ser Pro Leu Ser Pro Ile
    50                  55                  60

Thr Phe Leu Glu Arg Ser Ala Lys Val Tyr Arg Asp Arg Thr Ser Leu
65                  70                  75                  80

Val Phe Gly Ser Val Lys His Thr Trp Phe Gln Thr Tyr Gln Arg Cys
                85                  90                  95

Leu Arg Leu Ala Ser Ala Leu Thr Asn Leu Gly Ile Ser Arg Gly Asp
            100                 105                 110

Val Val Ala Ala Leu Ala Pro Asn Val Pro Ala Met His Glu Leu His
        115                 120                 125

Phe Ala Val Pro Met Ala Gly Leu Ile Leu Cys Pro Leu Asn Thr Arg
    130                 135                 140

Leu Asp Pro Ser Thr Leu Ser Val Leu Leu Ala His Ser Glu Ala Lys
145                 150                 155                 160

Ile Leu Phe Val Asp His Gln Leu Leu Glu Ile Ala His Gly Ala Leu
                165                 170                 175

Asp Leu Leu Ala Lys Ser Asp Lys Thr Arg Lys Ser Leu Lys Leu Val
            180                 185                 190

Leu Ile Ser Gln Ser Asn Asp Asp Asp Ser Asp Glu Asp Ser Ser
        195                 200                 205

Ser Thr Phe Ala Ser Lys Tyr Ser Phe Asp Tyr Glu Tyr Glu Thr Leu

```
          210                 215                 220
Leu Lys Ser Gly Asp Ser Glu Phe Glu Ile Ile Lys Pro Arg Cys Glu
225                 230                 235                 240

Trp Asp Pro Ile Ser Ile Asn Tyr Thr Ser Gly Thr Thr Ser Arg Pro
                245                 250                 255

Lys Gly Val Val Tyr Ser His Arg Gly Ala Tyr Leu Asn Ser Leu Ala
                260                 265                 270

Thr Val Phe Leu His Gln Met Ser Val Tyr Pro Val Tyr Leu Trp Thr
            275                 280                 285

Val Pro Met Phe His Cys Asn Gly Trp Cys Leu Val Trp Gly Val Ala
        290                 295                 300

Ala Gln Gly Gly Thr Asn Ile Cys Leu Arg Lys Val Ser Pro Lys Met
305                 310                 315                 320

Ile Phe Lys Asn Ile Ala Met His Lys Val Thr His Met Gly Gly Ala
                325                 330                 335

Pro Thr Val Leu Asn Met Ile Val Asn Tyr Thr Val Thr Glu His Lys
                340                 345                 350

Pro Leu Pro His Arg Val Glu Ile Met Thr Gly Gly Ser Pro Pro Leu
            355                 360                 365

Pro Gln Ile Leu Ala Lys Met Glu Glu Leu Gly Phe Asn Val Ser His
370                 375                 380

Leu Tyr Gly Leu Thr Glu Thr Tyr Gly Pro Gly Thr His Cys Val Trp
385                 390                 395                 400

Lys Pro Glu Trp Asp Ser Leu Ser Leu Glu Arg Thr Lys Leu Lys
                405                 410                 415

Ala Arg Gln Gly Val Gln His Leu Gly Leu Glu Gly Leu Asp Val Lys
                420                 425                 430

Asp Pro Leu Thr Met Glu Thr Val Pro Asp Gly Leu Thr Met Gly
            435                 440                 445

Glu Val Met Phe Arg Gly Asn Thr Val Met Ser Gly Tyr Phe Lys Asp
            450                 455                 460

Ile Glu Ala Thr Arg Lys Ala Phe Glu Gly Asp Trp Phe His Ser Gly
465                 470                 475                 480

Asp Leu Ala Val Lys Tyr Pro Asp Gly Tyr Ile Glu Ile Lys Asp Arg
                485                 490                 495

Leu Lys Asp Val Ile Ser Gly Gly Glu Asn Ile Ser Ser Val Glu
            500                 505                 510

Val Glu Arg Val Leu Cys Ser His Gln Ala Val Leu Glu Ala Ala Val
            515                 520                 525

Val Ala Arg Pro Asp His His Trp Gly Gln Thr Pro Cys Gly Phe Val
        530                 535                 540

Lys Leu Lys Glu Gly Phe Asp Thr Ile Lys Pro Glu Ile Ile Gly
545                 550                 555                 560

Phe Cys Arg Asp His Leu Pro His Tyr Met Ala Pro Lys Thr Ile Val
                565                 570                 575

Phe Gly Asp Ile Pro Lys Thr Ser Thr Gly Lys Val Gln Lys Tyr Leu
            580                 585                 590

Leu Arg Lys Lys Ala Asp Glu Met Gly Ser Leu
        595                 600

<210> SEQ ID NO 35
<211> LENGTH: 514
<212> TYPE: PRT
<213> ORGANISM: Arabidopsis thaliana
```

<400> SEQUENCE: 35

```
Met Asp Ser Asp Thr Leu Ser Gly Leu Leu Glu Asn Val Ala Lys Lys
1               5                   10                  15

Phe Pro Asp Arg Arg Ala Leu Ser Val Ser Gly Lys Phe Asn Leu Thr
            20                  25                  30

His Ala Arg Leu His Asp Leu Ile Glu Arg Ala Ala Ser Arg Leu Val
        35                  40                  45

Ser Asp Ala Gly Ile Lys Pro Gly Asp Val Val Ala Leu Thr Phe Pro
50                  55                  60

Asn Thr Val Glu Phe Val Ile Met Phe Leu Ala Val Ile Arg Ala Arg
65                  70                  75                  80

Ala Thr Ala Ala Pro Leu Asn Ala Ala Tyr Thr Ala Glu Glu Phe Glu
                85                  90                  95

Phe Tyr Leu Ser Asp Ser Asp Ser Lys Leu Leu Thr Ser Lys Glu
                100                 105                 110

Gly Asn Ala Pro Ala Gln Glu Ala Ser Lys Leu Lys Ile Ser His
            115                 120                 125

Val Thr Ala Thr Leu Leu Asp Ala Gly Ser Asp Leu Val Leu Ser Val
130                 135                 140

Ala Asp Ser Asp Ser Val Val Asp Ser Ala Thr Glu Leu Val Asn His
145                 150                 155                 160

Pro Asp Asp Gly Ala Leu Phe Leu His Thr Ser Gly Thr Thr Ser Arg
                165                 170                 175

Pro Lys Gly Val Pro Leu Thr Gln Leu Asn Leu Ala Ser Ser Val Lys
            180                 185                 190

Asn Ile Lys Ala Val Tyr Lys Leu Thr Glu Ser Asp Ser Thr Val Ile
            195                 200                 205

Val Leu Pro Leu Phe His Val His Gly Leu Leu Ala Gly Leu Leu Ser
210                 215                 220

Ser Leu Gly Ala Gly Ala Ala Val Thr Leu Pro Ala Ala Gly Arg Phe
225                 230                 235                 240

Ser Ala Thr Thr Phe Trp Pro Asp Met Lys Lys Tyr Asn Ala Thr Trp
                245                 250                 255

Tyr Thr Ala Val Pro Thr Ile His Gln Ile Ile Leu Asp Arg His Ala
                260                 265                 270

Ser His Pro Glu Thr Glu Tyr Pro Lys Leu Arg Phe Ile Arg Ser Cys
        275                 280                 285

Ser Ala Ser Leu Ala Pro Val Ile Leu Ser Arg Leu Glu Glu Ala Phe
290                 295                 300

Gly Ala Pro Val Leu Glu Ala Tyr Ala Met Thr Glu Ala Thr His Leu
305                 310                 315                 320

Met Ser Ser Asn Pro Leu Pro Glu Glu Gly Pro His Lys Pro Gly Ser
                325                 330                 335

Val Gly Lys Pro Val Gly Gln Glu Met Ala Ile Leu Asn Glu Lys Gly
            340                 345                 350

Glu Ile Gln Glu Pro Asn Asn Lys Gly Glu Val Cys Ile Arg Gly Pro
            355                 360                 365

Asn Val Thr Lys Gly Tyr Lys Asn Asn Pro Glu Ala Asn Lys Ala Gly
            370                 375                 380

Phe Glu Phe Gly Trp Phe His Thr Gly Asp Ile Gly Tyr Phe Asp Thr
385                 390                 395                 400

Asp Gly Tyr Leu His Leu Val Gly Arg Ile Lys Glu Leu Ile Asn Arg
```

```
                    405                 410                 415
Gly Gly Glu Lys Ile Ser Pro Ile Glu Val Asp Ala Val Leu Leu Thr
            420                 425                 430

His Pro Asp Val Ser Gln Gly Val Ala Phe Gly Val Pro Asp Glu Lys
            435                 440                 445

Tyr Gly Glu Glu Ile Asn Cys Ala Val Ile Pro Arg Glu Gly Thr Thr
            450                 455                 460

Val Thr Glu Glu Asp Ile Lys Ala Phe Cys Lys Lys Asn Leu Ala Ala
465                 470                 475                 480

Phe Lys Val Pro Lys Arg Val Phe Ile Thr Asp Asn Leu Pro Lys Thr
            485                 490                 495

Ala Ser Gly Lys Ile Gln Arg Arg Ile Val Ala Gln His Phe Leu Glu
            500                 505                 510

Lys Pro

<210> SEQ ID NO 36
<211> LENGTH: 545
<212> TYPE: PRT
<213> ORGANISM: Arabidopsis thaliana

<400> SEQUENCE: 36

Met Glu Leu Leu Leu Pro His Ala Ser Asn Ser Cys Pro Leu Thr Val
1               5                   10                  15

Leu Gly Phe Leu Glu Arg Ala Ala Ser Val Phe Gly Asp Ser Pro Ser
            20                  25                  30

Leu Leu His Thr Thr Val His Thr Trp Ser Glu Thr His Ser Arg
            35                  40                  45

Cys Leu Arg Ile Ala Ser Thr Leu Ser Ser Ala Ser Leu Gly Ile Asn
50                  55                  60

Arg Gly Gln Val Val Ser Val Ile Gly Pro Asn Val Pro Ser Val Tyr
65                  70                  75                  80

Glu Leu Gln Phe Ala Val Pro Met Ser Gly Ala Val Leu Asn Asn Ile
            85                  90                  95

Asn Pro Arg Leu Asp Ala His Ala Leu Ser Val Leu Leu Arg His Ser
            100                 105                 110

Glu Ser Lys Leu Val Phe Val Asp His His Leu Ser Ser Leu Val Leu
            115                 120                 125

Glu Ala Val Ser Phe Leu Pro Lys Asp Glu Arg Pro Arg Leu Val Ile
130                 135                 140

Leu Asn Asp Gly Asn Asp Met Pro Ser Ser Ser Ala Asp Met Asp
145                 150                 155                 160

Phe Leu Asp Thr Tyr Glu Gly Phe Met Glu Arg Gly Asp Leu Arg Phe
            165                 170                 175

Lys Trp Val Arg Pro Lys Ser Glu Trp Thr Pro Met Val Leu Asn Tyr
            180                 185                 190

Thr Ser Gly Thr Thr Ser Ser Pro Lys Gly Val Val His Ser His Arg
            195                 200                 205

Ser Val Phe Met Ser Thr Ile Asn Ser Leu Leu Asp Trp Ser Leu Pro
            210                 215                 220

Asn Arg Pro Val Tyr Leu Trp Thr Leu Pro Met Phe His Ala Asn Gly
225                 230                 235                 240

Trp Ser Tyr Thr Trp Ala Thr Ala Val Gly Ala Arg Asn Ile Cys
            245                 250                 255

Val Thr Arg Val Asp Val Pro Thr Ile Phe Asn Leu Ile Asp Lys Tyr
```

```
                        260                 265                 270
Gln Val Thr His Met Cys Ala Ala Pro Met Val Leu Asn Met Leu Thr
            275                 280                 285
Asn His Pro Ala Gln Lys Pro Leu Gln Ser Pro Val Lys Val Met Thr
            290                 295                 300
Ala Gly Ala Pro Pro Ala Thr Val Ile Ser Lys Ala Glu Ala Leu
305                 310                 315                 320
Gly Phe Asp Val Ser His Gly Tyr Gly Met Thr Glu Thr Gly Gly Leu
                325                 330                 335
Val Val Ser Cys Ala Leu Lys Pro Glu Trp Asp Arg Leu Glu Pro Asp
            340                 345                 350
Glu Arg Ala Lys Gln Lys Ser Arg Gln Gly Ile Arg Thr Ala Val Phe
            355                 360                 365
Ala Glu Val Asp Val Arg Asp Pro Ile Ser Gly Lys Ser Val Lys His
            370                 375                 380
Asp Gly Ala Thr Val Gly Glu Ile Val Phe Arg Gly Gly Ser Val Met
385                 390                 395                 400
Leu Gly Tyr Tyr Lys Asp Pro Glu Gly Thr Ala Ala Ser Met Arg Glu
                405                 410                 415
Asp Gly Trp Phe Tyr Thr Gly Asp Ile Gly Val Met His Pro Asp Gly
                420                 425                 430
Tyr Leu Glu Val Lys Asp Arg Ser Lys Asp Val Val Ile Cys Gly Gly
            435                 440                 445
Glu Asn Ile Ser Ser Thr Glu Leu Glu Ala Val Leu Tyr Thr Asn Pro
            450                 455                 460
Ala Ile Lys Glu Ala Ala Val Val Ala Lys Pro Asp Lys Met Trp Gly
465                 470                 475                 480
Glu Thr Pro Cys Ala Phe Val Ser Leu Lys Tyr His Asp Gly Ser Val
                485                 490                 495
Thr Glu Arg Glu Ile Arg Glu Phe Cys Lys Thr Lys Leu Pro Lys Tyr
            500                 505                 510
Met Val Pro Arg Asn Val Val Phe Leu Glu Glu Leu Pro Lys Thr Ser
            515                 520                 525
Thr Gly Lys Ile Gln Lys Phe Leu Leu Arg Gln Met Ala Lys Ser Leu
            530                 535                 540
Pro
545

<210> SEQ ID NO 37
<211> LENGTH: 552
<212> TYPE: PRT
<213> ORGANISM: Arabidopsis thaliana

<400> SEQUENCE: 37

Met Glu Gln Met Lys Pro Cys Ala Ala Asn Ser Pro Pro Leu Thr Pro
1               5                   10                  15
Ile Gly Phe Leu Glu Arg Ala Ala Thr Val Tyr Gly Asp Cys Thr Ser
                20                  25                  30
Ile Val Tyr Gly Ser Asn Thr Val Tyr Thr Trp Arg Glu Thr Asn Leu
            35                  40                  45
Arg Cys Leu Arg Val Ala Ser Ser Leu Ser Ser Ile Gly Ile Gly Arg
        50                  55                  60
Ser Asp Val Val Ser Val Leu Ser Pro Asn Thr Pro Ala Met Tyr Glu
65                  70                  75                  80
```

-continued

```
Leu Gln Phe Ala Val Pro Met Ser Gly Ala Ile Leu Asn Asn Ile Asn
            85                  90                  95
Thr Arg Leu Asp Ala Arg Thr Val Ser Val Leu Leu Arg His Cys Gly
            100                 105                 110
Ser Lys Leu Leu Phe Val Asp Val Phe Ser Val Asp Leu Ala Val Glu
            115                 120                 125
Ala Ile Ser Met Met Thr Thr Asp Pro Pro Ile Leu Val Phe Ile Ala
130                 135                 140
Asp Lys Glu Glu Glu Gly Gly Asp Ala Asp Val Ala Asp Arg Thr Lys
145                 150                 155                 160
Phe Ser Tyr Thr Tyr Asp Asp Leu Ile His Arg Gly Asp Leu Asp Phe
            165                 170                 175
Lys Trp Ile Arg Pro Glu Ser Glu Trp Asp Pro Val Val Leu Asn Tyr
            180                 185                 190
Thr Ser Gly Thr Thr Ser Ala Pro Lys Gly Val Val His Cys His Arg
            195                 200                 205
Gly Ile Phe Val Met Ser Ile Asp Ser Leu Ile Asp Trp Thr Val Pro
        210                 215                 220
Lys Asn Pro Val Tyr Leu Trp Thr Leu Pro Ile Phe His Ala Asn Gly
225                 230                 235                 240
Trp Ser Tyr Pro Trp Gly Ile Ala Ala Val Gly Gly Thr Asn Val Cys
            245                 250                 255
Leu Arg Lys Phe Asp Ala Pro Leu Ile Tyr Arg Leu Ile Arg Asp His
            260                 265                 270
Gly Val Thr His Met Cys Gly Ala Pro Val Val Leu Asn Met Leu Ser
        275                 280                 285
Ala Thr Asn Glu Phe Gln Pro Leu Asn Arg Pro Val Asn Ile Leu Thr
290                 295                 300
Ala Gly Ala Pro Pro Ala Ala Val Leu Leu Arg Ala Glu Ser Ile
305                 310                 315                 320
Gly Phe Val Ile Ser His Gly Tyr Gly Leu Thr Glu Thr Ala Gly Leu
            325                 330                 335
Asn Val Ser Cys Ala Trp Lys Pro Gln Trp Asn Arg Leu Pro Ala Ser
            340                 345                 350
Asp Arg Ala Arg Leu Lys Ala Arg Gln Gly Val Arg Thr Val Gly Phe
            355                 360                 365
Thr Glu Ile Asp Val Val Asp Pro Glu Ser Gly Arg Ser Val Glu Arg
370                 375                 380
Asn Gly Glu Thr Val Gly Glu Ile Val Met Arg Gly Ser Ser Ile Met
385                 390                 395                 400
Leu Gly Tyr Leu Lys Asp Pro Val Gly Thr Glu Lys Ala Leu Lys Asn
            405                 410                 415
Gly Trp Phe Tyr Thr Gly Asp Val Gly Val Ile His Ser Asp Gly Tyr
            420                 425                 430
Leu Glu Ile Lys Asp Arg Ser Lys Asp Ile Ile Thr Gly Gly Glu
        435                 440                 445
Asn Val Ser Ser Val Glu Val Glu Thr Val Leu Tyr Thr Asn Pro Ala
        450                 455                 460
Val Asn Glu Val Ala Val Val Ala Arg Pro Asp Val Phe Trp Gly Glu
465                 470                 475                 480
Thr Pro Cys Ala Phe Val Ser Leu Lys Ser Gly Leu Thr Gln Arg Pro
            485                 490                 495
Thr Glu Val Glu Met Ile Glu Tyr Cys Arg Lys Lys Met Pro Lys Tyr
```

```
                    500                 505                 510
Met Val Pro Lys Thr Val Ser Phe Val Asp Glu Leu Pro Lys Thr Ser
            515                 520                 525

Thr Gly Lys Val Met Lys Phe Val Leu Arg Glu Ile Ala Lys Lys Met
        530                 535                 540

Gly Thr Thr Arg Leu Ser Arg Met
545                 550

<210> SEQ ID NO 38
<211> LENGTH: 550
<212> TYPE: PRT
<213> ORGANISM: Arabidopsis thaliana

<400> SEQUENCE: 38

Met Glu Glu Met Lys Pro Cys Ala Ala Asn Ser Pro Leu Thr Pro
1               5                   10                  15

Ile Gly Phe Leu Glu Arg Ala Ala Thr Val Tyr Gly Asp Cys Thr Ser
            20                  25                  30

Ile Val Tyr Gly Ser Asn Thr Val Tyr Thr Trp Arg Glu Thr Asn Leu
        35                  40                  45

Arg Cys Leu Arg Val Ala Ser Ser Leu Ser Ser Ile Gly Ile Gly Arg
    50                  55                  60

Ser Asp Val Val Ser Val Leu Ser Pro Asn Thr Pro Ala Met Tyr Glu
65                  70                  75                  80

Leu Gln Phe Ala Val Pro Met Ser Gly Ala Ile Leu Asn Asn Ile Asn
                85                  90                  95

Thr Arg Leu Asp Ala Arg Thr Val Ser Val Leu Leu Arg His Cys Glu
            100                 105                 110

Ser Lys Leu Leu Phe Val Asp Val Phe Ser Val Asp Leu Ala Val Glu
        115                 120                 125

Ala Val Ser Met Met Thr Thr Asp Pro Pro Ile Leu Val Val Ile Ala
    130                 135                 140

Asp Lys Glu Glu Glu Gly Gly Val Ala Asp Val Ala Asp Leu Ser Lys
145                 150                 155                 160

Phe Ser Tyr Thr Tyr Asp Asp Leu Ile Glu Arg Gly Asp Pro Gly Phe
                165                 170                 175

Lys Trp Ile Arg Pro Glu Ser Glu Trp Asp Pro Val Val Leu Asn Tyr
            180                 185                 190

Thr Ser Gly Thr Thr Ser Ala Pro Lys Gly Val Val His Cys His Arg
        195                 200                 205

Gly Ile Phe Val Met Ser Val Asp Ser Leu Ile Asp Trp Ala Val Pro
    210                 215                 220

Lys Asn Pro Val Tyr Leu Trp Thr Leu Pro Ile Phe His Ser Asn Gly
225                 230                 235                 240

Trp Thr Asn Pro Trp Gly Ile Ala Ala Val Gly Gly Thr Asn Val Cys
                245                 250                 255

Leu Arg Lys Phe Asp Ala Pro Leu Ile Tyr Arg Leu Ile Arg Asp His
            260                 265                 270

Gly Val Thr His Met Cys Gly Ala Pro Val Val Leu Asn Met Leu Ser
        275                 280                 285

Ala Thr Gln Glu Ser Gln Pro Leu Asn His Pro Val Asn Ile Leu Thr
    290                 295                 300

Ala Gly Ser Pro Pro Pro Ala Thr Val Leu Leu Arg Ala Glu Ser Ile
305                 310                 315                 320
```

```
Gly Phe Val Ile Ser His Gly Tyr Gly Leu Thr Glu Thr Ala Gly Val
                325                 330                 335

Ile Val Ser Cys Ala Trp Lys Pro Lys Trp Asn His Leu Pro Ala Ser
            340                 345                 350

Asp Arg Ala Arg Leu Lys Ala Arg Gln Gly Val Arg Thr Val Gly Phe
        355                 360                 365

Thr Glu Ile Asp Val Val Asp Pro Glu Ser Gly Leu Ser Val Glu Arg
    370                 375                 380

Asn Gly Glu Thr Val Gly Glu Ile Val Met Arg Gly Ser Ser Val Met
385                 390                 395                 400

Leu Gly Tyr Leu Lys Asp Pro Val Gly Thr Glu Lys Ala Leu Lys Asn
                405                 410                 415

Gly Trp Phe Tyr Thr Gly Asp Val Gly Val Ile His Ser Asp Gly Tyr
            420                 425                 430

Leu Glu Ile Lys Asp Arg Ser Lys Asp Ile Ile Thr Gly Gly Glu
        435                 440                 445

Asn Val Ser Ser Val Glu Val Glu Thr Val Leu Tyr Thr Ile Pro Ala
    450                 455                 460

Val Asn Glu Val Ala Val Val Ala Arg Pro Asp Glu Phe Trp Gly Glu
465                 470                 475                 480

Thr Pro Cys Ala Phe Val Ser Leu Lys Asn Gly Phe Ser Gly Lys Pro
                485                 490                 495

Thr Glu Glu Glu Leu Met Glu Tyr Cys Arg Lys Lys Met Pro Lys Tyr
            500                 505                 510

Met Val Pro Lys Thr Val Ser Phe Met Asp Glu Leu Pro Lys Ser Ser
        515                 520                 525

Thr Gly Lys Val Thr Lys Phe Val Leu Arg Asp Ile Ala Lys Lys Met
    530                 535                 540

Gly Asp Lys Thr Ile Ser
545                 550

<210> SEQ ID NO 39
<211> LENGTH: 569
<212> TYPE: PRT
<213> ORGANISM: Arabidopsis thaliana

<400> SEQUENCE: 39

Met Ala Ala Thr Lys Trp Arg Asp Ile Asp Asp Leu Pro Lys Ile Pro
1               5                   10                  15

Ala Asn Tyr Thr Ala Leu Thr Pro Leu Trp Phe Leu Asp Arg Ala Ala
            20                  25                  30

Val Val His Pro Thr Arg Lys Ser Val Ile His Gly Ser Arg Glu Tyr
        35                  40                  45

Thr Trp Arg Gln Thr Tyr Asp Arg Cys Arg Arg Leu Ala Ser Ala Leu
    50                  55                  60

Ala Asp Arg Ser Ile Gly Pro Gly Ser Thr Val Ala Ile Ile Ala Pro
65                  70                  75                  80

Asn Ile Pro Ala Met Tyr Glu Ala His Phe Gly Val Pro Met Cys Gly
                85                  90                  95

Ala Val Leu Asn Cys Val Asn Ile Arg Leu Asn Ala Pro Thr Val Ala
            100                 105                 110

Phe Leu Leu Ser His Ser Gln Ser Ser Val Ile Met Val Asp Gln Glu
        115                 120                 125

Phe Phe Thr Leu Ala Glu Asp Ser Leu Arg Leu Met Glu Glu Lys Ala
    130                 135                 140
```

-continued

```
Gly Ser Ser Phe Lys Arg Pro Leu Leu Ile Val Ile Gly Asp His Thr
145                 150                 155                 160

Cys Ala Pro Glu Ser Leu Asn Arg Ala Leu Ser Lys Gly Ala Ile Glu
            165                 170                 175

Tyr Glu Asp Phe Leu Ala Thr Gly Asp Pro Asn Tyr Pro Trp Gln Pro
            180                 185                 190

Pro Ala Asp Glu Trp Gln Ser Ile Ala Leu Gly Tyr Thr Ser Gly Thr
            195                 200                 205

Thr Ala Ser Pro Lys Gly Val Val Leu His His Arg Gly Ala Tyr Ile
210                 215                 220

Met Ala Leu Ser Asn Pro Leu Ile Trp Gly Met Gln Asp Gly Ala Val
225                 230                 235                 240

Tyr Leu Trp Thr Leu Pro Met Phe His Cys Asn Gly Trp Cys Phe Pro
            245                 250                 255

Trp Ser Leu Ala Val Leu Ser Gly Thr Ser Ile Cys Leu Arg Gln Val
            260                 265                 270

Thr Ala Lys Glu Val Tyr Ser Met Ile Ala Lys Tyr Lys Val Thr His
            275                 280                 285

Phe Cys Ala Ala Pro Val Val Leu Asn Ala Ile Val Asn Ala Pro Lys
290                 295                 300

Glu Asp Thr Ile Leu Pro Leu Pro His Thr Val His Val Met Thr Ala
305                 310                 315                 320

Gly Ala Ala Pro Pro Pro Ser Val Leu Phe Ser Met Asn Gln Lys Gly
            325                 330                 335

Phe Arg Val Ala His Thr Tyr Gly Leu Ser Glu Thr Tyr Gly Pro Ser
            340                 345                 350

Thr Val Cys Ala Trp Lys Pro Glu Trp Asp Ser Leu Pro Pro Glu Thr
            355                 360                 365

Gln Ala Lys Leu Asn Ala Arg Gln Gly Val Arg Tyr Thr Gly Met Glu
370                 375                 380

Gln Leu Asp Val Ile Asp Thr Gln Thr Gly Lys Pro Val Pro Ala Asp
385                 390                 395                 400

Gly Lys Thr Ala Gly Glu Ile Val Phe Arg Gly Asn Met Val Met Lys
            405                 410                 415

Gly Tyr Leu Lys Asn Pro Glu Ala Asn Lys Glu Thr Phe Ala Gly Gly
            420                 425                 430

Trp Phe His Ser Gly Asp Ile Ala Val Lys His Pro Asp Asn Tyr Ile
            435                 440                 445

Glu Ile Lys Asp Arg Ser Lys Asp Val Ile Ile Ser Gly Gly Glu Asn
450                 455                 460

Ile Ser Ser Val Glu Val Glu Asn Val Val Tyr His His Pro Ala Val
465                 470                 475                 480

Leu Glu Ala Ser Val Val Ala Arg Pro Asp Glu Arg Trp Gln Glu Ser
            485                 490                 495

Pro Cys Ala Phe Val Thr Leu Lys Ser Asp Tyr Glu Lys His Asp Gln
            500                 505                 510

Asn Lys Leu Ala Gln Asp Ile Met Lys Phe Cys Arg Glu Lys Leu Pro
            515                 520                 525

Ala Tyr Trp Val Pro Lys Ser Val Val Phe Gly Pro Leu Pro Lys Thr
            530                 535                 540

Ala Thr Gly Lys Ile Gln Lys His Ile Leu Arg Thr Lys Ala Lys Glu
545                 550                 555                 560
```

Met Gly Pro Val Pro Arg Ser Arg Leu
            565

<210> SEQ ID NO 40
<211> LENGTH: 542
<212> TYPE: PRT
<213> ORGANISM: Arabidopsis thaliana

<400> SEQUENCE: 40

Met Glu Glu Pro Ser Ala Ala Asn Ser Leu Pro Thr Leu Leu Gly
1               5                   10                  15

Phe Leu Glu Arg Ala Ala Thr Val Tyr Gly Asp Cys Thr Ser Ile Val
                20                  25                  30

Tyr Gly Asn Ser Thr Val Tyr Thr Trp Arg Glu Thr Asn His Arg Cys
            35                  40                  45

Leu Cys Val Ala Ser Ala Leu Ser Ser Ile Gly Ile Gly Arg Ser Asp
        50                  55                  60

Val Val Ser Val Leu Ser Ala Asn Thr Pro Glu Met Tyr Glu Leu Gln
65                  70                  75                  80

Phe Ser Val Pro Met Ser Gly Ala Ile Leu Asn Asn Ile Asn Thr Arg
                85                  90                  95

Leu Asp Ala Arg Thr Val Ser Val Leu Leu Arg His Cys Glu Ser Lys
                100                 105                 110

Leu Leu Phe Val Asp Phe Phe Tyr Ser Asp Leu Ala Val Glu Ala Ile
            115                 120                 125

Thr Met Leu Leu Asn Pro Ile Leu Val Leu Ile Ala Asn Glu Glu
        130                 135                 140

Glu Glu Glu Gly Gly Ala Glu Val Thr Glu Arg Ser Lys Phe Cys Tyr
145                 150                 155                 160

Leu Tyr Ser Asp Leu Ile Thr Arg Gly Asn Pro Asp Phe Lys Trp Ile
                165                 170                 175

Arg Pro Gly Ser Glu Trp Asp Pro Ile Val Val Asn Tyr Thr Ser Gly
                180                 185                 190

Thr Thr Ser Ser Pro Lys Gly Val Val His Cys His Arg Gly Ile Phe
            195                 200                 205

Val Met Thr Leu Asp Ser Leu Thr Asp Trp Ala Val Pro Lys Thr Pro
        210                 215                 220

Val Tyr Leu Trp Thr Leu Pro Ile Phe His Ala Asn Gly Trp Thr Tyr
225                 230                 235                 240

Pro Trp Gly Ile Ala Ala Val Gly Gly Thr Asn Val Cys Val Arg Lys
                245                 250                 255

Leu His Ala Pro Ser Ile Tyr His Leu Ile Arg Asp His Gly Val Thr
                260                 265                 270

His Met Tyr Gly Ala Pro Ile Val Leu Gln Ile Leu Ser Ala Ser Gln
            275                 280                 285

Glu Ser Asp Gln Pro Leu Lys Ser Pro Val Asn Phe Leu Thr Ala Gly
        290                 295                 300

Ser Ser Pro Pro Ala Thr Val Leu Leu Arg Ala Glu Ser Leu Gly Phe
305                 310                 315                 320

Ile Val Ser His Gly Tyr Gly Leu Thr Glu Thr Ala Gly Val Ile Val
                325                 330                 335

Ser Cys Ala Trp Lys Pro Asn Trp Asn Arg Leu Pro Ala Ser Asp Gln
                340                 345                 350

Ala Gln Leu Lys Ser Arg Gln Gly Val Arg Thr Val Gly Phe Ser Glu
            355                 360                 365

-continued

```
Ile Asp Val Val Asp Pro Glu Ser Gly Arg Ser Val Glu Arg Asp Gly
    370                 375                 380
Glu Thr Val Gly Glu Ile Val Leu Arg Gly Ser Ser Ile Met Leu Gly
385                 390                 395                 400
Tyr Leu Lys Asn Pro Ile Gly Thr Gln Asn Ser Phe Lys Asn Gly Trp
                405                 410                 415
Phe Phe Thr Gly Asp Leu Gly Val Ile His Gly Asp Gly Tyr Leu Glu
            420                 425                 430
Ile Lys Asp Arg Ser Lys Asp Val Ile Ile Ser Gly Gly Glu Asn Val
        435                 440                 445
Ser Ser Val Glu Val Glu Ala Val Leu Tyr Thr Asn Pro Ala Val Asn
    450                 455                 460
Glu Ala Val Val Ala Arg Pro Asp Glu Phe Trp Gly Glu Thr Pro
465                 470                 475                 480
Cys Ala Phe Val Ser Leu Lys Pro Gly Leu Thr Arg Lys Pro Thr Asp
                485                 490                 495
Lys Glu Ile Ile Glu Tyr Cys Lys Tyr Lys Met Pro Arg Tyr Met Ala
            500                 505                 510
Pro Lys Thr Val Ser Phe Leu Glu Glu Leu Pro Lys Thr Ser Thr Gly
        515                 520                 525
Lys Ile Ile Lys Ser Leu Leu Lys Glu Ile Ala Lys Asn Met
    530                 535                 540

<210> SEQ ID NO 41
<211> LENGTH: 550
<212> TYPE: PRT
<213> ORGANISM: Arabidopsis thaliana

<400> SEQUENCE: 41

Met Glu Leu Leu Leu Pro His Pro Ser Asn Ser Thr Pro Leu Thr Val
1               5                   10                  15
Leu Gly Phe Leu Asp Arg Ala Ala Ser Val Tyr Gly Asp Cys Pro Ser
                20                  25                  30
Ile Leu His Thr Thr Asn Thr Val His Thr Trp Ser Glu Thr His Asn
            35                  40                  45
Arg Cys Leu Arg Ile Ala Ser Ala Leu Thr Ser Ser Ser Leu Gly Ile
        50                  55                  60
Asn Arg Gly Gln Val Ser Val Val Gly Pro Asn Val Pro Ser Val
65                  70                  75                  80
Tyr Glu Leu Gln Phe Ala Val Pro Met Ser Gly Ala Ile Leu Asn Asn
                85                  90                  95
Ile Asn Pro Arg Leu Asp Ala His Ala Leu Ser Val Leu Leu Arg His
            100                 105                 110
Ser Glu Ser Lys Leu Val Phe Val Asp Pro Asn Ser Ile Ser Val Val
        115                 120                 125
Leu Glu Ala Val Ser Phe Met Arg Gln Asn Glu Lys Pro His Leu Val
    130                 135                 140
Leu Leu Asp Asp Asp Gln Glu Asp Gly Ser Leu Ser Pro Ser Ala Ala
145                 150                 155                 160
Ser Asp Phe Leu Asp Thr Tyr Gln Gly Val Met Glu Arg Gly Asp Ser
                165                 170                 175
Arg Phe Lys Trp Ile Arg Pro Gln Thr Glu Trp Gln Pro Met Ile Leu
            180                 185                 190
Asn Tyr Thr Ser Gly Thr Thr Ser Ser Pro Lys Gly Val Val Leu Ser
```

```
                195                 200                 205
His Arg Ala Ile Phe Met Leu Thr Val Ser Ser Leu Leu Asp Trp His
210                 215                 220

Phe Pro Asn Arg Pro Val Tyr Leu Trp Thr Leu Pro Met Phe His Ala
225                 230                 235                 240

Asn Gly Trp Gly Tyr Thr Trp Gly Thr Ala Ala Val Gly Ala Thr Asn
                245                 250                 255

Val Cys Thr Arg Arg Val Asp Ala Pro Thr Ile Tyr Asp Leu Ile Asp
                260                 265                 270

Lys His His Val Thr His Met Cys Ala Ala Pro Met Val Leu Asn Met
                275                 280                 285

Leu Thr Asn Tyr Pro Ser Arg Lys Pro Leu Lys Asn Pro Val Gln Val
290                 295                 300

Met Thr Ala Gly Ala Pro Pro Ala Ala Ile Ile Ser Arg Ala Glu
305                 310                 315                 320

Thr Leu Gly Phe Asn Val Gly His Gly Tyr Gly Leu Thr Glu Thr Gly
                325                 330                 335

Gly Pro Val Val Ser Cys Ala Trp Lys Ala Glu Trp Asp His Leu Asp
                340                 345                 350

Pro Leu Glu Arg Ala Arg Leu Lys Ser Arg Gln Gly Val Arg Thr Ile
                355                 360                 365

Gly Phe Ala Glu Val Asp Val Arg Asp Pro Arg Thr Gly Lys Ser Val
                370                 375                 380

Glu His Asp Gly Val Ser Val Gly Glu Ile Val Leu Lys Gly Gly Ser
385                 390                 395                 400

Val Met Leu Gly Tyr Tyr Lys Asp Pro Glu Gly Thr Ala Ala Cys Met
                405                 410                 415

Arg Glu Asp Gly Trp Phe Tyr Ser Gly Asp Val Gly Val Ile His Glu
                420                 425                 430

Asp Gly Tyr Leu Glu Val Lys Asp Arg Ser Lys Asp Val Ile Ile Cys
                435                 440                 445

Gly Gly Glu Asn Ile Ser Ser Ala Glu Val Glu Thr Val Leu Tyr Thr
450                 455                 460

Asn Pro Val Val Lys Glu Ala Ala Val Ala Lys Pro Asp Lys Met
465                 470                 475                 480

Trp Gly Glu Thr Pro Cys Ala Phe Val Ser Leu Lys Tyr Asp Ser Asn
                485                 490                 495

Gly Asn Gly Leu Val Thr Glu Arg Glu Ile Arg Glu Phe Cys Lys Thr
                500                 505                 510

Arg Leu Pro Lys Tyr Met Val Pro Arg Lys Val Ile Phe Gln Glu Glu
                515                 520                 525

Leu Pro Lys Thr Ser Thr Gly Lys Ile Gln Lys Phe Leu Arg Gln
530                 535                 540

Met Ala Lys Ser Leu Pro
545                 550

<210> SEQ ID NO 42
<211> LENGTH: 547
<212> TYPE: PRT
<213> ORGANISM: Arabidopsis thaliana

<400> SEQUENCE: 42

Met Glu Leu Leu Leu Pro His Pro Ser Asn Ser Thr Pro Leu Thr Val
1               5                   10                  15
```

```
Leu Gly Phe Leu Asp Arg Ala Ala Ser Val Tyr Gly Asp Cys Pro Ser
         20              25              30
Ile Leu His Thr Ala Asn Thr Val His Thr Trp Ser Glu Thr His Asn
         35              40              45
Arg Cys Leu Arg Ile Ala Ser Ala Leu Thr Ser Ser Ile Gly Ile
 50              55              60
Lys Gln Gly Gln Val Val Ser Val Val Gly Pro Asn Val Pro Ser Val
 65              70              75              80
Tyr Glu Leu Gln Phe Ala Val Pro Met Ser Gly Ala Ile Leu Asn Asn
             85              90              95
Ile Asn Pro Arg Leu Asp Ala His Ala Leu Ser Val Leu Leu Arg His
         100             105             110
Ser Glu Ser Arg Leu Val Phe Val Asp His Arg Ser Ile Ser Leu Val
         115             120             125
Leu Glu Ala Val Ser Leu Phe Thr Gln His Glu Lys Pro His Leu Val
 130             135             140
Leu Leu Asp Asp Asp Gln Glu Asn Asp Ser Ser Ser Ala Ser Asp Phe
 145             150             155             160
Leu Asp Thr Tyr Glu Glu Ile Met Glu Arg Gly Asn Ser Arg Phe Lys
             165             170             175
Trp Ile Arg Pro Gln Thr Glu Trp Gln Pro Met Val Leu Asn Tyr Thr
         180             185             190
Ser Gly Thr Thr Ser Ser Pro Lys Gly Val Val Leu Ser His Arg Ala
         195             200             205
Ile Phe Met Leu Thr Val Ser Ser Leu Leu Asp Trp Ser Val Pro Asn
 210             215             220
Arg Pro Val Tyr Leu Trp Thr Leu Pro Met Phe His Ala Asn Gly Trp
 225             230             235             240
Gly Tyr Thr Trp Gly Thr Ala Ala Val Gly Ala Thr Asn Ile Cys Thr
             245             250             255
Arg Arg Val Asp Ala Pro Thr Ile Tyr Asn Leu Ile Asp Lys His Asn
         260             265             270
Val Thr His Met Cys Ala Ala Pro Met Val Leu Asn Met Leu Ile Asn
         275             280             285
Tyr Pro Leu Ser Thr Pro Leu Lys Asn Pro Val Met Thr Ser Gly Ala
 290             295             300
Pro Pro Pro Ala Thr Ile Ile Ser Arg Ala Glu Ser Leu Gly Phe Asn
 305             310             315             320
Val Ser His Ser Tyr Gly Leu Thr Glu Thr Ser Gly Pro Val Val Ser
             325             330             335
Cys Ala Trp Lys Pro Lys Trp Asp His Leu Asp Pro Leu Glu Arg Ala
         340             345             350
Arg Leu Lys Ser Arg Gln Gly Val Arg Thr Leu Gly Phe Thr Glu Val
         355             360             365
Asp Val Arg Asp Arg Lys Thr Gly Lys Ser Val Lys His Asp Gly Val
 370             375             380
Ser Val Gly Glu Ile Val Phe Arg Gly Ser Ser Val Met Leu Gly Tyr
 385             390             395             400
Tyr Lys Asp Pro Gln Gly Thr Ala Ala Cys Met Arg Glu Asp Gly Trp
             405             410             415
Phe Tyr Ser Gly Asp Ile Gly Val Ile His Lys Asp Gly Tyr Leu Glu
         420             425             430
Ile Lys Asp Arg Ser Lys Asp Val Ile Ile Cys Gly Gly Glu Asn Ile
```

-continued

```
                435                 440                 445
Ser Ser Ala Glu Ile Glu Thr Val Leu Tyr Thr Asn Pro Val Val Lys
    450                 455                 460

Glu Ala Ala Val Val Ala Lys Pro Asp Lys Met Trp Gly Glu Thr Pro
465                 470                 475                 480

Cys Ala Phe Val Ser Leu Lys Cys Asp Asn Asn Gly Asp Gly Ser Val
                485                 490                 495

Pro Val Thr Glu Arg Glu Ile Arg Glu Phe Cys Lys Thr Lys Leu Pro
                500                 505                 510

Lys Tyr Met Val Pro Arg Lys Val Ile Phe Gln Glu Glu Leu Pro Lys
                515                 520                 525

Thr Ser Thr Gly Lys Ile Gln Lys Phe Leu Leu Arg Gln Met Ala Lys
                530                 535                 540

Thr Leu Ser
545
```

<210> SEQ ID NO 43
<211> LENGTH: 8
<212> TYPE: PRT
<213> ORGANISM: Arabidopsis thaliana
<220> FEATURE:
<221> NAME/KEY: SITE
<222> LOCATION: (2)..(2)
<223> OTHER INFORMATION: The residue at this position can be Pro or Thr.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: SITE
<222> LOCATION: (3)..(3)
<223> OTHER INFORMATION: The residue at this position can be Leu or Ile.
<220> FEATURE:
<221> NAME/KEY: SITE
<222> LOCATION: (5)..(5)
<223> OTHER INFORMATION: The residue at this position can be Asp, Ala,
    or Ser.
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: SITE
<222> LOCATION: (6)..(6)
<223> OTHER INFORMATION: The residue at this position can be Thr or Ser.

<400> SEQUENCE: 43

```
Val Xaa Xaa Tyr Xaa Xaa Leu Gly
1               5
```

<210> SEQ ID NO 44
<211> LENGTH: 14
<212> TYPE: PRT
<213> ORGANISM: Arabidopsis thaliana
<220> FEATURE:
<221> NAME/KEY: SITE
<222> LOCATION: (2)..(2)
<223> OTHER INFORMATION: The residue at this position can  be Met or
    Cys.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: SITE
<222> LOCATION: (3)..(3)
<223> OTHER INFORMATION: The residue at this position can  be Tyr, Phe
    or Lys.
<220> FEATURE:

```
<221> NAME/KEY: SITE
<222> LOCATION: (7)..(7)
<223> OTHER INFORMATION: The residue at this position can  be Thr or
      Ser.
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: SITE
<222> LOCATION: (8)..(8)
<223> OTHER INFORMATION: The residue at this position can  be Thr or
      Ser.
<220> FEATURE:
<221> NAME/KEY: SITE
<222> LOCATION: (10)..(10)
<223> OTHER INFORMATION: The residue at this position can  be Asp, Leu,
      Thr, Asn or Glu.
<220> FEATURE:
<221> NAME/KEY: misc_feature
<222> LOCATION: (10)..(10)
<223> OTHER INFORMATION: Xaa can be any naturally occurring amino acid

<400> SEQUENCE: 44

Ile Xaa Xaa Thr Ser Gly Xaa Xaa Gly Xaa Pro Lys Gly Val
1               5                   10

<210> SEQ ID NO 45
<211> LENGTH: 7
<212> TYPE: PRT
<213> ORGANISM: Arabidopsis thaliana
<220> FEATURE:
<221> NAME/KEY: SITE
<222> LOCATION: (1)..(1)
<223> OTHER INFORMATION: The residue at this position can be Ser or Ala.
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: SITE
<222> LOCATION: (2)..(2)
<223> OTHER INFORMATION: The residue at this position can be Tyr, Met
      or Phe.
<220> FEATURE:
<221> NAME/KEY: SITE
<222> LOCATION: (5)..(5)
<223> OTHER INFORMATION: The residue at this position can be Leu or Ser.
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: SITE
<222> LOCATION: (6)..(6)
<223> OTHER INFORMATION: The residue at this position can be Ala or Trp.

<400> SEQUENCE: 45

Xaa Xaa Leu Pro Xaa Xaa His
1               5

<210> SEQ ID NO 46
<211> LENGTH: 4
<212> TYPE: PRT
<213> ORGANISM: Arabidopsis thaliana
<220> FEATURE:
<221> NAME/KEY: SITE
<222> LOCATION: (1)..(1)
<223> OTHER INFORMATION: The residue at this position can be Leu or Gln.
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: SITE
```

```
<222> LOCATION: (2)..(2)
<223> OTHER INFORMATION: The residue at this position can be Lys or Arg.
<220> FEATURE:
<221> NAME/KEY: SITE
<222> LOCATION: (4)..(4)
<223> OTHER INFORMATION: The residue at this position can be Thr, Pro
      or Ser.
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

Xaa Xaa Pro Xaa
1

<210> SEQ ID NO 47
<211> LENGTH: 6
<212> TYPE: PRT
<213> ORGANISM: Arabidopsis thaliana
<220> FEATURE:
<221> NAME/KEY: SITE
<222> LOCATION: (1)..(1)
<223> OTHER INFORMATION: The residue at this position can be Ser, Gly,
      or Val.
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: SITE
<222> LOCATION: (3)..(3)
<223> OTHER INFORMATION: The residue at this position can be Ala, Gly
      or Ser.
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: SITE
<222> LOCATION: (4)..(4)
<223> OTHER INFORMATION: The residue at this position can be Ala, Leu or
      Ser.
<220> FEATURE:
<221> NAME/KEY: SITE
<222> LOCATION: (6)..(6)
<223> OTHER INFORMATION: The residue at this position can be Leu, Ile or
      Met.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 47

Xaa Gly Xaa Xaa Pro Xaa
1               5

<210> SEQ ID NO 48
<211> LENGTH: 7
<212> TYPE: PRT
<213> ORGANISM: Arabidopsis thaliana
<220> FEATURE:
<221> NAME/KEY: SITE
<222> LOCATION: (4)..(4)
<223> OTHER INFORMATION: The residue at this position can be Leu or Met.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: SITE
<222> LOCATION: (7)..(7)
<223> OTHER INFORMATION: The residue at this position can be Thr or Ser.
<220> FEATURE:
<221> NAME/KEY: misc_feature
```

```
<222> LOCATION: (7)..(7)
<223> OTHER INFORMATION: Xaa can be any naturally occurring amino acid

<400> SEQUENCE: 48

Gly Tyr Gly Xaa Thr Glu Xaa
1               5

<210> SEQ ID NO 49
<211> LENGTH: 9
<212> TYPE: PRT
<213> ORGANISM: Arabidopsis thaliana
<220> FEATURE:
<221> NAME/KEY: SITE
<222> LOCATION: (1)..(1)
<223> OTHER INFORMATION: The residue at this position can be Pro, Ser or
      Ala.
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: SITE
<222> LOCATION: (2)..(2)
<223> OTHER INFORMATION: The residue at this position can be Arg or Lys.
<220> FEATURE:
<221> NAME/KEY: SITE
<222> LOCATION: (3)..(3)
<223> OTHER INFORMATION: The residue at this position can be Gly or Ala.
<220> FEATURE:
<221> NAME/KEY: SITE
<222> LOCATION: (4)..(4)
<223> OTHER INFORMATION: The residue at this position can be Glu or Ile.
<220> FEATURE:
<221> NAME/KEY: SITE
<222> LOCATION: (5)..(5)
<223> OTHER INFORMATION: The residue at this position can be Ile or Val.
<220> FEATURE:
<221> NAME/KEY: SITE
<222> LOCATION: (6)..(6)
<223> OTHER INFORMATION: The residue at this position can be Cys, Lys or
      Val.
<220> FEATURE:
<221> NAME/KEY: SITE
<222> LOCATION: (7)..(7)
<223> OTHER INFORMATION: The residue at this position can be Ile, Val or
      Leu.
<220> FEATURE:
<221> NAME/KEY: SITE
<222> LOCATION: (8)..(8)
<223> OTHER INFORMATION: The residue at this position can be Arg or Gly.

<400> SEQUENCE: 49

Xaa Xaa Xaa Xaa Xaa Xaa Xaa Xaa Gly
1               5

<210> SEQ ID NO 50
<211> LENGTH: 6
<212> TYPE: PRT
<213> ORGANISM: Arabidopsis thaliana

<400> SEQUENCE: 50

Ile Ile Asp Arg Lys Lys
1               5

<210> SEQ ID NO 51
<211> LENGTH: 10
<212> TYPE: PRT
<213> ORGANISM: Arabidopsis thaliana
<220> FEATURE:
<221> NAME/KEY: SITE
<222> LOCATION: (2)..(2)
<223> OTHER INFORMATION: The residue at this position can be Leu, Val,
      Met or Ile.
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: SITE
<222> LOCATION: (4)..(4)
<223> OTHER INFORMATION: The residue at this position can be Pro or Ala.
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: SITE
<222> LOCATION: (5)..(5)
<223> OTHER INFORMATION: The residue at this position can be Thr, Ala or
      Ser.
<220> FEATURE:
<221> NAME/KEY: SITE
<222> LOCATION: (6)..(6)
<223> OTHER INFORMATION: The residue at this position can be Phe, Leu,
      Met, or Tyr.
<220> FEATURE:
<221> NAME/KEY: SITE
<222> LOCATION: (8)..(8)
<223> OTHER INFORMATION: The residue at this position can be Ile, Lys,
      Met, Asn or Leu.
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: The residue at this position can be Lys or Arg.

<400> SEQUENCE: 51

Leu Xaa Thr Xaa Xaa Xaa Lys Xaa Xaa Arg
1               5                   10

<210> SEQ ID NO 52
<211> LENGTH: 18
<212> TYPE: DNA
<213> ORGANISM: Artificial
<220> FEATURE:
<223> OTHER INFORMATION: Synthetic

<400> SEQUENCE: 52
aaggcgattc atcttgac                                                 18

<210> SEQ ID NO 53
<211> LENGTH: 29
<212> TYPE: DNA
<213> ORGANISM: Artificial
<220> FEATURE:
<223> OTHER INFORMATION: Synthetic

<400> SEQUENCE: 53
ctggtaccat gacgcagcag aagaaatac                                     29

<210> SEQ ID NO 54
<211> LENGTH: 28
<212> TYPE: DNA
<213> ORGANISM: Artificial
<220> FEATURE:
<223> OTHER INFORMATION: Synthetic

<400> SEQUENCE: 54
ctctcgagct accctctgga agcaaatt                                      28

<210> SEQ ID NO 55
```

```
<211> LENGTH: 28
<212> TYPE: DNA
<213> ORGANISM: Artificial
<220> FEATURE:
<223> OTHER INFORMATION: Synthetic

<400> SEQUENCE: 55
atgacgtcgc agaaaagatt catctttg                                    28

<210> SEQ ID NO 56
<211> LENGTH: 29
<212> TYPE: DNA
<213> ORGANISM: Artificial
<220> FEATURE:
<223> OTHER INFORMATION: Synthetic

<400> SEQUENCE: 56
ttactgtccg gaagctagac tttccttc                                    29

<210> SEQ ID NO 57
<211> LENGTH: 19
<212> TYPE: DNA
<213> ORGANISM: Artificial
<220> FEATURE:
<223> OTHER INFORMATION: Synthetic

<400> SEQUENCE: 57
gagtctatct gccgaaacc                                              19

<210> SEQ ID NO 58
<211> LENGTH: 31
<212> TYPE: DNA
<213> ORGANISM: Artificial
<220> FEATURE:
<223> OTHER INFORMATION: Synthetic

<400> SEQUENCE: 58
atggcgactg gtcgatacat cgttgaggtt g                                31

<210> SEQ ID NO 59
<211> LENGTH: 23
<212> TYPE: DNA
<213> ORGANISM: Artificial
<220> FEATURE:
<223> OTHER INFORMATION: Synthetic

<400> SEQUENCE: 59
ttacactcgt agctgcactt ctc                                         23

<210> SEQ ID NO 60
<211> LENGTH: 20
<212> TYPE: DNA
<213> ORGANISM: Artificial
<220> FEATURE:
<223> OTHER INFORMATION: Synthetic

<400> SEQUENCE: 60
aactcaatta ccaatctccc                                             20

<210> SEQ ID NO 61
<211> LENGTH: 20
<212> TYPE: DNA
<213> ORGANISM: Artificial
<220> FEATURE:
<223> OTHER INFORMATION: Synthetic

<400> SEQUENCE: 61
```
cgccatgaac accgagtcag                    20

<210> SEQ ID NO 62
<211> LENGTH: 21
<212> TYPE: DNA
<213> ORGANISM: Artificial
<220> FEATURE:
<223> OTHER INFORMATION: Synthetic

<400> SEQUENCE: 62
gagccattca gagcttcgac g                    21

<210> SEQ ID NO 63
<211> LENGTH: 18
<212> TYPE: DNA
<213> ORGANISM: Artificial
<220> FEATURE:
<223> OTHER INFORMATION: Synthetic

<400> SEQUENCE: 63
atccgagagt gaaagcag                    18

<210> SEQ ID NO 64
<211> LENGTH: 28
<212> TYPE: DNA
<213> ORGANISM: Artificial
<220> FEATURE:
<223> OTHER INFORMATION: Synthetic

<400> SEQUENCE: 64
ctggtaccat ggattcttct tcttcgtc                    28

<210> SEQ ID NO 65
<211> LENGTH: 29
<212> TYPE: DNA
<213> ORGANISM: Artificial
<220> FEATURE:
<223> OTHER INFORMATION: Synthetic

<400> SEQUENCE: 65
agctcgagtt cacaaacctc tattagcag                    29

<210> SEQ ID NO 66
<211> LENGTH: 18
<212> TYPE: DNA
<213> ORGANISM: Artificial
<220> FEATURE:
<223> OTHER INFORMATION: Synthetic

<400> SEQUENCE: 66
cttgctgaga tggatgac                    18

<210> SEQ ID NO 67
<211> LENGTH: 23
<212> TYPE: DNA
<213> ORGANISM: Artificial
<220> FEATURE:
<223> OTHER INFORMATION: Synthetic

<400> SEQUENCE: 67
catggaattt gcttcgccgg aac                    23

<210> SEQ ID NO 68
<211> LENGTH: 27
<212> TYPE: DNA

```
<213> ORGANISM: Artificial
<220> FEATURE:
<223> OTHER INFORMATION: Synthetic

<400> SEQUENCE: 68
gtaccatgga atttgcttcg ccggaac                                        27

<210> SEQ ID NO 69
<211> LENGTH: 23
<212> TYPE: DNA
<213> ORGANISM: Artificial
<220> FEATURE:
<223> OTHER INFORMATION: Synthetic

<400> SEQUENCE: 69
ctcacagttt agaaggaatg ggg                                            23

<210> SEQ ID NO 70
<211> LENGTH: 27
<212> TYPE: DNA
<213> ORGANISM: Artificial
<220> FEATURE:
<223> OTHER INFORMATION: Synthetic

<400> SEQUENCE: 70
catgctcaca gtttagaagg aatgggg                                        27

<210> SEQ ID NO 71
<211> LENGTH: 24
<212> TYPE: DNA
<213> ORGANISM: Artificial
<220> FEATURE:
<223> OTHER INFORMATION: Synthetic

<400> SEQUENCE: 71
atggcttcga cttcttcttt ggga                                           24

<210> SEQ ID NO 72
<211> LENGTH: 27
<212> TYPE: DNA
<213> ORGANISM: Artificial
<220> FEATURE:
<223> OTHER INFORMATION: Synthetic

<400> SEQUENCE: 72
caaatgtctt aactgtagag ttgatca                                        27

<210> SEQ ID NO 73
<211> LENGTH: 37
<212> TYPE: DNA
<213> ORGANISM: Artificial
<220> FEATURE:
<223> OTHER INFORMATION: Synthetic

<400> SEQUENCE: 73
tgcatggagc tcatggcttc gacttcttct ttgggac                             37

<210> SEQ ID NO 74
<211> LENGTH: 36
<212> TYPE: DNA
<213> ORGANISM: Artificial
<220> FEATURE:
<223> OTHER INFORMATION: Synthetic

<400> SEQUENCE: 74
acgatcctcg agttaactgt agagttgatc aatctc                              36
```

<210> SEQ ID NO 75
<211> LENGTH: 39
<212> TYPE: DNA
<213> ORGANISM: Artificial
<220> FEATURE:
<223> OTHER INFORMATION: Synthetic

<400> SEQUENCE: 75
cgaatggtac caatggcttc aacgtctctc ggagcttcg                    39

<210> SEQ ID NO 76
<211> LENGTH: 36
<212> TYPE: DNA
<213> ORGANISM: Artificial
<220> FEATURE:
<223> OTHER INFORMATION: Synthetic

<400> SEQUENCE: 76
atactgcatg cctacttgta gagtctttct atttca                       36

<210> SEQ ID NO 77
<211> LENGTH: 18
<212> TYPE: DNA
<213> ORGANISM: Artificial
<220> FEATURE:
<223> OTHER INFORMATION: Synthetic

<400> SEQUENCE: 77
acggcagaaa agaacaag                                           18

<210> SEQ ID NO 78
<211> LENGTH: 29
<212> TYPE: DNA
<213> ORGANISM: Artificial
<220> FEATURE:
<223> OTHER INFORMATION: Synthetic

<400> SEQUENCE: 78
ctggtaccat gaagtctttt gcggctaag                               29

<210> SEQ ID NO 79
<211> LENGTH: 29
<212> TYPE: DNA
<213> ORGANISM: Artificial
<220> FEATURE:
<223> OTHER INFORMATION: Synthetic

<400> SEQUENCE: 79
actctagatt attgatacat ataacgtac                               29

<210> SEQ ID NO 80
<211> LENGTH: 27
<212> TYPE: DNA
<213> ORGANISM: Artificial
<220> FEATURE:
<223> OTHER INFORMATION: Synthetic

<400> SEQUENCE: 80
atggaagatt ctggagtgaa tccaatg                                 27

<210> SEQ ID NO 81
<211> LENGTH: 27
<212> TYPE: DNA
<213> ORGANISM: Artificial
<220> FEATURE:

<223> OTHER INFORMATION: Synthetic

<400> SEQUENCE: 81
ttaggcatat aacttgctga gttcatc 27

<210> SEQ ID NO 82
<211> LENGTH: 20
<212> TYPE: DNA
<213> ORGANISM: Artificial
<220> FEATURE:
<223> OTHER INFORMATION: Synthetic

<400> SEQUENCE: 82
cttcaaagca aggaatagac 20

<210> SEQ ID NO 83
<211> LENGTH: 22
<212> TYPE: DNA
<213> ORGANISM: Artificial
<220> FEATURE:
<223> OTHER INFORMATION: Synthetic

<400> SEQUENCE: 83
atgattcctt atgctgctgg tg 22

<210> SEQ ID NO 84
<211> LENGTH: 24
<212> TYPE: DNA
<213> ORGANISM: Artificial
<220> FEATURE:
<223> OTHER INFORMATION: Synthetic

<400> SEQUENCE: 84
ttaggcatat aacttggtga gatc 24

<210> SEQ ID NO 85
<211> LENGTH: 22
<212> TYPE: DNA
<213> ORGANISM: Artificial
<220> FEATURE:
<223> OTHER INFORMATION: Synthetic

<400> SEQUENCE: 85
atggagggaa ctatcaaatc tc 22

<210> SEQ ID NO 86
<211> LENGTH: 22
<212> TYPE: DNA
<213> ORGANISM: Artificial
<220> FEATURE:
<223> OTHER INFORMATION: Synthetic

<400> SEQUENCE: 86
tcataacttg cttctgcctt tc 22

<210> SEQ ID NO 87
<211> LENGTH: 23
<212> TYPE: DNA
<213> ORGANISM: Artificial
<220> FEATURE:
<223> OTHER INFORMATION: Synthetic

<400> SEQUENCE: 87
atgagattct tgttaaccaa aag 23

```
<210> SEQ ID NO 88
<211> LENGTH: 23
<212> TYPE: DNA
<213> ORGANISM: Artificial
<220> FEATURE:
<223> OTHER INFORMATION: Synthetic

<400> SEQUENCE: 88
ttacaagcta cccatttcat cag                                             23

<210> SEQ ID NO 89
<211> LENGTH: 19
<212> TYPE: DNA
<213> ORGANISM: Artificial
<220> FEATURE:
<223> OTHER INFORMATION: Synthetic

<400> SEQUENCE: 89
tgagaaatat ggggaagag                                                  19

<210> SEQ ID NO 90
<211> LENGTH: 22
<212> TYPE: DNA
<213> ORGANISM: Artificial
<220> FEATURE:
<223> OTHER INFORMATION: Synthetic

<400> SEQUENCE: 90
atggatagcg atactctctc ag                                              22

<210> SEQ ID NO 91
<211> LENGTH: 21
<212> TYPE: DNA
<213> ORGANISM: Artificial
<220> FEATURE:
<223> OTHER INFORMATION: Synthetic

<400> SEQUENCE: 91
tcagggcttc tcaaggaaat g                                               21

<210> SEQ ID NO 92
<211> LENGTH: 22
<212> TYPE: DNA
<213> ORGANISM: Artificial
<220> FEATURE:
<223> OTHER INFORMATION: Synthetic

<400> SEQUENCE: 92
atggaacttt tactcccaca cg                                              22

<210> SEQ ID NO 93
<211> LENGTH: 21
<212> TYPE: DNA
<213> ORGANISM: Artificial
<220> FEATURE:
<223> OTHER INFORMATION: Synthetic

<400> SEQUENCE: 93
tcatcaaggc aaggacttag c                                               21

<210> SEQ ID NO 94
<211> LENGTH: 28
<212> TYPE: DNA
<213> ORGANISM: Artificial
<220> FEATURE:
<223> OTHER INFORMATION: Synthetic
```

```
<400> SEQUENCE: 94
gaaaacaata cattgaccac tcaagatg                                    28

<210> SEQ ID NO 95
<211> LENGTH: 28
<212> TYPE: DNA
<213> ORGANISM: Artificial
<220> FEATURE:
<223> OTHER INFORMATION: Synthetic

<400> SEQUENCE: 95
tcgcaagttc taattttaca tccgactc                                    28

<210> SEQ ID NO 96
<211> LENGTH: 27
<212> TYPE: DNA
<213> ORGANISM: Artificial
<220> FEATURE:
<223> OTHER INFORMATION: Synthetic

<400> SEQUENCE: 96
tttgattacc actaggagga agagatg                                     27

<210> SEQ ID NO 97
<211> LENGTH: 28
<212> TYPE: DNA
<213> ORGANISM: Artificial
<220> FEATURE:
<223> OTHER INFORMATION: Synthetic

<400> SEQUENCE: 97
cggtgaaaga aagacgttta agaaattg                                    28

<210> SEQ ID NO 98
<211> LENGTH: 22
<212> TYPE: DNA
<213> ORGANISM: Artificial
<220> FEATURE:
<223> OTHER INFORMATION: Synthetic

<400> SEQUENCE: 98
atggcggcaa cgaagtggcg tg                                          22

<210> SEQ ID NO 99
<211> LENGTH: 28
<212> TYPE: DNA
<213> ORGANISM: Artificial
<220> FEATURE:
<223> OTHER INFORMATION: Synthetic

<400> SEQUENCE: 99
ctataacctg cttcttggta ctggtccc                                    28

<210> SEQ ID NO 100
<211> LENGTH: 24
<212> TYPE: DNA
<213> ORGANISM: Artificial
<220> FEATURE:
<223> OTHER INFORMATION: Synthetic

<400> SEQUENCE: 100
atggaagatt tgaagccaag tgcc                                        24

<210> SEQ ID NO 101
<211> LENGTH: 28
```

```
<212> TYPE: DNA
<213> ORGANISM: Artificial
<220> FEATURE:
<223> OTHER INFORMATION: Synthetic

<400> SEQUENCE: 101
ttacatgttt ttggcaatct ctttaagc                                28

<210> SEQ ID NO 102
<211> LENGTH: 30
<212> TYPE: DNA
<213> ORGANISM: Artificial
<220> FEATURE:
<223> OTHER INFORMATION: Synthetic

<400> SEQUENCE: 102
tacaaaacat taacaaaaat caaagtatgg                              30

<210> SEQ ID NO 103
<211> LENGTH: 29
<212> TYPE: DNA
<213> ORGANISM: Artificial
<220> FEATURE:
<223> OTHER INFORMATION: Synthetic

<400> SEQUENCE: 103
ataactcaag cgaatcttta aggcagaga                               29

<210> SEQ ID NO 104
<211> LENGTH: 30
<212> TYPE: DNA
<213> ORGANISM: Artificial
<220> FEATURE:
<223> OTHER INFORMATION: Synthetic

<400> SEQUENCE: 104
acgatactat agtttcttgc agctaactaa                              30

<210> SEQ ID NO 105
<211> LENGTH: 29
<212> TYPE: DNA
<213> ORGANISM: Artificial
<220> FEATURE:
<223> OTHER INFORMATION: Synthetic

<400> SEQUENCE: 105
ttatttaatg gacttgttca agacagggt                               29

<210> SEQ ID NO 106
<211> LENGTH: 30
<212> TYPE: DNA
<213> ORGANISM: Artificial
<220> FEATURE:
<223> OTHER INFORMATION: Synthetic

<400> SEQUENCE: 106
gaaagttaaa ctcaattcct ccgtcgatca                              30

<210> SEQ ID NO 107
<211> LENGTH: 31
<212> TYPE: DNA
<213> ORGANISM: Artificial
<220> FEATURE:
<223> OTHER INFORMATION: Synthetic

<400> SEQUENCE: 107
```

```
gcatataact tggtgagatc ttcagagaat t                                     31
```

<210> SEQ ID NO 108
<211> LENGTH: 29
<212> TYPE: DNA
<213> ORGANISM: Artificial
<220> FEATURE:
<223> OTHER INFORMATION: Synthetic

<400> SEQUENCE: 108

```
tgcactcgaa atcagccaat tttagacaa                                        29
```

<210> SEQ ID NO 109
<211> LENGTH: 25
<212> TYPE: PRT
<213> ORGANISM: Artificial
<220> FEATURE:
<223> OTHER INFORMATION: Synthetic
<220> FEATURE:
<221> NAME/KEY: SITE
<222> LOCATION: (11)..(11)
<223> OTHER INFORMATION: Xaa at this position can be any amino acid.
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: SITE
<222> LOCATION: (13)..(13)
<223> OTHER INFORMATION: Xaa at this position can be any amino acid.
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: SITE
<222> LOCATION: (15)..(15)
<223> OTHER INFORMATION: Xaa at this position can be any amino acid.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: SITE
<222> LOCATION: (17)..(17)
<223> OTHER INFORMATION: Xaa at this position can be any amino acid.
<220> FEATURE:
<221> NAME/KEY: misc_feature
<222> LOCATION: (17)..(17)
<223> OTHER INFORMATION: Xaa can be any naturally occurring amino acid

<400> SEQUENCE: 109

```
Asp Gly Trp Leu His Thr Gly Asp Ile Gly Xaa Trp Xaa Pro Xaa Gly
1               5                   10                  15

Xaa Leu Lys Ile Ile Asp Arg Lys Lys
            20                  25
```

<210> SEQ ID NO 110
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 110

```
Pro Arg Val Leu Asp Arg Val Tyr Ser Gly Leu Asp Lys Leu Val Phe
1               5                   10                  15

Ser Lys Val Lys
            20
```

```
<210> SEQ ID NO 111
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 111

Pro Arg Val Leu Asp Arg Val Tyr Thr Gly Leu Asp Lys Leu Val Phe
1               5                   10                  15

Asn Lys Val Lys
            20

<210> SEQ ID NO 112
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 112

Pro Arg Val Leu Glu Arg Ile Tyr Thr Gly Leu Asp Lys Ile Val Phe
1               5                   10                  15

Lys Lys Val Lys
            20

<210> SEQ ID NO 113
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 113

Pro Arg Val Tyr Asp Lys Leu Tyr Ala Gly Ile Asp Arg Leu Met Phe
1               5                   10                  15

Asp Lys Ile Lys
            20

<210> SEQ ID NO 114
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 114

Pro Arg Leu Tyr Asn Arg Ile Tyr Ala Gly Ile Asp Arg Leu Val Phe
1               5                   10                  15

Asn Lys Ile Lys
            20

<210> SEQ ID NO 115
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 115
```

```
Pro Arg Leu Tyr Asn Arg Ile Tyr Asp Gly Ile Asp Lys Leu Val Phe
1               5                   10                  15

Asn Lys Ile Lys
            20

<210> SEQ ID NO 116
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 116

Pro Leu Val Tyr Glu Thr Leu Tyr Ser Gly Ile Lys Lys Leu Ile Tyr
1               5                   10                  15

Lys Lys Ile His
            20

<210> SEQ ID NO 117
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 117

Pro Leu Val Tyr Glu Thr Leu Tyr Ser Gly Ile Glu Lys Leu Val His
1               5                   10                  15

Arg Lys Ile Arg
            20

<210> SEQ ID NO 118
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 118

Pro Arg Val Phe Glu Arg Ile His Glu Gly Ile Lys Phe Ile Ala Phe
1               5                   10                  15

Arg Lys Ile Arg
            20

<210> SEQ ID NO 119
<211> LENGTH: 20
<212> TYPE: PRT
<213> ORGANISM: Arabidopsis thaliana
<220> FEATURE:
<221> NAME/KEY: NON_CONS
<222> LOCATION: (11)..(12)

<400> SEQUENCE: 119

Pro Ala Ile Leu Asp Arg Val Arg Glu Gly Val Asp Ala Leu Val Phe
1               5                   10                  15

Lys Lys Ile Arg
            20

<210> SEQ ID NO 120
<211> LENGTH: 20
<212> TYPE: PRT
<213> ORGANISM: Arabidopsis thaliana
```

```
<220> FEATURE:
<221> NAME/KEY: NON_CONS
<222> LOCATION: (11)..(12)

<400> SEQUENCE: 120

Pro Ala Ile Leu Asp Arg Val Arg Asp Gly Val Asp Val Leu Val Phe
1               5                   10                  15

Arg Lys Ile Arg
            20

<210> SEQ ID NO 121
<211> LENGTH: 2001
<212> TYPE: DNA
<213> ORGANISM: Arabidopsis thaliana

<400> SEQUENCE: 121
atgtcgcagc agaagaaata catcttccaa gttgaagaag caaagaagg tagcgatgga      60
agaccatcag ttggtccagt gtaccggagt atctttgcca aggacggatt tcccgacccg    120
atcgaaggaa tggatagttg ttgggatgtt ttccgcatgt ctgttgagaa gtatccaaac    180
aatccaatgc tgggacgccg cgagattgta gatggaaagc cgggtaagta tgtctggcaa    240
acataccaag aagtctacga cattgtcatg aaacttggaa attctctcag aagtgttgga    300
gttaaggacg aagcaaaatg tggtatctat ggtgcaaatt ctcctgagtg gattatcagc    360
atggaggctt gtaatgcaca tggactctat tgtgtaccgt tatatgatac actaggtgct    420
gatgctgtgg aattcatcat ttcccattca gaggtttcaa ttgtctttgt ggaagagaag    480
aagatctctg agttgttcaa gacatgccca actcgacag agtacatgaa actgttgtg     540
agcttcgggg gtgtctcacg tgaacaaaaa gaagaagctg aaactttgg ttggttata     600
tatgcttggg atgaattttt gaagctgggt gaaggaaagc aatatgatct cccaatcaaa    660
aagaaaagcg acatttgcac gattatgtat acgagtggaa ccactggtga cccaaaggga    720
gtgatgatat ctaacgaaag cattgtgact ctaatcgctg gagtgatccg tctactgaaa    780
agtgctaacg aggctctgac tgtgaaagat gtgtatcttt cttatcttcc tcttgcccac    840
atctttgacc gagttatcga ggagtgtttc attcaacatg gtgctgcaat ggcttctgg     900
cgagggatg taaaattgtt gatcgaagac cttgctgagc ttaaaccaac tattttttgt    960
gctgtacctc gtgtcctgga tagagtatac tcaggtcttc agaagaagct ttctgatggt   1020
ggattcttaa aaagttcat atttgattct gcatttttcct ataaatttgg ttatatgaag   1080
aagggacagt ctcatgtgga ggcctctcca ctttttgaca aacttgtgtt cagcaaggtt   1140
aaacaaggac tcggaggcaa tgtgaggatt attctatctg gagctgctcc tcttgctagt   1200
cacgtagagt catttctaag agtggtggca tgctgtcatg ttctccaagg atacggtctt   1260
actgaaagct gtgctggaac ttttgtctcg ctgccagatg aactaggtat gctcggcaca   1320
gttggtccac cagtgccaaa cgttgatata cgccttgaat ccgtccccga gatggaatat   1380
gatgctcttg cgagtactgc acgtggtgaa atctgcattc ggggaaagac ccttttctct   1440
ggttactaca acgtgaagaa tctcacgaaa gaggttctca ttgatggatg gctgcacaca   1500
ggtgatgttg gtgagtggca accagatgga agcatgaaga taattgacag gaagaagaat   1560
atctttaaac tctcacaagg agagtatgtt gcggtggaga acatagaaaa catatacggt   1620
gaagtacaag ctgttgattc cgtgtgggtg tacggtaaca gctttgagtc cttcctaata   1680
gctatcgcca acccaaacca gcatatcctt gaacgctggg ctgcagaaaa cggtgtgagt   1740
ggtgactatg acgctctctg tcaaaatgaa aaggcaaagg aattcattct cggagaactt   1800
```

-continued

| | |
|---|---|
| gttaaaatgg ccaaagagaa aaagatgaaa gggttcgaga tcatcaaggc gattcatctt | 1860 |
| gacccagtgc catttgacat ggaacgagat cttcttacgc cgaccttcaa aaagaaaagg | 1920 |
| cctcagttgc tgaaatacta ccagagtgtg atcgacgaaa tgtacaagac cataaatgca | 1980 |
| aaatttgctt ccagagggta g | 2001 |

<210> SEQ ID NO 122
<211> LENGTH: 2001
<212> TYPE: DNA
<213> ORGANISM: Arabidopsis thaliana

<400> SEQUENCE: 122

| | |
|---|---|
| atgacgtcgc agaaaagatt catctttgag gtggaagccg ctaaggaagc cacagatgga | 60 |
| aatccctcgg ttggtcctgt ctatcgtagt acttttgctc agaacggatt cccgaacccg | 120 |
| atcgatggta tccaaagctg ctgggatatt ttccgcacgg ctgttgagaa gtatccaaac | 180 |
| aatcgaatgc ttggtcgccg tgagatttcg aacgggaagg caggaaagta cgtgtggaaa | 240 |
| acatacaaag aagtatacga cattgtcata aaacttggaa attctctacg tagttgcggg | 300 |
| attaaggagg gagaaaaatg tggtatatat ggtataaatt gttgtgagtg gatcattagc | 360 |
| atggaggcat gtaatgcaca tggcctttat tgtgtcccct tatacgatac gttaggcgct | 420 |
| ggtgcagtgg aattcatcat ttctcatgca gaggtttcaa ttgctttcgt ggaggagaag | 480 |
| aagatccctg agcttttttaa gacttgtcca aactcaacaa aatatatgaa gactgttgtg | 540 |
| agctttggcg gtgtcaaacc ggaacaaaaa gaagaagctg aaaaattggg attggtaata | 600 |
| cattcgtggg atgagttttt gaagctgggt gagggtaagc aatatgagct tcccattaaa | 660 |
| aagccaagcg acatatgcac gattatgtat actagcggaa caactggtga cccgaaggga | 720 |
| gttatgattt caaatgaaag cattgttact ataactactg gagtgatgca tttcctaggg | 780 |
| aatgtgaatg caagcctatc tgagaaggat gtgtatattt cttatcttcc tctcgcgcac | 840 |
| gtctttgatc gggcaatcga ggaatgtatt attcaagtag gtggttcaat tggtttctgg | 900 |
| cgcggggatg tcaaattgtt gattgaagac cttggtgagc taaaaccaag tatcttttgc | 960 |
| gccgttcctc gtgtcctaga tcgagtatac acaggactac agcagaaact atctggtggt | 1020 |
| ggtttcttca aaagaaggt gtttgatgtt gcttttttcct ataaatttgg aaatatgaag | 1080 |
| aaaggacagt ctcatgtggc agcttctcca ttttgtgaca aacttgtatt caacaaggtt | 1140 |
| aaacaaggac ttggaggcaa tgtgaggatt attctgtctg gagcggctcc tctcgctagt | 1200 |
| cacatagaat cttttctaag agttgttgca tgttgtaatg ttctacaagg atatggtcta | 1260 |
| actgagagtt gtgctggaac ttttgcaacg ttcccagacg aactagacat gcttgggact | 1320 |
| gttggtccac ccgtgccaaa cgtcgatata cgccttgaat ctgtcccgga atgaattat | 1380 |
| gatgctcttg gaagtactcc gcgaggcgaa atatgcatac gaggaaaaac tttatttttca | 1440 |
| gggtactaca acgtgaaga cctcacaaaa gaggttttta tcgacggatg gttgcacaca | 1500 |
| ggtgatgttg tgagtggca accaaatgga agcatgaaga taattgaccg gaaaagaac | 1560 |
| atcttcaaac tcgcgcaagg agagtatgtc gctgttgaga atttagaaaa tgtctacagt | 1620 |
| caagtagaag ttattgaatc gatatgggta tatggaaaca gctttgagtc cttccttgtc | 1680 |
| gcaatcgcta acccggccca acaaactctt gaacgatggg ctgtgagaa tggagtgaat | 1740 |
| ggagacttca actccatctg ccaaaacgca aaggcaaaag cattcatact tggagaactc | 1800 |
| gttaaaacag ccaaagagaa caagttgaag ggttttgaga tcataaaaga tgttcatctg | 1860 |

| | |
|---|---|
| gaaccagtgg cgttcgacat ggaacgagac cttcttactc caacctacaa aaagaagagg | 1920 |
| cctcaattgc tcaaatacta tcagaatgtg atccatgaaa tgtacaagac aacaaaggaa | 1980 |
| actctagctt ccggacagta a | 2001 |

<210> SEQ ID NO 123
<211> LENGTH: 1998
<212> TYPE: DNA
<213> ORGANISM: Arabidopsis thaliana

<400> SEQUENCE: 123

| | |
|---|---|
| atgtctttag ccgcggataa tgtgttgttg gtggaagaag gaaggccagc cacagcggaa | 60 |
| catccatcgg ccggaccggt ttatcgatgt aaatacgcta agatggcct cctcgatctc | 120 |
| cctaccgata ttgattctcc ttggcagttc tttagtgagg ctgtgaagaa atatccgaat | 180 |
| gagcaaatgt tgggccaacg cgtaacgact gattctaagg tcggtccata cacgtggatc | 240 |
| acatataagg aagcgcacga cgctgcaatt cggattggat cagcaatcag aagccgaggc | 300 |
| gttgatccgg gacactgttg tggtatttac ggagctaatt gtccagaatg gattattgca | 360 |
| atggaggcct gcatgagcca aggatcacc tacgtgcctc tatatgattc tttaggcgta | 420 |
| aacgcagttg aattcatcat caaccacgcc gaggtttcgc tagtatttgt tcaagagaag | 480 |
| acagtttcat ctatcttatc gtgccaaaag ggatgttctt cgaatttgaa gactattgtg | 540 |
| agcttcgggg aagtctcgag tacacaaaag gaagaagcta agaaccaatg tgtttcttta | 600 |
| ttttcatgga atgagttctc actaatggga aacttagatg aggcaaatct acctagaaag | 660 |
| cgaaagacag acatctgcac aataatgtac acaagcggga cgactggaga acccaaaggt | 720 |
| gtaatcttaa acaacgcagc aatttcggtc caggttttat ccatagacaa aatgcttgaa | 780 |
| gtcactgatc gatcgtgtga cacgagcgat gtgttcttct cgtacttgcc attagcacat | 840 |
| tgctatgatc aagtcatgga gatttacttt ttatctagag ctcctctgt tggatactgg | 900 |
| cgtggcgaca ttcggtacct gatggatgat gttcaagctc ttaaacctac tgtgttttgc | 960 |
| ggtgttccac gagtttacga caaactatat gccggtataa tgcaaaaaat atcagctagt | 1020 |
| ggcttgatac gcaagaaact gtttgatttt gcttataact acaaattggg aaatatgaga | 1080 |
| aaaggattct ctcaagaaga agcttctcct cgtctagaca gacttatgtt cgataagata | 1140 |
| aaagaagcat taggaggaag agctcatatg ttgttatcag gagcagcgcc tctacctcgt | 1200 |
| catgtagagg agttcttgag aatcattcct gcctctaatc tctctcaagg ttatggattg | 1260 |
| actgagagtt gtgggggaag cttcacgacc ttagccggaa tattttctat ggtggggaca | 1320 |
| gtgggtgtgc caatgcccac ggtggaggca aggctagtgt ccgtaccaga gatgggttac | 1380 |
| gacgcctttt ccgctgacgt gccgagagga gagatttgtc ttagaggaaa ttcaatgttt | 1440 |
| tctggttacc ataaaagaca agatctaact gatcaagtcc taatcgatgg atggttccac | 1500 |
| acaggagata ttggagaatg gcaagaagat ggatcaatga agatcatcga taggaagaag | 1560 |
| aacatcttca gttgtctca aggtgaatat gttgctgttg aaaacctcga aacacttac | 1620 |
| tcaagatgtc ccctcattgc tcagatatgg gtctatggca acagcttcga gtcatttttg | 1680 |
| gtaggtgtgg ttgtacctga tagaaaagct attgaagatt gggctaaact caattaccaa | 1740 |
| tctcccaatg atttcgaatc tctatgtcaa aatctcaaag ctcaaaaata cttcttggat | 1800 |
| gagcttaact ctaccgcaaa gcaatatcaa cttaaaggat tgaaatgtt aaaagctatt | 1860 |
| catttagaac caaaccctt tgatattgaa agagatctta ttactccaac tttcaagctg | 1920 |
| aaaaggccac agctcctcca acattacaag ggcatagttg atcaactta ttcagaagca | 1980 |

```
aagaggtcca tggcatag                                                    1998

<210> SEQ ID NO 124
<211> LENGTH: 2103
<212> TYPE: DNA
<213> ORGANISM: Arabidopsis thaliana

<400> SEQUENCE: 124
atggaatttg cttcgccgga caacgtcgt ctcgaaacca ttcgatctca catcgatact          60
tctccgacca acgatcaatc atcatctcta ttcctcaacg ccaccgcttc ttctgcttca        120
cctttcttta aagaggatag ctacagtgtt gtgcttccag aaaagcttga tactggaaaa        180
tggaatgtct acagatctaa aagatcgcct acgaaactcg ttagtaggtt cccggatcat        240
cctgaaatcg ggactttaca tgacaatttt gtacatgctg ttgaaacata tgctgaaaac        300
aagtatcttg gtacacgagt tcggtccgat ggaaccattg agagtattc atggatgaca         360 tatggagaag cagcgtctga gcgacaagcc attggttcag gactcttgtt tcatggagtt        420
aaccaaggag cttgcgttgg actctatttt attaacagac cagagtggtt ggttgtggat        480
catgcttgtg cagcatattc atttgtctct gttcctttat atgatacact tggtccagac        540
gctgttaagt ttgtggtgaa tcatgctaat ctgcaagcta tattttgtgt accacaaacc        600
ttgaatattt tgctaagctt cctagcggaa atcccatcca ttcgtctcat tgtggtggtg        660 ggagggctg atgagcattt gccatcactt cctcgaggaa ctggagtcac aattgtatca         720
taccaaaagc tattgagtca gggtcgaagt agcttacatc catttcgcc tccaaagcca        780 gaagacattg caaccatatg ctacacaagt ggaaccacag gaacaccaaa gggtgttgtg        840
ttgactcatg gaaacttgat cgcgaatgtc gctggttcca gtgtgaagc agaattcttt        900 ccttcagatg tktacatatc atatcttcct ttggcgcaca tatatgaacg tgcaaatcag        960
attatggggg tgtatggtgg tgttgctgtc ggtttctatc aggggatgt cttcaagctg       1020 atggatgatt tgctgtgtt aagaccaaca atattctgta gtgtccctcg cttatataat       1080
cgaatatatg atggcattac aagtgccgta aaatcatctg gggttgtgaa aaaaaggctt       1140
ttcgaaattg cctataactc aaagaagcaa gcgatcatta tgggcggac tccttctgca       1200 tttttgggaca agctggtgtt caacaaaata aagaaaagc ttggtggacg ggttcggttt       1260
atggggtctg gtgcttctcc tttgtcacct gatgtcatgg atttcttgag aatatgctt        1320 ggatgttcgg tgcgtgaagg gtatggtatg accgagactt cttgtgtcat aagtgctatg       1380
gatgatggtg acaatttatc tggccatgtc ggttcccta atccagcttg cgaggtaaaa       1440
cttgtggatt tccccgaaat gaattacaca tcagacgatc aaccataccc acgtggtgaa       1500
atctgtgtaa gaggaccaat catcttcaaa ggctactaca agatgaaga acaaacgaga       1560 gaaattcttg atggagatgg ctggctacac acaggagata tcgggttgtg gttacctggt      1620
ggtcggctca agatcataga caggaagaag aacatattta gttggcgca aggagaatat       1680 atagcaccag agaagatcga aaatgtttat accaaatgta gattcgtttc gcagtgtttc      1740
attcacggtg atagcttcaa ttcctctcta gtagctatag tttcagtcga ccccgaagtt       1800
atgaaagatt gggctgcatc agaaggcatc aagtatgagc atctaggaca gctctgtaac       1860
gatccaagag tgcgaaagac tgttcttgct gagatggatg accttggaag agaagctcag       1920
ttgagagggt ttgagtttgc aaaggctgtg actttggtgc cagaaccatt gaccttggag       1980
aatggacttc tcacaccaac attcaagata aagagacctc aagcaaaagc ctactttgca      2040
```

| gaagcaatta gcaaaatgta tgcggaaatc gcagcctcga accccattcc ttctaaactg | 2100 |
| tga | 2103 |

<210> SEQ ID NO 125
<211> LENGTH: 2130
<212> TYPE: DNA
<213> ORGANISM: Arabidopsis thaliana

<400> SEQUENCE: 125

| atggcttcga cttcttcttt gggaccttct acactactct cttacggttc tccttctcgt | 60 |
| cagtttcctg attttgggtt cagattgatt tcgggtcacg aaagtgttcg aattccatca | 120 |
| ttccggcgat ttcgggttca ctgcgagtca aggaaaaag aagtgaagcc gtcttctcca | 180 |
| tttcttgaaa gctcctcgtt ttcgggagat gccgctttgc gctctagtga atggaaggct | 240 |
| gttcctgata tttggagatc atctgcagaa agtatggtg atagagttgc attggtggat | 300 |
| ccttatcatg atcctccttt gaaactgacg tacaagcagt tggaacaaga attttggac | 360 |
| tttgctgagg gcttacgagt tcttggagtg aaagcagatg agaagattgc acttttgct | 420 |
| gataactcct gccgatggct tgtttcagat caaggtataa tggccacagg ggcagtcaat | 480 |
| gttgtcagag gatctaggtc tctgttgaa gagttactgc agatataccg tcattctgaa | 540 |
| agcgtagcca ttgttgtgga taatcctgag ttttttcaacc gcattgctga gtcatttacg | 600 |
| tcaaaggcat ctctgagatt tttgatactt ctctggggtg agaaatcatc actggtcaca | 660 |
| caggggatgc agattccagt ttacagttat gcagaaatta taaaccaagg acaggagagt | 720 |
| cgtgcaaaat tatcagcatc taatgatacc aggagctata gaaatcaatt catcgattca | 780 |
| gatgatacag ctgcaattat gtataccagt ggtaccacgg gaaatccaaa aggcgttatg | 840 |
| cttacacatc ggaatctctt acaccagata aaacatttat ccaaatatgt acctgctcta | 900 |
| gctggggata aatttctaag catgctacca tcatggcatg cctatgaacg tgctagtgaa | 960 |
| tacttcatat tcacttgtgg agttgagcaa atgtatacat ctataagata cttaaaggat | 1020 |
| gatctaaagc ggtaccaacc gaactatatt gtgtccgttc ctctagtata tgagacactt | 1080 |
| tacagtggga ttcaaaagca aatttctgca agttctgctg gccgtaaatt tctagcactt | 1140 |
| acattgatca aagtcagtat ggcatatatg gagatgaaaa ggatatatga gggtatgtgt | 1200 |
| ctgacaaaag agcaaaagcc tccaatgtat attgttgctt ttgtggattg gttgtgggcg | 1260 |
| agagtaattg ctgccttgtt gtggccatta catatgttgg ccaaaaagct tatctacaag | 1320 |
| aaaattcatt cgtctattgg gatatcgaag ctggtatta gcggaggtgg tagtttaccc | 1380 |
| attcatgttg acaagttttt tgaggccatc ggtgtgattc tacaaaatgg ttatggtttg | 1440 |
| acagagacct cacctgttgt ctgtgcacgg acacttagct gcaatgttct tggctcagct | 1500 |
| gggcatccaa tgcatggtac agaattcaaa attgtagatc ctgagactaa taatgtactc | 1560 |
| cctcctggtt caagggcat tatcaaagtc agaggtccac aggttatgaa gggttattat | 1620 |
| aagaatccat cgactacaaa gcaagttcta atgagagtg atggttcaa tacaggagac | 1680 |
| accggttgga ttgctcctca tcactcaaaa gggcggagtc gccactgtgc aggtgtcatt | 1740 |
| gttcttgaag gccgtgcaaa agacacaatt gtactttcca caggtgaaaa tgtggaaccg | 1800 |
| ttggagattg aagaagccgc catgagagc agggtgattg aacaaattgt tgttattgga | 1860 |
| caggaccgac gtcgccttgg agctatcatt atcccaaaca aagaggaagc acaaagagta | 1920 |
| gatcctgaaa catccaaaga aacactaaag agcttggtct accaagaact gagaaaatgg | 1980 |
| acatcagaat gttcgtttca agtcggacca gtcttgatcg tcgacgaccc tttcacgata | 2040 |

| | |
|---|---:|
| gacaacgggt taatgacacc aactatgaag attagacggg acatggtcgt ggctaaatac | 2100 |
| aaagaggaga ttgatcaact ctacagttaa | 2130 |

<210> SEQ ID NO 126
<211> LENGTH: 2163
<212> TYPE: DNA
<213> ORGANISM: Arabidopsis thaliana

<400> SEQUENCE: 126

| | |
|---|---:|
| atggaagatt ctggagtgaa tccaatggat tcaccatcta aaggcagtga ctttggagtc | 60 |
| tatggaatca taggaggtgg aatcgtggct ttacttgtgc ctgtgttact ctctgtggtg | 120 |
| ttgaatggaa ccaaaaaggg gaaaagaga ggtgttccca tcaaagtagg tggcgaggaa | 180 |
| ggttacacaa tgcgtcatgc tcgagctcct gaattggttg atgtaccttg ggaaggagct | 240 |
| gctactatgc ctgctttgtt tgagcagtct tgtaagaagt attcgaaaga tcggttacta | 300 |
| ggaactagag agtttataga taaggaattt attactgcta gtgatgggag gaagtttgag | 360 |
| aagcttcatt taggagagta taatggcaa agttatggag aggtttttga acgtgtttgt | 420 |
| aactttgcgt cggggttagt taatgtagga cataatgttg atgatcgtgt tgctatcttt | 480 |
| tcggatactc gtgctgagtg gtttatcgcg tttcagggat gtttcaggca gagcataacc | 540 |
| gttgttacta tttatgcttc tttaggagaa gaggctttga tttactcact caatgagact | 600 |
| cgagtgtcaa ccttaatatg tgactcaaaa caacttaaga agttgtctgc gatacaatca | 660 |
| agcttgaaaa ctgtgaagaa cattatttac attgaagaag atggagtaga tgttgcttct | 720 |
| agtgatgtca atagtatggg tgatataact gtttcgtcga tctctgaagt tgagaaactt | 780 |
| gggcagaaga acgctgttca accgatctta ccttcgaaga atggagttgc tgttataatg | 840 |
| tttaccagtg gtagtactgg tctaccaaag ggagttatga ttacccacgg aaatcttgtc | 900 |
| gcaactgctg caggagttat gaaggtggtt ccaaagttgg ataaaaatga tacatatatt | 960 |
| gcgtacttac ctttggctca tgtgtttgag ctggaagctg agattgtggt ctttacctca | 1020 |
| ggtagtgcca tcggttacgg ctcagcaatg actttaactg acacttcaaa taagttaag | 1080 |
| aaaggaacca aaggagatgt ttcagctctg aagccaacta atgactgca gttccagct | 1140 |
| attctggatc gtgtccgaga aggagttctt aaaaaggttg aggaaaaggg agggatggcg | 1200 |
| aagaccctt tgactttgc atacaagcgc cggttagcag ctgtggatgg aagttggttt | 1260 |
| ggtgcctggg gtttggagaa aatgttatgg gatgctcttg tcttcaagaa atacgcgct | 1320 |
| gtgcttggag gacacatccg ttttatgctc gttggaggag ctcctctgtc tcctgattcg | 1380 |
| caacgcttca tcaatatctg catggggtct cccatcggcc aaggatatgg attgactgaa | 1440 |
| acgtgtgctg gagctacgtt ttctgagtgg gacgatcctg ctgttggtcg tgttggaccct | 1500 |
| ccacttccat gcggctacgt taagctcgtt tcttgggaag aaggtggcta cagaatttca | 1560 |
| gataaaccaa tgcctagagg ggagattgtg gtaggtggta acagtgtaac agcaggttac | 1620 |
| ttcaacaatc aagaaaaaac cgatgaggtt tacaaggtcg atgagaaggg cacaaggtgg | 1680 |
| ttttacaccg gagatattgg gagattccac cctgatggat gtctcgaagt catcgataga | 1740 |
| aagaaagata ttgttaaact tcaacatggg gaatacgtat cccttggaaa ggtggaggca | 1800 |
| gctttgggtt cgagcaatta cgttgataac atcatggtcc acgcagaccc aattaacagc | 1860 |
| tactgtgtag ctcttgttgt tccatcacga ggagcattag agaaatgggc agaggaagct | 1920 |
| ggagttaaac acagcgaatt cgctgagcta tgcgagaaag tgaagcagt caaggaggtt | 1980 |

-continued

| | |
|---|---|
| caacaatctc ttaccaaggc cgggaaggcg gcaaagctcg aaaagtttga gcttccagca | 2040 |
| aagatcaagt tgctgtcaga gccgtggaca ccggagtcgg gattggtcac tgctgctctt | 2100 |
| aagataaaga gagaacaaat aaagtccaag ttcaaagatg aactcagcaa gttatatgcc | 2160 |
| taa | 2163 |

<210> SEQ ID NO 127
<211> LENGTH: 2076
<212> TYPE: DNA
<213> ORGANISM: Arabidopsis thaliana

<400> SEQUENCE: 127

| | |
|---|---|
| atgattcctt atgctgctgg tgttattgtg ccattggctt tgacgtttct ggttcagaaa | 60 |
| tctaagaaag aaaagaaaag aggtgttgtt gttgatgttg tggtgaacc aggttatgct | 120 |
| attaggaatc acaggtttac tgagcctgtt agttcccatt ggaacatat ctcaacgctt | 180 |
| ccagagctct ttgagatatc gtgtaatgct cacagtgata gggttttcct ggcacccga | 240 |
| aagctgatct ctagagagat tgagactagt gaggatggaa aaacgttcga gaaactgcat | 300 |
| ttaggtgact acgagtggct cacttttggg aagactctcg aagcagtgtg tgattttgcc | 360 |
| tctgggttag ttcagattgg gcacaagacg gaagagcgtg tcgccatttt tgcagatact | 420 |
| agagaagaat ggttcatctc cctacagggt tgcttcaggc gcaacgtcac tgtggtaact | 480 |
| atctattcat ctttgggaga ggaagctctt tgtcactcgc tgaatgagac agaggtcaca | 540 |
| accgtaatat gtggtagcaa agaactcaaa aagctcatgg acataagcca acagcttgaa | 600 |
| actgtgaaac gtgtgatatg catggatgat gaattcccat ctgatgtgaa cagtaattgg | 660 |
| atggcgactt catttactga tgttcagaaa cttggccgcg aaaatcctgt ggatcctaat | 720 |
| ttccctctct cagcagatgt tgctgttata atgtacacca gtggaagcac tggacttccc | 780 |
| aagggtgtta tgatgacgca tggtaatgtc ctagctacag tttcggcagt gatgacaatt | 840 |
| gttcctgacc ttggaaagag ggatatatac atggcatatt tacctttggc tcacatcctt | 900 |
| gagttagcag ctgagagcgt aatggcatact attgggagtg ctattggata tgggtctccc | 960 |
| ttgacgctaa cggatacttc aaacaagata aaaaagggta caaaggaga tgtcacagca | 1020 |
| ctaaagccca ctataatgac agctgttcca gccattcttg atcgtgtcag ggatggtgtc | 1080 |
| cgcaaaaagg ttgatgcaaa gggcggattg tcaaagaaat tgtttgactt tgcatatgct | 1140 |
| cggcgattat ctgcaatcaa tggaagttgg tttggagcct ggggattgga aaagcttttg | 1200 |
| tgggatgtgc ttgtgttcag gaaaatccgt gcagttttgg gaggtcaaat ccgctatttg | 1260 |
| ctctctggtg gtgcccctct ttctggtgac actcagagat tcattaacat ctgcgttggg | 1320 |
| gctccaatcg gtcagggata tgggctcaca gagacttgtg ctggtggaac cttctcggag | 1380 |
| tttgaggaca catccgttgg ccgtgttggt gctccacttc cttgctcctt tgtaaagcta | 1440 |
| gtagactggg cggaaggtgg gtatctaact agtgataagc cgatgccccg tggtgaaatt | 1500 |
| gtaattggtg gctcaaatat cacgcttggg tatttcaaaa atgaggagaa aactaaagaa | 1560 |
| gtgtacaagg ttgatgaaaa gggaatgagg tggttctaca caggagacat aggacgattt | 1620 |
| caccctgatg gctgcctcga gataatagac cgaaaaaagg atatcgttaa acttcagcat | 1680 |
| ggagaatatg tctccttggg caaagttgaa gctgctctaa gtataagtcc ctatgttgaa | 1740 |
| aacataatgg ttcatgctga ttcgttctac agttactgtg tggctcttgt ggtcgcgtcc | 1800 |
| caacatacag ttgaaggttg ggcttcaaag caaggaatag actttgccaa cttcgaagaa | 1860 |
| ctgtgcacga aagagcaagc cgtgaaagaa gtgtatgcgt cccttgtgaa ggcggctaaa | 1920 |

-continued

```
caatcacgat tggagaagtt tgagatacca gcaaagatca aattattggc atctccatgg      1980
acgccagagt caggattagt cacagcagct ctaaagctga aaagagatgt aattaggagg      2040
gaattctctg aagatctcac caagttatat gcctaa                                2076
```

<210> SEQ ID NO 128
<211> LENGTH: 666
<212> TYPE: PRT
<213> ORGANISM: Arabidopsis thaliana

<400> SEQUENCE: 128

```
Met Ser Gln Gln Lys Lys Tyr Ile Phe Gln Val Glu Glu Gly Lys Glu
1               5                   10                  15

Gly Ser Asp Gly Arg Pro Ser Val Gly Pro Val Tyr Arg Ser Ile Phe
            20                  25                  30

Ala Lys Asp Gly Phe Pro Asp Pro Ile Glu Gly Met Asp Ser Cys Trp
        35                  40                  45

Asp Val Phe Arg Met Ser Val Glu Lys Tyr Pro Asn Asn Pro Met Leu
    50                  55                  60

Gly Arg Arg Glu Ile Val Asp Gly Lys Pro Gly Lys Tyr Val Trp Gln
65                  70                  75                  80

Thr Tyr Gln Glu Val Tyr Asp Ile Val Met Lys Leu Gly Asn Ser Leu
                85                  90                  95

Arg Ser Val Gly Val Lys Asp Glu Ala Lys Cys Gly Ile Tyr Gly Ala
            100                 105                 110

Asn Ser Pro Glu Trp Ile Ile Ser Met Glu Ala Cys Asn Ala His Gly
        115                 120                 125

Leu Tyr Cys Val Pro Leu Tyr Asp Thr Leu Gly Ala Asp Ala Val Glu
    130                 135                 140

Phe Ile Ile Ser His Ser Glu Val Ser Ile Val Phe Val Glu Glu Lys
145                 150                 155                 160

Lys Ile Ser Glu Leu Phe Lys Thr Cys Pro Asn Ser Thr Glu Tyr Met
                165                 170                 175

Lys Thr Val Val Ser Phe Gly Gly Val Ser Arg Glu Gln Lys Glu Glu
            180                 185                 190

Ala Glu Thr Phe Gly Leu Val Ile Tyr Ala Trp Asp Glu Phe Leu Lys
        195                 200                 205

Leu Gly Glu Gly Lys Gln Tyr Asp Leu Pro Ile Lys Lys Ser Asp
    210                 215                 220

Ile Cys Thr Ile Met Tyr Thr Ser Gly Thr Thr Gly Asp Pro Lys Gly
225                 230                 235                 240

Val Met Ile Ser Asn Glu Ser Ile Val Thr Leu Ile Ala Gly Val Ile
                245                 250                 255

Arg Leu Leu Lys Ser Ala Asn Glu Ala Leu Thr Val Lys Asp Val Tyr
            260                 265                 270

Leu Ser Tyr Leu Pro Leu Ala His Ile Phe Asp Arg Val Ile Glu Glu
        275                 280                 285

Cys Phe Ile Gln His Gly Ala Ala Ile Gly Phe Trp Arg Gly Asp Val
    290                 295                 300

Lys Leu Leu Ile Glu Asp Leu Ala Glu Leu Lys Pro Thr Ile Phe Cys
305                 310                 315                 320

Ala Val Pro Arg Val Leu Asp Arg Val Tyr Ser Gly Leu Gln Lys Lys
                325                 330                 335

Leu Ser Asp Gly Gly Phe Leu Lys Lys Phe Ile Phe Asp Ser Ala Phe
```

```
                    340                 345                 350
Ser Tyr Lys Phe Gly Tyr Met Lys Lys Gly Gln Ser His Val Glu Ala
            355                 360                 365

Ser Pro Leu Phe Asp Lys Leu Val Phe Ser Lys Val Lys Gln Gly Leu
        370                 375                 380

Gly Gly Asn Val Arg Ile Ile Leu Ser Gly Ala Ala Pro Leu Ala Ser
385                 390                 395                 400

His Val Glu Ser Phe Leu Arg Val Val Ala Cys Cys His Val Leu Gln
                405                 410                 415

Gly Tyr Gly Leu Thr Glu Ser Cys Ala Gly Thr Phe Val Ser Leu Pro
            420                 425                 430

Asp Glu Leu Gly Met Leu Gly Thr Val Gly Pro Pro Val Pro Asn Val
        435                 440                 445

Asp Ile Arg Leu Glu Ser Val Pro Glu Met Glu Tyr Asp Ala Leu Ala
    450                 455                 460

Ser Thr Ala Arg Gly Glu Ile Cys Ile Arg Gly Lys Thr Leu Phe Ser
465                 470                 475                 480

Gly Tyr Tyr Lys Arg Glu Asp Leu Thr Lys Glu Val Leu Ile Asp Gly
                485                 490                 495

Trp Leu His Thr Gly Asp Val Gly Glu Trp Gln Pro Asp Gly Ser Met
            500                 505                 510

Lys Ile Ile Asp Arg Lys Lys Asn Ile Phe Lys Leu Ser Gln Gly Glu
        515                 520                 525

Tyr Val Ala Val Glu Asn Ile Glu Asn Ile Tyr Gly Glu Val Gln Ala
    530                 535                 540

Val Asp Ser Val Trp Val Tyr Gly Asn Ser Phe Glu Ser Phe Leu Ile
545                 550                 555                 560

Ala Ile Ala Asn Pro Asn Gln His Ile Leu Glu Arg Trp Ala Ala Glu
                565                 570                 575

Asn Gly Val Ser Gly Asp Tyr Asp Ala Leu Cys Gln Asn Glu Lys Ala
            580                 585                 590

Lys Glu Phe Ile Leu Gly Glu Leu Val Lys Met Ala Lys Glu Lys Lys
        595                 600                 605

Met Lys Gly Phe Glu Ile Ile Lys Ala Ile His Leu Asp Pro Val Pro
    610                 615                 620

Phe Asp Met Glu Arg Asp Leu Leu Thr Pro Thr Phe Lys Lys Lys Arg
625                 630                 635                 640

Pro Gln Leu Leu Lys Tyr Tyr Gln Ser Val Ile Asp Glu Met Tyr Lys
                645                 650                 655

Thr Ile Asn Ala Lys Phe Ala Ser Arg Gly
            660                 665

<210> SEQ ID NO 129
<211> LENGTH: 666
<212> TYPE: PRT
<213> ORGANISM: Arabidopsis thaliana

<400> SEQUENCE: 129

Met Thr Ser Gln Lys Arg Phe Ile Phe Glu Val Glu Ala Ala Lys Glu
1               5                  10                  15

Ala Thr Asp Gly Asn Pro Ser Val Gly Pro Val Tyr Arg Ser Thr Phe
            20                  25                  30

Ala Gln Asn Gly Phe Pro Asn Pro Ile Asp Gly Ile Gln Ser Cys Trp
        35                  40                  45
```

-continued

```
Asp Ile Phe Arg Thr Ala Val Glu Lys Tyr Pro Asn Asn Arg Met Leu
         50                  55                  60
Gly Arg Arg Glu Ile Ser Asn Gly Lys Ala Gly Lys Tyr Val Trp Lys
 65                  70                  75                  80
Thr Tyr Lys Glu Val Tyr Asp Ile Val Ile Lys Leu Gly Asn Ser Leu
                 85                  90                  95
Arg Ser Cys Gly Ile Lys Glu Gly Lys Cys Gly Ile Tyr Gly Ile
                100                 105                 110
Asn Cys Cys Glu Trp Ile Ile Ser Met Glu Ala Cys Asn Ala His Gly
                115                 120                 125
Leu Tyr Cys Val Pro Leu Tyr Asp Thr Leu Gly Ala Gly Ala Val Glu
    130                 135                 140
Phe Ile Ile Ser His Ala Glu Val Ser Ile Ala Phe Val Glu Glu Lys
145                 150                 155                 160
Lys Ile Pro Glu Leu Phe Lys Thr Cys Pro Asn Ser Thr Lys Tyr Met
                165                 170                 175
Lys Thr Val Val Ser Phe Gly Val Lys Pro Glu Gln Lys Glu Glu
                180                 185                 190
Ala Glu Lys Leu Gly Leu Val Ile His Ser Trp Asp Glu Phe Leu Lys
                195                 200                 205
Leu Gly Glu Gly Lys Gln Tyr Glu Leu Pro Ile Lys Lys Pro Ser Asp
    210                 215                 220
Ile Cys Thr Ile Met Tyr Thr Ser Gly Thr Thr Gly Asp Pro Lys Gly
225                 230                 235                 240
Val Met Ile Ser Asn Glu Ser Ile Val Thr Ile Thr Thr Gly Val Met
                245                 250                 255
His Phe Leu Gly Asn Val Asn Ala Ser Leu Ser Glu Lys Asp Val Tyr
                260                 265                 270
Ile Ser Tyr Leu Pro Leu Ala His Val Phe Asp Arg Ala Ile Glu Glu
                275                 280                 285
Cys Ile Ile Gln Val Gly Gly Ser Ile Gly Phe Trp Arg Gly Asp Val
    290                 295                 300
Lys Leu Leu Ile Glu Asp Leu Gly Glu Leu Lys Pro Ser Ile Phe Cys
305                 310                 315                 320
Ala Val Pro Arg Val Leu Asp Arg Val Tyr Thr Gly Leu Gln Gln Lys
                325                 330                 335
Leu Ser Gly Gly Gly Phe Phe Lys Lys Lys Val Phe Asp Val Ala Phe
                340                 345                 350
Ser Tyr Lys Phe Gly Asn Met Lys Lys Gly Gln Ser His Val Ala Ala
    355                 360                 365
Ser Pro Phe Cys Asp Lys Leu Val Phe Asn Lys Val Lys Gln Gly Leu
    370                 375                 380
Gly Gly Asn Val Arg Ile Ile Leu Ser Gly Ala Ala Pro Leu Ala Ser
385                 390                 395                 400
His Ile Glu Ser Phe Leu Arg Val Val Ala Cys Cys Asn Val Leu Gln
                405                 410                 415
Gly Tyr Gly Leu Thr Glu Ser Cys Ala Gly Thr Phe Ala Thr Phe Pro
                420                 425                 430
Asp Glu Leu Asp Met Leu Gly Thr Val Gly Pro Val Pro Asn Val
                435                 440                 445
Asp Ile Arg Leu Glu Ser Val Pro Glu Met Asn Tyr Asp Ala Leu Gly
    450                 455                 460
Ser Thr Pro Arg Gly Glu Ile Cys Ile Arg Gly Lys Thr Leu Phe Ser
```

```
                465                 470                 475                 480
Gly Tyr Tyr Lys Arg Glu Asp Leu Thr Lys Glu Val Phe Ile Asp Gly
                    485                 490                 495
Trp Leu His Thr Gly Asp Val Gly Glu Trp Gln Pro Asn Gly Ser Met
                500                 505                 510
Lys Ile Ile Asp Arg Lys Lys Asn Ile Phe Lys Leu Ala Gln Gly Glu
                515                 520                 525
Tyr Val Ala Val Glu Asn Leu Glu Asn Val Tyr Ser Gln Val Glu Val
                530                 535                 540
Ile Glu Ser Ile Trp Val Tyr Gly Asn Ser Phe Glu Ser Phe Leu Val
545                 550                 555                 560
Ala Ile Ala Asn Pro Ala Gln Gln Thr Leu Glu Arg Trp Ala Val Glu
                565                 570                 575
Asn Gly Val Asn Gly Asp Phe Asn Ser Ile Cys Gln Asn Ala Lys Ala
                580                 585                 590
Lys Ala Phe Ile Leu Gly Glu Leu Val Lys Thr Ala Lys Glu Asn Lys
                595                 600                 605
Leu Lys Gly Phe Glu Ile Ile Lys Asp Val His Leu Glu Pro Val Ala
                610                 615                 620
Phe Asp Met Glu Arg Asp Leu Leu Thr Pro Thr Tyr Lys Lys Arg
625                 630                 635                 640
Pro Gln Leu Leu Lys Tyr Tyr Gln Asn Val Ile His Glu Met Tyr Lys
                645                 650                 655
Thr Thr Lys Glu Thr Leu Ala Ser Gly Gln
                660                 665

<210> SEQ ID NO 130
<211> LENGTH: 700
<212> TYPE: PRT
<213> ORGANISM: Arabidopsis thaliana

<400> SEQUENCE: 130

Met Glu Phe Ala Ser Pro Glu Gln Arg Arg Leu Glu Thr Ile Arg Ser
1               5                   10                  15

His Ile Asp Thr Ser Pro Thr Asn Asp Gln Ser Ser Ser Leu Phe Leu
                20                  25                  30

Asn Ala Thr Ala Ser Ser Ala Ser Pro Phe Phe Lys Glu Asp Ser Tyr
                35                  40                  45

Ser Val Val Leu Pro Glu Lys Leu Asp Thr Gly Lys Trp Asn Val Tyr
                50                  55                  60

Arg Ser Lys Arg Ser Pro Thr Lys Leu Val Ser Arg Phe Pro Asp His
65                  70                  75                  80

Pro Glu Ile Gly Thr Leu His Asp Asn Phe Val His Ala Val Glu Thr
                85                  90                  95

Tyr Ala Glu Asn Lys Tyr Leu Gly Thr Arg Val Arg Ser Asp Gly Thr
                100                 105                 110

Ile Gly Glu Tyr Ser Trp Met Thr Tyr Gly Glu Ala Ala Ser Glu Arg
                115                 120                 125

Gln Ala Ile Gly Ser Gly Leu Leu Phe His Gly Val Asn Gln Gly Asp
                130                 135                 140

Cys Val Gly Leu Tyr Phe Ile Asn Arg Pro Glu Trp Leu Val Val Asp
145                 150                 155                 160

His Ala Cys Ala Ala Tyr Ser Phe Val Ser Val Pro Leu Tyr Asp Thr
                165                 170                 175
```

-continued

```
Leu Gly Pro Asp Ala Val Lys Phe Val Val Asn His Ala Asn Leu Gln
            180                 185                 190
Ala Ile Phe Cys Val Pro Gln Thr Leu Asn Ile Leu Leu Ser Phe Leu
        195                 200                 205
Ala Glu Ile Pro Ser Ile Arg Leu Ile Val Val Gly Gly Ala Asp
    210                 215                 220
Glu His Leu Pro Ser Leu Pro Arg Gly Thr Gly Val Thr Ile Val Ser
225                 230                 235                 240
Tyr Gln Lys Leu Leu Ser Gln Gly Arg Ser Ser Leu His Pro Phe Ser
                245                 250                 255
Pro Pro Lys Pro Glu Asp Ile Ala Thr Ile Cys Tyr Thr Ser Gly Thr
            260                 265                 270
Thr Gly Thr Pro Lys Gly Val Val Leu Thr His Gly Asn Leu Ile Ala
        275                 280                 285
Asn Val Ala Gly Ser Ser Val Glu Ala Glu Phe Phe Pro Ser Asp Val
    290                 295                 300
Tyr Ile Ser Tyr Leu Pro Leu Ala His Ile Tyr Glu Arg Ala Asn Gln
305                 310                 315                 320
Ile Met Gly Val Tyr Gly Gly Val Ala Val Gly Phe Tyr Gln Gly Asp
                325                 330                 335
Val Phe Lys Leu Met Asp Asp Phe Ala Val Leu Arg Pro Thr Ile Phe
            340                 345                 350
Cys Ser Val Pro Arg Leu Tyr Asn Arg Ile Tyr Asp Gly Ile Thr Ser
        355                 360                 365
Ala Val Lys Ser Ser Gly Val Val Lys Lys Arg Leu Phe Glu Ile Ala
    370                 375                 380
Tyr Asn Ser Lys Lys Gln Ala Ile Ile Asn Gly Arg Thr Pro Ser Ala
385                 390                 395                 400
Phe Trp Asp Lys Leu Val Phe Asn Lys Ile Lys Glu Lys Leu Gly Gly
                405                 410                 415
Arg Val Arg Phe Met Gly Ser Gly Ala Ser Pro Leu Ser Pro Asp Val
            420                 425                 430
Met Asp Phe Leu Arg Ile Cys Phe Gly Cys Ser Val Arg Glu Gly Tyr
        435                 440                 445
Gly Met Thr Glu Thr Ser Cys Val Ile Ser Ala Met Asp Asp Gly Asp
    450                 455                 460
Asn Leu Ser Gly His Val Gly Ser Pro Asn Pro Ala Cys Glu Val Lys
465                 470                 475                 480
Leu Val Asp Val Pro Glu Met Asn Tyr Thr Ser Asp Asp Gln Pro Tyr
                485                 490                 495
Pro Arg Gly Glu Ile Cys Val Arg Gly Pro Ile Ile Phe Lys Gly Tyr
            500                 505                 510
Tyr Lys Asp Glu Glu Gln Thr Arg Glu Ile Leu Asp Gly Asp Gly Trp
        515                 520                 525
Leu His Thr Gly Asp Ile Gly Leu Trp Leu Pro Gly Gly Arg Leu Lys
    530                 535                 540
Ile Ile Asp Arg Lys Lys Asn Ile Phe Lys Leu Ala Gln Gly Glu Tyr
545                 550                 555                 560
Ile Ala Pro Glu Lys Ile Glu Asn Val Tyr Thr Lys Cys Arg Phe Val
                565                 570                 575
Ser Gln Cys Phe Ile His Gly Asp Ser Phe Asn Ser Ser Leu Val Ala
            580                 585                 590
Ile Val Ser Val Asp Pro Glu Val Met Lys Asp Trp Ala Ala Ser Glu
```

```
                595               600                605
Gly Ile Lys Tyr Glu His Leu Gly Gln Leu Cys Asn Asp Pro Arg Val
        610                 615                 620

Arg Lys Thr Val Leu Ala Glu Met Asp Asp Leu Gly Arg Glu Ala Gln
625                 630                 635                 640

Leu Arg Gly Phe Glu Phe Ala Lys Ala Val Thr Leu Val Pro Glu Pro
                645                 650                 655

Phe Thr Leu Glu Asn Gly Leu Leu Thr Pro Thr Phe Lys Ile Lys Arg
                660                 665                 670

Pro Gln Ala Lys Ala Tyr Phe Ala Glu Ala Ile Ser Lys Met Tyr Ala
            675                 680                 685

Glu Ile Ala Ala Ser Asn Pro Ile Pro Ser Lys Leu
690                 695                 700

<210> SEQ ID NO 131
<211> LENGTH: 709
<212> TYPE: PRT
<213> ORGANISM: Arabidopsis thaliana

<400> SEQUENCE: 131

Met Ala Ser Thr Ser Ser Leu Gly Pro Ser Thr Leu Ser Tyr Gly
1               5                   10                  15

Ser Pro Ser Arg Gln Phe Pro Asp Phe Gly Phe Arg Leu Ile Ser Gly
                20                  25                  30

His Glu Ser Val Arg Ile Pro Ser Phe Arg Arg Phe Arg Val His Cys
            35                  40                  45

Glu Ser Lys Glu Lys Glu Val Lys Pro Ser Ser Pro Phe Leu Glu Ser
        50                  55                  60

Ser Ser Phe Ser Gly Asp Ala Ala Leu Arg Ser Ser Glu Trp Lys Ala
65                  70                  75                  80

Val Pro Asp Ile Trp Arg Ser Ala Glu Lys Tyr Gly Asp Arg Val
                85                  90                  95

Ala Leu Val Asp Pro Tyr His Asp Pro Pro Leu Lys Leu Thr Tyr Lys
                100                 105                 110

Gln Leu Glu Gln Glu Ile Leu Asp Phe Ala Glu Gly Leu Arg Val Leu
        115                 120                 125

Gly Val Lys Ala Asp Glu Lys Ile Ala Leu Phe Ala Asp Asn Ser Cys
130                 135                 140

Arg Trp Leu Val Ser Asp Gln Gly Ile Met Ala Thr Gly Ala Val Asn
145                 150                 155                 160

Val Val Arg Gly Ser Arg Ser Ser Val Glu Glu Leu Leu Gln Ile Tyr
                165                 170                 175

Arg His Ser Glu Ser Val Ala Ile Val Val Asp Asn Pro Glu Phe Phe
            180                 185                 190

Asn Arg Ile Ala Glu Ser Phe Thr Ser Lys Ala Ser Leu Arg Phe Leu
        195                 200                 205

Ile Leu Leu Trp Gly Glu Lys Ser Ser Leu Val Thr Gln Gly Met Gln
    210                 215                 220

Ile Pro Val Tyr Ser Tyr Ala Glu Ile Ile Asn Gln Gly Gln Glu Ser
225                 230                 235                 240

Arg Ala Lys Leu Ser Ala Ser Asn Asp Thr Arg Ser Tyr Arg Asn Gln
                245                 250                 255

Phe Ile Asp Ser Asp Asp Thr Ala Ala Ile Met Tyr Thr Ser Gly Thr
                260                 265                 270
```

-continued

```
Thr Gly Asn Pro Lys Gly Val Met Leu Thr His Arg Asn Leu Leu His
        275                 280                 285
Gln Ile Lys His Leu Ser Lys Tyr Val Pro Ala Leu Ala Gly Asp Lys
    290                 295                 300
Phe Leu Ser Met Leu Pro Ser Trp His Ala Tyr Glu Arg Ala Ser Glu
305                 310                 315                 320
Tyr Phe Ile Phe Thr Cys Gly Val Gln Met Tyr Thr Ser Ile Arg
                325                 330                 335
Tyr Leu Lys Asp Asp Leu Lys Arg Tyr Gln Pro Asn Tyr Ile Val Ser
                340                 345                 350
Val Pro Leu Val Tyr Glu Thr Leu Tyr Ser Gly Ile Gln Lys Gln Ile
            355                 360                 365
Ser Ala Ser Ser Ala Gly Arg Lys Phe Leu Ala Leu Thr Leu Ile Lys
    370                 375                 380
Val Ser Met Ala Tyr Met Glu Met Lys Arg Ile Tyr Glu Gly Met Cys
385                 390                 395                 400
Leu Thr Lys Glu Gln Lys Pro Pro Met Tyr Ile Val Ala Phe Val Asp
                405                 410                 415
Trp Leu Trp Ala Arg Val Ile Ala Ala Leu Leu Trp Pro Leu His Met
                420                 425                 430
Leu Ala Lys Lys Leu Ile Tyr Lys Lys Ile His Ser Ser Ile Gly Ile
            435                 440                 445
Ser Lys Ala Gly Ile Ser Gly Gly Ser Leu Pro Ile His Val Asp
    450                 455                 460
Lys Phe Phe Glu Ala Ile Gly Val Ile Leu Gln Asn Gly Tyr Gly Leu
465                 470                 475                 480
Thr Glu Thr Ser Pro Val Val Cys Ala Arg Thr Leu Ser Cys Asn Val
                485                 490                 495
Leu Gly Ser Ala Gly His Pro Met His Gly Thr Glu Phe Lys Ile Val
            500                 505                 510
Asp Pro Glu Thr Asn Asn Val Leu Pro Pro Gly Ser Lys Gly Ile Ile
            515                 520                 525
Lys Val Arg Gly Pro Gln Val Met Lys Gly Tyr Tyr Lys Asn Pro Ser
530                 535                 540
Thr Thr Lys Gln Val Leu Asn Glu Ser Gly Trp Phe Asn Thr Gly Asp
545                 550                 555                 560
Thr Gly Trp Ile Ala Pro His His Ser Lys Gly Arg Ser Arg His Cys
                565                 570                 575
Ala Gly Val Ile Val Leu Glu Gly Arg Ala Lys Asp Thr Ile Val Leu
            580                 585                 590
Ser Thr Gly Glu Asn Val Glu Pro Leu Glu Ile Glu Glu Ala Ala Met
        595                 600                 605
Arg Ser Arg Val Ile Glu Gln Ile Val Val Ile Gly Gln Asp Arg Arg
    610                 615                 620
Arg Leu Gly Ala Ile Ile Pro Asn Lys Glu Glu Ala Gln Arg Val
625                 630                 635                 640
Asp Pro Glu Thr Ser Lys Glu Thr Leu Lys Ser Leu Val Tyr Gln Glu
                645                 650                 655
Leu Arg Lys Trp Thr Ser Glu Cys Ser Phe Gln Val Gly Pro Val Leu
            660                 665                 670
Ile Val Asp Asp Pro Phe Thr Ile Asp Asn Gly Leu Met Thr Pro Thr
            675                 680                 685
Met Lys Ile Arg Arg Asp Met Val Val Ala Lys Tyr Lys Glu Glu Ile
```

-continued

```
              690                 695                 700

Asp Gln Leu Tyr Ser
705

<210> SEQ ID NO 132
<211> LENGTH: 691
<212> TYPE: PRT
<213> ORGANISM: Arabidopsis thaliana

<400> SEQUENCE: 132

Met Ile Pro Tyr Ala Ala Gly Val Ile Val Pro Leu Ala Leu Thr Phe
  1               5                  10                  15

Leu Val Gln Lys Ser Lys Glu Lys Lys Arg Gly Val Val Val Asp
                 20                  25                  30

Val Gly Gly Glu Pro Gly Tyr Ala Ile Arg Asn His Arg Phe Thr Glu
             35                  40                  45

Pro Val Ser Ser His Trp Glu His Ile Ser Thr Leu Pro Glu Leu Phe
         50                  55                  60

Glu Ile Ser Cys Asn Ala His Ser Asp Arg Val Phe Leu Gly Thr Arg
 65                  70                  75                  80

Lys Leu Ile Ser Arg Glu Ile Glu Thr Ser Glu Asp Gly Lys Thr Phe
                 85                  90                  95

Glu Lys Leu His Leu Gly Asp Tyr Glu Trp Leu Thr Phe Gly Lys Thr
            100                 105                 110

Leu Glu Ala Val Cys Asp Phe Ala Ser Gly Leu Val Gln Ile Gly His
            115                 120                 125

Lys Thr Glu Glu Arg Val Ala Ile Phe Ala Asp Thr Arg Glu Glu Trp
130                 135                 140

Phe Ile Ser Leu Gln Gly Cys Phe Arg Arg Asn Val Thr Val Val Thr
145                 150                 155                 160

Ile Tyr Ser Ser Leu Gly Glu Glu Ala Leu Cys His Ser Leu Asn Glu
                165                 170                 175

Thr Glu Val Thr Thr Val Ile Cys Gly Ser Lys Glu Leu Lys Lys Leu
            180                 185                 190

Met Asp Ile Ser Gln Gln Leu Glu Thr Val Lys Arg Val Ile Cys Met
            195                 200                 205

Asp Asp Glu Phe Pro Ser Asp Val Asn Ser Asn Trp Met Ala Thr Ser
        210                 215                 220

Phe Thr Asp Val Gln Lys Leu Gly Arg Glu Asn Pro Val Asp Pro Asn
225                 230                 235                 240

Phe Pro Leu Ser Ala Asp Val Ala Val Ile Met Tyr Thr Ser Gly Ser
                245                 250                 255

Thr Gly Leu Pro Lys Gly Val Met Met Thr His Gly Asn Val Leu Ala
            260                 265                 270

Thr Val Ser Ala Val Met Thr Ile Val Pro Asp Leu Gly Lys Arg Asp
            275                 280                 285

Ile Tyr Met Ala Tyr Leu Pro Leu Ala His Ile Leu Glu Leu Ala Ala
        290                 295                 300

Glu Ser Val Met Ala Thr Ile Gly Ser Ala Ile Gly Tyr Gly Ser Pro
305                 310                 315                 320

Leu Thr Leu Thr Asp Thr Ser Asn Lys Ile Lys Lys Gly Thr Lys Gly
                325                 330                 335

Asp Val Thr Ala Leu Lys Pro Thr Ile Met Thr Ala Val Pro Ala Ile
            340                 345                 350
```

Leu Asp Arg Val Arg Asp Gly Val Arg Lys Val Asp Ala Lys Gly
                355                 360                 365

Gly Leu Ser Lys Lys Leu Phe Asp Phe Ala Tyr Ala Arg Arg Leu Ser
        370                 375                 380

Ala Ile Asn Gly Ser Trp Phe Gly Ala Trp Gly Leu Glu Lys Leu Leu
385                 390                 395                 400

Trp Asp Val Leu Val Phe Arg Lys Ile Arg Ala Val Leu Gly Gly Gln
                405                 410                 415

Ile Arg Tyr Leu Leu Ser Gly Ala Pro Leu Ser Gly Asp Thr Gln
            420                 425                 430

Arg Phe Ile Asn Ile Cys Val Gly Ala Pro Ile Gly Gln Gly Tyr Gly
                435                 440                 445

Leu Thr Glu Thr Cys Ala Gly Gly Thr Phe Ser Glu Phe Glu Asp Thr
    450                 455                 460

Ser Val Gly Arg Val Gly Ala Pro Leu Pro Cys Ser Phe Val Lys Leu
465                 470                 475                 480

Val Asp Trp Ala Glu Gly Gly Tyr Leu Thr Ser Asp Lys Pro Met Pro
                485                 490                 495

Arg Gly Glu Ile Val Ile Gly Gly Ser Asn Ile Thr Leu Gly Tyr Phe
                500                 505                 510

Lys Asn Glu Glu Lys Thr Lys Glu Val Tyr Lys Val Asp Glu Lys Gly
            515                 520                 525

Met Arg Trp Phe Tyr Thr Gly Asp Ile Gly Arg Phe His Pro Asp Gly
    530                 535                 540

Cys Leu Glu Ile Ile Asp Arg Lys Lys Asp Ile Val Lys Leu Gln His
545                 550                 555                 560

Gly Glu Tyr Val Ser Leu Gly Lys Val Glu Ala Ala Leu Ser Ile Ser
                565                 570                 575

Pro Tyr Val Glu Asn Ile Met Val His Ala Asp Ser Phe Tyr Ser Tyr
                580                 585                 590

Cys Val Ala Leu Val Val Ala Ser Gln His Thr Val Glu Gly Trp Ala
            595                 600                 605

Ser Lys Gln Gly Ile Asp Phe Ala Asn Phe Glu Glu Leu Cys Thr Lys
    610                 615                 620

Glu Gln Ala Val Lys Glu Val Tyr Ala Ser Leu Val Lys Ala Ala Lys
625                 630                 635                 640

Gln Ser Arg Leu Glu Lys Phe Glu Ile Pro Ala Lys Ile Lys Leu Leu
                645                 650                 655

Ala Ser Pro Trp Thr Pro Glu Ser Gly Leu Val Thr Ala Ala Leu Lys
                660                 665                 670

Leu Lys Arg Asp Val Ile Arg Arg Glu Phe Ser Glu Asp Leu Thr Lys
            675                 680                 685

Leu Tyr Ala
    690

<210> SEQ ID NO 133
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X can be Leu, Ile, Val, Met, Phe or Tyr.
<220> FEATURE:
<221> NAME/KEY: MISC_FEATURE

```
<222> LOCATION: (2)..(3)
<223> OTHER INFORMATION: X can be any amino acid.
<220> FEATURE:
<221> NAME/KEY: MISC_FEATURE
<222> LOCATION: (4)..(4)
<223> OTHER INFORMATION: X can be Ser, Thr, or Gly.
<220> FEATURE:
<221> NAME/KEY: MISC_FEATURE
<222> LOCATION: (5)..(5)
<223> OTHER INFORMATION: X can be Ser, Thr, Ala, or Gly.
<220> FEATURE:
<221> NAME/KEY: MISC_FEATURE
<222> LOCATION: (7)..(7)
<223> OTHER INFORMATION: X can be Ser or Thr.
<220> FEATURE:
<221> NAME/KEY: MISC_FEATURE
<222> LOCATION: (8)..(8)
<223> OTHER INFORMATION: X can be Ser, Thr, Glu, or Ile.
<220> FEATURE:
<221> NAME/KEY: MISC_FEATURE
<222> LOCATION: (9)..(9)
<223> OTHER INFORMATION: X can be Ser or Gly.
<220> FEATURE:
<221> NAME/KEY: MISC_FEATURE
<222> LOCATION: (10)..(10)
<223> OTHER INFORMATION: X can be any amino acid.
<220> FEATURE:
<221> NAME/KEY: MISC_FEATURE
<222> LOCATION: (11)..(11)
<223> OTHER INFORMATION: X can be Pro, Ala, Ser, Leu, Ile, Val, or Met.
<220> FEATURE:
<221> NAME/KEY: MISC_FEATURE
<222> LOCATION: (12)..(12)
<223> OTHER INFORMATION: X can be Lys or Arg.

<400> SEQUENCE: 133

Xaa Xaa Xaa Xaa Xaa Gly Xaa Xaa Xaa Xaa Xaa Xaa
1               5                   10

<210> SEQ ID NO 134
<211> LENGTH: 12
<212> TYPE: DNA
<213> ORGANISM: Arabidopsis thaliana

<400> SEQUENCE: 134
gtgtttgatg tt                                                         12

<210> SEQ ID NO 135
<211> LENGTH: 12
<212> TYPE: DNA
<213> ORGANISM: Arabidopsis thaliana

<400> SEQUENCE: 135 gcttttcct at                                                          12

<210> SEQ ID NO 136
<211> LENGTH: 4
<212> TYPE: PRT
<213> ORGANISM: Arabidopsis thaliana

<400> SEQUENCE: 136

Val Phe Asp Val
1

<210> SEQ ID NO 137
<211> LENGTH: 4
<212> TYPE: PRT
<213> ORGANISM: Arabidopsis thaliana

<400> SEQUENCE: 137
```

Ala Phe Ser Tyr
1

<210> SEQ ID NO 138
<211> LENGTH: 21
<212> TYPE: DNA
<213> ORGANISM: Artificial Sequence
<220> FEATURE:
<223> OTHER INFORMATION: Synthetic

<400> SEQUENCE: 138
tttttttttt tttttttttt c                                                    21

<210> SEQ ID NO 139
<211> LENGTH: 21
<212> TYPE: DNA
<213> ORGANISM: Artificial Sequence
<220> FEATURE:
<223> OTHER INFORMATION: Synthetic

<400> SEQUENCE: 139
tttttttttt tttttttttt a                                                    21

<210> SEQ ID NO 140
<211> LENGTH: 21
<212> TYPE: DNA
<213> ORGANISM: Artificial Sequence
<220> FEATURE:
<223> OTHER INFORMATION: Synthetic

<400> SEQUENCE: 140
tttttttttt tttttttttt g                                                    21

<210> SEQ ID NO 141
<211> LENGTH: 24
<212> TYPE: DNA
<213> ORGANISM: Arabidopsis thaliana

<400> SEQUENCE: 141
gtgtttgatg ttgcttttc ctat                                                  24